(12) United States Patent
Scobie et al.

(10) Patent No.: US 10,179,790 B2
(45) Date of Patent: *Jan. 15, 2019

(54) MTH1 INHIBITORS FOR TREATMENT OF CANCER

(71) Applicant: THOMAS HELLEDAYS STIFTELSE FOR MEDICINSK FORSKNING, Stocksund (SE)

(72) Inventors: Martin Scobie, Uppsala (SE); Olov Wallner, Solna (SE); Tobias Koolmeister, Stockholm (SE); Karl Sven Axel Vallin, Stockholm (SE); Carl Martin Henriksson, Bromma (SE); Sylvain Jacques, Lyons (FR); Evert Homan, Sollentuna (SE); Thomas Helleday, Stocksund (SE)

(73) Assignee: THOMAS HELLEDAYS STIFTELSE FOR MEDICINSK FORSKNING, Stocksund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/315,461

(22) PCT Filed: Jun. 4, 2015

(86) PCT No.: PCT/SE2015/050653
§ 371 (c)(1),
(2) Date: Dec. 1, 2016

(87) PCT Pub. No.: WO2015/187088
PCT Pub. Date: Dec. 10, 2015

(65) Prior Publication Data
US 2017/0197976 A1    Jul. 13, 2017

(30) Foreign Application Priority Data

Jun. 4, 2014  (SE) ...................... 1450680

(51) Int. Cl.
| | | |
|---|---|---|
| *A61K 31/505* | (2006.01) |
| *C07D 491/044* | (2006.01) |
| *A61K 31/506* | (2006.01) |
| *C07D 239/48* | (2006.01) |
| *C07D 409/04* | (2006.01) |
| *C07D 413/12* | (2006.01) |
| *C07D 417/12* | (2006.01) |
| *A61K 45/06* | (2006.01) |
| *A61K 31/517* | (2006.01) |
| *A61K 31/52* | (2006.01) |
| *A61K 31/53* | (2006.01) |

(Continued)

(52) U.S. Cl.
CPC ........ *C07D 491/044* (2013.01); *A61K 31/505* (2013.01); *A61K 31/506* (2013.01); *A61K 31/517* (2013.01); *A61K 31/52* (2013.01); *A61K 31/53* (2013.01); *A61K 31/538* (2013.01); *A61K 31/5377* (2013.01); *A61K 45/06* (2013.01); *C07D 239/48* (2013.01); *C07D 401/04* (2013.01); *C07D 401/12* (2013.01); *C07D 403/04* (2013.01); *C07D 403/12* (2013.01); *C07D 405/04* (2013.01); *C07D 405/12* (2013.01); *C07D 409/04* (2013.01); *C07D 413/12* (2013.01); *C07D 413/14* (2013.01); *C07D 417/12* (2013.01); *C07D 473/16* (2013.01); *C07D 473/34* (2013.01); *C07D 487/04* (2013.01); *C07D 491/048* (2013.01)

(58) Field of Classification Search
CPC .............. C07D 491/044; C07D 239/48; C07D 401/04; C07D 401/12; C07D 403/04; C07D 403/12; C07D 405/04; C07D 405/12; C07D 413/14; C07D 417/12; C07D 473/16; C07D 491/048; C07D 409/04; C07D 413/12; C07D 473/34; C07D 487/04; A61K 31/505; A61K 31/506; A61K 31/517; A61K 31/52; A61K 31/53; A61K 31/5377; A61K 31/538; A61K 45/06

See application file for complete search history.

(56) References Cited

U.S. PATENT DOCUMENTS

| | | | |
|---|---|---|---|
| 6,169,086 B1 | 1/2001 | Ejima et al. | |
| 8,268,846 B2 * | 9/2012 | Wakefield | C07D 491/048 514/267 |

(Continued)

FOREIGN PATENT DOCUMENTS

| | | |
|---|---|---|
| CN | 104288170 A | 1/2015 |
| GB | 0 681 712 | 10/1952 |

(Continued)

OTHER PUBLICATIONS

CAS Registry No. 1214470-09-3 (2010).*

(Continued)

*Primary Examiner* — Alexander R Pagano
(74) *Attorney, Agent, or Firm* — Foley & Lardner LLP

(57) ABSTRACT

A compound of formula I, (I) or a pharmaceutically-acceptable salt thereof. The compound is useful in the treatment of cancer.

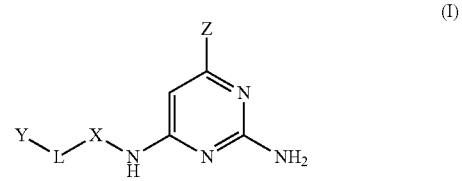

46 Claims, 1 Drawing Sheet

(51) Int. Cl.

| | |
|---|---|
| A61K 31/5377 | (2006.01) |
| A61K 31/538 | (2006.01) |
| C07D 403/12 | (2006.01) |
| C07D 413/14 | (2006.01) |
| C07D 401/12 | (2006.01) |
| C07D 405/12 | (2006.01) |
| C07D 473/16 | (2006.01) |
| C07D 473/34 | (2006.01) |
| C07D 491/048 | (2006.01) |
| C07D 401/04 | (2006.01) |
| C07D 403/04 | (2006.01) |
| C07D 405/04 | (2006.01) |
| C07D 487/04 | (2006.01) |

(56) References Cited

U.S. PATENT DOCUMENTS

| | | | | |
|---|---|---|---|---|
| 8,486,950 | B2* | 7/2013 | Goodacre | C07D 401/12 514/256 |
| 9,604,937 | B2* | 3/2017 | Scobie | A61K 31/505 |
| 9,944,640 | B2* | 4/2018 | Scobie | C07D 471/04 |
| 2004/0204386 | A1 | 10/2004 | Bhatt et al. | |
| 2008/0194577 | A1 | 8/2008 | Cai et al. | |
| 2010/0016344 | A1 | 1/2010 | Wakefield et al. | |
| 2010/0035863 | A1 | 2/2010 | Raphy et al. | |
| 2011/0275611 | A1 | 11/2011 | Axten et al. | |
| 2017/0196873 | A1* | 7/2017 | Scobie | A61K 31/538 |

FOREIGN PATENT DOCUMENTS

| | | | |
|---|---|---|---|
| WO | WO-86/04583 | 8/1986 | |
| WO | WO-02/096867 | 12/2002 | |
| WO | WO-03/015776 | 2/2003 | |
| WO | WO-2004/080979 | 9/2004 | |
| WO | WO-2005/026129 A1 | 3/2005 | |
| WO | WO-2005035507 A2 * | 4/2005 | C04B 35/632 |
| WO | WO-2005/092899 A1 | 10/2005 | |
| WO | WO-2006/078886 A2 | 7/2006 | |
| WO | WO-2009/105220 | 8/2009 | |
| WO | WO-2010/059658 | 5/2010 | |
| WO | WO-2011/056916 | 5/2011 | |
| WO | WO-2011/100285 | 8/2011 | |
| WO | WO-2012/080729 | 6/2012 | |
| WO | WO-2013/066839 A2 | 5/2013 | |
| WO | WO-2014/033480 A1 | 3/2014 | |

OTHER PUBLICATIONS

CAS Registry No. 1269067-56-2 (2011).*
CAS Registry No. 1381398-05-5 (2011).*
CAS Abstract and Indexed Compounds U.S. Pat. No. 8,268,846 (Sep. 18, 2012) (Year: 2012).*
H. Engelhardt, 56 Journal of Medicinal Chemistry, 4264-4276 (2013) (Year: 2013).*
Database CAPLUS in STN Acc. No. 1955:60839, Hitchings et al., U.S. Pat. No. 2691655 (Oct. 12, 1954)(abstract).
Database CAPLUS in STN, Acc. No. 2010:84378, Wakefield et al., U.S. Pat. No. 8,268,846 B2 (Sep. 18, 2012)(abstract).
Engelhardt et al. "Bispyrimidines as Potent Histamine H4 Receptor Ligands: Delineation of Structure—Activity Relationships and Detailed H4 Receptor Binding Mode," Journal of Medicinal Chemistry, vol. 56, May 13, 2013, pp. 4264-4276.
Extract from STN Registry—database, STN International, File Registry—RN: 634582-11-9 Entered STN: Jan. 6, 2004; RN: 634195-10-1 Entered STN: Jan. 5, 2004; RN: 634195-07-6 Entered STN: Jan. 5, 2004, 1 page.
Gad et al., "MTH1 inhibition eradicates cancer by preventing sanitation of the dNTP pool." Nature 508: 215-221 (2014).
Huber et al., "Stereospecific targeting of MTH1 by (S)-crizotinib as an anticancer strategy," Nature 508: 222-227 (2014).
International Search Report and Written Opinion for PCT/SE2013/051387, dated Mar. 10, 2014.
International Search Report and Written Opinion in PCT/SE2015/050654 dated Sep. 22, 2015.
Kambe et al., "Mapping the Protein Interaction Landscape for Fully Functionalized Small-Molecule Probes in Human Cells," J Am Chem Soc 136(30): 10777-10782 (2014).
Katiyar et al., "Syntheses of 2,4,6-trisubstituted pyrimidine derivatives as a new class of antifilarial topoisomerase II inhibitors," Bioorganic & Medicinal Chemistry Letters 15 (2005) pp. 47-50.
Koketsu et al., "Expression of DNA Repair Protein: MYH, NTH1, and MTH1 in Colorectal Cancer." Hepato-Gastroenterology 51: 638-642 (2004).
Kumar et al., "A novel and convenient synthesis of 2-amino-4-(N-alkyl-N-arylamino)-pyrimidines using polarized ketene S,S- and S,N-acetals." Synthesis 1980(9): 748-751 (1980).
Lee et al., "Discovery of a novel class of 2-aminopyrimidines as CDK1 and CDK2 inhibitors," Bioorganic & Medicinal Chemistry Letters vol. 21, 2001, pp. 4203-4205.
Medina et al., "Structure-Based Design of Potent and Selective 3-Phosphoinositide-Depdendent Kinase-1 (PDK1) Inhibitors," Journal of Medicinal Chemistry, vol. 54, No. 6, Mar. 24, 2011, pp. 1871-1895.
Mizar et al., "Three-component synthesis of 5:6 and 6:6 fused pyrimidines using KF-alumina as a catalyst," Tetrahedron letters 49 (2008), pp. 5283-5285.
Rabbani et al., "Prevention of prostate-cancer metastasis in vivo by a novel synthetic inhibitor of urokinase-type plasminogen activator (uPA)," International Journal of Cancer (1995), 63, pp. 840-845.
Rai et al., "A roadblock for the tumor-suppressive effects of oncogenic RAS-induced ROS," Small TGPASES 2012, vol. 3, No. 2, Apr. 1, 2012, pp. 120-125.
Rai et al., "Continuous elimination of oxidized nucleotides is necessary to prevent rapid onset of cellular senescence." PNAS 106(1): 169-174 (2009).
Sakumi et al., "Ogg1 Knockout-associated Lung Tumorigenesis and Its Suppression by Mth1 Gene Disruption." Cancer Research 63: 902-905 (2003).
Saleh et al., "Development and validation of method for TH588 and TH287, potent MTH1 inhibitors and new anti-cancer agents, for pharmacokinetic studies in mice plasma," J Pharm Biomed Analysis 104: 1-11 (2015).
Sekiguchi et al., "Oxidative nucleotide damage: consequences and prevention." Oncogene 21: 8895-8904 (2002).
Shi et al., "Modulation of Peripheral Serotonin Levels by Novel Tryptophan Hydroxylase Inhibitors for the Potential Treatment of Functional Gastrointestinal Disorders," Journal of Medicinal Chemistry, vol. 51, No. 13, Jul. 10, 2008, pp. 3684-3687.
Streib et al., "An Organometallic Inhibitor for the Human Repair Enzyme 7,8-Dihydro-8-oxoguanosine Triphosphatase," Angewandte Chemie 53(1): 305-309 (Jan. 2014).
Sunduru et al., "Discovery of new 1,3,5-triazine scaffolds with potent activity against *Mycobacterium tuberculosis* H37Rv," European Journal of Medicinal Chemistry, vol. 45, 2010, pp. 3335-3345.
Supplementary European Search Report issued on EP Application EP13859400, dated Jul. 11, 2016.
Svennson et al., "Crystall structure of human MTH1 and the 8-oxo-dGMP product complex," FEBS Letters, vol. 585, 2011, pp. 2617-2621.
Tani, Database CAPLUS 1975:140168, JP 4921147B, abstract, 1974.
Tani, Database CAPLUS 1975:140173, JP 4921147B, abstract, 1974.
Non-Final Rejection dated Apr. 26, 2016 in U.S. Appl. No. 14/647,400.
Notice of Allowance dated Nov. 28, 2016 in U.S. Appl. No. 14/647,400.
Vishwakarma et al., Database Accession No. 1986:406471, 2 pages.
Zhang et al., "Redox Control of the Survival of Healthy and Diseased Cells." Antioxidants & Redox Signaling 15(11): 2867-2908 (2011).
Database Registry Extract, American Chemical Society [database online], Jul. 22, 2016 [retrieved on Aug. 1, 2016] (856972-52-6/RN, 856972-54-8/RN, 856972-56-0/RN, 856972-52-6/RN).

(56) References Cited

OTHER PUBLICATIONS

Gong, et al., "Synthesis, SAR, and Antitumor Properties of Diamino-C, N-Diarylpyrimidine Positional Isomers: Inhibitors of Lysophosphatidic Acid Acyltransferase-beta," Bioorganic & Medicinal Chemistry Letters, 2004, 14, pp. 2303-2308.

Sander, et al., "2, 4-Diaminopyrimidines as Histamine H4 Receptor Ligands-Scaffold Optimization and Pharmacological Characterization," Bioorganic & Medicinal Chemistry, 2009, 17, pp. 7186-7196.

Schreeb, et al., "Piperazine Modification in 2, 4, 6-Triaminopyrimidine Derivatives as Histamine H4, Receptor Ligands," Pharmazine, 2013, 68, pp. 521-525.

* cited by examiner

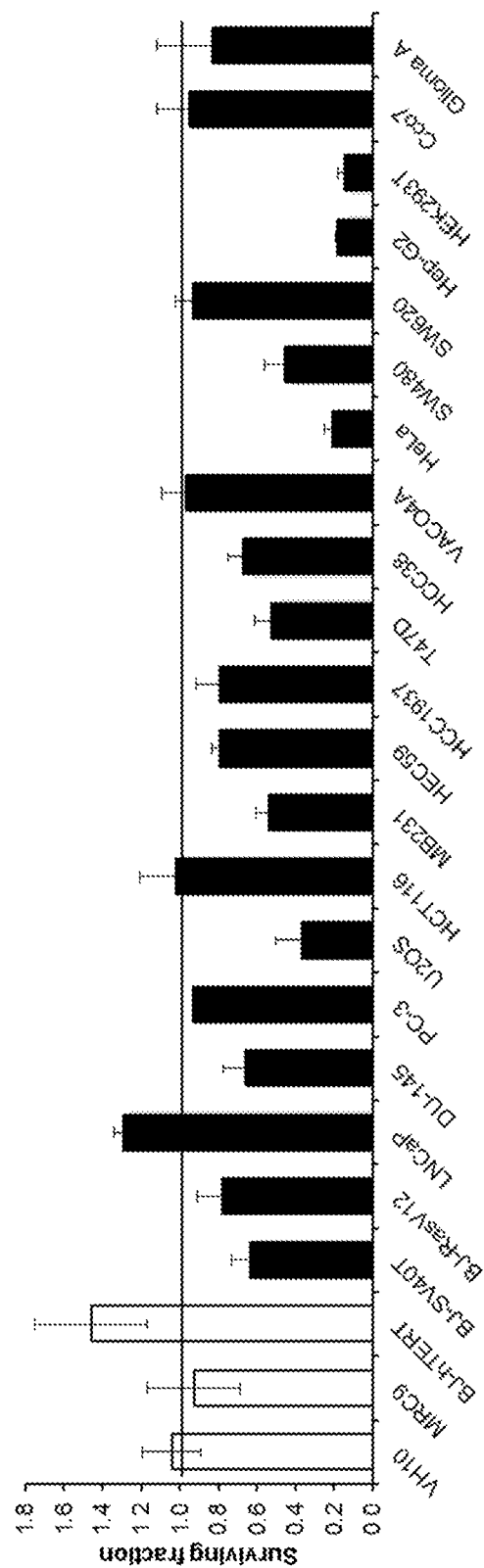

MTH1 INHIBITORS FOR TREATMENT OF CANCER

CROSS REFERENCE TO RELATED APPLICATIONS

This application is a U.S. National Stage Application under 35 U.S.C. § 371 of International Application of PCT/SE2015/050653, filed Jun. 4, 2015, which claims the benefit of and priority to SE Application 1450680-2, filed Jun. 4, 2014, the contents of which are incorporated herein by reference in their entireties.

FIELD OF THE INVENTION

The invention relates to novel compounds, compositions and methods for treatment of cancer. In particular, the invention relates to novel compounds, compositions and methods for the treatment of cancers through inhibition of MTH1.

BACKGROUND OF THE INVENTION

The listing or discussion of an apparently prior-published document in this specification should not necessarily be taken as an acknowledgement that the document is part of the state of the art or is common general knowledge.

BACKGROUND

Dysfunctional redox regulation of cellular signalling and an increased ROS (Reactive oxygen species) tension have been demonstrated to play a crucial role in cancer etiology, progression and metastasis (Zhang et al., Antioxid Redox Signal 15(11)2011:2876-2908). ROS mediates tumor-promoting characteristics, such as e.g. unrestrained proliferation, survival signaling, increased migration, angiogenesis. ROS are generated during cell metabolism and are highly reactive with macromolecules such as DNA, proteins and lipids. Exposure of nucleic acids to ROS can create more than 20 oxidatively modified nucleotides, of which 8-oxo-7,8-dihydroxyguanine (8-oxo-dG) is most abundant. 8-oxo-dG plays a pivotal role in mutagenesis (Sekiguchi and Tsuzuki., Oncogene 21(58)2002:8895-906). To protect themselves from carcinogenic effects, mammalian cells are armed with a set of repair enzymes to remove the oxidized nucleotides to maintain genome integrity. One of these protective enzymes is MTH1 (MutT homologue 1, 8-oxo-dGTPase, NUDT1). Interestingly, MTH1 is upregulated in various cancer forms, suggesting that the cancer cell rely on MTH1 function to survive the increased DNA lesion (Human Proteinatlas, Koketsu et al., Hepatogastroenterology, 51(57)2004:638-41). Suppression of MTH1 level and activity by using RNAi technology, leads to reduced cancer cell survival, premature senescence and DNA strand breaks (Rai et al, PNAS, 106(1)2009:169-174), Helleday et al unpublished data). Interestingly, lung cancers which spontaneously form in OGG–/– mice are prevented from forming in crosses with the MTH1–/– mice, suggesting that MTH1 is required for lung cancer cells to survive (Sakumi et al., Cancer Res 63, 2003: 902). We have observed that downregulation of MTH1 protein levels in human colon cancer tumors in xenograft mice model reduced tumor growth and significantly shrinked the tumour (Helleday et al, unpublished data).

In tumour cells, reducing the capacity to eliminate oxidised dNTPs by inhibiting MTH1 activity, will reduce cancer cell survival and hence be a promising novel anticancer therapy, either as monotherapy in cancer forms with high oxidative stress levels and/or in combination with radiotherapy and chemotherapy drugs.

Shortcomings and Complications with Current Treatment

Today's treatment of cancer is not effective for all patients with diagnosed disease also including a large proportion of patients that experience adverse effects from treatments with existing therapies or where resistance to on-going therapy is developed over time.

PRIOR ART

Engelhardt, H. et al. *Journal of Medicinal Chemistry* (2013), 56(11), 4264-4276 discloses certain 6-aryl-2,4-diaminopyrimidines having an additional pyrimidine appendage as histamine H4 receptor modulators. The compounds are claimed to be useful for a various diseases including cancer pain, but their use in the treatment of cancer as such is neither disclosed or suggested.

US patent application US 2010/0016344 disclose certain 6-aryl-2,4-diaminopyrimidines having an additional pyrimidine appendage as histamine H4 receptor modulators. The compounds are claimed to be useful for a various diseases including cancer.

International patent application WO 2013/066839 discloses 6-(3-pyridyl)-(2,4-diaminopyrimidines as HDAC inhibitors useful in the treatment for cancer. However, the substituent on the 4-amino group contains an essential (5-trifluoromethyl-1,2,4-oxadiazol-3-yl)benzyl group.

2,4-Diaminopyrimidines substituted in the 6-position with indazolyl or 3-cyano-2-fluorophenyl are described in international patent application WO 2010/059658. However, when the 4-amino group is substituted by aryl —CH$_2$CH$_2$—, the aryl is either phenyl, 2-fluorophenyl or 2-methylphenyl. In addition, the compounds with a 3-cyano-2-fluorophenyl substituent in the 6-position are merely precursors to the 3-aminoindazoles mentioned above and there is no disclosure or suggestions in the document that they possess any anti-cancer activity.

International patent application WO 2006/078886 describes 2,4-diaminopyrimidines substituted in the 6-position by an aryl group but where the 4-amine is substituted by a benzylic group.

MTH1 inhibitors have been described in Streib, M. et al. *Angewandte Chemie, Int., Ed.* (2014), 52, 305-309. The compounds are organometallic and are not substituted 2,4-diaminopyrimidines.

Huber, K. V. M. et al. *Nature* (2014), 508, 222-227 describe certain compounds, i.e. (S)-crizotinib, as MTH1 inhibitors. However, the compounds are not substituted 2,4-diaminopyrimidines.

Gad, H. et al. *Nature* (2014), 508, 215-221 and Saleh, A. et al. *Journal of Pharmaceutical and Biomedical Analysis* (2015), 104, 1, describe certain 2,4-diaminopyrimidines as MTH1 inhibitors. However, there are no compounds disclosed or suggested that have an aryl or heteroaryl connected to the 4-amino group of the pyrimidine core.

International patent application WO 2013/066839 discloses certain 2,4-diaminopyrimidines as HDAC inhibitors. However, the 4-amino group is substituted with arylmethyl- or heteroarylmethyl that contain a prerequisite 5-trifluoromethyl-1,2,4-oxadiazol-3-yl group.

Chinese patent application CN104288170 describes the natural product echinacoside as an inhibitor of MTH1. However this compound is a sugar derivative and not a pyrimidine Kambe, T. et al. *Journal of the American Chemical Society* (2014), 136, 10777 demonstrate a tetrazole-based MTH1 ligand.

SUMMARY OF THE INVENTION

Although the finding of oncogenes and development of new anticancer treatments and diagnosis have improved the life length of cancer patients, there is still a high medical need to find more effective and less toxic treatments for e.g. breast cancer, leukemia, colon or lung cancer. Our data suggests that MTH1 inhibitors have the potential to be very effective against cancer forms with dysfunctional redox status, with minimal general toxic effects. MTH1 inhibition may also be a suitable adjuvant therapy to be used in conjunction with radiotherapies or other chemotherapeutic approaches.

The present invention aims at providing new treatments for cancer that can be achieved by inhibition of MTH1

BRIEF DESCRIPTION OF THE DRAWINGS

FIG. 1. Effect on cell survival following MTH1 siRNA depletion in various human cancer and normal cell lines.

DETAILED DESCRIPTION OF THE INVENTION

There is provided a compound of formula I,

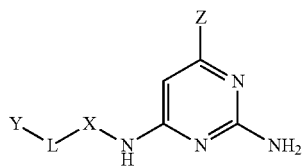

(I)

or a pharmaceutically acceptable salt thereof,
wherein:
X represents —$C_{2-6}$alkylene- optionally substituted by one or more $T^1$, or —$(C(R^A)_2)_p$—$C_{2-5}$heterocycloalkylene-$(C(R^A)_2)_q$— where the heterocycloalkylene is optionally substituted by one or more $T^2$;
L represents a single bond or -$L^1$-$L^2$-;
$L^1$ represents —N($R^B$)—, —O—, —S(O)$_m$—, —C(O)N($R^C$)—, —N($R^D$)C(O)— or —N($R^E$)C(O)N($R^F$)—;
$L^2$ represents a single bond or —$C_{1-6}$alkylene-;
Y represents
(i) a 6- to 10-membered aryl substituted by $D^1$ and optionally substituted by one or more groups selected from $R^1$, or
(ii) a 6-membered heteroaryl substituted by $D^2$ and optionally substituted by one or more groups selected from $R^2$, or
(iii) a 5-membered heteroaryl substituted by $D^3$ and optionally substituted by one or more groups selected from $R^3$, or
(iv) a 9-membered bicyclic heteroaryl, in which one ring is 5-membered and the other 6-membered, which heteroaryl is connected to L via its 5-membered ring and substituted by one or more groups selected from $D^4$, and optionally substituted by one or more groups selected from $R^4$, or
(v) a 9- to 11-membered bicyclic heteroaryl, in which one ring is 6-membered and the other 5-7-membered, which heteroaryl is connected to L via its 6-membered ring and optionally substituted by one or more groups selected from $D^5$, or
(vi) an 8-membered bicyclic heteroaryl optionally substituted by one or more groups selected from $D^6$;
$D^1$ represents $R^a$, -A-C(Q)$R^c$, -A-C(Q)N($R^d$)$R^e$, -A-C(Q)O$R^f$, -A-S(O)$_n$$R^g$, -A-S(O)$_n$C(O)$R^h$, -A-S(N$R^i$)(O)$R^j$, -A-S(O)$_n$N($R^k$)$R^l$, -A-S(O)$_n$O$R^m$, —B(O$R^n$)$_2$, —$N_3$, —N($R^o$)$R^p$, —N(H)CN, —$NO_2$, —$ONO_2$, —O$R^q$, —S$R^r$ or, when Y is partly aromatic, =Q;
$D^2$ represents $R^b$, -A-C(Q)$R^c$, -A-C(Q)N($R^d$)$R^e$, -A-C(Q)O$R^f$, -A-S(O)$_n$$R^g$, -A-S(O)$_n$C(O)$R^h$, -A-S(N$R^i$)(O)$R^j$, -A-S(O)$_n$N($R^k$)$R^l$, -A-S(O)$_n$O$R^m$, —B(O$R^n$)$_2$, —$N_3$, —N($R^o$)$R^p$, —N(H)CN, —$NO_2$, —$ONO_2$, —O$R^q$ or —S$R^r$;
$D^3$ represents —CN, $R^a$, -A-C(Q)$R^c$, -A-C(Q)N($R^d$)$R^e$, -A-C(Q)O$R^f$, -A-S(O)$_n$$R^g$, -A-S(O)$_n$C(O)$R^h$, -A-S(N$R^i$)(O)$R^j$, -A-S(O)$_n$N($R^k$)$R^l$, -A-S(O)$_n$O$R^m$, —B(O$R^n$)$_2$, —$N_3$, —N($R^o$)$R^p$, —N(H)CN, —$NO_2$, —$ONO_2$, —O$R^q$ or —S$R^r$;
$D^4$ represents —CN, $R^b$, -A-C(Q)$R^c$, -A-C(Q)N($R^d$)$R^e$, -A-C(Q)O$R^f$, -A-S(O)$_n$$R^g$, -A-S(O)$_n$C(O)$R^h$, -A-S(N$R^i$)(O)$R^j$, -A-S(O)$_n$N($R^k$)$R^l$, -A-S(O)$_n$O$R^m$, —B(O$R^n$)$_2$, —$N_3$, —N($R^o$)$R^p$, —N(H)CN, —$NO_2$, —$ONO_2$, —O$R^q$, —S$R^r$ or, when Y is partly aromatic, =Q;
$D^5$ and $D^6$ represent halogen, —CN, $R^b$, -A-C(Q)$R^c$, -A-C(Q)N($R^d$)$R^e$, -A-C(Q)O$R^f$, -A-S(O)$_n$$R^g$, -A-S(O)$_n$C(O)$R^h$, -A-S(N$R^i$)(O)$R^j$, -A-S(O)$_n$N($R^k$)$R^l$, -A-S(O)$_n$O$R^m$, —B(O$R^n$)$_2$, —$N_3$, —N($R^o$)$R^p$, —N(H)CN, —$NO_2$, —$ONO_2$, —O$R^q$, —S$R^r$ or, when Y is partly aromatic, =Q;
each $R^1$, $R^2$, $R^3$ and $R^4$ independently represents halogen, —CN, $R^y$, —$NO_2$, —O$R^z$ or =O;
A represents a single bond, —N($R^G$)—, —C(Q)N($R^H$)— or —O—;
Q represents =O, =S, =N$R^s$, =NN($R^t$)$R^u$, =N(O$R^v$), =NS(O)$_2$N($R^w$)$R^x$ or =C(H)$NO_2$;
Z represents
(i) a 6- to 10-membered aryl optionally substituted by one or more groups selected from $D^7$, or
(ii) a 5- to 10-membered monocyclic or bicyclic heteroaryl optionally substituted by one or more groups selected from $D^8$, or
(iii) a 3- to 8-membered nonaromatic ring, which ring optionally contains one or two heteroatoms and/or one or two double bonds, and which ring is optionally substituted by one or more groups selected from $D^9$;
$D^7$ and $D^8$ represent halogen, —CN, $R^{a1}$, -$A^1$-C($Q^1$)$R^{b1}$, -$A^1$-C($Q^1$)N($R^{c1}$)$R^{d1}$, -$A^1$-C($Q^1$)O$R^{e1}$, -$A^1$-S(O)$_n$$R^{f1}$, -$A^1$-S(O)$_n$C(O)$R^{g1}$, -$A^1$-S(N$R^{h1}$)(O)$R^{i1}$, -$A^1$-S(O)$_n$N($R^{j1}$)$R^{k1}$, -$A^1$-S(O)$_n$O$R^{l1}$, —B(O$R^{m1}$)$_2$, —$N_3$, —N($R^{n1}$)$R^{o1}$, —N(H)CN, —$NO_2$, —$ONO_2$, —O$R^{p1}$, —S$R^{q1}$ or, when Z is partly aromatic, =$Q^1$;
$D^9$ represents halogen, —CN, $R^{a1}$, -$A^1$-C($Q^1$)$R^{b1}$, -$A^1$-C($Q^1$)N($R^{c1}$)$R^{d1}$, -$A^1$-C($Q^1$)O$R^{e1}$, -$A^1$-S(O)$_n$$R^{f1}$, -$A^1$-S(O)$_n$N($R^{j1}$)$R^{k1}$, —N($R^{n1}$)$R^{o1}$, —O$R^{p1}$ or =$Q^1$;
$A^1$ represents a single bond, —N($R^I$)— or —C($Q^1$)N($R^J$)—;
$Q^1$ represents =O, =S, =N$R^{r1}$, =NN($R^{s1}$)$R^{t1}$, =N(O$R^{u1}$), =NS(O)$_2$N($R^{v1}$)$R^{w1}$ or =C(H)$NO_2$;
$R^a$ and $R^q$ represent $C_1$alkyl substituted by one or more groups selected from $G^1$, $C_{2-6}$alkyl optionally substituted by one or more groups selected from $G^1$, heterocycloalkyl optionally substituted by one or more groups selected from $G^2$, aryl optionally substituted by one or more groups selected from $G^3$ or heteroaryl optionally substituted by one or more groups selected from $G^4$;
$R^d$ represents hydrogen, $R^b$, —C(O)O$R^f$, —S(O)$_n$$R^g$, —S(O)$_n$N($R^k$)$R^l$, —N($R^o$)$R^p$ or —O$R^q$;

each $R^c$, $R^e$, $R^f$, $R^h$, $R^i$, $R^k$, $R^l$, $R^m$, $R^n$, $R^o$, $R^p$, $R^r$, $R^s$, $R^u$, $R^t$, $R^u$, $R^v$, $R^w$, $R^x$, $R^y$ and $R^z$ independently represents hydrogen, $C_{1-6}$alkyl optionally substituted by one or more groups selected from $G^1$, heterocycloalkyl optionally substituted by one or more groups selected from $G^2$, aryl optionally substituted by one or more groups selected from $G^3$ or heteroaryl optionally substituted by one or more groups selected from $G^4$; or any two $R^d$ and $R^e$, $R^k$ and $R^l$, $R^o$ and $R^p$, $R^t$ and $R^u$ and/or $R^w$ and $R^x$ are linked together to form, along with the nitrogen atom to which they are attached, a 3- to 6-membered ring, which ring optionally contains one further heteroatom and which ring optionally is substituted by one or more groups selected from halogen, $C_{1-3}$alkyl optionally substituted by one or more halogens, and =O; or two $R^m$ are linked together to form, along with the boron, and the oxygen atoms to which they are attached, a 5- to 8-membered heterocyclic ring, which ring optionally contains one or more further heteroatoms and which ring optionally is substituted by one or more groups independently selected from halogen, $C_{1-3}$alkyl optionally substituted by one or more halogens, and/or =O;

each $R^b$, $R^g$ and $R^j$ independently represents $C_{1-6}$alkyl optionally substituted by one or more groups selected from $G^1$, heterocycloalkyl optionally substituted by one or more groups selected from $G^2$, aryl optionally substituted by one or more groups selected from $G^3$ or heteroaryl optionally substituted by one or more groups selected from $G^4$;

$R^{c1}$ represents $R^{a1}$, $-S(O)_nR^{g1}$, $-S(O)_nN(R^{j1})R^{k1}$, $-N(R^{m1})R^{o1}$ or $-OR^{p1}$;

each $R^{b1}$, $R^{d1}$, $R^{e1}$, $R^{g1}$, $R^{h1}$, $R^{j1}$, $R^{k1}$, $R^{l1}$, $R^{m1}$, $R^{n1}$, $R^{o1}$, $R^{p1}$, $R^{q1}$, $R^{r1}$, $R^{s1}$, $R^{t1}$, $R^{u1}$, $R^{v1}$ and $R^{w1}$ independently represents hydrogen, $C_{1-6}$alkyl optionally substituted by one or more groups selected from $G^5$, heterocycloalkyl optionally substituted by one or more groups selected from $G^6$, aryl optionally substituted by one or more groups selected from $G^7$ or heteroaryl optionally substituted by one or more groups selected from $G^8$; or any two $R^{c1}$ and $R^{d1}$, $R^{j1}$ and $R^{k1}$, $R^{n1}$ and $R^{o1}$, $R^{s1}$ and $R^{t1}$ and/or $R^{v1}$ and $R^{w1}$ are linked together to form, along with the nitrogen atom to which they are attached, a 3- to 6-membered ring, which ring optionally contains one further heteroatom and which ring optionally is substituted by one or more groups selected from halogen, $C_{1-3}$alkyl optionally substituted by one or more halogens, and =O; or two $R^{m1}$ are linked together to form, along with the boron, and the oxygen atoms to which they are attached, a 5- to 8-membered heterocyclic ring, which ring optionally contains one or more further heteroatoms and which ring optionally is substituted by one or more groups independently selected from halogen, $C_{1-3}$alkyl optionally substituted by one or more halogens, and/or =O;

each $R^{a1}$, $R^{f1}$ and $R^{l1}$ independently represents $C_{1-6}$alkyl optionally substituted by one or more groups selected from $G^5$, heterocycloalkyl optionally substituted by one or more groups selected from $G^6$, aryl optionally substituted by one or more groups selected from $G^7$ or heteroaryl optionally substituted by one or more groups selected from $G^8$;

each $G^1$ and $G^5$ independently represent a group selected from halogen, $-CN$, $-N_3$, $-N(R^{b2})R^{c2}$, $-N(H)C(O)R^{d2}$, $-N(H)S(O)_nR^{h2}$, $-OR^{k2}$, $-S(O)_mR^{l2}$ or =O; each $G^2$ and $G^6$ independently represents a group selected from halogen, $R^{a2}$, $-CN$, $-N_3$, $-N(R^{b2})R^{c2}$, $-N(H)C(O)R^{d2}$, $-N(H)S(O)_nR^{h2}$, $-OR^{k2}$, $-S(O)_mR^{l2}$ or =O;

each $G^3$, $G^4$, $G^7$ and $G^8$ independently represents a group selected from halogen, $-CN$, $R^{a2}$, $-N(R^{b2})R^{c2}$, $-A^2-C(O)$ $R^{d2}$, $-A^2-C(O)N(R^{e2})R^{f2}$, $-A^2-C(O)OR^{g2}$, $-A^2-S(O)_nR^{h2}$, $-A^2-S(O)_nN(R^{i2})R^{j2}$, $-OR^{k2}$ or =O;

$A^2$ represents a single bond or $-N(H)-$;

each $R^{a2}$ and $R^{h2}$ independently represents $C_{1-6}$ alkyl optionally substituted by one or more halogens;

each $R^{b2}$, $R^{c2}$, $R^{d2}$, $R^{e2}$, $R^{f2}$, $R^{g2}$, $R^{i2}$, $R^{j2}$, $R^{k2}$ and $R^{l2}$ independently represents hydrogen or $C_{1-6}$ alkyl optionally substituted by one or more halogens; or any two $R^{b2}$ and $R^{c2}$, $R^{e2}$ and $R^{f2}$ and/or $R^{i2}$ and $R^{j2}$ are linked together to form, along with the nitrogen atom to which they are attached, a 3- to 6-membered ring, which ring optionally contains one further heteroatom and which ring optionally is substituted by one or more groups selected from halogen, $C_{1-3}$alkyl optionally substituted by one or more halogens, and =O;

each $R^A$, $R^B$, $R^C$, $R^D$, $R^E$, $R^F$, $R^G$, $R^H$, $R^I$ and $R^J$ independently represents hydrogen or $C_{1-3}$alkyl optionally substituted by one or more halogens;

$T^1$ represents halogen, $-CN$, $-N(R^{b3})R^3$ or $-OR^{d3}$;

$T^2$ represents halogen, $-CN$, $R^{a3}$, $-OR^{d3}$ or =O;

each $R^{a3}$ independently represents $C_{1-6}$alkyl optionally substituted by one or more halogens;

each $R^{b3}$, $R^{c3}$ and $R^{d3}$ independently represents hydrogen or $C_{1-6}$alkyl optionally substituted by one or more halogens; or $R^{b3}$ and $R^{c3}$ are linked together to form, along with the nitrogen atom to which they are attached, a 3- to 6-membered ring;

each p and q independently represents 0, 1 or 2, provided that the sum of p and q is 0, 1 or 2;

each m independently represents 0, 1 or 2; and each n independently represents 1 or 2;

provided that when X represents $-CH_2CH_2-$, Y represents pyrimidin-4-yl, L represents $-L^1-L^2-$, $L^1$ represents $-N(H)-$, $L^2$ represents a single bond and Z represents phenyl, 3-chlorophenyl, 3,5-dichlorophenyl or 5-chloro-2-methoxyphenyl, then $R^b$ does not represent $-CH_3$, $R^o$ does not represent hydrogen and $R^p$ does not represent hydrogen or $-CH_2CH(CH_3)_2$, and provided that when X represents $-CH_2CH_2-$, Y represents pyrimidin-4-yl, L represents $-L^1-L^2-$, $L^1$ represents $-N(Me)-$, $L^2$ represents a single bond and Z represents phenyl, then $R^o$ does not represent hydrogen; and provided that formula I does not represent 4-(2-{[2-amino-6-(2,3-dichlorophenyl)pyrimidin-4-yl]amino}ethyl)benzene-1-sulfonamide, 4-(2-{[2-amino-6-(3-chloro-2-methylphenyl)pyrimidin-4-yl]amino}ethyl)benzene-1-sulfonamide, 4-(2-{[2-amino-6-(2,3-dimethylphenyl)pyrimidin-4-yl]amino}ethyl)benzene-1-sulfonamide, 6-(2,3-dimethylphenyl)-4-N-[2-(4-methanesulfonylphenyl)ethyl]pyrimidine-2,4-diamine, N-[3-(3-{[2-amino-6-(2,3-dimethylphenyl)pyrimidin-4-yl]amino}propoxy)phenyl]-acetamide, 6-(2,3-dimethylphenyl)-4-N-{2-[5-(4-fluorophenyl)-1,3,4-oxadiazol-2-yl]ethyl}-pyrimidine-2,4-diamine, 6-(2,3-dimethylphenyl)-4-N-[2-(4-methanesulfonylphenyl)ethyl]pyrimidine-2,4-diamine, 4-(2-{[2-amino-6-(3-chloro-2-methylphenyl)pyrimidin-4-yl]amino}ethyl)-N,N-dimethylbenzene-1-sulfonamide, 4-(2-{[2-amino-6-(2,3-dichlorophenyl)pyrimidin-4-yl]amino}ethyl)-N,N-dimethylbenzene-1-sulfonamide, 4-(2-{[2-amino-6-(2,3-dimethylphenyl)pyrimidin-4-yl]amino}ethyl)-N,N-dimethylbenzene-1-sulfonamide, 4-(2-{[2-amino-6-(4-fluoro-2,3-dimethylphenyl)pyrimidin-4-yl]amino}ethyl)-benzene-1-sulfonamide, 4-(2-{[2-amino-6-(3-cyano-2-methylphenyl)pyrimidin-4-yl]amino}ethyl)benzene-1-sulfonamide,
4-(2-{[2-amino-6-(5-chloro-2-methylphenyl)pyrimidin-4-yl]amino}ethyl)benzene-1-sulfonamide,
4-(2-{[2-amino-6-(3,4-dichloro-2-methylphenyl)pyrimidin-4-yl]amino}ethyl)-benzene-1-sulfonamide,
6-(4-fluoro-2,3-dimethylphenyl)-4-N-[2-(4-methanesulfonylphenyl)ethyl]pyrimidine-2,4-diamine,
6-(3,4-dichloro-2-methylphenyl)-4-N-[2-(4-methanesulfonylphenyl)ethyl]-pyrimidine-2,4-diamine,
4-(2-{[2-amino-6-(4-chloro-2-methylphenyl)pyrimidin-4-yl]amino}ethyl)benzene-1-sulfonamide,
4-(2-{[2-amino-6-(2-chloro-4-fluorophenyl)pyrimidin-4-yl]amino}ethyl)benzene-1-sulfonamide,
4-(2-{[2-amino-6-(2,3,4-trifluorophenyl)pyrimidin-4-yl]amino}ethyl)benzene-1-sulfonamide,
4-(2-{[2-amino-6-(4-fluoro-3-methylphenyl)pyrimidin-4-yl]amino}ethyl)benzene-1-sulfonamide,
4-(2-{[2-amino-6-(4-fluoro-2,5-dimethylphenyl)pyrimidin-4-yl]amino}ethyl)-benzene-1-sulfonamide,
6-[(2-{[2-amino-6-(2,3-dimethylphenyl)pyrimidin-4-yl]amino}ethyl)amino]pyridine-3-sulfonamide,
6-(2,3-dichlorophenyl)-4-N-[2-(4-methanesulfonylphenyl)ethyl]pyrimidine-2,4-diamine or
4-[(2-{[2-amino-6-(2,3-dimethylphenyl)pyrimidin-4-yl]amino}ethyl)amino]benzene-1-sulfonamide.

The compounds of formula (I) as defined herein above may be referred to herein as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin. For the avoidance of doubt, solvates are also included within the scope of the invention.

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

The terms "halo" or "halogen", when used herein, includes fluoro, chloro, bromo and iodo (for example, fluoro and chloro).

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). When there is a sufficient number (i.e. a minimum of four) of carbon atoms, such groups may also be part cyclic. Part cyclic alkyl groups that may be mentioned include cyclopropylmethyl and cyclohexylethyl. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

Unless otherwise specified, $C_{1-q}$ alkylene groups (where q is the upper limit of the range) defined herein may (in a similar manner to the definition of $C_{1-q}$ alkyl) be straight-chain or, when there is a sufficient number (i.e. a minimum of two or three, as appropriate) of carbon atoms, be branched-chain, and/or cyclic (so forming a $C_{3-q}$-cycloalkylene group). When there is a sufficient number (i.e. a minimum of four) of carbon atoms, such groups may also be part cyclic. Such alkylene groups may also be saturated or, when there is a sufficient number (i.e. a minimum of two) of carbon atoms, be unsaturated (forming, for example, a $C_{2-q}$alkenylene or a $C_{2-q}$alkynylene group). Particular alkylene groups that may be mentioned include those that are straight-chained or cyclic and saturated.

Heterocycloalkyl groups that may be mentioned include non-aromatic monocyclic and bicyclic heterocycloalkyl groups (which groups may further be bridged) in which at least one (e.g. one to four) of the atoms in the ring system is other than carbon (i.e. a heteroatom), and in which the total number of atoms in the ring system is between three and twelve (e.g. between five and ten and, most preferably, between three and eight, e.g. a 5- or 6-membered heterocycloalkyl group). Further, such heterocycloalkyl groups may be saturated or unsaturated containing one or more double and/or triple bonds, forming for example a $C_{2-q}$ (e.g. $C_{4-q}$) heterocycloalkenyl (where q is the upper limit of the range) or a $C_{7-q}$ heterocycloalkynyl group. $C_{2-q}$ heterocycloalkyl groups that may be mentioned include 7-azabicyclo-[2.2.1] heptanyl, 6-azabicyclo[3.1.1]heptanyl, 6-azabicyclo[3.2.1]-octanyl, 8-azabicyclo[3.2.1]octanyl, aziridinyl, azetidinyl, dihydropyranyl, dihydropyridyl, dihydropyrrolyl (including 2,5-dihydropyrrolyl), 1,3,2-dioxaborinane, 1,3,6,2-dioxazaborocane, 1,3,2☐ dioxaborolane, dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuryl, tetrahydropyridyl (such as 1,2,3,4-tetrahydropyridyl and 1,2,3,6-tetrahydropyridyl), thietanyl, thiiranyl, thiolanyl, tetrahydrothiopyranyl, thiomorpholinyl, trithianyl (including 1,3,5-trithianyl), tropanyl and the like. Substituents on heterocycloalkyl groups may, where appropriate, be located on any atom in the ring system including a heteroatom. Further, in the case where the substituent is another cyclic compound, then the cyclic compound may be attached through a single atom on the heterocycloalkyl group, forming a so-called "spiro"-compound. The point of attachment of heterocycloalkyl groups may be via any atom in the ring system including (where appropriate) a further heteroatom (such as a nitrogen atom), or an atom on any fused carbocyclic ring that may be present as part of the ring system. Heterocycloalkyl groups may also be in the N- or S-oxidised form. At each occurrence when mentioned herein, a heterocycloalkyl group is preferably a 3- to 8-membered heterocycloalkyl group (e.g. a 5- or 6-membered heterocycloalkyl group).

The term "aryl", when used herein, includes $C_{6-10}$ aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl and the like). For the avoidance of doubt, the point of attachment of substituents on aryl groups may be via any carbon atom of the ring system.

The term "heteroaryl" (or heteroaromatic), when used herein, includes 5- to 11-membered heteroaromatic groups containing one or more heteroatoms selected from oxygen, nitrogen and/or sulfur. Such heteroaryl group may comprise one, or two rings, of which at least one is aromatic. Substituents on heteroaryl/heteroaromatic groups may, where appropriate, be located on any atom in the ring system including a heteroatom. The point of attachment of heteroaryl/heteroaromatic groups may be via any atom in the ring system including (where appropriate) a heteroatom. Bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocycloalkyl ring. Examples of heteroaryl/heteroaromatic groups that may be mentioned include pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, imidazothiazolyl, thienothiophenyl, pyrimidinyl, furopyridinyl, indolyl, azaindolyl, pyrazinyl, indazolyl, pyrimidinyl, quinolinyl, isoquinolinyl, quinazolinyl, benzofuranyl, benzothiophenyl, benzoimidazolyl, benzoxazolyl, benzothiazolyl, benzotriazolyl and purinyl. The oxides of heteroaryl/heteroaromatic groups are also embraced within the scope of the invention (e.g. the N-oxide). As stated above, heteroaryl includes polycyclic (e.g. bicyclic) groups where all rings are aromatic, and partly aromatic groups where at least one ring is aromatic and at least one other ring is not aromatic. Hence, other heteroaryl groups that may be mentioned include e.g. benzo[1,3]dioxolyl, benzo[1,4]dioxinyl, dihydrobenzo[d]isothiazolyl, 1,2-dihydrobenzo[d][1,2,3]diazaborininyl, 3,4-dihydro-1H-benzo[c][1,2]oxaborininyl, 1,3-dihydrobenzo[c][1,2]oxaborolyl, 3,4-dihydrobenz[1,4]oxazinyl, dihydrobenzothiophenyl, indolinyl, 5H, 6H, 7H-pyrrolo[1,2-b]pyrimidinyl, 1,2,3,4-tetrahydroquinolinyl, thiochromanyl and the like.

Heteroatoms that may be mentioned include phosphorus, silicon, preferably boron and, more preferably, oxygen, nitrogen and sulfur.

For the avoidance of doubt, in cases in which the identity of two or more substituents in a compound of the invention may be the same, the actual identities of the respective substituents are not in any way interdependent. For the avoidance of doubt, when L represents $-L^1-L^2-$, $L^1$ represents $—C(O)N(R^C)—$ and $L^2$ represents a single bond, then formula I can be represented by

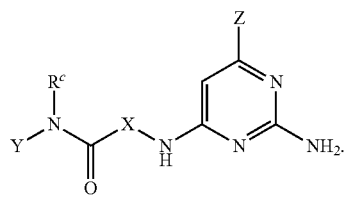

Likewise, when X represent

and L represents a single bond, then formula I can be represented by

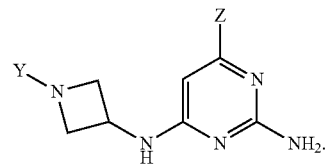

Likewise, when Y is phenyl substituted in the 4-position by $D^1$, $D^1$ is defined as $-A-S(O)_nR^g$ and A is defined as $—C(Q)N(R^H)—$, then formula I can be represented by

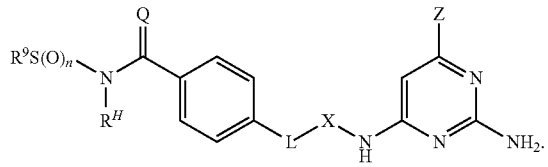

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. in which one or more hydrogen atoms are replaced by the hydrogen isotope deuterium.

All individual features (e.g. preferred features) mentioned herein may be taken in isolation or in combination with any other feature (including preferred features) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

In a compound of formula I as defined herein above, X represents: —C$_{2-6}$alkylene-, optionally substituted by one or more T$^1$, or —(C(R$^A$)$_2$)$_p$—C$_{2-5}$heterocycloalkylene-(C(R$^A$)$_2$)$_q$—, where the heterocycloalkylene is optionally substituted by one or more T$^2$.

In some embodiments, X represents —C$_{2-6}$alkylene-, more particularly X represents —C$_{2-4}$alkylene-, especially —C$_{2-3}$alkylene-, e.g. X is —CH$_2$CH$_2$—, or —CH$_2$CH$_2$CH$_2$—.

Particular compounds of formula I that may be mentioned include those in which X represents

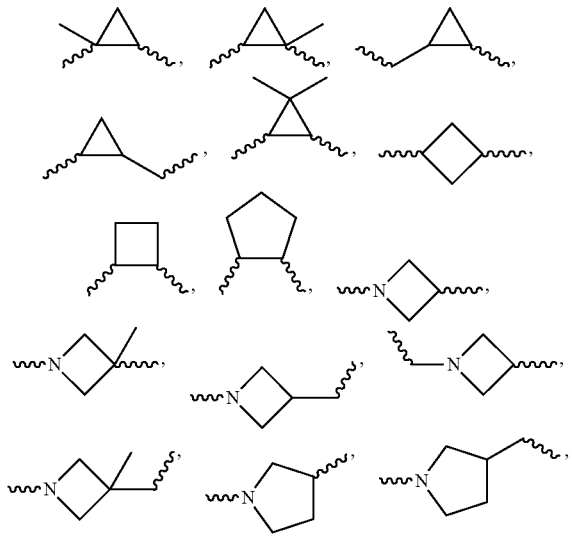

preferably —CH$_2$CH$_2$CH$_2$—, —CH$_2$CH$_2$CH$_2$CH$_2$—, —CH$_2$C(CH$_3$)$_2$CH$_2$—, -cyclopropylene-, —CH$_2$=CH$_2$—, or more preferably, —CH$_2$CH$_2$—.

In some embodiments, X represents —C$_{2-4}$alkylene-substituted by T$^1$;
T$^1$ represents —OR$^{d3}$; and
R$^{d3}$ represents C$_{1-4}$alkyl, or preferably, hydrogen.

Particular compounds of formula I that may be mentioned include those in which X represents —CH$_2$CH(OH)—.

In some embodiments, X represents —(C(R$^A$)$_2$)$_p$—C$_{2-5}$heterocycloalkylene-(C(R$^A$)$_2$)$_q$— where the heterocycloalkylene is optionally substituted by one or more T$^2$;

In some embodiments L represents a single bond.
In some embodiments L represents -L$^1$-L$^2$-.

In a compound of formula I as defined herein above, L$^1$ represents, —N(R$^B$)—, —O—, —S(O)$_m$—, —C(O)N(R$^C$)—, —N(R$^D$)C(O)— or —N(R$^E$)C(O)N(R$^F$)—. In some embodiments, L$^1$ represents —N(R$^B$)—, —O—, —S(O)$_m$— or —N(R$^E$)C(O)N(R$^F$)—. In some more particular embodiments, L$^1$ represents —O— or —N(R$^B$)—, e.g. L$^1$ represents —N(R$^B$)—.

Particular compounds of formula I that may be mentioned include those in which L$^1$ represents —C(O)N(H)—, —N(H)C(O)N(H)—, preferably —S(O)$_2$—, or more preferably, a single bond, —N(H)—, —O—, —S— or —S(O)—.

Other particularly preferred compounds of formula I that may be mentioned include those in which L$^1$ represents —N(H)—.

Other particularly preferred compounds of formula I that may be mentioned include those in which L$^1$ represents —O—.

Other particularly preferred compounds of formula I that may be mentioned include those in which L$^1$ represents —S— or —S(O)—.

Compounds of formula I that may be mentioned include those in which L$^2$ represents a single bond or —C$_{1-2}$alkylene-.

In some embodiments, L$^2$ is a single bond.
In some embodiments, L$^2$ represents —C$_{1-2}$alkylene-, preferably —CH$_2$—.

In a compound of formula I as defined herein above, A represents a single bond, —N(R$^G$)—, —C(Q)N(R$^H$)— or —O—.

In some embodiments, A represents a single bond or —N(R$^G$)—, e.g. a single bond or —NH—. In some particular embodiments A is single bond. In some other particular embodiments, A is —N(R$^G$)—, e.g. A is —NH—.

In a compound of formula I as defined herein above, Q represents =O, =S, =NR$^s$, =NN(R$^t$)R$^u$, =N(OR$^v$), =NS(O)$_2$N(R$^w$)R$^x$ or =C(H)NO$_2$. In some embodiments, Q represents =O, =S, =NR$^s$, =NN(R$^t$)R$^u$, =N(OR$^v$). In some particular embodiments, Q represents =O, =S, =NR$^s$, or =N(OR$^v$), e.g. =O, =S, =NH, or =N(OH). In some embodiments, Q represents =O or =S, e.g. Q represents =O.

When Y is a 6- to 10-membered aryl, e.g. phenyl, substituted by D$^1$ and optionally substituted by one or more groups selected from R$^1$, D$^1$ in particular may represent R$^a$, -A-C(Q)R$^c$, -A-C(Q)N(R$^d$)R$^e$, -A-C(Q)OR$^f$, -A-S(O)$_n$R$^g$, -A-S(O)$_n$C(O)R$^h$, -A-S(NR$^i$)(O)R$^j$, -A-S(O)$_n$N(R$^k$)R$^l$, -A-S(O)$_n$OR$^m$, —B(OR$^n$)$_2$, —N(R$^o$)R$^p$, —N(H)CN, —NO$_2$, —SR$^r$ or a 5-membered heteroaryl;

Q in particular may represent =O, =S, =NR$^s$ or =N(OR$^v$); and

R$^1$ in particular may represent halogen, R$^y$ or —OR$^z$.

Preferred compounds of formula I that may be mentioned include those in which Y represents phenyl substituted by -A-C(Q)R$^c$, -A-C(Q)N(R$^d$)R$^e$, -A-C(O)OR$^f$, -A-S(O)$_n$R$^g$, —S(O)$_n$N(R$^k$)R$^l$, —S(O)$_2$OR$^m$, —N(H)CN, —NO$_2$ or —SR$^r$, which phenyl is optionally substituted by R$^1$; Q represents =O, =S, =NR$^s$ or =N(OR$^v$);

R$^1$ represents halogen, R$^y$ or —OR$^z$;
R$^e$, R$^f$, R$^m$, R$^s$ and R$^v$ represents hydrogen;
each R$^b$, R$^f$, R$^k$, R$^r$, and R$^z$ independently represents hydrogen or C$_{1-6}$alkyl optionally substituted by one or more groups selected from G$^1$;

R$^c$, R$^g$ and R$^y$ represents C$_{1-6}$alkyl optionally substituted by one or more groups selected from G$^1$;

R$^d$ represents R$^b$ or —C(O)OR$^f$; or

R$^d$ and R$^e$ are linked together to form, along with the nitrogen atom to which they are attached, a 5- to 6-membered ring, which ring optionally contains one further heteroatom;

G$^1$ represents fluoro, —OR$^{k2}$ or —S(O)R$^2$;
R$^{k2}$ represents hydrogen or C$_{1-3}$alkyl; and
R$^{l2}$ represents C$_{1-3}$alkyl.

Particularly preferred compounds of formula I that may be mentioned include those in which Y represents phenyl substituted, preferably in the 3- or 4-position, by ethyl, ethynyl, trifluoromethyl, —C(O)NH$_2$, —C(NH)NH$_2$, —C(NOH)NH$_2$, —C(S)NH$_2$, —C(O)N(H)Me, —C(O)NHCH(CH$_3$)CH$_2$OH, —C(O)N(CH$_3$)propargyl, —C(O)OH, —C(O)OCH$_3$, —C(O)OCH$_2$CH$_3$, —C(O)OCH$_2$CH$_2$CH$_3$, —C(O)OCH$_2$CH(CH$_3$)$_2$, —C(O)OCH$_2$CH$_2$OH, —C(O)OCH$_2$CH$_2$SO$_2$Me, —C(O)OCH$_2$CH(OH)CH$_2$OH, —NH$_2$, —N(H)CN, —NHC(O)Me, —NH(CO)cyclopropyl, —NH(CO)C(Me)$_3$, —NHC(O)OEt, —NHC(O)OCH(Me)$_2$, —NHC(O)OC(Me)$_3$, —NHC(O)OCH$_2$CH(Me)$_2$, —NHC(O)OCH$_2$C(Me)$_3$, —NHC(O)OCH$_2$CH$_2$OMe, —N(H)C(O)N(H)Et, —N(H)C(O)N(H)CH(Me)$_2$, —N(H)C(O)N(H)C(Me)$_3$, —N(H)C(O)N(H)CH$_2$CH=CH$_2$, —N(H)C(O)N(CH$_3$)$_2$, —N(H)C(O)N(H)C(O)OEt, —N(H)C(S)N(H)Et, —NO$_2$, —NHS(O)$_2$Me, —NHS(O)$_2$Et, —NHS(O)$_2$CH(Me)$_2$, —NHS(O)$_2$CH$_2$CH(Me)$_2$, —NHS(O)$_2$CH$_2$CF$_3$, —SMe, —S(O)Me, —SO$_2$Me, —S(O)$_2$CF$_3$, —S(O)$_2$CH(Me)$_2$, —S(O)$_2$CH$_2$CH$_2$N(Me)$_2$, —S(O)$_2$NH$_2$, —S(O)$_2$NHMe, —S(O)$_2$NHCH$_2$CH$_2$OMe, —S(O)$_2$OH, tetrazolyl,

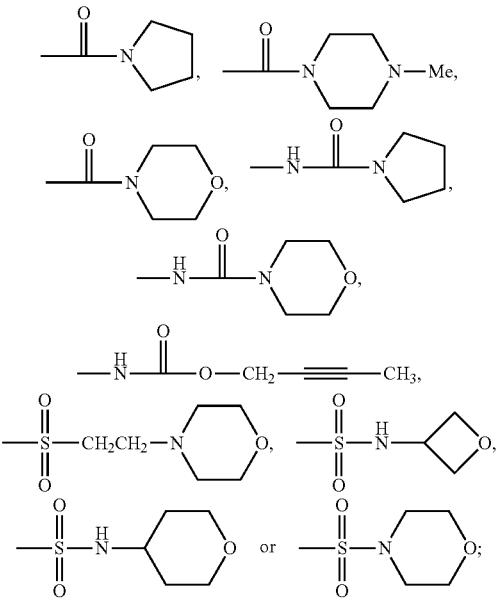

and

R$^1$ represents fluoro, —CH$_3$, —CF$_3$, —OH or —OCH$_3$.

Examples of particularly preferred compounds of formula I that may be mentioned include those in which Y represents phenyl substituted, preferably in the 4-position, by —C(O)OCH$_3$, —C(O)OCH$_2$CH$_3$, —C(O)OCH$_2$CH$_2$CH$_3$, —C(O)OCH$_2$CH(CH$_3$)$_2$, —C(O)OCH$_2$CH$_2$OH, —C(O)OCH$_2$CH$_2$SO$_2$Me and —C(O)OCH$_2$CH(OH)CH$_2$OH.

Examples of particularly preferred compounds of formula I that may be mentioned include those in which Y represents phenyl substituted, preferably in the 4-position, by —SO$_2$CH(CH$_3$)$_2$, —SO$_2$CH$_2$CH$_2$N(Me)$_2$, —SO$_2$NHCH$_2$CH$_2$OMe,

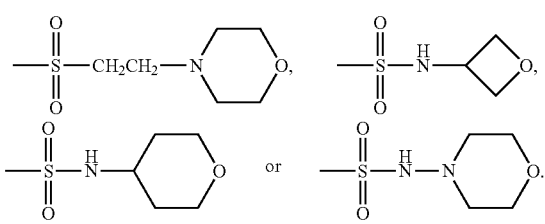

More particularly preferred compounds of formula I that may be mentioned include those in which Y represents phenyl substituted in the 3- or 4-position by —C(O)NH$_2$, —C(O)N(H)Me, —NHC(O)Me, —NH(CO)cyclopropyl, —NH(CO)C(Me)$_3$, —NHSO$_2$Me, —NHS(O)$_2$Et, —NHS(O)$_2$CH(Me)$_2$, —NHSO$_2$CH$_2$CF$_3$, —SO$_2$Me, —SO$_2$NH$_2$ or —SO$_2$NHMe.

For example, more particularly preferred compounds of formula I that may be mentioned include those in which Y represents phenyl substituted in the 3- or 4-position (e.g. in the 4-position) by —C(O)NH$_2$, —C(O)N(H)Me, —NHC(O)Me, —NH(CO)cyclopropyl, —NH(CO)C(Me)$_3$, —NHSO$_2$Me, —NHS(O)$_2$Et, —NHS(O)$_2$CH(Me)$_2$ or, —NHSO$_2$CH$_2$CF$_3$.

In some embodiments of the invention Y is a 6- to 10-membered aryl, preferably phenyl, substituted by D$^1$ and optionally substituted by one or more groups selected from R$^1$, e.g. optionally substituted by 1, 2 or 3 groups R$^1$, or 1 or 2 groups R$^1$, or 1 group R$^1$, or having no substituent R$^1$.

In some embodiments of the invention, when Z is phenyl optionally substituted by one or more groups selected from D$^7$, X is —CH$_2$CH$_2$—, and L is a single bond, Y is not phenyl substituted in the 4-position with —SO$_2$NH$_2$.

In other embodiments of the inventions, when Z is phenyl optionally substituted by one or more groups selected from D$^7$, X is —CH$_2$CH$_2$—, and L is a single bond, Y is not phenyl substituted in the 4-position with —SO$_2$Me, —SO$_2$NH$_2$ or —SO$_2$N(H)Me.

In some embodiments of the invention, when Z is phenyl optionally substituted by one or more groups selected from D$^7$, X is —CH$_2$CH$_2$—, L is -L$^1$-L$^2$-, L$^1$ is —S(O)$_m$— and L$^2$ is C$_{1-6}$alkylene, e.g. —CH$_2$CH$_2$—, or preferably —CH$_2$—, Y is phenyl substituted in the 4-position with —C(O)OR$^f$ or —SO$_2$R$^g$.

In some embodiments of the invention, when Z is phenyl optionally substituted by one or more groups selected from D$^7$, X is —CH$_2$CH$_2$—, L is -L$^1$-L$^2$-, L$^1$ is —S(O)$_m$— (e.g. —S—) and L$^2$ is C$_{1-6}$alkylene, e.g. —CH$_2$CH$_2$—, or preferably —CH$_2$—, Y is heteroaryl, e.g. a 5-membered heteroaryl substituted by R$^a$ and optionally substituted by one or more (e.g. two, or preferably one) groups selected from R$^3$.

Examples of compounds of formula I that may be mentioned include those in which when Z is phenyl, X is —CH$_2$CH$_2$—, L is -L$^1$-L$^2$-, L$^1$ is —S— and L$^2$ is —CH$_2$—, Y is a 5-membered heteroaryl substituted by C$_{1-6}$alkyl (e.g. —CH$_3$) substituted by one or more halogens or, preferably, by —N(R$^d$)R$^e$.

In some embodiments, Y is a 6-membered heteroaryl substituted by D$^2$ and optionally substituted by one or more groups selected from R$^2$, e.g. optionally substituted by 1, 2 or 3 groups R$^2$, or 1 or 2 groups R$^2$, or 1 group R$^2$, or having no substituent R$^2$. Such a 6-membered heteroaryl e.g. may be pyridyl, pyrimidinyl or pyrazinyl.

When Y is 6-membered heteroaryl, in particular pyridyl, substituted by D$^2$ and optionally substituted by one or more groups selected from R$^2$, D$^2$ in particular may represent R$^b$, -A-C(Q)R$^c$, -A-C(Q)N(R$^d$)R$^e$, -A-C(Q)OR$^f$, -A-S(O)$_n$R$^g$, -A-S(O)$_n$C(O)R$^h$, -A-S(O)$_n$N(R$^k$)R$^l$, -A-S(O)$_n$OR$^m$, —B(OR$^n$)$_2$, —N(R$^o$)R$^p$, or —NO$_2$;

Q in particular may represent =O, =S, =NR$^s$ or =N(OR$^v$); and

R$^2$ in particular may represent halogen or C$_{1-3}$ alkyl optionally substituted by F.

Preferred compounds of formula I that may be mentioned include those in which Y represents pyridyl substituted by R$^b$, -A-C(Q)R$^c$, -A-C(O)N(R$^d$)R$^e$, -A-C(O)OR$^f$, -A-S(O)$_n$R$^g$, —S(O)$_n$N(R$^k$)R$^l$, —N(R$^o$)R$^p$ or —NO$_2$, which pyridyl is optionally substituted by R$^2$;

R$^2$ represents R$^y$;

each R$^d$, R$^e$, R$^l$, R$^o$ and R$^p$ represent hydrogen;

each R$^c$, R$^g$ and R$^y$ represent C$_{1-6}$alkyl; and each R$^f$ and R$^k$ represents hydrogen or C$_{1-6}$alkyl.

For example, preferred compounds of formula I that may be mentioned include those in which Y represents pyridinyl substituted by $C_{1-6}$ alkyl optionally substituted by one or more fluoro, —C(O)NH$_2$, —C(O)OR$^f$, —N(H)C(O)R$^c$, —N(H)C(O)N(R$^d$)R$^e$, —N(H)C(O)OR$^f$, —N(H)S(O)$_n$R$^g$, —S(O)$_n$R$^g$, —N(R$^o$)R$^p$ or —NO$_2$.

Particularly preferred compounds of formula I that may be mentioned include those in which Y represents 2-pyridinyl substituted in the 4-position by —C(O)NH$_2$ or in the 5-position by —CF$_3$, —C(O)NH$_2$, —C(O)OEt, —N(H)C(O)Me, —N(H)C(O)N(H)C(CH$_3$)$_3$, —N(H)C(O)OC(CH$_3$)$_3$, —N(H)SO$_2$Me, —NO$_2$, —SO$_2$Me, —SO$_2$NH$_2$ or —SO$_2$N(H)Me, 3-pyridinyl substituted in the 4-position by —NH$_2$ or —SO$_2$Me, substituted in the 5-position by —SO$_2$NH$_2$ or substituted in the 6-position by —SO$_2$Me, or 4-pyridinyl substituted in the 2-position by —C(O)NH$_2$.

In some embodiments of the invention Y is pyridyl substituted by D$^2$ and optionally substituted by one or more groups selected from R$^2$.

In some embodiments, when Y is 6-membered heteroaryl, in particular pyrimidinyl, substituted by D$^2$ and optionally substituted by one or more groups selected from R$^2$, D$^2$ in particular may represent -A-C(Q)R$^c$, -A-C(Q)N(R$^d$)R$^e$, -A-C(Q)OR$^f$, -A-S(O)$_n$R$^g$, -A-S(O)$_n$N(R$^k$)R$^l$, -A-S(O)$_n$OR$^m$, —B(OR$^n$)$_2$, —C(O)OR$^f$ or —N(R$^o$)R$^p$;

Q in particular may represent =O, =S, =NR$^s$ or =N(OR$^v$);

R$^2$ in particular may represent halogen or R$^y$; and

R$^y$ in particular may represent $C_{1-6}$alkyl optionally substituted by one or more halogens.

Preferred compounds of formula I that may be mentioned include those in which Y represents pyrimidinyl substituted by —C(O)N(R$^d$)R$^e$, —C(O)OR$^f$ or —N(R$^o$)R$^p$, which pyrimidinyl is optionally substituted by R$^2$;

R$^2$ represents R$^y$;

R$^d$, R$^e$, R$^o$ and R$^p$ represent hydrogen;

R$^f$ represents hydrogen or $C_{1-6}$alkyl; and

R$^y$ represents $C_{1-6}$alkyl optionally substituted by one or more fluoro.

Particularly preferred compounds of formula I that may be mentioned include those in which Y represents 2-pyrimidinyl substituted in the 4-position by —C(O)NH$_2$, —C(O)OH or —C(O)OMe, —NH$_2$, —S(O)$_2$Me or —S(O)$_2$NH$_2$, or substituted in the 5-position by —C(O)NH$_2$, or 4-pyrimidinyl substituted in the 2-position by —C(O)NH$_2$, —NH$_2$, —S(O)$_2$Me or —S(O)$_2$NH$_2$; and R$^2$ represents halogen (e.g. fluoro or chloro) or preferably, —CF$_3$.

More particularly preferred compounds of formula I that may be mentioned include those in which Y represents 2-pyrimidinyl substituted in the 4-position by —C(O)NH$_2$, —C(O)OH or —C(O)OMe.

In some embodiments of the invention Y is pyrimidinyl substituted by D$^2$ and optionally substituted by one or more groups selected from R$^2$.

In some embodiments, when Y is 6-membered heteroaryl, in particular pyrazinyl, substituted by D$^2$ and optionally substituted by one or more groups selected from R$^2$, D$^2$ in particular may represent -A-C(Q)R$^c$, -A-C(Q)N(R$^d$)R$^e$, -A-C(Q)OR$^f$, -A-S(O)$_n$R$^g$, -A-S(O)$_n$N(R$^k$)R$^l$, -A-S(O)$_n$OR$^m$, —B(OR$^n$)$_2$, —C(O)OR$^f$ or —N(R$^o$)R$^p$; and Q in particular may represent =O, =S, =NR$^W$ or =N(OR$^z$).

Preferred compounds of formula I that may be mentioned include those in which Y represents pyrazinyl substituted by —C(O)N(R$^d$)R$^e$, —C(O)OR$^f$ or —S(O)$_2$NH$_2$;

R$^d$ and R$^e$ represent hydrogen; and

R$^f$ represents $C_{1-6}$alkyl.

Particularly preferred compounds of formula I that may be mentioned include those in which Y represents 2-pyrazinyl substituted in the 3-position by —C(O)NH$_2$ or in the 5-position by —C(O)OMe.

In some embodiments of the invention Y is pyrazinyl substituted by D$^2$ and optionally substituted by one or more groups selected from R$^2$.

In some embodiments, when Y represents 6-membered heteroaryl, in particular 1,3,5-triazinyl, substituted by D$^2$ and optionally substituted by one or more groups selected from R$^2$, D$^2$ in particular may represent -A-C(O)R$^c$, -A-C(O)N(R$^d$)R$^e$, -A-C(O)OR$^f$, -A-S(O)$_n$R$^g$, -A-S(O)$_n$N(R$^k$)R$^l$, or —N(R$^o$)R$^p$.

Particularly preferred compounds of formula I that may be mentioned include those in which Y represents 1,3,5-triazinyl substituted by —C(O)NH$_2$, —C(O)OR$^f$, —S(O)$_2$R$^g$, —S(O)$_2$NH$_2$, or in particular, —NH$_2$.

In some embodiments of the invention Y represents 1,3,5-triazinyl substituted by D$^2$ and optionally substituted by one or more groups selected from R$^2$.

When Y is a 5-membered heteroaryl, substituted by D$^3$ and optionally substituted by one or more groups selected from R$^3$, D$^3$ in particular may represent —CN, -A-C(Q)R$^c$, -A-C(Q)N(R$^d$)R$^e$, -A-C(Q)OR$^f$, -A-S(O)$_n$R$^g$, -A-S(O)$_n$N(R$^k$)R$^l$, —B(OR$^o$)$_2$, —C(O)OR$^f$, —N(R$^p$)R$^q$, or —NO$_2$;

Q in particular may represent =O, =S, =NR$^s$ or =N(OR$^v$); and

R$^3$ in particular may represent halogen or $C_{1-3}$ alkyl optionally substituted by one or more fluoro.

Some preferred compounds wherein Y in formula I is a 5-membered heteroaryl include those in which Y represents imidazolyl, isoxazolyl, oxazolyl, 1,2,4-oxadiazolyl, 1,3,4-oxadiazolyl, 1,3,4-thiadiazolyl, thiazolyl, 1,2,3-triazolyl or thiophenyl, each substituted by —C(O)NH$_2$, —C(O)OMe, —NH$_2$, —NO$_2$, —S(O)$_2$Me or —S(O)$_2$NH$_2$, and each optionally substituted by halogen or $C_{1-6}$alkyl optionally substituted by one or more halogens.

Particularly preferred compounds of formula I wherein Y is a 5-membered heteroaryl include those in which Y represents 2-methyl-5-nitro-1-imidazolyl.

In some embodiments of the invention Y is a 5-membered heteroaryl substituted by D$^3$ and optionally substituted by one or more groups selected from R$^3$, e.g. optionally substituted by one group R$^3$, or having no group R$^3$.

When Y a 9-membered bicyclic heteroaryl, in which one ring is 5-membered and the other 6-membered, which heteroaryl is connected to L via its 5-membered ring and substituted by one or more groups selected from D$^4$, and optionally substituted by one or more groups selected from R$^4$, D$^4$ in particular may represent —CN, R$^b$, —CN, -A-C(O)R$^c$, -A-C(O)N(R$^d$)R$^e$, -A-C(Q)OR$^f$, -A-S(O)$_n$R$^g$, -A-S(O)$_n$N(R$^k$)R$^l$, —C(O)OR$^f$, —N(R$^o$)R$^p$, —OR$^q$, or, when Y is partly aromatic, =O; and R$^4$ in particular may represent halogen, $C_{1-3}$ alkyl optionally substituted by one or more fluoro or —OC$_{1-3}$ alkyl optionally substituted by one or more fluoro.

Preferred compounds of formula I that may be mentioned include those in which Y represents 2-benzimidazolyl, 2-benzoxazolyl, 2-benzothiazolyl, 2-indolyl, 2-indolinyl or 2-isoindolinyl, all substituted by one or more groups selected from D$^4$ and optionally substituted by one or more groups selected from R$^4$;

D$^4$ represents R$^b$, —CN, —N(R$^o$)R$^p$, —OR$^q$, or, when Y is partly aromatic, =O, =S or =NR$^s$;

$R^4$ represents halogen or $R^y$;

each $R^b$ and $R^y$ independently represents $C_{1-6}$alkyl optionally substituted by one or more fluoro; and each $R^o$, $R^p$, $R^q$ and $R^s$ independently represents hydrogen or $C_{1-6}$alkyl optionally substituted by one or more fluoro.

Particularly preferred compounds of formula I that may be mentioned include those in which L is a single bond and Y represents 1-oxo-2-indolinyl.

In some embodiments of the invention Y is a 9-membered bicyclic heteroaryl, in which one ring is 5-membered and the other 6-membered, which heteroaryl is connected to L via its 5-membered ring and substituted by one or more groups selected from $D^4$, and optionally substituted by one or more groups selected from $R^4$, e.g. 1, 2 or 3 groups $R^4$, or 1 or 2 groups $R^4$, or 1 group $R^4$, or having no $R^4$.

When Y is a 9- to 11-membered bicyclic heteroaryl, in which one ring is 6-membered and the other 5-7-membered, which heteroaryl is connected to L via its 6-membered ring and optionally substituted by one or more groups selected from $D^5$, $D^5$ in particular may represent halogen, —CN, $R^b$, —CN, -A-C(O)$R^c$, -A-C(O)N($R^d$)$R^e$, -A-C(Q)O$R^f$, -A-S(O)$_n$ $R^g$, -A-S(O)$_n$N($R^h$)$R^i$, —C(O)O$R^f$, —N($R^o$)$R^p$, —O$R^q$, or, when Y is partly aromatic, =O.

Preferred compounds of formula I that may be mentioned include those in which Y represents benzimidazol-5-yl, benzoxazol-5-yl, benzothiazol-5-yl, benzothiazol-6-yl, benzothiophen-6-yl, 2,3-dihydrobenz[1,3]oxazin-6-yl, 3,4-dihydrobenz[1,4]-oxazin-6-yl, 2,3-dihydro-benzo[d]isothiazol-6-yl, dihydrobenzothiophen-6-yl, furo[2,3-c]pyridin-5-yl, 1-oxo-1-iminobenzothiophen-6-yl, indol-5-yl, indol-6-yl, indolin-5-yl, indolin-6-yl, isoindolin-5-yl, isoquinolin-6-yl, isoquinolin-7-yl, tetrahydroquinolin-6-yl, tetrahydroquinolin-7-yl, tetrahydroisoquinolin-6-yl, tetrahydroisoquinolin-6-yl, tetrahydroquinazolin-6-yl, tetrahydroquinazolin-7-yl, thiochroman-7-yl, quinolin-6-yl, quinolin-7-yl, quinazolin-6-yl, quinazolin-7-yl, or purin-6-yl, all optionally substituted by one or more groups selected from $D^5$; $D^5$ represents $R^b$, —CN, —N($R^o$)$R^p$, —O$R^q$, or, when Y is partly aromatic, =O, =S or =N$R^s$;

$R^b$ represents $C_{1-6}$alkyl optionally substituted by one or more fluoro; and each $R^o$, $R^p$, $R^q$ and $R^s$ independently represents hydrogen or $C_{1-6}$alkyl optionally substituted by one or more fluoro.

Particularly preferred compounds of formula I that may be mentioned include those in which L is a single bond and Y represents benzoxazol-5-yl, 2,3-dihydro-2,2-dimethyl-4-oxobenz[1,3]oxazin-6-yl, 4,4-dimethyl-1,2,3,4-tetrahydroquinazolin-7-yl, 1-methyl-2-oxo-1,3-dihydrobenzimidazol-6-yl, or preferably 3,4-dihydro-3-oxo-1,4-benzoxazin-6-yl, or L is —N(H)— and Y represents 2-methyl-1,3-benzothiazol-5-yl, 2-methyl-1,3-benzothiazol-6-yl, 4-oxo-quinazolin-7-yl, 3,4-dihydro-3-oxo-1,4-benzoxazin-6-yl, 3,4-dihydro-4-methyl-3-oxo-1,4-benzoxazin-6-yl, 3,4-dihydro-2,2-dimethyl-3-oxo-1,4-benzoxazin-6-yl, purin-6-yl or 2-aminopurin-6-yl.

In some embodiments of the invention L is a single bond, Y is 9- to 11-membered bicyclic heteroaryl, in which one ring is 6-membered and the other 5-7-membered, which heteroaryl is connected to L via its 6-membered ring and optionally substituted by one or more groups selected from $D^5$, e.g. optionally substituted with 1, 2 or 3 groups $D^5$.

When Y is an 8-membered bicyclic heteroaryl optionally substituted by one or more groups selected from $D^6$, $D^6$ in particular may represent halogen, $R^b$, —CN, —C(O)N($R^d$) $R^e$, -A-S(O)$_n$$R^g$, —S(O)$_n$N($R^h$)$R^i$, —N($R^p$)$R^q$, —O$R^s$, or, when Y is partly aromatic, =O.

For example, compounds of formula I that may be mentioned include those in which Y represents imidazo[2,1-b]thiazol-6-yl, substituted in the 5-position by —SO$_2$NH$_2$ or —SO$_2$Me, or thieno[3,2-b]thiophen-2-yl substituted in the 5-position by —SO$_2$NH$_2$ or —SO$_2$Me.

In some embodiments of the invention Y is an 8-membered bicyclic heteroaryl optionally substituted by one or more groups selected from $D^6$, e.g. 1, 2 or 3 groups selected from $D^6$, or 1 or 2 groups selected from $D^6$, or one group $D^6$, or having no substituent $D^6$.

When Z is 6- to 10-membered aryl, e.g. phenyl, optionally substituted by one or more groups selected from $D^7$, $D^7$ in particular may represent halogen, —CN, —$R^{a1}$, -A$^1$-C(Q$^1$)$R^{b1}$, -A$^1$-C(Q$^1$) N($R^{c1}$)$R^{d1}$, -A$^1$-S(O)$_n$$R^1$, -A$^1$-S(O)$_n$N($R^{j1}$)$R^{k1}$, —NO$_2$ or —OR; each $R^{a1}$, $R^{b1}$, $R^{c1}$, $R^{d1}$, $R^{j1}$, $R^{k1}$ and $R^{p1}$ independently may represent hydrogen or $C_{1-6}$alkyl optionally substituted by one or more fluoro; or any two $R^{c1}$ and $R^{d1}$ and/or $R^{j1}$ and $R^{k1}$ may be linked together to form, along with the nitrogen atom to which they are attached, a 3- to 6-membered ring, which ring optionally contains one further heteroatom and which ring optionally is substituted by one or more fluoro, $C_{1-3}$alkyl optionally substituted by one or more fluoro, or =O; and $R^{f1}$ may represent $C_{1-3}$ alkyl optionally substituted by one or more fluoro.

For example, compounds of formula I that may be mentioned include those in which Z represents phenyl substituted by one or more substituents selected from halogen $R^{a1}$, —CN, —NO$_2$ or —S(O)$_m$$R^{f1}$.

Preferred compounds of formula I that may be mentioned include those in which Z represents phenyl substituted:

(i) in the 3-position by fluoro, chloro, —CF$_3$, —CH$_2$OH, —OH, —OS(O)$_2$CH$_3$ or —OS(O)$_2$CF$_3$; or (ii) by two substituents selected from fluoro, chloro, -Me, —CF$_3$ or —OMe (i.e. Z is e.g. 2,3-dichlorophenyl, 3-chloro-2-fluorophenyl, 2-chloro-3-methylphenyl, 3-chloro-2-methylphenyl, 5-fluoro-2-methylphenyl, 2,5-dimethylphenyl, 2,3-dimethylphenyl or 2-methyl-3-trifluoromethyl); or (ii) by three substituents selected from fluoro, chloro, -Me, —CF$_3$ or —OMe (i.e. Z is e.g. 5-chloro-2-fluoro-3-methylphenyl, 5-chloro-4-methoxy-2-methylphenyl, 3,4-dichloro-2-methoxyphenyl, 3,4-dichloro-2-methylphenyl, 3,5-dichloro-2-methylphenyl, 4,5-dichloro-2-methylphenyl, 2,3-dimethyl-4-fluorophenyl, 2,5-dimethyl-4-fluorophenyl, 2,5-dimethyl-4-methoxyphenyl, 2,3,4-trichlorophenyl, 2,3,5-trichlorophenyl and 2,4,5-trimethylphenyl; or (iv) by four substituents selected from fluoro, chloro or -Me (e.g. 2-methyl-3,4,5-trichlorophenyl).

Particularly preferred compounds of formula I that may be mentioned include those in which Z represents phenyl substituted in the 2- and 3-position by fluoro, chloro, —CH$_3$ or —CF$_3$ (i.e. Z is e.g. 3-chloro-2-fluorophenyl, 2-chloro-3-methyl-phenyl, 3-chloro-2-methylphenyl, 2,3-dichlorophenyl, 2,3-dimethylphenyl and 2-methyl-3-trifluoromethyl).

In some embodiments of the invention Z is phenyl optionally substituted by $D^7$.

When Z is 5- to 10-membered monocyclic or bicyclic heteroaryl optionally substituted by one or more groups selected from $D^8$, said heteroaryl in particular may represent benzothiophenyl, furanyl, indolyl, pyrazolyl or thiophenyl and $D^8$ in particular may represent halogen, —CN, -A$^1$-C(O)$R^{b1}$, -A$^1$-C(O)N($R^{c1}$)$R^{d1}$, -A$^1$-S(O)$_n$$R^{f1}$, -A$^1$-SO$_2$N($R^j$)$R^{k1}$, —NO$_2$, —OR$^{p1}$ or, when Z is partly aromatic, =O; each $R^{a1}$, $R^{b1}$, $R^{c1}$, $R^{d1}$, $R^{j1}$, $R^{k1}$ and $R^{p1}$ independently may in particular represent hydrogen or $C_{1-6}$alkyl optionally substituted by one or more fluoro; or any two $R^{c1}$ and $R^{d1}$ and/or $R^{j1}$ and $R^{k1}$ may be linked together to form, along with the nitrogen atom to which they are attached, a 3- to 6-membered ring, which ring optionally contains one further heteroatom and which ring optionally is substituted by one or more fluoro, one or more $C_{1-3}$alkyl optionally substituted by one or more fluoro, and/or =O; and each $R^{a1}$ and $R^{f1}$ may independently represent $C_{1-3}$ alkyl optionally substituted by one or more fluoro.

For example, compounds of formula I that may be mentioned include those in which Z represents indolyl (e.g. 4-indolyl), furanyl (e.g. 5-methyl-2-furanyl) or thiophenyl (e.g. 2-acetyl-3-thiophenyl, 2-(N-tert-butylaminosulfonyl)-3-thiophenyl and 2-(N-tert-butyloxycarbonylaminomethyl)-3-thiophenyl).

In some embodiments of the invention Z is 5- to 10-membered monocyclic or bicyclic heteroaryl, optionally substituted by one or more groups selected from $D^8$, e.g. 1, 2 or 3 groups selected from $D^8$, or 1 or 2 groups selected from $D^8$, or one group $D^8$, or having no substituent $D^8$. In some embodiments, said heteroaryl is a 5- to 7-membered monocyclic heteroaryl, e.g. 5- or 6-membered monocyclic heteroaryl. In some other embodiments, said heteroaryl is an 8- to 10-membered bicyclic heteroaryl, e.g. a 9- or 10-membered bicyclic heteroaryl.

When Z is a 3- to 8-membered, preferably a 5- to 7-membered nonaromatic ring optionally substituted by one or more groups selected from $D^9$, said ring is preferably connected via a carbon atom to the pyrimidine core of formula I, and preferably contains one heteroatom and/or one optional double bond; $D^9$ in particular may represent $R^{a1}$, —C(O)$R^{b1}$, —C(O)N($R^{c1}$)$R^{d1}$, —C(O)O$R^{e1}$, —SO$_2R^{f1}$, —SO$_2$N($R^{j1}$)$R^{k1}$ or =O;

each $R^{a1}$, $R^{b1}$, $R^{c1}$, $R^{d1}$, $R^{e1}$, $R^{f1}$, $R^{j1}$ and $R^{k1}$ in particular may independently represent $C_{1-6}$alkyl optionally substituted by one or more fluoro, phenyl optionally substituted by one or more groups selected from halogen or $C_{1-3}$alkyl optionally substituted by one or more fluoro, or heteroaryl optionally substituted by one or more groups selected from halogen or $C_{1-3}$alkyl optionally substituted by one or more fluoro; or any two $R^{c1}$ and $R^{d1}$ and/or $R^{j1}$ and $R^{k1}$ may be linked together to form, along with the nitrogen atom to which they are attached, a 5- to 6-membered ring, which ring optionally contains one further heteroatom and which ring optionally is substituted by one or more $C_{1-3}$alkyl or =O; and $R^{e1}$ in particular may represent $C_{1-6}$alkyl optionally substituted by one or more fluoro.

For example, compounds of formula I that may be mentioned include those in which Z represents cycloheptanyl, cyclohexanyl, cyclopentanyl, piperidin-3-yl, pyrrolidin-3-yl, or preferably, cyclohepten-1-yl, piperidin-4-yl or 1,2,3, 6-tetrahydropiperidin-4-yl and where the piperidine, pyrrolidine and the 1,2,3,6-tetrahydropiperidine are preferably substituted in the 1-position by —C(O)Me, —C(O)CH(CH$_3$)$_2$, —C(O)cyclopentyl, —C(O)methylcyclopentyl, —C(O)(4-methyl-phenyl), —C(O)(5-isoxazolyl), —C(O)OC(CH$_3$)$_3$, —SO$_2$Me or —SO$_2$(4-methylphenyl).

In some embodiments, Z is a 3- to 8-membered nonaromatic ring, which ring optionally contains one or two heteroatoms and/or one or two double bonds, and which ring is optionally substituted by one or more groups selected from $D^9$, e.g. 1, 2 or 3 groups selected from $D^9$, or 1 or 2 groups selected from $D^9$, or one group $D^9$, or having no substituent $D^9$.

In one embodiment, the compound according to the invention is selected from the compounds of Examples 1-218.

As discussed hereinbefore, compounds of the invention are indicated as pharmaceuticals. According to a further aspect of the invention there is provided a compound of the invention, as hereinbefore defined, for use as a pharmaceutical.

In another aspect of the invention the use of a compound of the invention, as hereinbefore defined, is provided for the manufacture of a medicament for the treatment of cancer.

Although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention.

By "prodrug of a compound of the invention", we include compounds that form a compound of the invention, in an experimentally-detectable amount, within a predetermined time, following enteral or parenteral administration (e.g. oral or parenteral administration). All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds, which possess pharmacological activity.

It is stated herein that the compounds of the invention may be useful in the treatment of cancer. For the purposes of this specification, and for the avoidance of doubt, the term "treatment" includes treatment per se, prevention and prophylaxis.

Preferably the cancer is selected from the group comprising: Soft Tissue Cancers: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood and bone marrow (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Kaposi's sarcoma, moles dysplastic nevi, lipoma, angioma, dermatofibroma, keloids; neurofibromatosis and Adrenal glands: neuroblastoma. The term "cancerous cell" as provided herein, includes a cell afflicted by any one of the above identified conditions.

In certain embodiments of the present invention, the cancer is a solid tumor cancer.

In certain embodiments of the present invention, the cancer is selected from pancreatic cancer, ovarian cancer and colorectal cancer.

In certain embodiments of the present invention, the cancer is selected from colorectal cancer (including Ras mutations), small cell lung cancer, non-small cell lung cancer, and glioma.

In certain embodiments of the present invention, the cancer is selected from non-small cell lung cancer, ovarian cancer, metastatic breast cancer, pancreatic cancer, hepatobiliary cancer (including hepatocellular cancer, bile duct cancer and cholangiocarcinoma), and gastric cancer.

In certain embodiments of the present invention, the cancer is selected from colorectal cancer (including Ras mutations), small cell lung cancer, non-small cell lung cancer, ovarian cancer, hepatobiliary cancer (including hepatocellular cancer, bile duct cancer and cholangiocarcinoma), gastric cancer, testicular cancer, and head and neck squamous cell carcinoma.

In certain embodiments of the present invention, the cancer is selected from leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostate cancer Compounds of the invention will normally be administered orally, intravenously, subcutaneously, buccally, rectally, dermally, nasally, tracheally, bronchially, sublingually, intranasally, topically, by any other parenteral route or via inhalation, in a pharmaceutically acceptable dosage form.

Compounds of the invention may be administered alone, but are preferably administered by way of known pharmaceutical compositions/formulations, including tablets, capsules or elixirs for oral administration, suppositories for rectal administration, sterile solutions or suspensions for parenteral or intramuscular administration, and the like.

Compounds of the invention (i.e. compounds that inhibit MTH1) may be administered in the form of tablets or capsules, e.g., time-release capsules that are taken orally. Alternatively, the compounds of the invention may be in a liquid form and may be taken orally or by injection. The compounds of the invention may also be in the form of suppositories, or, creams, gels, and foams e.g. that can be applied to the skin. In addition, they may be in the form of an inhalant that is applied nasally.

Such compositions/formulations may be prepared in accordance with standard and/or accepted pharmaceutical practice.

According to a further aspect of the invention there is thus provided a pharmaceutical composition/formulation including a compound of the invention, as hereinbefore defined, optionally in admixture with a pharmaceutically acceptable adjuvant, diluent and/or carrier. Such compositions/formulations may be of use in the treatment, prevention and/or prophylaxis of cancer.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The invention further provides a process for the preparation of a pharmaceutical formulation, as hereinbefore defined, which process comprises bringing into association a compound of the invention, as hereinbefore defined, or a pharmaceutically acceptable salt thereof with a pharmaceutically-acceptable adjuvant, diluent or carrier.

In yet another aspect the present invention provides methods for the treatment of cancer comprising administering a therapeutically effective amount of a compound of the invention to a subject (e.g. patient) in need of such treatment.

"Patients" include mammalian (including human) patients.

The term "effective amount" refers to an amount of a compound, which confers a therapeutic effect on the treated patient. The effect may be objective (i.e. measurable by some test or marker) or subjective (i.e. the subject gives an indication of or feels an effect).

Compounds of the invention may also be combined with other therapeutic agents that are useful in the treatment of cancer.

According to a further aspect of the invention, there is provided a combination product comprising:

(A) a compound of the invention, as hereinbefore defined; and (B) another therapeutic agent that is useful in the in the treatment of cancer, wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, another therapeutic agent that is useful in the treatment of cancer, and a pharmaceutically-acceptable adjuvant, diluent or carrier; and
(2) a kit of parts comprising components:
(a) a pharmaceutical formulation including a compound of the invention, as hereinbefore defined, in admixture with a pharmaceutically-acceptable adjuvant, diluent or carrier; and
(b) a pharmaceutical formulation including another therapeutic agent that is useful in the treatment of cancer in admixture with a pharmaceutically-acceptable adjuvant, diluent or carrier, which components (a) and (b) are each provided in a form that is suitable for administration in conjunction with the other.

The invention further provides a process for the preparation of a combination product as hereinbefore defined, which process comprises bringing into association a compound of the invention, as hereinbefore defined, or a pharmaceutically acceptable salt thereof with the other therapeutic agent that is useful in the treatment of cancer, and at least one pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Compounds of the invention may be administered at varying doses. Oral, pulmonary and topical dosages (and subcutaneous dosages, although these dosages may be relatively lower) may range from between about 0.01 mg/kg of body weight per day (mg/kg/day) to about 100 mg/kg/day, preferably about 0.01 to about 10 mg/kg/day, and more preferably about 0.1 to about 5.0 mg/kg/day. For e.g. oral administration, the compositions typically contain between about 0.01 mg to about 2000 mg, for example between about 0.1 mg to about 500 mg, or between 1 mg to about 100 mg, of the active ingredient. Intravenously, the most preferred doses will range from about 0.001 to about 10 mg/kg/hour during constant rate infusion. Advantageously, compounds may be administered in a single daily dose, or the total daily dosage may be administered in divided doses of two, three or four times daily.

In any event, the physician, or the skilled person, will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, compounds of the invention may have the advantage that they are more efficacious and/or exhibit advantageous properties in vivo.

It is contemplated that any method or composition described herein can be implemented with respect to any other method or composition described herein.

Unless otherwise defined, all technical and scientific terms used herein have the same meaning as commonly understood by one of ordinary skill in the art to which this invention pertains.

EXAMPLES

The invention is illustrated by way of the following examples, in which the following abbreviations may be employed.

aq aqueous
DMF dimethylformamide
DMSO dimethyl sulfoxide
EtOAc ethyl acetate
EtOH ethanol
MeOH methanol
MeCN acetonitrile
Pd—C palladium on carbon
sat. saturated
TFA trifluoroacetic acid
THF tetrahydrofuran
min. minutes
h. hours
Hunigs base N,N-diisopropylethylamine
DCM dichloromethane
n-BuOH butan-1-ol
iPrOH propan-2-ol
$NEt_3$ triethylamine
Boc tert-butoxycabonyl
HATU (1-[Bis(dimethylamino)methylene]-1H-1,2,3-triazolo-[4,5-b]pyridinium 3-oxid hexafluorophosphate
NMP N-methylpyrrolidine
LC liquid chromatography
LCMS liquid chromatography electrospray mass spectroscopy
NMR nuclear magnetic resonance
NCS N-chlorosuccinimide
$Pd(PPh_3)_4$ tetrakis(triphenylphosphine)palladium (0)

B(OMe)$_3$ trimethylborate
n-BuLi n-butyl lithium
MeI iodomethane
NaOMe sodium methoxide
CHCl$_3$ chloroform
MgSO$_4$ anhydrous magnesium sulphate
K$_2$CO$_3$ anhydrous potassium carbonate
NH$_4$OH ammonium hydroxide
Ac$_2$O acetic anhydride
POCl$_3$ phosphorus oxychloride
TBTU O-(Benzotriazol-1-yl)-N,N,N',N'-tetramethyluronium tetrafluoroborate
CuCl copper(I) chloride
NaHCO3 sodium bicarbonate
KOH potassium hydroxide
RuPhos 2-Dicyclohexylphosphino-2',6'-diisopropoxybiphenyl
SPhos 2-Dicyclohexylphosphino-2',6'-dimethoxybiphenyl
PdCl$_2$dppf.DCM 1,1'-Bis(diphenylphosphino)ferrocene-palladium(II)dichloride dichloromethane complex
TMPMgCl LiCl 2,2,6,6-Tetramethylpiperidinylmagnesium chloride lithium chloride complex
Oxone Potassium peroxymonosulfate Starting materials and chemical reagents specified in the syntheses described below are commercially available, e.g. from Sigma-Aldrich, Fine Chemicals, Combi-Blocks and other vendors.

In the event that there is a discrepancy between nomenclature and any compounds depicted graphically, then it is the latter that presides (unless contradicted by any experimental details that may be given or unless it is clear from the context). Final compounds were named using Marvin software version 6.1. 6.2. or ChemBioDraw Ultra 13.

Purification of compounds may be carried out using silica gel column chromatography or preparative reverse phase HPLC (ACE column, acidic gradients with MeCN—H$_2$O containing 0.1% TFA or XBridge column, basic gradients using MeCN—H$_2$O containing ammonium bicarbonate) to give the products as their free bases or trifluoroacetic acid salts.

Intermediate 1

4-chloro-6-(2,3-dimethylphenyl)pyrimidin-2-amine

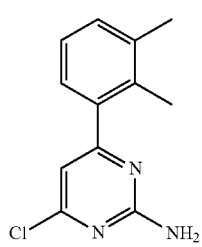 [SMILES: Cc1cccc(-c2cc(Cl)nc(N)n2)c1C]

A mixture of 2-amino-4,6-dichloropyrimidine (0.82 g, 5.0 mmol), 2,3-dimethylphenylboronic acid (0.75 g, 5.0 mmol), K$_2$CO$_3$ (1.38 g, 10.0 mmol,) and palladium tetrakis(triphenylphosphine)palladium (0) (0.12 g, 0.10 mmol) in 1,4-dioxane (20 mL) and water (5 mL) was heated in a sealed tube at 90° C. for 2.5 hours. The mixture was run through a plug of silica using EtOAc as eluent, concentrated and purified by column chromatography (1:4 EtOAc/pentane) to give the desired product as a white solid (0.76 g, 65%).

LCMS [M+H]$^+$ 234; $^1$H NMR (400 MHz, CD$_3$OD) δ ppm 7.21-7.29 (1H, m), 7.20-7.09 (2H, m), 6.70 (1H, s), 2.34 (3H, s), 2.23 (3H, s).

Intermediate 2

6-chloro-4-N-methylpyrimidine-2,4-diamine

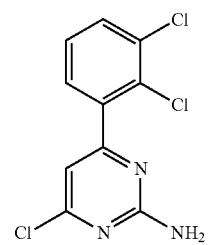 [SMILES: Nc1nc(Cl)cc(-c2cccc(Cl)c2Cl)n1]

A mixture of 4,6-dichloropyrimidin-2-amine (0.50 g, 3.05 mmol), (2,3-dichlorophenyl)boronic acid (0.64 g, 3.35 mmol), sodium carbonate (0.65 g, 6.10 mmol) and palladium tetrakis(triphenylphosphine)palladium (0) (0.088 g, 0.076 mmol) in 1,4-dioxane/water (30 mL; 4:1) was heated in a sealed tube at 95° C. for 2 h. The reaction mixture was run through a plug of silica (EtOAc) and then concentrated. Purification by column chromatography (1:4→1:3 EtOAc/hexane) afforded the desired product as a white solid (0.26 g, 31%). LCMS [M+H]$^+$ 274; $^1$H NMR (400 MHz, DMSO-d$_6$) δ ppm 6.89 (1H, s) 7.33 (2H, br s) 7.44-7.52 (2H, m) 7.71-7.81 (1H, m).

Intermediate 3

4-chloro-6-(3-chloro-2-methylphenyl)pyrimidin-2-amine

A stirred mixture of 2-amino-4,6-dichloropyrimidine (0.50 g, 3.1 mmol), 3-chloro-2-methylphenylboronic acid (0.57 g, 3.4 mmol), Na$_2$CO$_3$ (1.0 g, 9.8 mmol), palladium tetrakis(triphenylphosphine)palladium (0) (0.088 g, 0.076 mmol), dioxane (22 mL) and water (8 mL) were heated in a sealed tube at 90° C. for 2 hours. The solvents were removed and the resulting solid was dissolved in EtOAc (20 mL) and washed with water. The organic phase was dried over MgSO$_4$ and concentrated. The crude material was purified by flash chromatography (1:4 EtOAc/petroleum ether) to give the desired product as a white solid (0.36 g, 47%).

LCMS [M+H]$^+$ 254; $^1$H NMR (400 MHz, DMSO-d$_6$) δ ppm 7.52-7.56 (1H, dd, J$_1$=6.5 Hz, J$_2$=2.5 Hz) 7.30-7.33 (2H, m) 7.26 (2H, s) 6.79 (1H, s) 2.32 (3H, s).

Intermediate 4

4-{2-[(2-amino-6-chloropyrimidin-4-yl)amino]ethyl}benzene-1-sulfonamide

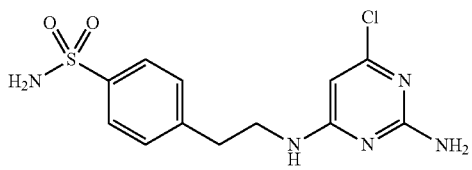 [SMILES: Nc1nc(Cl)cc(NCCc2ccc(S(N)(=O)=O)cc2)n1]

To a suspension of 4,6-dichloropyrimidin-2-amine (800 mg, 4.9 mmol) and 4-(2-aminoethyl)benzenesulfonamide (980 mg, 4.9 mmol) in 2-propanol (10 mL), was added Hünig's base (1.0 mL, 5.7 mmol) and the resulting mixture was heated at reflux for 15 h. The mixture was then poured into NaHCO$_3$ (aq) and extracted three times with DCM. The combined organic layers were dried and concentrated and the crude mixture was purified by column chromatography to afford the title compound. LCMS [M+H]$^+$ 328; $^1$H NMR (400 MHz, CD$_3$OD) δ ppm 7.80-7.85 (m, 2H), 7.41 (d, J=8.6 Hz, 2H), 5.76-5.81 (m, 1H), 3.54-3.64 (m, 2H), 2.95 (t, J=7.1 Hz, 2H).

Intermediate 5

4-chloro-6-(2,3,4-trichlorophenyl)pyrimidin-2-amine

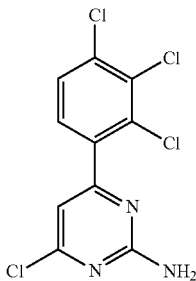 [SMILES: Nc1nc(Cl)cc(-c2ccc(Cl)c(Cl)c2Cl)n1]

A mixture of 4,6-dichloropyrimidin-2-amine (82 mg, 0.50 mmol), (2,3,4-trichlorophenyl)-boronic acid (113 mg, 0.50 mmol), potassium carbonate (138 mg, 1.0 mmol), and palladium tetrakis(triphenylphosphine)palladium (0) (14 mg, 0.013 mmol) in 1,4-dioxane/water (8 mL; 4:1) was heated in a sealed tube at 90° C. for 2 h. The reaction mixture was passed through a plug of silica, concentrated, and purified by preparative LC. LCMS [M+H]$^+$ 308.

Intermediate 6

6-chloro-4-N-[2-(4-methanesulfonylphenyl)ethyl]pyrimidine-2,4-diamine

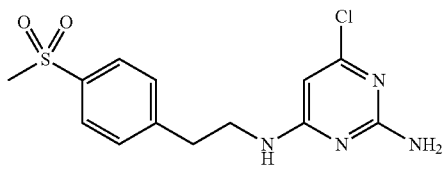 [SMILES: CS(=O)(=O)c1ccc(CCNc2cc(Cl)nc(N)n2)cc1]

A mixture of 4,6-dichloropyrimidin-2-amine (500 mg, 3.0 mmol), 2-(4-methylsulfonylphenyl)ethanamine (600 mg, 3.0 mmol) and Hünig's base (0.63 mL, 3.6 mmol) in 2-propanol (10 mL) was heated at reflux for 15 h. The reaction mixture was poured into NaHCO$_3$ (aq) and extracted three times with DCM. The combined organic layers were dried and concentrated. The crude mixture was purified by column chromatography which afforded the title compound. LCMS [M+H]+ 327; $^1$H NMR (400 MHz, CDCl3) δ ppm 7.90 (d, J=8.3 Hz, 2H), 7.41 (d, J=8.3 Hz, 2H), 5.77 (s, 1H), 4.80-4.89 (m, 2H), 4.69-4.79 (m, 1H), 3.56-3.67 (m, 2H), 3.07 (s, 3H), 3.00 (t, J=6.8 Hz, 2H).

Intermediate 7

4-N-(2-aminoethyl)-6-(2,3-dimethylphenyl)pyrimidine-2,4-diamine

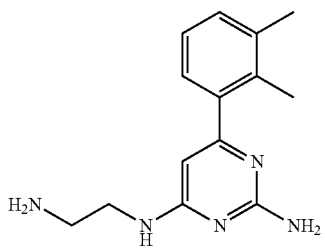 [SMILES: Cc1cccc(-c2cc(NCCN)nc(N)n2)c1C]

Step 1: To a suspension of 4,6-dichloropyrimidin-2-amine (500 mg, 3.1 mmol) and Hünig's base (0.80 mL) in 2-propanol (3.0 mL) was added tert-butyl N-(2-aminoethyl)carbamate (590 mg, 3.7 mmol) and the mixture was stirred at 150° C. for 15 min. The crude mixture was poured into NaHCO$_3$ (aq) and extracted three times with DCM. The combined organic layers were dried and concentrated. Purification by column chromatography (0→10% MeOH in DCM) afforded tert-butyl N-[2-[(2-amino-6-chloro-pyrimidin-4-yl)amino]ethyl]carbamate (850 mg, 2.9 mmol).

Step 2: tert-Butyl N-[2-[(2-amino-6-chloro-pyrimidin-4-yl)amino]ethyl]carbamate (850 mg, 3.0 mmol), (2,3-dimethylphenyl)boronic acid (530 mg, 3.5 mmol), palladium tetrakis(triphenylphosphine)palladium (0) (34 mg, 0.030 mmol), and K$_2$CO$_3$ (1020 mg, 7.4 mmol) were suspended in 1,4-dioxane (10 ml) and H$_2$O (2.0 ml). The vial was flushed with nitrogen and the resulting mixture was stirred at 90° C. for 16 h. The crude mixture was poured into NaHCO$_3$ (aq) and extracted three times with DCM. The combined organic layers were dried and concentrated. Purification by column chromatography (0→10% MeOH in DCM) afforded tert-butyl N-[2-[[2-amino-6-(2,3-dimethylphenyl)pyrimidin-4-yl]amino]ethyl]carbamate (770 mg, 2.1 mmol).

Step 3: tert-Butyl N-[2-[[2-amino-6-(2,3-dimethylphenyl)pyrimidin-4-yl]amino]ethyl]carbamate (770 mg, 2.1 mmol) was dissolved in TFA (6.0 mL) and the resulting mixture was stirred for 1 h at 20° C., after which the TFA was distilled off. Purification by column chromatography (5→30% MeOH [containing 1 v/v % NH$_4$OH] in DCM) afforded 4-N-(2-aminoethyl)-6-(2,3-dimethylphenyl)pyrimidine-2,4-diamine (500 mg, 1.9 mmol). LCMS [M+H]$^+$ 258.

Intermediate 8

4-N-(3-aminopropyl)-6-(2,3-dimethylphenyl)pyrimidine-2,4-diamine

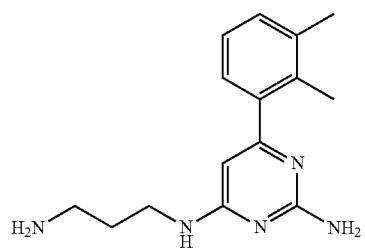 [SMILES: Cc1cccc(-c2cc(NCCCN)nc(N)n2)c1C]

Step 1: A vial was charged with 4,6-dichloropyrimidin-2-amine (500 mg, 3.0 mmol) and tert-butyl N-(2-aminopropyl)carbamate (640 mg, 3.7 mmol). Then 2-propanol (3.0 ml) and Hünig's base (0.80 ml) were added and the resulting mixture was heated at 150° C. using microwave irradiation for 15 min. The mixture was then concentrated and purified by column chromatography (2→10% MeOH in DCM) to afford tert-butyl N-[3-[(2-amino-6-chloro-pyrimidin-4-yl)amino]propyl]-carbamate (790 mg, 2.6 mmol).

Step 2: tert-Butyl N-[3-[(2-amino-6-chloro-pyrimidin-4-yl)amino]propyl]carbamate (790 mg, 2.6 mmol), (2,3-dimethylphenyl)boronic acid (470 mg, 3.1 mmol), palladium tetrakis(triphenylphosphine)palladium (0) (60 mg, 0.050 mmol), and $K_2CO_3$ (720 mg 5.2 mmol) were suspended in 1,4-dioxane (6.0 ml) and $H_2O$ (1.5 ml). The resulting mixture was heated at 90° C. for 16 h and then poured into $H_2O$ and extracted three times with DCM. The combined organic layers were dried and concentrated. Purification by column chromatography (1→10% MeOH in DCM) afforded tert-butyl N-[3-[[2-amino-6-(2,3-dimethylphenyl)pyrimidin-4-yl]amino]propyl]carbamate (800 mg, 2.1 mmol).

Step 3: tert-Butyl N-[3-[[2-amino-6-(2,3-dimethylphenyl)pyrimidin-4-yl]amino]propyl]carbamate (800 mg, 2.1 mmol) was dissolved in TFA and heated at reflux for 1 h. The TFA was evaporated and the crude residue was purified by column chromatography (2→30% MeOH [containing 1 v/v % $NH_4OH$] in DCM) to afford 4-N-(3-aminopropyl)-6-(2,3-dimethylphenyl)pyrimidine-2,4-diamine (540 mg, 2.0 mmol). LCMS $[M+H]^+$ 272.

Intermediate 9

4-chloro-6-(2-chloro-3-methylphenyl)pyrimidin-2-amine

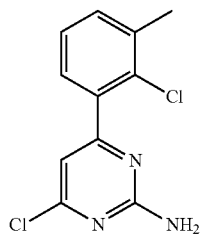 [SMILES: Cc1cccc(-c2cc(Cl)nc(N)n2)c1Cl]

To a suspension of 4,6-dichloropyrimidin-2-amine (250 mg, 1.5 mmol) in dioxane/$H_2O$ (5 mL, 4:1) was added (2-chloro-3-methylphenyl)boronic acid (260 mg, 1.5 mmol) followed by potassium carbonate (420 mg, 3.0 mmol) and $Pd(PPh_3)_4$ (44 mg, 0.040 mmol). The resulting mixture was stirred at 90° C. for 12 hrs. The solvent was removed and the residue was taken up in DMF and purified by preparative to afford the desired product as an off-white solid (170 mg, 43%). LCMS $[M+H]^+$ 254; $^1$H NMR (400 MHz, $CDCl_3$) δ ppm 7.32-7.28 (2H, m), 7.25-7.21 (1H, m), 6.92 (1H, s), 5.31 (2H, br s), 2.42 (3H, s).

Intermediate 10

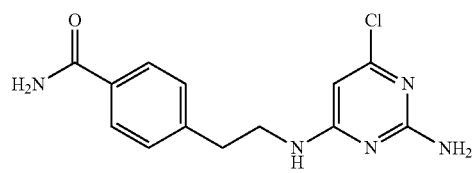 [SMILES: NC(=O)c1ccc(CCNc2cc(Cl)nc(N)n2)cc1]

4-[2-[(2-amino-6-chloro-pyrimidin-4-yl)amino]ethyl]benzamide

Step 1. A mixture of 2-(4-carboxyphenyl)ethylammonium chloride (1.0 equiv.), 4,6-dichloropyrimidin-2-amine (1.0 equiv.), diisopropylethylamine (3.2 equiv.), and 2-propanol was heated to 110° C. in a sealed vial for 16 h.

The mixture was then concentrated and purified by silica gel chromatography which afforded 4-[2-[(2-amino-6-chloro-pyrimidin-4-yl)amino]ethyl]benzoic acid. LCMS $[M+H]^+$ 293.

Step 2. A mixture of 4-[2-[(2-amino-6-chloro-pyrimidin-4-yl)amino]ethyl]benzoic acid (1.0 equiv.), HATU (1.1 equiv.), and DMF was stirred at 20° C. for 5 min, thereafter ammonium hydroxide (3 equiv.) was added. The mixture was stirred at 20° C. for 16 h and then the mixture was diluted with $NaHCO_3$ (aq) and extracted with DCM×3. The combined organics were dried, concentrated, and purified by silica gel chromatography. $[M+H]^+$ 292.

Intermediate 11

4-N-(4-aminobutyl)-6-(2,3-dimethylphenyl)pyrimidine-2,4-diamine

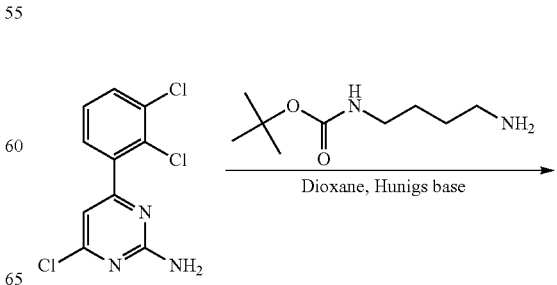

-continued

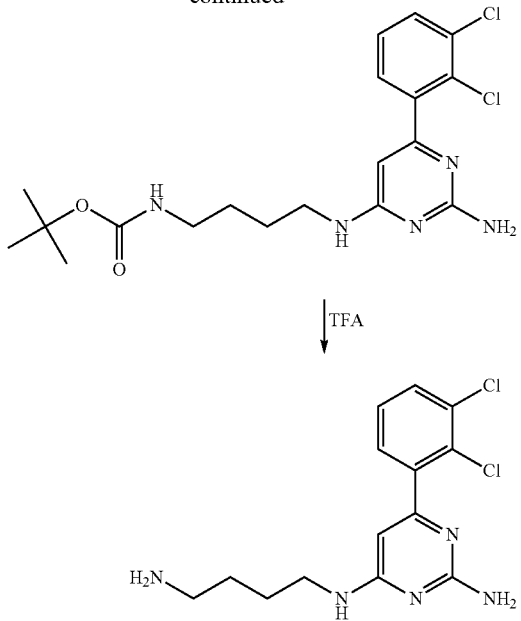

Step 1: A mixture of intermediate 2 (1 equiv.), tert-butyl N-(4-aminobutyl)carbamate (1.9 equiv.), and diisopropylethylamine (2.1 equiv.) in 1,4-dioxane was stirred at 150° C. in a microwave reactor for 30 min. The crude reaction mixture was then purified by preparative LC. LCMS [M+H]+ 426.

Step 2: tert-butyl N-[4-[[2-amino-6-(2,3-dichlorophenyl)pyrimidin-4-yl]amino]butyl]carbamate was stirred in TFA at 20° C. for 1 h. The TFA was then removed and the crude residue was purified by silica gel chromatography. LCMS [M+H]+ 326.

Intermediate 12

4-N-[2-(3-aminophenyl)ethyl]-6-(3-chloro-2-methyl-phenyl)pyrimidine-2,4-diamine

Step 1: A mixture of 2-amino-4,6-dichloropyrimidine (1.0 equiv.), 2-(3-nitrophenyl)ethylammonium chloride (1.3 equiv.), and diisopropylethylamine (2.5 equiv.) in 2-propanol was stirred at 100° C. in a sealed vial for 16 h. The reaction mixture was then diluted with NaHCO$_3$ (aq) and extracted with DCM (×3). The combined organics were dried, concentrated, and purified by silica gel chromatography.

Step 2: A mixture of 6-(3-chloro-2-methyl-phenyl)-N4-[2-(3-nitrophenyl)ethyl]pyrimidine-2,4-diamine (1.0 equiv.), (3-chloro-2-methyl-phenyl)boronic acid (1.2 equiv.), K$_2$CO$_3$ (3.0 equiv.) and Pd(PPh$_3$)$_4$ (0.05 equiv.) in 1,4-dioxane and water was stirred at 90° C. for 16 h. Thereafter water was added and the mixture was extracted with DCM×3. The combined organic phases were concentrated and purified by silica gel chromatography. LCMS [M+H]+ 384.

Step 3: A mixture of 6-(3-chloro-2-methyl-phenyl)-N4-[2-(3-nitrophenyl)ethyl]pyrimidine-2,4-diamine (1.0 equiv.) and SnCl$_2$.H$_2$O (5.0 equiv.) was stirred in ethanol at reflux for 16 h. Then KOH (1 M) was added and the mixture was extracted with DCM×5. The organics were dried, concentrated and purified by silica gel chromatography.

LCMS [M+H]+ 354. $^1$H NMR (400 MHz, CHLOROFORM-d) δ ppm 7.37 (d, J=1.6 Hz, 1H), 7.19 (d, J=1.6 Hz, 1H), 7.14-7.18 (m, 1H), 7.09-7.14 (m, 1H), 6.61-6.64 (m, 1H), 6.54-6.60 (m, 2H), 5.77 (s, 1H), 4.77 (br. s., 3H), 3.66 (br. s., 2H), 3.51-3.62 (m, 2H), 2.83 (t, J=7.0 Hz, 2H), 2.37 (s, 3H).

Intermediate 13

4-N-[2-(4-aminophenyl)ethyl]-6-(3-chloro-2-methyl-phenyl)pyrimidine-2,4-diamine

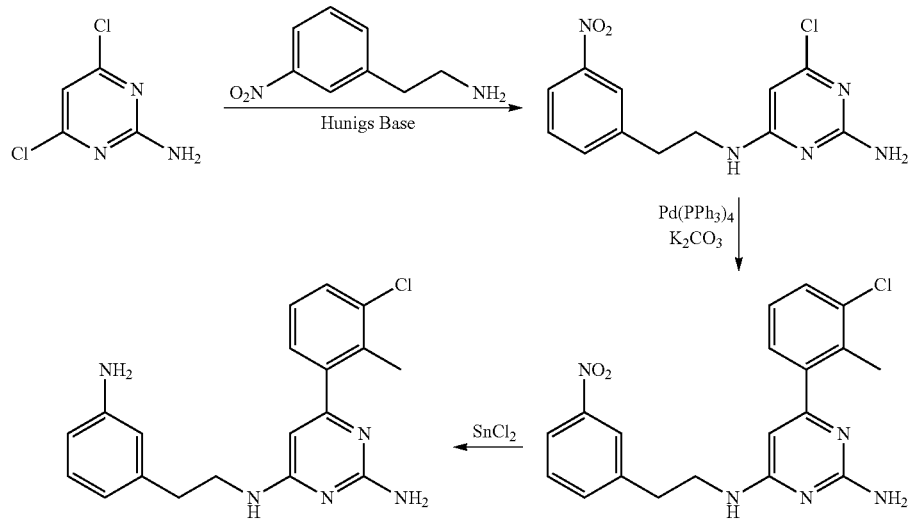

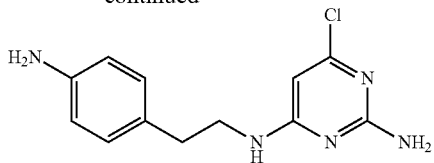

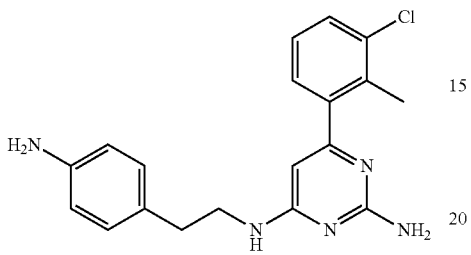

Step 1: A mixture of 2-amino-4,6-dichloropyrimidine (1.0 equiv.), 4-(2-aminoethyl)aniline (1.3 equiv.), and diisopropylethylamine (2.0 equiv.) in 2-propanol was stirred at 90° C. in a sealed vial for 16 h. The reaction mixture was then diluted with NaHCO₃ (aq) and extracted with DCM×3. The combined organics were dried, concentrated, and purified by silica gel chromatography. [M+H]⁺ 264.

Step 2: A mixture of N4-[2-(4-aminophenyl)ethyl]-6-chloro-pyrimidine-2,4-diamine (1.0 equiv.), (3-chloro-2-methyl-phenyl)boronic acid (1.2 equiv.), K₂CO₃ (3.0 equiv.) and Pd(PPh₃)₄ (0.05 equiv.) in 1,4-dioxane and water was stirred at 90° C. for 16 h. Thereafter water was added and the mixture was extracted with DCM×3. The combined organic phases were dried, concentrated, and purified by silica gel chromatography.

LCMS [M+H]⁺ 354.

Intermediate 14

4-chloro-6-(4-fluoro-2,5-dimethylphenyl)pyrimidin-2-amine

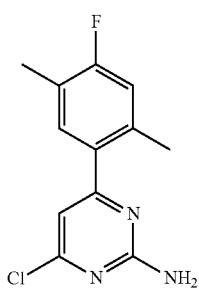 [SMILES: Cc1cc(-c2cc(Cl)nc(N)n2)c(C)cc1F]

A mixture of 2-amino-4,6-dichloropyrimidine (0.72 g, 4.4 mmol), 4-fluoro-2,5-dimethylphenylboronic acid (0.78 g, 4.6 mmol), K₂CO₃ (1.2 g, 8.8 mmol,) and tetrakis(triphenylphosphine)palladium (0.17 g, 0.15 mmol) in 1,4-dioxane (10 mL) and water (2.0 mL) was heated in a sealed tube at 60° C. for 23 hours. The mixture was diluted with NaHCO₃ and extracted with DCM×3. The combined organics were concentrated and purified by column chromatography.

LCMS [M+H]⁺ 252. ¹H NMR (400 MHz, CHLOROFORM-d) δ ppm 7.23 (d, J=7.83 Hz, 1H), 6.92 (d, J=10.61 Hz, 1H), 6.73 (s, 1H), 5.37 (br. s., 2H), 2.37 (s, 3H), 2.27 (d, J=0.76 Hz, 3H).

Intermediate 15

4-N-[2-(4-aminophenyl)ethyl]-6-(2,3-dimethylphenyl)pyrimidine-2,4-diamine

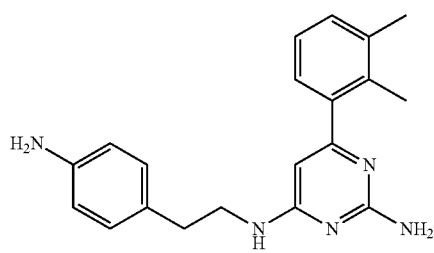 [SMILES: Cc1cccc(-c2cc(NCCc3ccc(N)cc3)nc(N)n2)c1C]

This compound was produced according to general procedure 2 from intermediate 1 and 4-(2-aminoethyl)aniline. LCMS [M+H]⁺ 334. ¹H NMR (400 MHz, CHLOROFORM-d) δ ppm 7.19 (br. s., 1H), 7.13 (s, 1H), 7.08 (s, 1H), 7.00 (d, J=8.34 Hz, 2H), 6.68 (d, J=8.34 Hz, 2H), 0.80 (s, 1H), 3.48-3.60 (m, 2H), 2.77 (t, J=7.45 Hz, 2H), 2.32 (s, 3H), 2.20 (s, 3H).

Intermediate 16

[4-[2-[(2-amino-6-chloro-pyrimidin-4-yl)amino]ethyl]phenyl]-morpholino-methanone

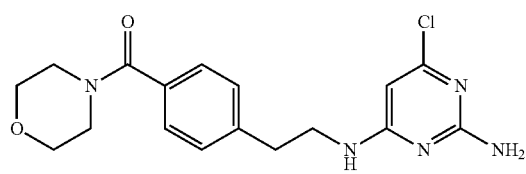 [SMILES: Nc1nc(Cl)cc(NCCc2ccc(C(=O)N3CCOCC3)cc2)n1]

A mixture of 4-[2-[(2-amino-6-chloro-pyrimidin-4-yl)amino]ethyl]benzoic acid (from step 1 of the synthesis of intermediate 10) and TBTU in DMF was stirred at 20° C. for 10 min, then morpholine was added and the resulting mixture was stirred at 20° C. for 20 h.

The mixture was then diluted with NaHCO₃ (aq) and extracted with DCM×3. The combined organics were dried, concentrated, and purified by silica gel chromatography. LCMS [M+H]⁺ 362.

Intermediate 17

4-(2-{[2-amino-6-(3-chloro-2-methylphenyl)pyrimidin-4-yl]amino}ethyl)benzonitrile

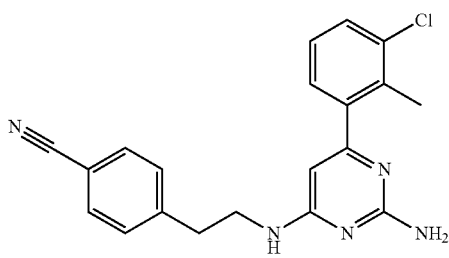 [SMILES: Cc1c(Cl)cccc1-c1cc(NCCc2ccc(C#N)cc2)nc(N)n1]

A mixture of 4-chloro-6-(3-chloro-2-methylphenyl)pyrimidin-2-amine (150 mg, 0.59 mmol), 4-(2-aminoethyl)benzonitrile hydrochloride (110 mg, 0.59 mmol), $K_2CO_3$ (240 mg, 1.8 mmol) and MeCN (5 mL) was heated for 1 hour at 170° C. in a sealed vial. Thereafter the mixture was diluted with MeOH and purified by preparative LC to afford 4-(2-{[2-amino-6-(3-chloro-2-methylphenyl)pyrimidin-4-yl]amino}ethyl)benzonitrile. LCMS [M+H]$^+$ 364.

Intermediate 18

2-{[2-amino-6-(2,3-dimethylphenyl)pyrimidin-4-yl]amino}ethan-1-ol

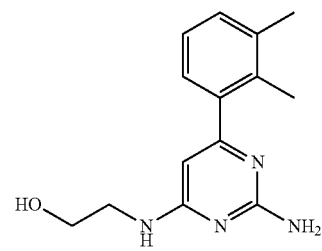 [SMILES: Cc1cccc(-c2cc(NCCO)nc(N)n2)c1C]

A mixture of Intermediate 1 (1.0 equiv.) and 2-aminoethanol (2.2 equiv.) in ethanol was heated in a sealed tube at 130° C. for 4 h. After cooling a precipitate formed which was filtered and washed with cold ethanol and dried to furnish the title compound. LCMS [M+H]$^+$ 259. $^1$H NMR (400 MHz, DMSO-d6) δ ppm 7.12-7.17 (m, 1H), 7.08 (t, J=7.5 Hz, 1H), 7.00-7.05 (m, 1H), 6.88 (br. s., 1H), 5.93 (s, 2H), 5.73 (s, 1H), 4.74 (t, J=5.3 Hz, 1H), 3.51 (q, J=5.8 Hz, 2H), 3.28-3.33 (m, 2H), 2.26 (s, 3H), 2.15 (s, 3H).

Intermediate 19

2-[[2-amino-6-(3-chloro-2-methyl-phenyl)pyrimidin-4-yl]amino]ethanol

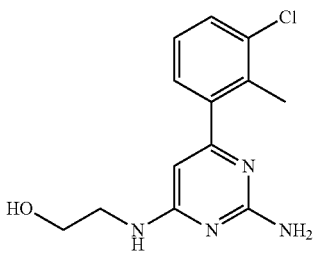 [SMILES: Cc1c(Cl)cccc1-c1cc(NCCO)nc(N)n1]

A mixture of Intermediate 3 (1.0 equiv.) and 2-aminoethanol (2.2 equiv.) in isopropanol was heated in a sealed tube at 130° C. for 1 h. After cooling a precipitate formed which was filtered and washed with cold isopropanol and dried to furnish the title compound. LCMS [M+H]$^+$ 279.

Intermediate 20

4-[2-[[2-amino-6-(1,2,3,6-tetrahydropyridin-4-yl)pyrimidin-4-yl]amino]ethyl]-benzenesulfonamide

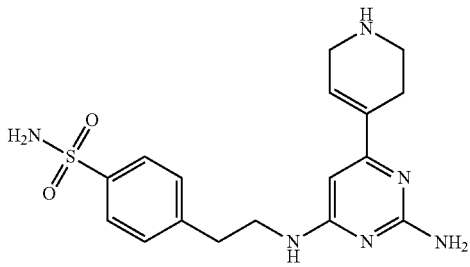 [SMILES: Nc1nc(NCCc2ccc(S(N)(=O)=O)cc2)cc(C2=CCNCC2)n1]

To tert-butyl 4-[2-amino-6-[2-(4-sulfamoylphenyl)ethylamino]pyrimidin-4-yl]-3,6-dihydro-2H-pyridine-1-carboxylate was added HCl (5 M in 1,4-dioxane) and methanol and the mixture was stirred at 20° C. for 40 min. Then the solvent was removed to obtain the title compound. LCMS [M+H]$^+$ 375.

Intermediate 21

4-N-[2-(4-methanesulfonylphenyl)ethyl]-6-(1,2,3,6-tetrahydropyridin-4-yl)pyrimidine-2,4-diamine

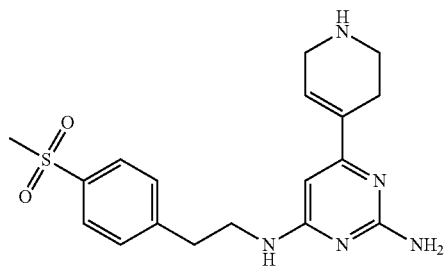 [SMILES: CS(=O)(=O)c1ccc(CCNc2cc(C3=CCNCC3)nc(N)n2)cc1]

To tert-butyl 4-(2-amino-6-{[2-(4-methanesulfonylphenyl)ethyl]amino}pyrimidin-4-yl)-1,2,3,6-tetrahydropyridine-1-carboxylate was added HCl (5 M) in 1,4-dioxane), then the mixture was stirred at 20° C. for 20 min. The solvent was removed to obtain the title compound. LCMS [M+H]$^+$ 374.

Intermediate 22

N4-(2-aminoethyl)-6-(3-chloro-2-methyl-phenyl)pyrimidine-2,4-diamine

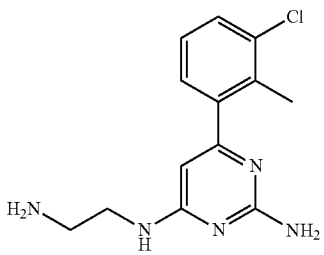 [SMILES: Cc1c(Cl)cccc1-c1cc(NCCN)nc(N)n1]

Step 1. A mixture of 4,6-dichloropyrimidin-2-amine (1 equiv.), tert-butyl N-(2-aminoethyl)carbamate (1.2 equiv.), and diisopropylethylamine (3 equiv.) in 2-propanol was stirred at 90° C. for 16 h. The reaction mixture was then poured into water and extracted with DCM×3. The combined organics were dried (MgSO$_4$) and concentrated. The crude material was used in step 2 without further purification.

Step 2. The crude material from step 1 was dissolved in dioxane, then K$_2$CO$_3$ (2 equiv.), Pd(PPh$_3$)$_4$ (0.05 equiv.), and (3-chloro-2-methyl-phenyl)boronic acid (1.2 equiv.) were added. The flask was flushed with N2 and the mixture was stirred at reflux for 16 h. The reaction mixture was then poured into water and extracted with DCM×3. The combined organics were dried (MgSO$_4$) and concentrated. The crude material was purified by silica gel chromatography using MeOH (0-9%) in DCM.

Step 3. The material from step 2 was dissolved in TFA and stirred at 20° C. for 2 h. The solvent was removed and the crude residue was purified by silica gel chromatography using 5-30% MeOH (containing 1 v/v % NH$_4$OH) in DCM.

LCMS [M+H]$^+$ 278. $^1$H NMR (400 MHz, DMSO-d$_6$) δ ppm 7.97 (br. s., 2H), 7.62-7.70 (m, 1H), 7.38-7.44 (m, 1H), 7.33-7.37 (m, 1H), 7.27 (br. s., 1H), 7.14 (br. s., 1H), 7.01 (br. s., 1H), 6.08 (s, 1H), 3.61 (d, J=4.7 Hz, 2H), 3.10 (br. s., 2H), 2.31 (s, 3H).

Intermediate 23

N4-(3-aminopropyl)-6-(3-chloro-2-methylphenyl)pyrimidine-2,4-diamine

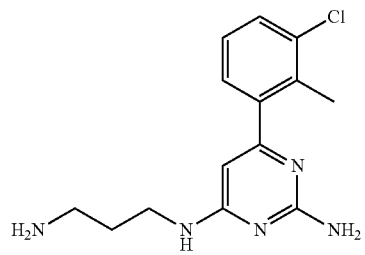 [SMILES: Cc1c(Cl)cccc1-c1cc(NCCCN)nc(N)n1]

Step 1. tert-butyl N-[3-[[2-amino-6-(3-chloro-2-methyl-phenyl)pyrimidin-4-yl]amino]propyl]carbamate A mixture of tert-butyl N-(3-aminopropyl)carbamate (1.25 equiv.), 4,6-dichloropyrimidin-2-amine (1 equiv.), and Hünig's base (1.5 equiv.) in 2-propanol was stirred at 100° C. for 16 h. The reaction mixture was then poured into water and extracted with DCM×3. The combined organics were dried (MgSO$_4$) and concentrated. The crude material was purified by silica gel chromatography which afforded tert-butyl N-[3-[(2-amino-6-chloro-pyrimidin-4-yl)amino]propyl]carbamate Step 2. The title compound was prepared according to general procedure 1 from tert-butyl N-[3-[(2-amino-6-chloro-pyrimidin-4-yl)amino]propyl]carbamate (prepared in step 1) and (3-chloro-2-methyl-phenyl)boronic acid. LCMS [M+H]$^+$ 392. $^1$H NMR (400 MHz, METHANOL-d4) δ ppm 7.57-7.63 (m, 1H), 7.31-7.40 (m, 2H), 6.04 (s, 1H), 3.55 (t, J=6.8 Hz, 2H), 3.14 (t, J=7.0 Hz, 2H), 2.39 (s, 3H), 1.81 (t, J=7.0 Hz, 2H), 1.44 (s, 9H).

Step 3. A mixture of tert-butyl N-[3-[[2-amino-6-(3-chloro-2-methyl-phenyl)pyrimidin-4-yl]amino]propyl]carbamate (prepared in step 2) and TFA was stirred at 20° C. for 2 h, thereafter the solvent was removed by co-evaporation with 2-propanol. The crude residue was purified by silica gel chromatography.

LCMS [M+H]$^+$ 292.

Intermediate 24

3-{[2-amino-6-(3-chloro-2-methylphenyl)pyrimidin-4-yl]amino}propan-1-ol

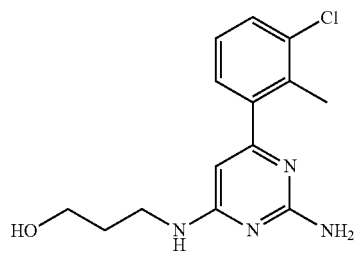 [SMILES: Cc1c(Cl)cccc1-c1cc(NCCCO)nc(N)n1]

A mixture of 4-chloro-6-(3-chloro-2-methylphenyl)pyrimidin-2-amine (intermediate 3), 3-aminopropan-1-ol (2.2 equiv.) in 2-propanol was microwave heated in a sealed tube at 130° C. for 30 min. Purification by column chromatography afforded the title compound (10% MeOH in DCM). LCMS [M+H]$^+$ 293.

Intermediate 25

4-(2-{[2-amino-6-(3-chloro-2-methylphenyl)pyrimidin-4-yl]amino}ethoxy)benzonitrile

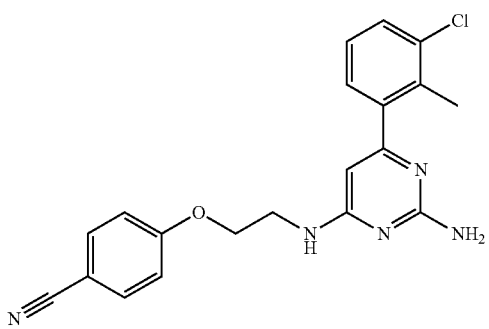 [SMILES: Cc1c(Cl)cccc1-c1cc(NCCOc2ccc(C#N)cc2)nc(N)n1]

A mixture of 4-chloro-6-(3-chloro-2-methylphenyl)pyrimidin-2-amine (intermediate 3), 4-(2-aminoethoxy)benzonitrile (1.5 equiv.) and N,N-diisopropylethylamine (2 equiv.) in 2-propanol (0.3 mL) was heated in a sealed tube at 100° C. for 30 h. Purification by column chromatography afforded the title compound (70% EtOAc in iso-Hexane). LCMS [M+H]$^+$ 380. $^1$H NMR (400 MHz, DMSO-d$_6$) δ ppm 7.75-7.82 (m, 2H), 7.44 (dd, J=7.7, 1.4 Hz, 1H), 7.17-7.28 (m, 3H), 7.15 (d, J=8.8 Hz, 2H), 6.10 (br. s., 2H), 5.79 (s, 1H), 4.20 (t, J=5.7 Hz, 2H), 3.60-3.76 (m, 2H), 2.29 (s, 3H),

Intermediate 26

4-(2-acetamidoethyl)benzene-1-sulfonyl chloride

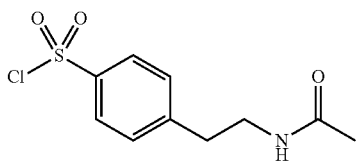 [SMILES: CC(=O)NCCc1ccc(S(=O)(=O)Cl)cc1]

Chlorosulfuric acid (5 equiv.) was slowly added to N-(2-phenylethyl)acetamide (1 equiv.). The mixture was stirred for 2 hours at r.t. and dropped on a mixture of water and ice. The title compound was collected by filtration and washed with water. LCMS [M+H]$^+$ 262.

General Procedures

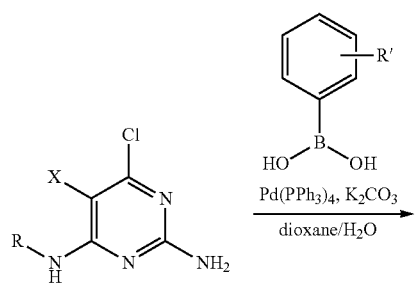

General Procedure 1:

To a mixture of a suitable chloropyrimidine derivative (1 equiv.) in 1,4-dioxane/water (4:1) was added the appropriate boronic acid (or boronic ester) derivative (1.3 equiv.), K$_2$CO$_3$ (2 equiv.) and Pd(PPh$_3$)$_4$ (0.1 equiv.).

The mixture is heated at 95° C. overnight or in a microwave reactor until the reaction is complete as shown by LCMS. The crude mixture is then purified by preparative LC to afford the desired product.

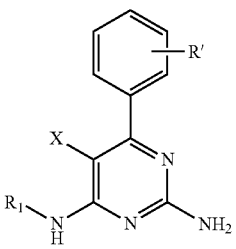

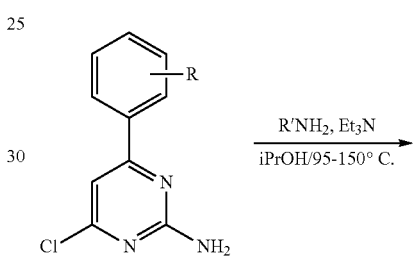

General Procedure 2:

A mixture of a suitable amine (1 equiv.), and a suitable chloropyrimidine derivative (1.2 equiv.) and triethylamine (1.5 equiv.) in 2-propanol was heated in a sealed tube at 95° C. overnight or at 150° C. for 15 min in a microwave reactor. The reaction mixture was then concentrated and purified by preparative LC or by silica gel chromatography.

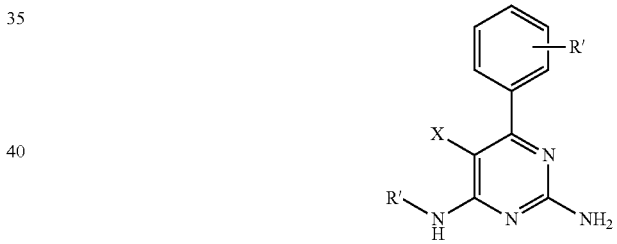

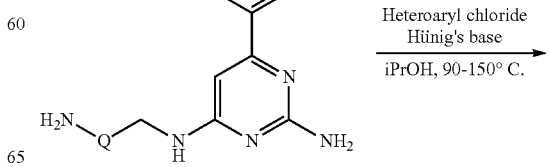

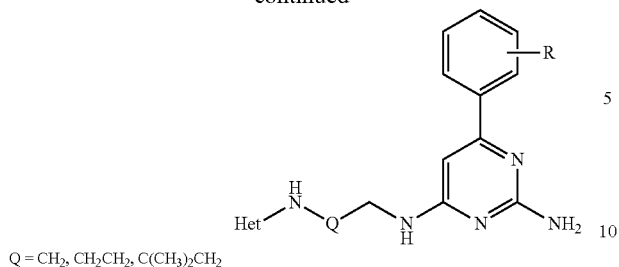

Q = CH₂, CH₂CH₂, C(CH₃)₂CH₂

General Procedure 3:

A mixture of the corresponding 4-N-(aminoalkyl)-6-(aryl)pyrimidine-2,4-diamine (1.0 equiv.) and the corresponding heteroaryl chloride (1.5 equiv.), and Hünig's base (1.5 equiv.) in 2-propanol was stirred in a sealed tube at 90-150° C. until the reaction was complete. The crude mixture was then concentrated and purified by preparative LC or by silica gel chromatography.

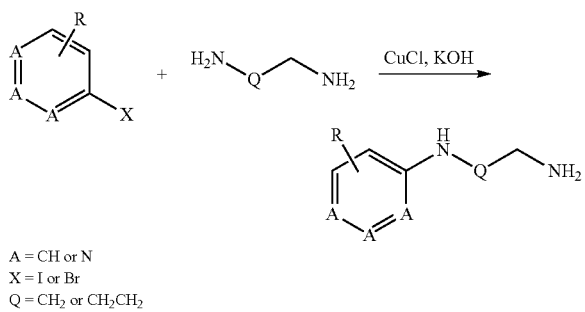

A = CH or N
X = I or Br
Q = CH₂ or CH₂CH₂

General Procedure 4:

A mixture of the corresponding aryl halide or heteroaryl halide (1.0 equiv.), CuCl (0.10 equiv.), KOH (2.0 equiv.), and ethylenediamine or propane-1,3-diamine (4.5 equiv.) was stirred at 20° C. (for aryl iodides) or 90° C. (for aryl bromides) for 12-24 h in a sealed vial. The mixture was allowed to cool and was then extracted with hot EtOAc (×5). The combined organics were concentrated and the excess of diamine was removed by co-evaporation with toluene. The crude material was used without further purification.

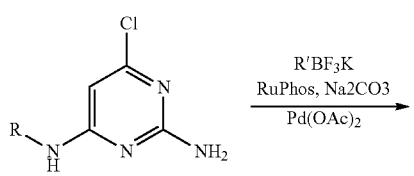

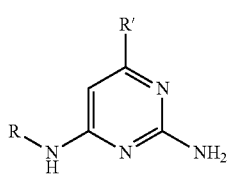

General Procedure 5:

A mixture of the corresponding 6-chloro-4-N-(alkyl)-pyrimidine-2,4-diamine compound (1.0 equiv.), the appropriate potassium (aryl)trifluoroborate (2.0 equiv.), Pd(OAc)₂ (0.10 equiv.), RuPhos (0.20 equiv), and Na₂CO₃ (3.0 equiv.) was stirred in ethanol at reflux for 16 h. The crude mixture was then diluted with NaHCO₃ (aq.) and extracted with DCM×3. The crude material was purified by preparative LC or by silica gel chromatography.

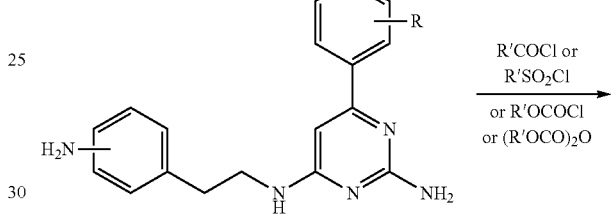

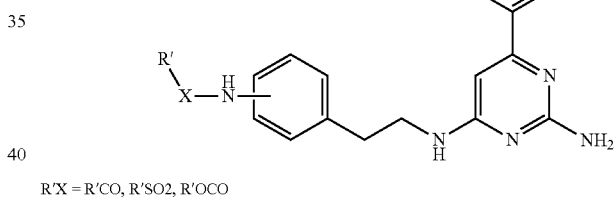

R'X = R'CO, R'SO2, R'OCO

General Procedure 6:

A mixture of the corresponding 4-N-(aminophenethyl) 6-(aryl)pyrimidine-2,4-diamine (1.0 equiv.), a suitable electrophile (acid chloride, sulfonyl chloride, chloroformate, or dicarbonate) (1.3 equiv.), and triethylamine or diisopropylethylamine (5.0 equiv.) in DCM or acetonitrile was stirred at 20-50° C. for 12-24 h. After completion the mixture was concentrated and purified by preparative LC or by silica gel chromatography.

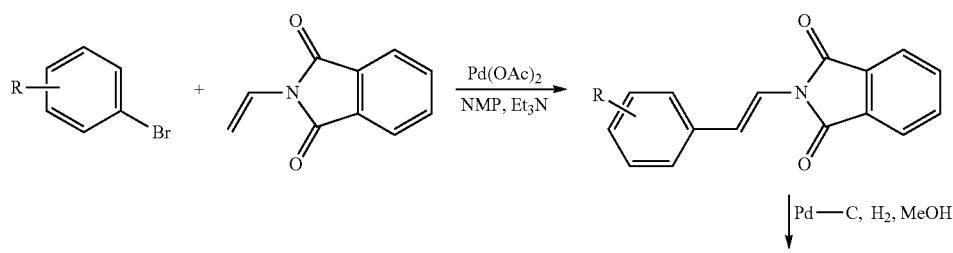

-continued

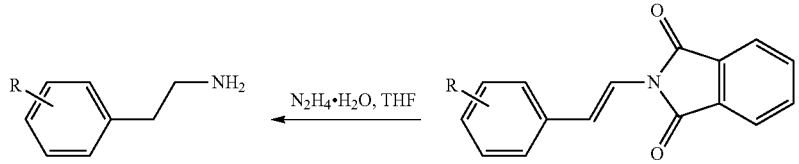

General Procedure 7:

Step 1: A mixture of the corresponding aryl halide (1.0 equiv.), N-vinylphthalimide (1.1 equiv.), Pd(OAc)$_2$ (0.0005 equiv.), and Et$_3$N (1.2 equiv.) were dissolved in NMP and stirred at 135° C. for 16 h. The reaction mixture was cooled to room temperature and then water was added which precipitated a solid. The solid was filtered off and washed with water.

Step 2: In a flask, the solid from step 1 was dissolved in MeOH and then Pd/C (0.10 equiv.) was added. The atmosphere in the flask was changed to H$_2$ and the resulting mixture was stirred at 60° C. for 16-24 h. The solution was then passed through a syringe filter and concentrated.

Step 3: The crude material from step 2 was dissolved in THF, and then hydrazine hydrate (1.25 equiv.) was added. The resulting mixture was stirred at reflux for 16-24 h. The reaction mixture was concentrated and purified by preparative LC.

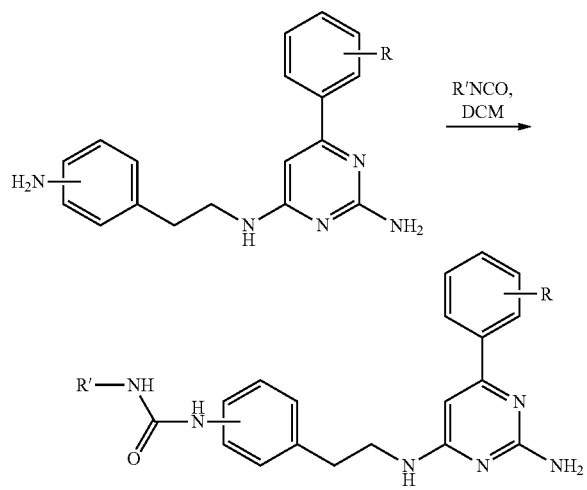

General Procedure 8:

A mixture of the corresponding amine, a suitable isocyanate, and DCM was stirred at 20-60° C. for 1-48 hours. Thereafter the mixture was concentrated and purified by preparative LC or by silica gel chromatography.

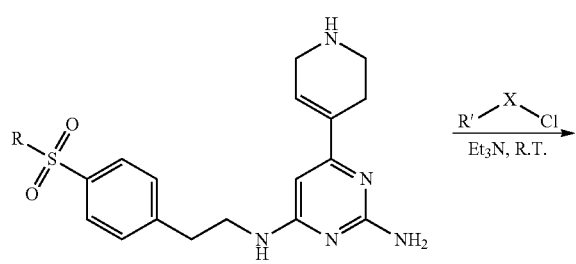

-continued

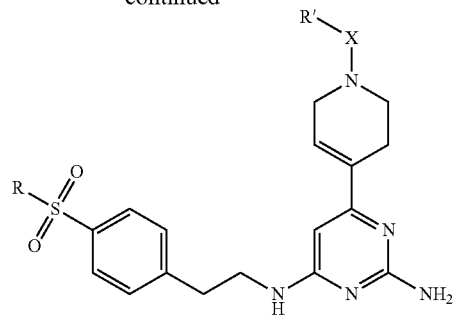

R = Me or NH$_2$
X = CO or SO$_2$

General Procedure 9:

A mixture of N4-[2-(4-methylsulfonylphenyl)ethyl]-6-(1,2,3,6-tetrahydropyridin-4-yl)pyrimidine-2,4-diamine hydrochloride or 4-[2-[[2-amino-6-(1,2,3,6-tetrahydropyridin-4-yl)pyrimidin-4-yl]amino]ethyl]benzenesulfonamide hydrochloride, a suitable sulfonyl chloride or acid chloride (1.2 equiv.), and triethylamine (3.0 equiv.) in DCM is stirred in a sealed tube at 20° C. After completion of the reaction the crude mixture was purified by preparative LC.

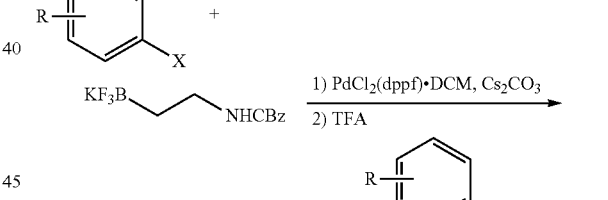

General Procedure 10:

Step 1. A mixture of the corresponding aryl halide (1.0 equiv.), potassium 2-(benzyloxycarbonylamino)ethyl-trifluoro-boranuide (1.0 equiv.), PdCl$_2$(dppf).DCM (0.05 equiv.), and Cs$_2$CO$_3$ (3.0 equiv.) in toluene and water was stirred at 90° C. under N$_2$ for 16 h. The reaction mixture was then poured into water and extracted with DCM. The combined organics were dried (MgSO$_4$) and concentrated. The crude material was purified by silica gel chromatography.

Step 2. The material from step 1 was stirred in refluxing TFA until the reaction was complete. The solvent was removed by co-evaporation with 2-propanol. The crude material was used without further purification.

EXAMPLES

The utility of the compounds of the present invention can be illustrated, for example, by their activity in vitro in the cancer cell clonogenic and/or viability assay described below. The link between activity in tumor cell clonogenic assay and anti-tumor activity in the clinical setting has been well established in the art (e.g. see ref Silverstini et al Stem Cells 1993, 11(6), 258-35).

Example 1

6-(3-chloro-2-methylphenyl)-4-N-[2-(4-methanesulfonylphenyl)ethyl]pyrimidine-2,4-diamine A solution of 4-chloro-6-(3-chloro-2-methylphenyl)pyrimidin-2-amine (300 mg; 1.2 mmol) and the 2-(4-methylsulfonylphenyl)ethanamine (HCl salt) (300 mg; 1.27 mmol) in n-Butanol (2.0 ml) was treated with Hünig's base (400 mg; 3 mmol) and heated at 140° C. overnight. The mixture was purified by preparative LC to afford the title compound (390 mg). LCMS [M+H]$^+$ 417; $^1$H NMR (400 MHz, CD$_3$OD) δ ppm 7.89 (d, J=8.53 Hz, 2H), 7.56 (d, J=8.53 Hz, 2H), 7.44-7.41 (m, 1H), 7.25-7.18 (m, 2H), 5.79 (s, 1H), 3.68 (m, 2H), 3.11 (s, 3H), 3.05 (t, J=7.11 Hz, 2H) and 2.33 (s, 3H).

Example 2

6-[(3-{[2-amino-6-(2,3-dimethylphenyl)pyrimidin-4-yl]amino}propyl)amino]pyridine-3-sulfonamide In a closed vial a mixture of intermediate 8 and 6-chloropyridine-3-sulfonamide (1.2 equiv.) were stirred neat at 150° C. for 16 h. The reaction mixture was then purified by preparative LC. LCMS [M+H]$^+$ 428. $^1$H NMR (400 MHz, METHANOL-d4) δ ppm 8.34-8.37 (m, 2H), 8.01-8.08 (m, 2H), 7.35-7.41 (m, 2H), 7.24-7.29 (m, 2H), 7.19-7.24 (m, 3H), 6.96-7.02 (m, 2H), 6.04 (s, 1H), 3.68 (s, 2H), 3.55 (s, 2H), 2.38 (s, 3H), 2.27 (s, 3H), 2.05 (s, 2H).

Example 3

6-[(2-{[2-amino-6-(2,3-dimethylphenyl)pyrimidin-4-yl]amino}ethyl)amino]-N-methylpyridine-3-sulfonamide The title compound was prepared according to general procedure 3 from 6-chloro-N-methyl-pyridine-3-sulfonamide and intermediate 7. LCMS [M+H]$^+$ 428. $^1$H NMR (400 MHz, METHANOL-d4) δ ppm 8.36-8.39 (m, 1H), 7.74-7.79 (m, 1H), 7.33-7.38 (m, 1H), 7.22-7.27 (m, 1H), 7.15-7.19 (m, 1H), 6.65-6.71 (m, 1H), 5.96-5.99 (m, 1H), 3.75-3.79 (m, 2H), 3.68-3.73 (m, 2H), 2.51 (s, 3H), 2.35-2.37 (m, 2H), 2.23-2.25 (m, 3H).

Example 4

4-(2-{[2-amino-6-(5-methylfuran-2-yl)pyrimidin-4-yl]amino}ethyl)benzene-1-sulfonamide The title compound was prepared according to General procedure 5 from intermediate 4 and potassium trifluoro(5-methylfuran-2-yl)boranuide. LCMS [M+H]$^+$ 374. $^1$H NMR (400 MHz, METHANOL-d4) δ ppm 7.86 (d, J=8.3 Hz, 2H), 7.46 (d, J=8.3 Hz, 2H), 7.15 (d, J=3.5 Hz, 1H), 6.37 (dd, J=3.5, 1.0 Hz, 1H), 6.25 (s, 1H), 3.77-3.83 (m, 2H), 3.02-3.07 (m, 2H), 2.44 (s, 3H).

Example 5

6-[(2-{[2-amino-6-(2,3-dimethylphenyl)pyrimidin-4-yl]amino}ethyl)amino]pyridine-3-carboxamide The title compound was prepared according to general procedure 3 from intermediate 7 and 6-chloropyridine-3-carboxamide. LCMS [M+H]$^+$ 378. $^1$H NMR (400 MHz, METHANOL-d4) δ ppm 8.49 (dd, J=2.3, 0.8 Hz, 1H), 8.15 (dd, J=9.5, 1.9 Hz, 1H), 7.36 (d, J=7.6 Hz, 1H), 7.25 (t, J=7.5 Hz, 1H), 7.14-7.19 (m, 1H), 6.92 (d, J=8.8 Hz, 1H), 6.02 (s, 1H), 3.79-3.85 (m, 2H), 3.70-3.75 (m, 2H), 2.36 (s, 3H), 2.24 (s, 3H).

Example 6

3-(4-{[2-amino-6-(2,3-dichlorophenyl)pyrimidin-4-yl]amino}butyl)-1-[4-(methylsulfanyl)phenyl]urea A mixture of intermediate 11 (1.0 equiv), 1-isocyanato-4-methylsulfanyl-benzene (1.1 equiv), diisopropylethylamine (2.1 equiv), and acetonitrile was stirred at 20° C. for 15 h. The mixture was concentrated and purified by preparative LC to afford the title compound. LCMS [M+H]$^+$ 491. $^1$H NMR (400 MHz, METHANOL-d4) δ ppm 7.74-7.79 (m, 1H), 7.47-7.49 (m, 2H), 7.28-7.32 (m, 2H), 7.17-7.21 (m, 2H), 6.11 (s, 1H), 3.56 (t, J=6.8 Hz, 2H), 3.26 (t, J=6.8 Hz, 2H), 2.42 (s, 3H), 1.66-1.75 (m, 2H), 1.57-1.66 (m, 2H).

Example 7

3-(4-{[2-amino-6-(2,3-dichlorophenyl)pyrimidin-4-yl]amino}butyl)-1-(4-methanesulfinylphenyl)urea In a vial 3-(4-{[2-amino-6-(2,3-dichlorophenyl)pyrimidin-4-yl]amino}butyl)-1-[4-(methylsulfanyl)phenyl]urea (from example 6) was dissolved in 2-propanol, then 0.2 ml H$_2$O$_2$ (30 wt %) was added and the resulting mixture was stirred 2 h at 20° C. The crude mixture was then purified by preparative LC. LCMS [M+H]$^+$ 507.

Example 8

6-(4-fluoro-2,5-dimethylphenyl)-4-N-{2-[(5-nitropyridin-2-yl)amino]ethyl}pyrimidine-2,4-diamine The title compound was prepared according to general procedure 2 from Intermediate 14 and N'-(5-nitro-2-pyridyl)ethane-1,2-diamine. LCMS [M+H]$^+$ 398. $^1$H NMR (400 MHz, CHLOROFORM-d) δ ppm 9.01 (d, J=2.8 Hz, 1H), 8.15 (dd, J=9.0, 2.7 Hz, 1H), 7.15 (d, J=8.1 Hz, 1H), 6.87 (d, J=10.6 Hz, 1H), 6.37 (dd, J=9.3, 0.5 Hz, 1H), 5.82 (s, 1H), 5.12-5.24 (m, 1H), 4.85-4.98 (m, 2H), 2.31 (s, 3H), 2.22-2.25 (m, 3H), 1.73-1.84 (m, 1H).

Example 9

4-(2-{[2-amino-6-(3-chloro-2-methylphenyl)pyrimidin-4-yl]amino}ethyl)benzoic acid A mixture of 4-chloro-6-(3-chloro-2-methylphenyl)pyrimidin-2-amine (25 mg, 0.10 mmol; Intermediate 3), 4-(2-aminoethyl)benzoic acid hydrochloride (30 mg, 0.15 mmol) and triethylamine (0.040 mL, 0.30 mmol) in n-butanol (1.5 mL) was heated in a sealed tube at 130° C. overnight. The mixture was then concentrated and purified by preparative LC. LCMS [M+H]$^+$ 383.

Example 10

4-(2-{[6-(2-acetylthiophen-3-yl)-2-aminopyrimidin-4-yl]amino}ethyl)benzene-1-sulfonamide The title compound was prepared according to general procedure 5 from intermediate 4 and potassium (2-acetylthiophen-3-yl)trifluoroboranuide. LCMS [M+H]$^+$ 418. $^1$H NMR (400 MHz, METHANOL-d4) δ ppm 7.96 (d, J=5.1 Hz, 1H), 7.84-7.88 (m, 2H), 7.46-7.50 (m, 2H), 7.39 (d, J=5.1 Hz, 1H), 6.12 (s, 1H), 3.82 (t, J=7.1 Hz, 2H), 3.06 (t, J=7.1 Hz, 2H), 2.62 (s, 3H).

Example 11

N-{6-[(2-{[2-amino-6-(4-fluoro-2,5-dimethylphenyl)pyrimidin-4-yl]amino}ethyl)amino]pyridin-3-yl}acetamide Step 1: In a flask 6-(4-fluoro-2,5-dimethyl-phenyl)-N4-[2-[(5-nitro-2-pyridyl)amino]ethyl]pyrimidine-2,4-diamine (from example 8) was dissolved in MeOH, then the flask was evacuated and the atmosphere was changed to H$_2$. The mixture was stirred at 20° C. for 16 h and then passed through a syringe filter and concentrated.

Step 2. The crude mixture from step 1 was dissolved in DCM, then Hünig's base (2.0 equiv) and acetyl chloride (1.1 equiv) were added and the mixture was stirred 3 h at 20° C. Then the mixture was concentrated and purified by preparative LC. LCMS [M+H]$^+$ 410. $^1$H NMR (400 MHz, METHANOL-d4) δ ppm 8.50 (dd, J=2.5, 0.8 Hz, 1H), 7.90 (dd, J=9.7, 2.4 Hz, 1H), 7.28 (d, J=7.6 Hz, 1H), 7.08-7.15 (m, 2H), 6.07 (s, 1H), 3.81-3.87 (m, 2H), 3.67-3.73 (m, 2H), 2.34 (s, 3H), 2.28-2.31 (m, 3H), 2.16 (s, 3H).

Example 12

N-{6-[(2-{[2-amino-6-(4-fluoro-2,5-dimethylphenyl)pyrimidin-4-yl]amino}ethyl)amino]pyridin-3-yl}methanesulfonamide Step 1: In a flask 6-(4-fluoro-2,5-dimethyl-phenyl)-N4-[2-[(5-nitro-2-pyridyl)amino]ethyl]pyrimidine-2,4-diamine (from example 8) was dissolved in MeOH, then the flask was evacuated and the atmosphere was changed to H$_2$. The mixture was stirred at 20° C. for 16 h and then passed through a syringe filter and concentrated.

Step 2: The crude mixture from step 1 was dissolved in DCM, then Hünig's base (2.0 equiv) and methanesulfonyl chloride (1.1 equiv) were added and the mixture was stirred 3 h at 20° C. Then the mixture was concentrated and purified by preparative LC. LCMS [M+H]$^+$ 446. $^1$H NMR (400 MHz, METHANOL-d4) δ ppm 7.84-7.88 (m, 2H), 7.29 (d, J=7.3 Hz, 2H), 7.08-7.13 (m, 5H), 6.07 (s, 2H), 3.81-3.86 (m, 2H), 3.68-3.73 (m, 2H), 3.04 (s, 3H), 2.35 (s, 3H), 2.29-2.32 (m, 3H).

Example 13

6-(2,3-dimethylphenyl)-4-N-{2-[(6-methanesulfonylpyridin-3-yl)amino]ethyl}pyrimidine-2,4-diamine Step 1: N'-(6-methylsulfonyl-3-pyridyl)ethane-1,2-diamine was prepared according to general procedure 4 from 5-bromo-2-methylsulfonyl-pyridine.

Step 2: The title compound was prepared according to general procedure 2 from the crude material in step 1 and intermediate 1. LCMS [M+H]$^+$ 413. $^1$H NMR (400 MHz, METHANOL-d4) δ ppm 8.13 (d, J=2.8 Hz, 1H), 7.85 (dd, J=8.6, 0.5 Hz, 1H), 7.38 (d, J=7.3 Hz, 1H), 7.23-7.29 (m, 1H), 7.15-7.21 (m, 2H), 6.01 (s, 1H), 3.75-3.80 (m, 2H), 3.55 (t, J=6.2 Hz, 2H), 3.12 (s, 3H), 2.38 (s, 3H), 2.26 (s, 3H).

Example 14

5-[(2-{[2-amino-6-(2,3-dimethylphenyl)pyrimidin-4-yl]amino}ethyl)amino]pyridine-3-sulfonamide Step 1: 5-(2-aminoethylamino)pyridine-3-sulfonamide was prepared according to General procedure 4 from 5-bromopyridine-3-sulfonamide.

Step 2: The title compound was prepared according to general procedure 2 from the crude material in step 1 and intermediate 1. LCMS [M+H]$^+$ 414. $^1$H NMR (400 MHz, METHANOL-d4) δ ppm 8.14-8.39 (m, 2H), 7.78 (s, 1H), 7.36-7.41 (m, 1H), 7.24-7.29 (m, 1H), 7.20-7.24 (m, 1H), 6.01 (s, 1H), 3.70-3.75 (m, 2H), 3.52-3.57 (m, 2H), 2.38 (s, 3H), 2.27 (s, 3H).

Example 15

4-[(1R,2S)-2-{[2-amino-6-(3-chloro-2-methylphenyl)pyrimidin-4-yl]amino}cyclopropyl]benzene-1-sulfonamide Step 1: 6-chloro-N4-[(1S,2R)-2-phenylcyclopropyl]pyrimidine-2,4-diamine A mixture of 4,6-dichloropyrimidin-2-amine, (1S,2R)-2-phenylcyclopropanamine hydrochloride and N,N-diisopropylethylamine in n-butanol was heated in a sealed tube at 80° C. for 16 h. After cooling the formed solid was washed with ethanol to obtain the title product. LCMS [M+H]$^+$ 261.

Step 2: 4-[(1R,2S)-2-[(2-amino-6-chloro-pyrimidin-4-yl)amino]cyclopropyl]benzenesulfonyl chloride To 6-chloro-N4-[(1S,2R)-2-phenylcyclopropyl]pyrimidine-2,4-diamine at 0° C. in DCM was chlorosulfonic acid (5.0 equiv.) added dropwise. The mixture was then stirred at 20° C. for 2 h. The solution was then poured onto crushed ice and extracted with DCM×3. The combined organic phases were washed with water, dried, filtered, and concentrated to obtain the title compound. LCMS [M+H]$^+$ 359.

Step 3: 4-[(1R,2S)-2-[(2-amino-6-chloro-pyrimidin-4-yl)amino]cyclopropyl]benzenesulfonamide Aqueous ammonia was added drop wise to a stirred, ice-chilled solution of 4-[(1R,2S)-2-[(2-amino-6-chloro-pyrimidin-4-yl)amino]cyclopropyl]benzenesulfonyl chloride in acetonitrile. The resulting mixture was stirred for 20 min at 20° C. and was then diluted with water and extracted with EtOAc. The organic layers were dried over Na$_2$SO$_4$ and concentrated in vacuo to give the title compound. LCMS [M+H]$^+$ 340.

Step 4: 4-[(1R,2S)-2-{[2-amino-6-(3-chloro-2-methylphenyl)pyrimidin-4-yl]amino}cyclopropyl]benzene-1-sulfonamide was prepared according to general procedure 1 from 4-[(1R,2S)-2-[(2-amino-6-chloro-pyrimidin-4-yl)amino]cyclopropyl]benzenesulfonamide and (3-chloro-2-methyl-phenyl)boronic acid. LCMS [M+H]$^+$ 430; $^1$H NMR (400 MHz, DMSO-d$_6$) δ ppm 7.69 (d, J=8.1 Hz, 2H), 7.42-7.45 (m, 1H), 7.40 (d, J=3.3 Hz, 1H), 7.32 (d, J=8.3 Hz, 2H), 7.15-7.28 (m, 4H), 6.07 (s, 2H), 5.71 (s, 1H), 2.52-2.52 (m, 1H), 2.28 (s, 3H), 2.10 (ddd, J=8.8, 6.2, 3.2 Hz, 1H), 1.28-1.42 (m, 2H).

Example 16

2-[(2-{[2-amino-6-(2,3-dimethylphenyl)pyrimidin-4-yl]amino}ethyl)amino]pyrimidine-4-carboxamide The title compound was prepared according to general procedure 3 from intermediate 7 and 2-chloropyrimidine-4-carboxamide. LCMS [M+H]+ 379. 1H NMR (400 MHz, METHANOL-d4) δ ppm 8.49 (d, J=4.8 Hz, 1H), 7.35 (d, J=7.3 Hz, 1H), 7.19-7.26 (m, 2H), 7.13-7.17 (m, 1H), 5.94 (s, 1H), 3.77 (s, 4H), 2.35 (s, 3H), 2.22 (s, 3H).

Example 17

3-(2-amino-6-{[2-(4-methanesulfonylphenyl)ethyl]amino}pyrimidin-4-yl)-N-tert-butylthiophene-2-sulfonamide The title compound was prepared according to General procedure 5 from intermediate 6 and potassium [2-(tert-butylsulfamoyl)-3-thienyl]-trifluoro-boranuide. LCMS [M+H]+ 510. 1H NMR (400 MHz, METHANOL-d4) δ ppm 7.87-7.92 (m, 2H), 7.64-7.67 (m, 2H), 7.55 (d, J=8.3 Hz, 2H), 6.31 (s, 1H), 3.82 (t, J=7.1 Hz, 2H), 3.10 (s, 3H), 3.05-3.09 (m, 2H), 1.28 (s, 9H).

Example 18 tert-butyl N-{[5-(2-amino-6-{[2-(4-methanesulfonylphenyl)ethyl]amino}pyrimidin-4-yl)thiophen-2-yl]methyl}carbamate The title compound was prepared according to General procedure 5 from intermediate 6 and potassium [2-(tert-butylsulfamoyl)-3-thienyl]-trifluoro-boranuide. LCMS [M+H]+ 504. 1H NMR (400 MHz, METHANOL-d4) δ ppm 7.89 (d, J=8.6 Hz, 2H), 7.56-7.60 (m, 1H), 7.54 (d, J=8.3 Hz, 2H), 7.07 (d, J=3.8 Hz, 1H), 6.19 (s, 1H), 4.42 (s, 2H), 3.79 (t, J=7.1 Hz, 2H), 3.10 (s, 3H), 3.06 (t, J=7.1 Hz, 2H), 1.46 (s, 9H).

Example 19

N-[4-(2-{[2-amino-6-(2,3-dimethylphenyl)pyrimidin-4-yl]amino}ethyl)phenyl]acetamide The title compound was prepared according to General procedure 6 from Intermediate 15 and acetyl chloride. LCMS [M+H]+ 376. 1H NMR (400 MHz, METHANOL-d4) δ ppm 7.46-7.51 (m, 2H), 7.33-7.37 (m, 1H), 7.20-7.26 (m, 3H), 7.15-7.19 (m, 1H), 5.96 (s, 1H), 3.75 (t, J=7.2 Hz, 2H), 2.91 (t, J=7.2 Hz, 2H), 2.35 (s, 3H), 2.24 (s, 3H), 2.11 (s, 3H).

Example 20

N-[4-(2-{[2-amino-6-(2,3-dimethylphenyl)pyrimidin-4-yl]amino}ethyl)phenyl]methanesulfonamide The title compound was prepared according to General procedure 6 from Intermediate 15 and methanesulfonyl chloride. LCMS [M+H]+ 412. 1H NMR (400 MHz, METHANOL-d4) δ ppm 7.35 (d, J=7.1 Hz, 1H), 7.14-7.28 (m, 6H), 5.97 (s, 1H), 3.76 (t, J=7.2 Hz, 2H), 2.91-2.95 (m, 5H), 2.36 (s, 3H), 2.24 (s, 3H).

Example 21

4-[(2-{[2-amino-6-(2,3-dimethylphenyl)pyrimidin-4-yl]amino}ethyl)amino]-N-methylbenzene-1-sulfonamide Step 1: 4-(2-aminoethylamino)-N-methyl-benzenesulfonamide was prepared according to General procedure 4 from 4-iodo-N-methyl-benzenesulfonamide.

Step 2: The title compound was prepared according to general procedure 2 from the crude material in step 1 and intermediate 1. LCMS [M+H]+ 427. 1H NMR (400 MHz, METHANOL-d4) δ ppm 7.54-7.59 (m, 2H), 7.33-7.37 (m, 1H), 7.21-7.27 (m, 1H), 7.15-7.20 (m, 1H), 6.71-6.75 (m, 2H), 5.98 (s, 1H), 3.75 (t, J=6.2 Hz, 2H), 3.49 (t, J=6.1 Hz, 2H), 2.45-2.47 (m, 3H), 2.36 (s, 3H), 2.24 (s, 3H).

Example 22

N-{4-[(2-{[2-amino-6-(2,3-dimethylphenyl)pyrimidin-4-yl]amino}ethyl)amino]-2-methylphenyl}acetamide Step 1: N-[4-(2-aminoethylamino)-2-methyl-phenyl]acetamide was prepared according to General procedure 4 from N-(4-iodo-2-methyl-phenyl)acetamide.

Step 2: The title compound was prepared according to general procedure 2 from the crude material in step 1 and intermediate 1. LCMS [M+H]+ 405. 1H NMR (400 MHz, METHANOL-d4) δ ppm 7.36 (d, J=7.6 Hz, 2H), 7.22-7.28 (m, 3H), 7.16-7.20 (m, 1H), 6.92 (d, J=2.5 Hz, 1H), 6.87 (dd, J=8.3, 2.5 Hz, 1H), 6.03 (s, 1H), 3.75-3.81 (m, 2H), 3.55 (t, J=5.9 Hz, 2H), 2.36 (s, 3H), 2.25 (s, 3H), 2.22 (s, 3H), 2.14 (s, 3H).

Example 23

6-[(2-{[2-amino-6-(2,3-dimethylphenyl)pyrimidin-4-yl]amino}ethyl)amino]-3,4-dihydro-2H-1,4-benzoxazin-3-one Step 1: 6-(2-aminoethylamino)-4H-1,4-benzoxazin-3-one was prepared according to General procedure 4 from (6-bromo-4H-1,4-benzoxazin-3-one.

Step 2: The title compound was prepared according to general procedure 2 from the crude material in step 1 and intermediate 1. LCMS [M+H]+ 405. 1H NMR (400 MHz, METHANOL-d4) δ ppm 7.35-7.38 (m, 1H), 7.25 (t, J=7.6 Hz, 1H), 7.16-7.20 (m, 1H), 6.93 (d, J=8.6 Hz, 1H), 6.70 (dd, J=8.7, 2.7 Hz, 1H), 6.65 (d, J=2.5 Hz, 1H), 6.03 (s, 1H), 4.53 (s, 2H), 3.79 (t, J=6.1 Hz, 2H), 3.53 (t, J=5.9 Hz, 2H), 2.36 (s, 3H), 2.25 (s, 3H).

Example 24

2-[(2-{[2-amino-6-(2,3-dimethylphenyl)pyrimidin-4-yl]amino}ethyl)amino]benzamide Step 1: 2-(2-aminoethylamino)benzamide was prepared according to General procedure 4 from 2-bromobenzamide.

Step 2: The title compound was prepared according to general procedure 2 from the crude material in step 1 and intermediate 1. LCMS [M+H]+ 377. 1H NMR (400 MHz, METHANOL-d4) δ ppm 7.57 (dd, J=7.8, 1.3 Hz, 1H), 7.31-7.37 (m, 2H), 7.22-7.27 (m, 1H), 7.17-7.21 (m, 1H), 6.83 (dd, J=8.3, 0.8 Hz, 1H), 6.64 (ddd, J=8.0, 7.1, 1.0 Hz, 1H), 6.01 (s, 1H), 3.79 (t, J=5.9 Hz, 2H), 3.49 (t, J=5.9 Hz, 2H), 2.36 (s, 3H), 2.25 (s, 3H).

Example 25

2-[(2-{[2-amino-6-(2,3-dimethylphenyl)pyrimidin-4-yl]amino}ethyl)amino]pyridine-4-carboxamide The title compound was prepared according to general procedure 3 from intermediate 7 and 6-chloropyridine-3-carboxamide. LCMS [M+H]+ 378.

Example 26

6-(2-{[2-amino-6-(2,3-dimethylphenyl)pyrimidin-4-yl]amino}ethoxy)pyridine-3-carboxamide A mixture of 2-[[2-amino-6-(2,3-dimethylphenyl)pyrimidin-4-yl]amino]ethanol, 6-chloropyridine-3-carboxamide (1.5 equiv.), and potassium carbonate (3.5 equiv.) in DMSO was heated in a sealed tube at 90° C. for 16 h. After cooling methanol was added followed by filtration and purification by preparative LC to furnish the title compound. LCMS [M+H]+ 379.

Example 27

4-(2-{[2-amino-6-(3-hydroxyphenyl)pyrimidin-4-yl]amino}ethyl)benzene-1-sulfonamide Prepared according to general procedure 1 from intermediate 4 and (3-hydroxyphenyl)boronic acid. LCMS [M+H]+ 386.

Example 28 ethyl 6-[(2-{[2-amino-6-(2,3-dimethylphenyl)pyrimidin-4-yl]amino}ethyl)amino]pyridine-3-carboxylate Step 1. A mixture of ethyl 6-chloropyridine-3-carboxylate (1.0 equiv.) and ethane-1,2-diamine (1.1 equiv.) were stirred at 90° C. for 16 h. The mixture was purified by preparative LC which afforded ethyl 6-(2-aminoethylamino)pyridine-3-carboxylate.
Step 2: The title compound was prepared according to general procedure 2 from ethyl 6-(2-aminoethylamino)pyridine-3-carboxylate and intermediate 1.
LCMS [M+H]+ 407. 1H NMR (400 MHz, METHANOL-d4) δ ppm 8.53 (dd, J=2.2, 0.6 Hz, 1H), 8.23 (d, J=9.2 Hz, 1H), 7.36 (d, J=7.6 Hz, 1H), 7.24 (t, J=7.6 Hz, 1H), 7.14-7.18 (m, 1H), 7.01 (d, J=8.2 Hz, 1H), 6.03 (s, 1H), 4.37 (q, J=7.3 Hz, 2H), 3.80-3.87 (m, 2H), 3.73-3.79 (m, 2H), 2.35 (s, 3H), 2.23 (s, 3H), 1.38 (t, J=7.1 Hz, 3H).

Example 29

4-[(2-{[2-amino-6-(2,3-dimethylphenyl)pyrimidin-4-yl]amino}ethyl)amino]-2-(trifluoromethyl)benzene-1-sulfonamide Step 1: 4-(2-aminoethylamino)-2-(trifluoromethyl)benzenesulfonamide was prepared according to general procedure 4 from 4-bromo-2-(trifluoromethyl)benzenesulfonamide.
Step 2: The title compound was prepared according to general procedure 2 from the compound from step 1 and intermediate 1. LCMS [M+H]+ 481. 1H NMR (400 MHz, METHANOL-d4) δ ppm 7.96 (d, J=8.8 Hz, 1H), 7.35 (d, J=7.6 Hz, 1H), 7.24 (t, J=7.7 Hz, 1H), 7.14-7.19 (m, 1H), 7.03 (d, J=2.5 Hz, 1H), 6.85 (dd, J=9.2, 2.5 Hz, 1H), 5.97 (s, 1H), 3.71-3.79 (m, 2H), 3.51-3.56 (m, 2H), 2.35 (s, 3H), 2.23 (s, 3H).

Example 30

4-[(2-{[2-amino-6-(2,3-dimethylphenyl)pyrimidin-4-yl]amino}ethyl)amino]benzamide Step 1: 4-(2-aminoethylamino)benzamide was prepared according to General procedure 4 from 4-iodobenzamide.
Step 2: The title compound was prepared according to general procedure 2 from the compound from step 1 and intermediate 1. LCMS [M+H]+ 377. 1H NMR (400 MHz, METHANOL-d4) δ ppm 7.66-7.72 (m, 2H), 7.35 (d, J=7.6 Hz, 1H), 7.23 (t, J=7.6 Hz, 1H), 7.13-7.17 (m, 1H), 6.64-6.69 (m, 2H), 5.97 (s, 1H), 3.75 (s, 2H), 3.48 (s, 2H), 2.35 (s, 3H), 2.22 (s, 3H).

Example 31 ethyl N-[4-(2-{[2-amino-6-(2,3-dimethylphenyl)pyrimidin-4-yl]amino}ethyl)phenyl]carbamate The title compound was prepared according to General procedure 6 Intermediate and ethyl chloroformate. LCMS [M+H]+ 406. 1H NMR (400 MHz, METHANOL-d4) δ ppm 7.34 (d, J=8.5 Hz, 1H), 7.16 (d, J=8.2 Hz, 2H), 7.10 (t, J=7.6 Hz, 1H), 7.02-7.06 (m, 1H), 5.75 (s, 1H), 4.17 (q, J=7.3 Hz, 2H), 3.55 (br. s., 2H), 2.84 (t, J=7.3 Hz, 2H), 2.30 (s, 3H), 2.18 (s, 3H), 1.29 (t, J=7.1 Hz, 3H).

Example 32

5-[(2-{[2-amino-6-(2,3-dimethylphenyl)pyrimidin-4-yl]amino}ethyl)amino]-2-methoxybenzene-1-sulfonamide Step 1: 5-(2-aminoethylamino)-2-methoxy-benzenesulfonamide was prepared according to General procedure 4 from 5-bromo-2-methoxy-benzenesulfonamide.
Step 2: The title compound was prepared according to general procedure 2 from the compound from step 1 and intermediate 1. LCMS [M+H]+ 443. 1H NMR (400 MHz, METHANOL-d4) δ ppm 7.44 (d, J=2.8 Hz, 1H), 7.34-7.38 (m, 1H), 7.22-7.27 (m, 1H), 7.18-7.22 (m, 1H), 7.07-7.11 (m, 1H), 7.01-7.05 (m, 1H), 6.00 (s, 1H), 3.92 (s, 3H), 3.70 (t, J=6.8 Hz, 2H), 3.43-3.48 (m, 2H), 2.36 (s, 3H), 2.25 (s, 3H).

Example 33

3-(2-amino-6-{[2-(4-sulfamoylphenyl)ethyl]amino}pyrimidin-4-yl)phenyl trifluoromethanesulfonate A mixture of 4-[2-[[2-amino-6-(3-hydroxyphenyl)pyrimidin-4-yl]amino]ethyl]benzenesulfonamide, N-phenylbis(trifluoromethane-sulfonimide), K2CO3, and THF was stirred at 90° C. for 2 h. After cooling methanol was added followed by filtration and purification by preparative LC to give the title compound.
LCMS [M+H]+ 518.

Example 34

4-(2-{[2-amino-6-(2,3-dimethylphenyl)pyrimidin-4-yl]amino}ethyl)benzoic acid

The title compound was prepared according to general procedure 2 from intermediate 1 and 2-(4-carboxyphenyl)ethylammonium chloride.
LCMS [M+H]$^+$ 363.

Example 35

6-[(2-{[2-amino-6-(3-chloro-2-methylphenyl)pyrimidin-4-yl]amino}ethyl)amino]-3,4-dihydro-2H-1,4-benzoxazin-3-one Step 1: 6-(2-aminoethylamino)-4H-1,4-benzoxazin-3-one was prepared according to General procedure 4 from 6-bromo-4H-1,4-benzoxazin-3-one.
Step 2: The title compound was prepared according to general procedure 2 from the compound from step 1 and intermediate 3. LCMS [M+H]$^+$ 425. $^1$H NMR (400 MHz, METHANOL-d4) δ ppm 7.61 (dd, J=7.7, 1.7 Hz, 1H), 7.30-7.39 (m, 2H), 6.90 (d, J=8.5 Hz, 1H), 6.58-6.67 (m, 2H), 6.06 (s, 1H), 4.52 (s, 2H), 3.79 (t, J=6.0 Hz, 2H), 3.51 (t, J=6.0 Hz, 2H), 2.38 (s, 3H).

Example 36

6-(2,3-dimethylphenyl)-4-N-{2-[(2-methyl-1,3-benzothiazol-6-yl)amino]ethyl}pyrimidine-2,4-diamine Step 1: N'-(2-methyl-1,3-benzothiazol-6-yl)ethane-1,2-diamine was prepared according to general procedure 4 from 6-iodo-2-methyl-1,3-benzothiazole.
Step 2: The title compound was prepared according to general procedure 2 from the compound from step 1 and intermediate 1. LCMS [M+H]$^+$ 405. $^1$H NMR (400 MHz, METHANOL-d4) δ ppm 7.68 (d, J=8.8 Hz, 1H), 7.34 (d, J=7.6 Hz, 1H), 7.26 (d, J=2.5 Hz, 1H), 7.22 (t, J=7.6 Hz, 1H), 7.11 (d, J=7.3 Hz, 1H), 7.01 (dd, J=8.8, 2.2 Hz, 1H), 5.97 (s, 1H), 3.79 (t, J=6.0 Hz, 2H), 3.53 (t, J=6.0 Hz, 2H), 2.79 (s, 3H), 2.34 (s, 3H), 2.21 (s, 3H).

Example 37

6-[(2-{[2-amino-6-(3-chlorophenyl)pyrimidin-4-yl]amino}ethyl)amino]-3,4-dihydro-2H-1,4-benzoxazin-3-one The title compound was isolated as a side product from the reaction mixture in example 38 (step 2). LCMS [M+H]$^+$ 411. $^1$H NMR (400 MHz, METHANOL-d4) δ ppm 7.77 (t, J=1.9 Hz, 1H), 7.62-7.67 (m, 2H), 7.55-7.61 (m, 1H), 6.87-6.97 (m, 2H), 6.66 (dd, J=8.5, 2.5 Hz, 1H), 6.61 (d, J=2.5 Hz, 1H), 6.35 (s, 1H), 4.50 (s, 2H), 3.79 (t, J=6.0 Hz, 2H), 3.51 (t, J=6.0 Hz, 2H).

Example 38

6-[(2-{[2-amino-6-(2,3-dichlorophenyl)pyrimidin-4-yl]amino}ethyl)amino]-3,4-dihydro-2H-1,4-benzoxazin-3-one Step 1: 6-(2-aminoethylamino)-4H-1,4-benzoxazin-3-one was prepared according to general procedure 4 from 6-bromo-4H-1,4-benzoxazin-3-one.
Step 2: The title compound was prepared according to general procedure 2 from the crude compound from step 1 and intermediate 2. LCMS [M+H]$^+$ 445. $^1$H NMR (400 MHz, METHANOL-d4) δ ppm 7.76-7.80 (m, 1H), 7.48-7.51 (m, 2H), 6.85 (d, J=8.5 Hz, 1H), 6.52 (dd, J=8.7, 2.7 Hz, 1H), 6.47 (d, J=2.5 Hz, 1H), 6.15 (s, 1H), 4.49 (s, 2H), 3.77 (t, J=6.0 Hz, 2H), 3.45 (t, J=6.0 Hz, 2H).

Example 39

6-(2,3-dichlorophenyl)-4-N-{2-[(2-methyl-1,3-benzothiazol-6-yl)amino]ethyl}pyrimidine-2,4-diamine Step 1: N'-(2-methyl-1,3-benzothiazol-6-yl)ethane-1,2-diamine was prepared according to general procedure 4 from 6-iodo-2-methyl-1,3-benzothiazole.
Step 2: The title compound was prepared according to general procedure 2 from the crude compound from step 1 and intermediate 2. LCMS [M+H]$^+$ 445. $^1$H NMR (400 MHz, METHANOL-d4) δ ppm 7.77 (dd, J=7.9, 1.6 Hz, 1H), 7.63 (d, J=8.8 Hz, 1H), 7.45-7.50 (m, 1H), 7.42 (d, J=1.6 Hz, 1H), 7.16 (d, J=2.2 Hz, 1H), 6.93 (d, J=2.5 Hz, 1H), 6.09 (s, 1H), 3.77-3.81 (m, 2H), 3.48-3.53 (m, 2H), 2.76 (s, 3H).

Example 40

6-(2,3-dimethylphenyl)-4-N-{2-[(3-methanesulfonylphenyl)amino]ethyl}pyrimidine-2,4-diamine Step 1: N'-(3-methylsulfonylphenyl)ethane-1,2-diamine was prepared according to General procedure 4 from 1-bromo-3-methylsulfonyl-benzene.
Step 2: The title compound was prepared according to general procedure 2 from the compound from step 1 and intermediate 1. LCMS [M+H]$^+$ 412. $^1$H NMR (400 MHz, METHANOL-d4) δ ppm 7.34 (s, 3H), 7.23 (d, J=7.6 Hz, 1H), 7.20 (d, J=1.3 Hz, 1H), 7.14 (ddd, J=7.6, 1.9, 0.9 Hz, 1H), 6.94 (ddd, J=8.2, 2.5, 0.9 Hz, 1H), 5.99 (s, 1H), 3.70 (s, 2H), 3.48 (s, 2H), 3.09 (s, 3H), 2.36 (s, 3H), 2.25 (s, 3H).

Example 41

5-[(2-{[2-amino-6-(2,3-dimethylphenyl)pyrimidin-4-yl]amino}ethyl)amino]-2-methoxybenzene-1-sulfonic acid Step 1: 5-(2-aminoethylamino)-2-methoxy-benzenesulfonic acid was prepared according to General procedure 4 from 4-bromo-2-methoxy-benzenesulfonic acid.
Step 2: The title compound was prepared according to general procedure 2 from the compound from step 1 and intermediate 1. LCMS [M+H]$^+$ 444.

Example 42

4-[(2-{[2-amino-6-(2,3-dimethylphenyl)pyrimidin-4-yl]amino}ethyl)amino]-3-fluorobenzene-1-sulfonamide Step 1: 4-(2-aminoethylamino)-3-fluoro-benzenesulfonamide was prepared according to General procedure 4 from 4-bromo-3-fluoro-benzenesulfonamide.
Step 2: The title compound was prepared according to general procedure 2 from the compound from step 1 and intermediate 1. LCMS [M+H]$^+$ 431.

Example 43

4-(2-{[2-amino-6-(3-chloro-2-methylphenyl)pyrimidin-4-yl]amino}ethyl)benzamide

Step 1: A mixture of 4,6-dichloropyrimidin-2-amine (600 mg, 3.66 mmol), 4-(2-aminoethyl)benzoic acid hydrochloride (812 mg, 4.02 mmol), and triethylamine (1.5 mL, 4.02 mmol) in n-butanol (20 mL) was heated in a sealed tube at 110° C. overnight. The reaction mixture was then concentrated and the crude material was recrystallized from a mixture of 2-propanol, methanol and water. The solid material was collected by filtration, washed with 2-propanol and dried under vacuum to afford 4-{2-[(2-amino-6-chloropyrimidin-4-yl)amino]ethyl}benzoic acid.

Step 2: A mixture of 4-{2-[(2-amino-6-chloropyrimidin-4-yl)amino]ethyl}benzoic acid (59 mg, 0.20 mmol), ammonia (1.0 mL, 0.50 mmol; as a 0.50 M solution in 1,4-dioxane), HATU (91 mg, 0.24 mmol), and triethylamine in DMF (3.0 mL) was stirred at 20° C. for 1.5 h. The mixture was then purified by preparative LC to afford 4-{2-[(2-amino-6-chloropyrimidin-4-yl)amino]ethyl}benzamide.

Step 3: A mixture of 4-{2-[(2-amino-6-chloropyrimidin-4-yl)amino]ethyl}benzamide (27 mg, 0.093 mmol), (3-chloro-2-methylphenyl)boronic acid (21 mg, 0.12 mmol), palladium tetrakis(triphenylphosphine)palladium (0) (12 mg, 0.010 mmol), and potassium carbonate (26 mg, 0.19 mmol) in 1,4-dioxane (4.0 mL) and water (1.0 mL) was heated in a sealed tube at 95° C. for 1 h. The mixture was then concentrated and purified by preparative LC. LCMS [M+H]$^+$ 382; $^1$H NMR (400 MHz, CD$_3$OD) δ ppm 7.79-7.84 (2H, m) 7.34-7.43 (3H, m) 7.15-7.24 (2H, m) 5.76 (1H, s) 3.61 (2H, s) 2.98 (2H, t, J=7.11 Hz) 2.31 (3H, s).

Example 44

4-(2-{[2-amino-6-(2,3-dimethylphenyl)pyrimidin-4-yl]amino}ethyl)benzamide

A mixture of 4-[2-[[2-amino-6-(2,3-dimethylphenyl)pyrimidin-4-yl]amino]ethyl]benzoic acid (from example 34) and O-(Benzotriazol-1-yl)-N,N,N',N'-tetramethyluronium tetrafluoroborate was dissolved in DMF. Then NH$_3$ (0.5 M in 1,4-dioxane) was added. The mixture was stirred at 20° C. for 4 h and then purified by preparative LC. LCMS [M+H]$^+$ 362. $^1$H NMR (400 MHz, METHANOL-d4) δ ppm 7.81-7.86 (m, 2H), 7.34-7.41 (m, 4H), 7.22-7.27 (m, 1H), 7.15-7.20 (m, 1H), 5.96 (s, 1H), 3.81 (t, J=7.3 Hz, 2H), 3.03 (t, J=7.1 Hz, 2H), 2.36 (s, 3H), 2.24 (s, 3H).

Example 45

4-N-{2-[(2-amino-9H-purin-6-yl)amino]ethyl}-6-(2,3-dimethylphenyl)pyrimidine-2,4-diamine Step 1: N6-(2-aminoethyl)-9H-purine-2,6-diamine was prepared according to General procedure 4 from 6-bromo-9H-purin-2-amine.

Step 2: The title compound was prepared according to general procedure 2 from the compound from step 1 and intermediate 1. LCMS [M+H]$^+$ 391. $^1$H NMR (400 MHz, METHANOL-d4) δ ppm 8.04 (s, 1H), 7.35 (d, J=7.3 Hz, 1H), 7.23 (t, J=7.7 Hz, 1H), 7.13-7.18 (m, 1H), 5.99 (s, 1H), 3.92 (d, J=6.0 Hz, 2H), 3.82-3.89 (m, 2H), 2.35 (s, 3H), 2.22 (s, 3H).

Example 46

N-[3-(2-{[2-amino-6-(3-chloro-2-methylphenyl)pyrimidin-4-yl]amino}ethyl)phenyl]acetamide The title compound was prepared according to General procedure 6 from Intermediate 12 and acetyl chloride. LCMS [M+H]$^+$ 396. $^1$H NMR (400 MHz, METHANOL-d4) δ ppm 7.63 (d, J=0.9 Hz, 1H), 7.58-7.61 (m, 1H), 7.32-7.38 (m, 2H), 7.24-7.26 (m, 2H), 7.02 (qd, J=2.8, 1.9 Hz, 1H), 6.00 (s, 1H), 3.78 (t, J=7.3 Hz, 2H), 2.94 (t, J=7.3 Hz, 2H), 2.37 (s, 3H), 2.12 (s, 3H).

Example 47 ethyl N-[3-(2-{[2-amino-6-(3-chloro-2-methylphenyl)pyrimidin-4-yl]amino}ethyl)phenyl]carbamate The title compound was prepared according to General procedure 6 from Intermediate 12 and ethyl chloroformate. LCMS [M+H]$^+$ 426. $^1$H NMR (400 MHz, METHANOL-d4) δ ppm 7.58-7.61 (m, 1H), 7.45-7.48 (m, 1H), 7.33-7.35 (m, 2H), 7.16-7.24 (m, 3H), 6.93-6.96 (m, 1H), 6.00 (s, 1H), 4.13-4.20 (m, 2H), 3.77 (s, 2H), 2.93 (s, 2H), 2.37 (s, 3H), 1.30 (t, J=7.1 Hz, 3H).

Example 48

6-(2-{[2-amino-6-(3-chloro-2-methylphenyl)pyrimidin-4-yl]amino}ethyl)-3,4-dihydro-2H-1,4-benzoxazin-3-one Step 1: 6-(2-aminoethyl)-4H-1,4-benzoxazin-3-one was prepared according to General procedure 7 from 6-bromo-4H-1,4-benzoxazin-3-one.

Step 2: The title compound was prepared according to general procedure 2 from 6-(2-aminoethyl)-4H-1,4-benzoxazin-3-one and intermediate 3. LCMS [M+H]$^+$ 410. $^1$H NMR (400 MHz, METHANOL-d4) δ ppm 7.38-7.42 (m, 1H), 7.19-7.23 (m, 1H), 7.15-7.19 (m, 1H), 6.86 (d, J=0.9 Hz, 2H), 6.78-6.81 (m, 1H), 5.73-5.77 (m, 1H), 4.52 (s, 2H), 3.52-3.61 (m, 2H), 2.79-2.85 (m, 2H), 2.31 (s, 3H).

Example 49 methyl 5-[(2-{[2-amino-6-(2,3-dimethylphenyl)pyrimidin-4-yl]amino}ethyl)amino]pyrazine-2-carboxylate The title compound was prepared according to general procedure 3 from intermediate 7 and methyl 5-chloropyrazine-2-carboxylate.

LCMS [M+H]$^+$ 394. $^1$H NMR (400 MHz, METHANOL-d4) δ ppm 8.63-8.72 (m, 1H), 7.86-7.97 (m, 1H), 7.33-7.39 (m, 1H), 7.20-7.27 (m, 1H), 7.13-7.17 (m, 1H), 5.93-5.96 (m, 1H), 3.90 (s, 3H), 3.73-3.81 (m, 4H), 2.36 (s, 3H), 2.23 (s, 3H).

Example 50 methyl 2-[(2-{[2-amino-6-(2,3-dimethylphenyl)pyrimidin-4-yl]amino}ethyl)amino]-6-methylpyrimidine-4-carboxylate The title compound was prepared according to general procedure 3 from intermediate 7 and methyl 2-chloro-6-methyl-pyrimidine-4-carboxylate. LCMS [M+H]$^+$ 408. $^1$H NMR (400 MHz, METHANOL-d4) δ ppm 7.36 (d, J=7.3 Hz, 1H), 7.24 (t, J=7.6 Hz, 1H), 7.16 (d, J=6.6 Hz, 1H), 7.12 (s, 1H), 6.02 (s, 1H), 3.91 (s, 3H), 3.70-3.78 (m, 4H), 2.40 (s, 3H), 2.36 (s, 3H), 2.24 (s, 3H).

Example 51

6-(2,3-dimethylphenyl)-4-N-{2-[(9H-purin-6-yl)amino]ethyl}pyrimidine-2,4-diamine The title compound was prepared according to general procedure 3 from intermediate 7 and 6-chloropurine. LCMS [M+H]+ 376. $^1$H NMR (400 MHz, METHANOL-d4) δ ppm 8.46 (br. s., 1H), 8.30 (s, 1H), 7.35 (d, J=7.3 Hz, 1H), 7.24 (t, J=7.6 Hz, 1H), 7.13-7.18 (m, 1H), 5.98 (s, 1H), 4.01 (br. s., 2H), 3.85-3.92 (m, 2H), 2.35 (s, 3H), 2.22 (s, 3H).

Example 52

6-(3-chloro-2-methylphenyl)-4-N-[2-(3-methanesulfonylphenyl)ethyl]pyrimidine-2,4-diamine Step 1: 2-(3-methylsulfonylphenyl)ethanamine was prepared according to General procedure 7 from 1-bromo-3-methylsulfonyl-benzene.
Step 2: The title compound was prepared according to general procedure 2 from 2-(3-methylsulfonylphenyl)ethanamine and intermediate 3. LCMS [M+H]+ 417. $^1$H NMR (400 MHz, METHANOL-d4) δ ppm 7.82-7.90 (m, 2H), 7.65-7.70 (m, 1H), 7.58-7.64 (m, 2H), 7.35-7.38 (m, 2H), 6.01 (s, 1H), 3.86 (s, 2H), 3.14 (s, 5H), 2.38 (s, 3H).

Example 53

3-(2-{[2-amino-6-(3-chloro-2-methylphenyl)pyrimidin-4-yl]amino}ethyl)benzene-1-sulfonamide Step 1: 3-(2-aminoethyl)benzenesulfonamide was prepared according to General procedure 7 from 3-bromobenzenesulfonamide.
Step 2: The title compound was prepared according to general procedure 2 from 3-(2-aminoethyl)benzenesulfonamide and intermediate 3. LCMS [M+H]+ 418.

Example 54

3-(2-{[2-amino-6-(2,3-dichlorophenyl)pyrimidin-4-yl]amino}ethyl)benzene-1-sulfonamide Step 1: 3-(2-aminoethyl)benzenesulfonamide was prepared according to General procedure 7 from 3-bromobenzenesulfonamide.
Step 2: The title compound was prepared according to general procedure 2 from 3-(2-aminoethyl)benzenesulfonamide and intermediate 2. LCMS [M+H]+ 438.

Example 55

6-(2-{[2-amino-6-(3-chloro-2-methylphenyl)pyrimidin-4-yl]amino}ethoxy)pyridine-3-carboxamide A mixture of 2-[[2-amino-6-(3-chloro-2-methyl-phenyl)pyrimidin-4-yl]amino]ethanol (intermediate 19), 6-chloropyridine-3-carboxamide (1.5 equiv.) and Cs$_2$CO$_3$ (2.0 equiv.) in DMSO was heated in a sealed tube at 90° C. for 16 h. After cooling methanol was added followed by filtration and purification by preparative LC to give the title compound. LCMS [M+H]+ 399.

Example 56

6-[(2-{[2-amino-6-(3-chloro-2-methylphenyl)pyrimidin-4-yl]amino}ethyl)amino]-2,2-dimethyl-3,4-dihydro-2H-1,4-benzoxazin-3-one Step 1: 6-(2-aminoethylamino)-2,2-dimethyl-4H-1,4-benzoxazin-3-one was prepared according to general procedure 4 from 6-bromo-2,2-dimethyl-4H-1,4-benzoxazin-3-one
Step 2: The title compound was prepared according to general procedure 2 from 6-(2-aminoethylamino)-2,2-dimethyl-4H-1,4-benzoxazin-3-one and intermediate 3. LCMS [M+H]+ 453. $^1$H NMR (400 MHz, METHANOL-d4) δ ppm 7.40 (dd, J=7.7, 1.7 Hz, 1H), 7.14-7.23 (m, 2H), 6.70 (d, J=8.5 Hz, 1H), 6.28-6.34 (m, 1H), 6.23 (d, J=2.5 Hz, 1H), 5.80 (s, 1H), 3.52-3.63 (m, 2H), 3.27 (t, J=6.2 Hz, 2H), 2.31 (s, 3H), 1.40 (s, 6H).

Example 57

2-(2-{[2-amino-6-(3-chloro-2-methylphenyl)pyrimidin-4-yl]amino}ethoxy)pyrimidine-4-carboxamide A mixture of 2-[[2-amino-6-(3-chloro-2-methyl-phenyl)pyrimidin-4-yl]amino]ethanol (intermediate 19), 2-chloropyrimidine-4-carboxamide (1.5 equiv.) and Cs$_2$CO$_3$ (2.0 equiv.) in DMSO was heated in a sealed tube at 90° C. for 16 h. After cooling methanol was added followed by filtration and purification by preparative LC to give the title compound. LCMS [M+H]+ 400. $^1$H NMR (400 MHz, METHANOL-d$_4$) δ ppm 8.78 (d, J=5.1 Hz, 1H), 7.68 (d, J=5.1 Hz, 1H), 7.40 (dd, J=7.4, 1.7 Hz, 1H), 7.16-7.24 (m, 2H), 5.82 (br. s., 1H), 4.67 (t, J=5.5 Hz, 2H), 3.73-3.92 (m, 2H), 2.31 (s, 3H).

Example 58

2-(2-{[2-amino-6-(3-chloro-2-methylphenyl)pyrimidin-4-yl]amino}ethoxy)pyrimidine-4-carboxylic acid A mixture of 2-[[2-amino-6-(3-chloro-2-methyl-phenyl)pyrimidin-4-yl]amino]ethanol (intermediate 19), 2-chloropyrimidine-4-carboxamide (1.5 equiv.) and Cs$_2$CO$_3$ (2.0 equiv.) in DMSO was heated in a sealed tube at 90° C. for 16 h. After cooling methanol was added followed by filtration and purification by preparative LC to give the title compound. LCMS [M+H]+ 401. $^1$H NMR (400 MHz, METHANOL-d$_4$) δ ppm 8.63 (br. s., 1H), 7.50 (dd, J=6.6, 2.5 Hz, 2H), 7.16-7.37 (m, 2H), 6.00 (s, 1H), 4.61-4.71 (m, 2H), 3.89 (br. s., 2H), 2.34 (s, 3H).

Example 59

N-[4-(2-{[2-amino-6-(3-chloro-2-methylphenyl)pyrimidin-4-yl]amino}ethyl)phenyl]-2,2-dimethylpropanamide The title compound was prepared according to general procedure 6 from Intermediate 13 and 2,2-dimethylpropanoyl chloride. LCMS [M+H]+ 438. $^1$H NMR (400 MHz, METHANOL-d4) δ ppm 7.42-7.47 (m, 2H), 7.41 (dd, J=7.4, 1.4 Hz, 1H), 7.14-7.24 (m, 4H), 5.76 (s, 1H), 3.50-3.66 (m, 2H), 2.83-2.91 (m, 2H), 2.31 (s, 3H), 1.29 (s, 9H).

Example 60

N-[4-(2-{[2-amino-6-(3-chloro-2-methylphenyl)pyrimidin-4-yl]amino}ethyl)phenyl]-2,2,2-trifluoroethane-1-sulfonamide The title compound was prepared according to general procedure 6 from Intermediate 13 and 2,2,2-trifluoroethane-sulfonyl chloride. LCMS [M+H]$^+$ 500. $^1$H NMR (400 MHz, METHANOL-d4) δ ppm 7.58-7.62 (m, 1H), 7.31-7.38 (m, 2H), 7.26-7.31 (m, 2H), 7.20-7.25 (m, 2H), 6.00 (s, 1H), 4.07 (q, J=9.5 Hz, 2H), 3.77 (t, J=7.1 Hz, 2H), 2.94 (t, J=7.1 Hz, 2H), 2.37 (s, 3H).

Example 61

1-[4-(2-{[2-amino-6-(3-chloro-2-methylphenyl)pyrimidin-4-yl]amino}ethyl)phenyl]-3-(propan-2-yl)urea The title compound was prepared according to general procedure 8 from Intermediate 13 and isopropyl isocyanate. LCMS [M+H]$^+$ 439. $^1$H NMR (400 MHz, METHANOL-d4) δ ppm 7.38-7.43 (m, 1H), 7.24-7.29 (m, 2H), 7.11-7.24 (m, 4H), 5.75 (s, 1H), 3.87 (dt, J=13.0, 6.6 Hz, 1H), 3.52-3.62 (m, 2H), 2.83 (t, J=7.3 Hz, 2H), 2.31 (s, 3H), 1.17 (d, J=6.6 Hz, 6H).

Example 62 tert-butyl N-[4-(2-{[2-amino-6-(3-chloro-2-methylphenyl)pyrimidin-4-yl]amino}ethyl)phenyl]carbamate The title compound was prepared according to General procedure 6 from Intermediate 13 and di-tert-butyl dicarbonate. LCMS [M+H]$^+$ 454. $^1$H NMR (400 MHz, METHANOL-d4) δ ppm 7.38-7.43 (m, 1H), 7.31 (d, J=8.5 Hz, 2H), 7.12-7.24 (m, 4H), 5.75 (s, 1H), 3.49-3.63 (m, 2H), 2.83 (s, 2H), 2.31 (s, 3H), 1.49-1.53 (m, 9H).

Example 63

N-[4-(2-{[2-amino-6-(3-chloro-2-methylphenyl)pyrimidin-4-yl]amino}ethyl)phenyl]cyclopropanecarboxamide The title compound was prepared according to General procedure 6 from Intermediate 13 and cyclopropanecarbonyl chloride. LCMS [M+H]$^+$ 422. $^1$H NMR (400 MHz, METHANOL-d4) δ ppm 7.44-7.49 (m, 2H), 7.41 (dd, J=7.6, 1.3 Hz, 1H), 7.14-7.24 (m, 4H), 5.75 (s, 1H), 3.58 (br. s., 2H), 2.86 (t, J=7.3 Hz, 2H), 2.31 (s, 3H), 1.75 (tt, J=7.9, 4.7 Hz, 1H), 0.91-0.96 (m, 2H), 0.81-0.87 (m, 2H).

Example 63

N-[4-(2-{[2-amino-6-(3-chloro-2-methylphenyl)pyrimidin-4-yl]amino}ethyl)phenyl]ethane-1-sulfonamide The title compound was prepared according to General procedure 6 from Intermediate 13 and ethanesulfonyl chloride.

LCMS [M+H]$^+$ 446. $^1$H NMR (400 MHz, METHANOL-d4) δ ppm 7.57-7.61 (m, 1H), 7.31-7.37 (m, 2H), 7.22-7.26 (m, 2H), 7.18-7.22 (m, 2H), 6.00 (s, 1H), 3.76 (t, J=7.1 Hz, 2H), 3.05 (q, J=7.4 Hz, 2H), 2.92 (t, J=7.1 Hz, 2H), 2.37 (s, 3H), 1.26-1.32 (m, 3H).

Example 65

4-(2-{[2-amino-6-(2,4,5-trimethylphenyl)pyrimidin-4-yl]amino}ethyl)benzene-1-sulfonamide The title compound was prepared according to general procedure 1 from (2,4,5-trimethylphenyl)boronic acid and intermediate 4. LCMS [M+H]$^+$ 412.

Example 66

4-(2-{[2-amino-6-(4-methoxy-2,5-dimethylphenyl)pyrimidin-4-yl]amino}ethyl)benzene-1-sulfonamide The title compound was prepared according to general procedure 1 from (4-methoxy-2,5-dimethyl-phenyl)boronic acid and intermediate 4. LCMS [M+H]$^+$ 428.

Example 67

4-(2-{[2-amino-6-(4,5-dichloro-2-methylphenyl)pyrimidin-4-yl]amino}ethyl)benzene-1-sulfonamide The title compound was prepared according to general procedure 1 from (4,5-dichloro-2-methyl-phenyl)boronic acid and intermediate 4. LCMS [M+H]$^+$ 452.

Example 68

4-(2-{[2-amino-6-(5-chloro-4-methoxy-2-methylphenyl)pyrimidin-4-yl]amino}ethyl)benzene-1-sulfonamide The title compound was prepared according to general procedure 1 from (5-chloro-4-methoxy-2-methyl-phenyl)boronic acid and intermediate 4. LCMS [M+H]$^+$ 448.

Example 69

4-(2-{[2-amino-6-(1H-indol-4-yl)pyrimidin-4-yl]amino}ethyl)benzene-1-sulfonamide The title compound was prepared according to general procedure 1 from 1H-indol-4-ylboronic acid and intermediate 4. LCMS [M+H]$^+$ 409.

Example 70

4-(2-{[2-amino-6-(2,5-dimethylphenyl)pyrimidin-4-yl]amino}ethyl)benzene-1-sulfonamide The title compound was prepared according to general procedure 1 from (2,5-dimethylphenyl)boronic acid and intermediate 4. LCMS [M+H]$^+$ 398.

Example 71

4-(2-{[2-amino-6-(5-fluoro-2-methylphenyl)pyrimidin-4-yl]amino}ethyl)benzene-1-sulfonamide The title compound was prepared according to general procedure 1 from (5-fluoro-2-methyl-phenyl)boronic acid and intermediate 4. LCMS [M+H]$^+$ 402.

Example 72

4-(2-{[2-amino-6-(3,4,5-trichloro-2-methylphenyl)pyrimidin-4-yl]amino}ethyl)benzene-1-sulfonamide The title compound was prepared according to general procedure 1 from (3,4,5-trichloro-2-methyl-phenyl)boronic acid and intermediate 4. LCMS [M+H]$^+$ 486.

Example 73

4-(2-{[2-amino-6-(5-chloro-2-fluoro-3-methylphenyl)pyrimidin-4-yl]amino}ethyl)benzene-1-sulfonamide The title compound was prepared according to general procedure 1 from (5-chloro-2-fluoro-3-methyl-phenyl)boronic acid and intermediate 4. LCMS [M+H]$^+$ 436.

Example 74

4-(2-{[2-amino-6-(3,5-dichloro-2-methylphenyl)pyrimidin-4-yl]amino}ethyl)benzene-1-sulfonamide The title compound was prepared according to general procedure 1 from (3,5-dichloro-2-methyl-phenyl)boronic acid and intermediate 4. LCMS [M+H]$^+$ 452.

Example 75

4-(2-{[2-amino-6-(3,4,5-trichloro-2-methylphenyl)pyrimidin-4-yl]amino}ethyl)benzamide The title compound was prepared according to general procedure 1 from (3,4,5-trichloro-2-methyl-phenyl)boronic acid and Intermediate 10. LCMS [M+H]$^+$ 450.

Example 76

4-(2-{[2-amino-6-(3,5-dichloro-2-methylphenyl)pyrimidin-4-yl]amino}ethyl)benzamide The title compound was prepared according to general procedure 1 from (3,5-dichloro-2-methyl-phenyl)boronic acid and Intermediate 10. LCMS [M+H]$^+$ 416.

Example 77

4-(2-{[2-amino-6-(4-fluoro-2,3-di methylphenyl)pyrimidin-4-yl]amino}ethyl)benzamide The title compound was prepared according to general procedure 1 from (4-fluoro-2,3-dimethyl-phenyl)boronic acid and Intermediate 10. LCMS [M+H]$^+$ 380.

Example 78

4-(2-{[2-amino-6-(3,4-dichloro-2-methylphenyl)pyrimidin-4-yl]amino}ethyl)benzamide The title compound was prepared according to general procedure 1 from (3,4-dichloro-2-methyl-phenyl)boronic acid and Intermediate 10. LCMS [M+H]$^+$ 416.

Example 79

4-(2-{[2-amino-6-(5-chloro-2-fluoro-3-methylphenyl)pyrimidin-4-yl]amino}ethyl)benzamide The title compound was prepared according to general procedure 1 from (5-chloro-2-fluoro-3-methyl-phenyl)boronic acid and Intermediate 10. LCMS [M+H]$^+$ 400.

Example 80

4-(2-{[2-amino-6-(3-chloro-2-fluorophenyl)pyrimidin-4-yl]amino}ethyl)benzamide

The title compound was prepared according to general procedure 1 from (3-chloro-2-fluoro-phenyl)boronic acid and Intermediate 10. LCMS [M+H]$^+$ 386.

Example 81

N-[3-(2-{[2-amino-6-(3-chloro-2-methylphenyl)pyrimidin-4-yl]amino}ethyl)phenyl]-2,2-dimethylpropanamide The title compound was prepared according to general procedure 6 from Intermediate 12 and 2,2-dimethylpropanoyl chloride. LCMS [M+H]$^+$ 438.

Example 82

1-[3-(2-{[2-amino-6-(3-chloro-2-methylphenyl)pyrimidin-4-yl]amino}ethyl)phenyl]-3-(propan-2-yl)urea The title compound was prepared according to general procedure 8 from Intermediate 12 and isopropyl isocyanate. LCMS [M+H]$^+$ 439.

Example 83 tert-butyl N-[3-(2-{[2-amino-6-(3-chloro-2-methylphenyl)pyrimidin-4-yl]amino}ethyl)phenyl]carbamate The title compound was prepared according to general procedure 6 from Intermediate 12 and di-tert-butyl dicarbonate. LCMS [M+H]$^+$ 454.

Example 84

N-[3-(2-{[2-amino-6-(3-chloro-2-methylphenyl)pyrimidin-4-yl]amino}ethyl)phenyl]cyclopropanecarboxamide The title compound was prepared according to general procedure 6 from Intermediate 12 and cyclopropanecarbonyl chloride. LCMS [M+H]$^+$ 422.

Example 85

N-[3-(2-{[2-amino-6-(3-chloro-2-methylphenyl)pyrimidin-4-yl]amino}ethyl)phenyl]-2-methylpropane-1-sulfonamide The title compound was prepared according to general procedure 6 from Intermediate 12 and isobutylsulfonyl chloride. LCMS [M+H]+ 474.

Example 86

N-[4-(2-{[2-amino-6-(3-chloro-2-methylphenyl)pyrimidin-4-yl]amino}ethyl)phenyl]propane-2-sulfonamide The title compound was prepared according to general procedure 6 from Intermediate 13 and isopropylsulfonyl chloride. LCMS [M+H]+ 460.

Example 87

N-[4-(2-{[2-amino-6-(3-chloro-2-methylphenyl)pyrimidin-4-yl]amino}ethyl)phenyl]-2-methylpropane-1-sulfonamide The title compound was prepared according to general procedure 6 from Intermediate 13 and isobutylsulfonyl chloride. LCMS [M+H]+ 474.

Example 88

3-[2-[[2-amino-6-(3-chloro-2-methyl-phenyl)pyrimidin-4-yl]amino]ethyl]benzamide

Step 1. 3-(2-aminoethyl)benzamide was prepared according to general procedure 7 from 3-bromobenzamide.
Step 2. The title compound was prepared according to general procedure 2 from 3-(2-aminoethyl)benzamide and intermediate 3. LCMS [M+H]+ 382.

Example 89

4-[2-[[2-amino-6-(3-chloro-2-methyl-phenyl)pyrimidin-4-yl]amino]ethyl]-N-methyl-benzamide Step 1. A mixture of 4-[2-[(2-amino-6-chloro-pyrimidin-4-yl)amino]ethyl]benzoic acid (from step 1 of the synthesis of intermediate 10, 1.0 equiv.), TBTU (1.2 equiv.), and DMF was stirred at 20° C. for 5 min. Then methyl amine (3.0 equiv.) was added and the resulting mixture was stirred at 20° C. for 16 h. The mixture was then diluted with NaHCO$_3$ (aq) and extracted with DCM (×3). The combined organics were dried, concentrated, and purified by silica gel chromatography. Step 2. The title compound was prepared according to general procedure 1 from the material from step 1 and (3-chloro-2-methyl-phenyl)boronic acid. LCMS [M+H]+ 396.

Example 90

[4-[2-[[2-amino-6-(3-chloro-2-methyl-phenyl)pyrimidin-4-yl]amino]ethyl]phenyl]-pyrrolidin-1-yl-methanone Step 1. A mixture of 4-[2-[(2-amino-6-chloro-pyrimidin-4-yl)amino]ethyl]benzoic acid (from step 1 of the synthesis of intermediate 10, 1.0 equiv.), TBTU (1.2 equiv.), and DMF was stirred at 20° C. for 5 min. Then pyrrolidine (3.0 equiv.) was added and the resulting mixture was stirred at 20° C. for 16 h. The mixture was then diluted with NaHCO$_3$ (aq) and extracted with DCM×3. The combined organics were dried, concentrated, and purified by silica gel chromatography.
Step 2. The title compound was prepared according to general procedure 1 from the material from step 1 and (3-chloro-2-methyl-phenyl)boronic acid. LCMS [M+H]+ 436.

Example 91

7-[2-[[2-amino-6-(3-chloro-2-methyl-phenyl)pyrimidin-4-yl]amino]ethylamino]-4H-1,4-benzoxazin-3-one Step 1. 7-(2-aminoethylamino)-4H-1,4-benzoxazin-3-one was prepared according to general procedure 4 from 7-bromo-4H-1,4-benzoxazin-3-one.
Step 2. The title compound was prepared according to general procedure 2 from the material from step 1 and intermediate 3. LCMS [M+H]+ 425. $^1$H NMR (400 MHz, METHANOL-d$_4$) δ ppm 7.59-7.62 (m, 1H), 7.30-7.39 (m, 2H), 6.77 (d, J=8.5 Hz, 1H), 6.56 (d, J=2.5 Hz, 1H), 6.49 (dd, J=8.5, 2.5 Hz, 1H), 6.04 (s, 1H), 4.52 (s, 2H), 3.74 (t, J=6.2 Hz, 2H), 3.45 (t, J=6.0 Hz, 2H), 2.38 (s, 3H).

Example 92

6-[2-[[2-amino-6-(3-chloro-2-methyl-phenyl)pyrimidin-4-yl]amino]ethylamino]-4-methyl-1,4-benzoxazin-3-one Step 1. 6-(2-aminoethylamino)-4-methyl-1,4-benzoxazin-3-one was prepared according to general procedure 4 from 6-bromo-4-methyl-1,4-benzoxazin-3-one.
Step 2. The title compound was prepared according to general procedure 2 from 6-(2-aminoethylamino)-4-methyl-1,4-benzoxazin-3-one and intermediate 3. LCMS [M+H]+ 439. $^1$H NMR (400 MHz, METHANOL-d$_4$) δ ppm 7.61 (dd, J=7.6, 1.3 Hz, 1H), 7.30-7.39 (m, 2H), 6.88 (d, J=8.5 Hz, 1H), 6.63 (d, J=2.8 Hz, 1H), 6.54 (dd, J=8.5, 2.5 Hz, 1H), 6.04 (s, 1H), 4.52 (d, J=0.6 Hz, 2H), 3.75-3.80 (m, 2H), 3.49 (t, J=6.0 Hz, 2H), 3.33 (s, 3H), 2.37 (s, 3H).

Example 93

7-[2-[[2-amino-6-(3-chloro-2-methyl-phenyl)pyrimidin-4-yl]amino]ethylamino]-3H-quinazolin-4-one Step 1. 6-(2-aminoethylamino)-3H-quinazolin-4-one was prepared according to general procedure 4 from 7-bromo-3H-quinazolin-4-one.
Step 2. The title compound was prepared according to general procedure 2 from 6-(2-aminoethylamino)-3H-quinazolin-4-one and intermediate 3. [M+H]+ 422. $^1$H NMR (400 MHz, METHANOL-d$_4$) δ ppm 8.08-8.10 (m, 1H), 7.69-7.72 (m, 1H), 7.59-7.63 (m, 1H), 7.48-7.52 (m, 1H), 7.32-7.40 (m, 1H), 7.20-7.25 (m, 1H), 6.04 (s, 1H), 3.68 (dd, J=8.8, 5.7 Hz, 2H), 3.49-3.54 (m, 2H), 2.39 (s, 3H).

Example 94

6-[2-[[2-amino-6-(2,3-dichlorophenyl)pyrimidin-4-yl]amino]ethylamino]-4-methyl-1,4-benzoxazin-3-one Step 1. 6-(2-aminoethylamino)-4-methyl-1,4-benzoxazin-3-one was prepared according to general procedure 4 from 6-bromo-4-methyl-1,4-benzoxazin-3-one.

Step 2. The title compound was prepared according to general procedure 2 from 6-(2-aminoethylamino)-4-methyl-1,4-benzoxazin-3-one and intermediate 2. [M+H]$^+$ 459. $^1$H NMR (400 MHz, METHANOL-d$_4$) δ ppm 7.79 (dd, J=7.0, 2.8 Hz, 1H), 7.47-7.53 (m, 2H), 6.93 (d, J=8.8 Hz, 1H), 6.77 (d, J=2.5 Hz, 1H), 6.67 (dd, J=8.5, 2.5 Hz, 1H), 6.15 (s, 1H), 4.55 (s, 2H), 3.77-3.83 (m, 2H), 3.53-3.58 (m, 2H), 3.34 (s, 3H).

Example 95

6-(3-chloro-2-methylphenyl)-4-N-[2-(3-nitrophenyl)ethyl]pyrimidine-2,4-diamine

Step 1: A mixture of 2-amino-4,6-dichloropyrimidine (1.0 equiv.), 2-(3-nitrophenyl)ethylammonium chloride (1.3 equiv.), and diisopropylethylamine (2.5 equiv.) in 2-propanol was stirred at 100° C. in a sealed vial for 16 h. The reaction mixture was then diluted with NaHCO$_3$ (aq) and extracted with DCM×3. The combined organics were dried, concentrated, and purified by silica gel chromatography.

Step 2: A mixture of 6-(3-chloro-2-methyl-phenyl)-N4-[2-(3-nitrophenyl)ethyl]pyrimidine-2,4-diamine (1.0 equiv.), (3-chloro-2-methyl-phenyl)boronic acid (1.2 equiv.), K$_2$CO$_3$ (3.0 equiv.) and Pd(PPh$_3$)$_4$ (0.05 equiv.) in 1,4-dioxane and water was stirred at 90° C. for 16 h. Thereafter water was added and the mixture was extracted with DCM×3. The combined organic phases were dried, concentrated, and purified by silica gel chromatography. LCMS [M+H]$^+$ 384.

Example 96

4-[2-[[2-amino-6-(2-chloro-3-methyl-phenyl)pyrimidin-4-yl]amino]ethyl]benzenesulfonamide The title compound was prepared according to general procedure 2 from 4-(2-aminoethyl)benzenesulfonamide and intermediate 9. LCMS [M+H]$^+$ 418. $^1$H NMR (400 MHz, METHANOL-d$_4$) δ ppm 7.83-7.87 (m, 2H), 7.51-7.55 (m, 1H), 7.44-7.49 (m, 2H), 7.36-7.41 (m, 1H), 7.33-7.36 (m, 1H), 6.06 (s, 1H), 3.81 (t, J=7.3 Hz, 2H), 3.05 (t, J=7.1 Hz, 2H), 2.47 (s, 3H).

Example 97

4-[2-[[2-amino-6-(2,3,5-trichlorophenyl)pyrimidin-4-yl]amino]ethyl]benzenesulfonamide Step 1. A mixture of 4,6-dichloropyrimidin-2-amine (100 mg, 0.64 mmol), (2,3,5-trichlorophenyl)boronic acid (120 mg, 0.53 mmol), potassium carbonate (220 m g, 1.6 mmol), and palladium tetrakis(triphenylphosphine)palladium (0) (31 mg, 0.027 mmol) in 1,4-dioxane/water (5.0 mL; 4:1) was heated in a sealed tube at 60° C. for 4 h. The mixture was then diluted with NaHCO$_3$ (aq) and extracted with DCM×3. The combined organics were dried, concentrated, and purified by silica gel chromatography. LCMS [M+H]$^+$ 308.

Step 2. The title compound was prepared according to general procedure 2 from 4-(2-aminoethyl)benzenesulfonamide and the material from step 1. LCMS [M+H]$^+$ 472. $^1$H NMR (400 MHz, METHANOL-d$_4$) δ ppm 7.89-7.90 (m, 1H), 7.85 (d, J=8.5 Hz, 2H), 7.61-7.62 (m, 1H), 7.46 (d, J=8.5 Hz, 2H), 6.11 (s, 1H), 3.82 (s, 2H), 3.05 (s, 2H).

Example 98

4-[2-[[2-amino-6-(2,3,4-trichlorophenyl)pyrimidin-4-yl]amino]ethyl]benzenesulfonamide The title compound was prepared according to general procedure 2 from 4-(2-aminoethyl)benzenesulfonamide and intermediate 5. LCMS [M+H]$^+$ 472. $^1$H NMR (400 MHz, METHANOL-d$_4$) δ ppm 7.82-7.87 (m, 2H), 7.71 (d, J=8.5 Hz, 1H), 7.44-7.50 (m, 3H), 6.10 (s, 1H), 3.81 (t, J=7.1 Hz, 2H), 3.05 (t, J=7.1 Hz, 2H).

Example 99

4-[2-[[2-amino-6-(2,4-dichloro-3-methoxy-phenyl)pyrimidin-4-yl]amino]ethyl]benzenesulfonamide Step 1. A mixture of 4,6-dichloropyrimidin-2-amine (100 mg, 0.64 mmol), (2,4-dichloro-3-methoxy-phenyl)boronic acid (120 mg, 0.53 mmol), potassium carbonate (220 mg, 1.60 mmol), and palladium tetrakis(triphenylphosphine)palladium (0) (31 mg, 0.027 mmol) in 1,4-dioxane/water (5.0 mL; 4:1) was heated in a sealed tube at 60° C. for 4 h. The mixture was then diluted with NaHCO$_3$ (aq) and extracted with DCM×3. The combined organics were concentrated and purified by silica gel chromatography. LCMS [M+H]$^+$ 304.

Step 2. The title compound was prepared according to general procedure 2 from 4-(2-aminoethyl)benzenesulfonamide and the material from step 1.

LCMS [M+H]$^+$ 468. $^1$H NMR (400 MHz, METHANOL-d$_4$) δ ppm 7.83-7.87 (m, 2H), 7.57 (d, J=8.5 Hz, 1H), 7.46 (d, J=8.5 Hz, 2H), 7.29 (d, J=8.5 Hz, 1H), 6.09 (s, 1H), 3.92-3.94 (m, 3H), 3.81 (t, J=7.3 Hz, 2H), 3.05 (t, J=7.1 Hz, 2H).

Example 100

6-(3-chloro-2-methyl-phenyl)-N4-[2-(2-methyl-5-nitro-imidazol-1-yl)ethyl]pyrimidine-2,4-diamine The title compound was prepared according to general procedure 2 from 2-(2-methyl-5-nitro-imidazol-3-ium-1-yl)ethylammonium dichloride and intermediate 3.

LCMS [M+H]$^+$ 388. $^1$H NMR (400 MHz, METHANOL-d$_4$) δ ppm 7.98 (br. s., 1H), 7.61 (dd, J=7.9, 1.6 Hz, 1H), 7.33-7.39 (m, 1H), 7.29-7.33 (m, 1H), 5.98 (s, 1H), 4.65-4.70 (m, 2H), 3.97 (t, J=5.8 Hz, 2H), 2.53 (s, 3H), 2.36 (s, 3H).

Example 101

6-(3-chloro-2-methyl-phenyl)-N4-[2-[(2-methyl-1,3-benzothiazol-6-yl)amino]ethyl]pyrimidine-2,4-diamine Step 1. N'-(2-methyl-1,3-benzothiazol-6-yl)ethane-1,2-diamine was prepared according to general procedure 4 from 6-iodo-2-methyl-1,3-benzothiazole.

Step 2. The title compound was prepared according to general procedure 2 from intermediate 3 and N'-(2-methyl-1,3-benzothiazol-6-yl)ethane-1,2-diamine.

LCMS [M+H]$^+$ 425. $^1$H NMR (400 MHz, CHLOROFORM-d) δ ppm 7.86 (d, J=8.8 Hz, 1H), 7.74 (br. s., 1H), 7.41-7.49 (m, 2H), 7.18 (dd, J=8.8, 2.2 Hz, 1H), 7.04-7.13 (m, 2H), 5.91 (s, 1H), 3.86-3.93 (m, 2H), 3.52-3.58 (m, 2H), 2.89 (s, 3H), 2.25 (s, 3H).

Example 102

4-[2-[[2-amino-6-(benzothiophen-3-yl)pyrimidin-4-yl]amino]ethyl]benzenesulfonamide The title compound was prepared according to general procedure 1 from intermediate 4 and benzothiophen-3-ylboronic acid. LCMS [M+H]$^+$ 426. $^1$H NMR (400 MHz, METHANOL-d$_4$) δ ppm 8.16 (s, 1H), 8.02-8.06 (m, 1H), 7.96-8.00 (m, 1H), 7.83-7.88 (m, 2H), 7.45-7.57 (m, 4H), 6.34 (s, 1H), 3.84 (t, J=7.1 Hz, 2H), 3.07 (t, J=7.1 Hz, 2H).

Example 103

6-[2-[[2-amino-6-(3-chlorophenyl)pyrimidin-4-yl]amino]ethylamino]-3,3-dimethyl-4H-1,4-benzoxazin-2-one The title compound was isolated as a side product from the experiment described in example 104. LCMS [M+H]$^+$ 439. $^1$H NMR (400 MHz, METHANOL-d$_4$) δ ppm 7.75-7.77 (m, 1H), 7.64 (dd, J=3.8, 1.9 Hz, 2H), 7.56-7.61 (m, 1H), 6.75 (d, J=8.8 Hz, 1H), 6.36-6.41 (m, 1H), 6.28-6.32 (m, 2H), 3.74 (t, J=6.2 Hz, 2H), 3.38 (t, J=6.0 Hz, 2H), 1.40 (s, 6H).

Example 104

6-[2-[[2-amino-6-(2,3-dichlorophenyl)pyrimidin-4-yl]amino]ethylamino]-3,3-dimethyl-4H-1,4-benzoxazin-2-one Step 1. 6-(2-aminoethylamino)-4H-1,4-benzoxazin-3-one was prepared according to general procedure 4 from 6-bromo-3,3-dimethyl-4H-1,4-benzoxazin-2-one.

Step 2. The title compound was prepared according to general procedure 2 from intermediate 2 and 6-(2-aminoethylamino)-4H-1,4-benzoxazin-3-one LCMS [M+H]$^+$ 473. $^1$H NMR (400 MHz, METHANOL-d$_4$) δ ppm 7.76-7.82 (m, 1H), 7.48-7.51 (m, 2H), 6.80 (d, J=8.5 Hz, 1H), 6.48 (dd, J=8.7, 2.7 Hz, 1H), 6.40 (d, J=2.5 Hz, 1H), 6.13 (s, 1H), 3.76 (t, J=6.0 Hz, 3H), 3.44 (t, J=6.0 Hz, 3H), 1.42 (s, 6H).

Example 105

6-(3-chloro-2-methyl-phenyl)-N4-[2-(3-methylsulfonylanilino)ethyl]pyrimidine-2,4-diamine Step 1. N'-(3-methylsulfonylphenyl)ethane-1,2-diamine was prepared according to general procedure 4 from 1-bromo-3-methylsulfonyl-benzene.

Step 2. The title compound was prepared according to general procedure 2 from intermediate 3 and N'-(3-methylsulfonylphenyl)ethane-1,2-diamine. LCMS [M+H]$^+$ 432. $^1$H NMR (400 MHz, CHLOROFORM-d) δ ppm 7.37 (dd, J=7.3, 1.9 Hz, 1H), 7.28-7.33 (m, 2H), 7.20-7.24 (m, 1H), 7.12-7.20 (m, 2H), 6.82 (ddd, J=8.2, 2.5, 0.9 Hz, 1H), 5.76 (s, 1H), 5.18 (br. s., 3H), 4.66-4.79 (m, 1H), 3.62 (d, J=6.3 Hz, 2H), 3.38-3.45 (m, 2H), 3.05-3.08 (m, 3H), 2.36 (s, 3H).

Example 106

6-(2,3-dichlorophenyl)-N4-[2-(3-methylsulfonylanilino)ethyl]pyrimidine-2,4-diamine Step 1. N'-(3-methylsulfonylphenyl)ethane-1,2-diamine was prepared according to general procedure 4 from 1-bromo-3-methylsulfonyl-benzene.

Step 2. The title compound was prepared according to general procedure 2 from intermediate 2 and N'-(3-methylsulfonylphenyl)ethane-1,2-diamine. LCMS [M+H]$^+$ 452. $^1$H NMR (400 MHz, CHLOROFORM-d) δ ppm 7.50 (dd, J=8.1, 1.7 Hz, 1H), 7.36-7.40 (m, 1H), 7.28-7.35 (m, 3H), 7.25 (t, J=1.4 Hz, 1H), 6.85 (d, J=0.9 Hz, 1H), 5.97 (s, 1H), 5.03-5.26 (m, 3H), 4.70 (br. s., 1H), 3.65 (q, J=6.1 Hz, 2H), 3.44 (q, J=6.4 Hz, 2H), 3.08 (s, 3H).

Example 107

4-[2-[[2-amino-6-(3-chloro-2-methyl-phenyl)pyrimidin-4-yl]amino]ethyl]-N'-hydroxy-benzamidine A mixture of 4-[2-[[2-amino-6-(3-chloro-2-methyl-phenyl)pyrimidin-4-yl]amino]ethyl]benzonitrile (intermediate 17) (1.0 equiv.) and hydroxylamine (2.0 equiv.) was stirred at reflux in ethanol for 3 h. The mixture was then purified by preparative LC. LCMS [M+H]$^+$ 397. $^1$H NMR (400 MHz, METHANOL-d$_4$) δ ppm 7.66-7.70 (m, 2H), 7.58-7.62 (m, 1H), 7.53-7.58 (m, 2H), 7.30-7.38 (m, 2H), 6.02 (s, 1H), 3.82 (t, J=7.3 Hz, 2H), 3.09 (t, J=7.4 Hz, 2H), 2.37 (s, 3H).

Example 108

[4-[2-[[2-amino-6-(3-chloro-2-methyl-phenyl)pyrimidin-4-yl]amino]ethyl]phenyl]-morpholino-methanone The title compound was prepared according to general procedure 1 from intermediate 16 and (3-chloro-2-methyl-phenyl)boronic acid. [M+H]$^+$ 452.

Example 109

[4-[2-[[2-amino-6-(3,5-dichloro-2-methyl-phenyl)pyrimidin-4-yl]amino]ethyl]phenyl]-morpholino-methanone The title compound was prepared according to general procedure 1 from intermediate 16 and (3,5-dichloro-2-methyl-phenyl)boronic acid.

LCMS [M+H]$^+$ 486.

Example 110

6-(3-chloro-2-methyl-phenyl)-N4-[3-(3-methylsulfonylanilino)propyl]pyrimidine-2,4-diamine Step 1. A mixture of 1-bromo-3-methylsulfonyl-benzene (1.0 equiv.), CuCl (0.10 equiv.), KOH (2.0 equiv.), and 1,3-propanediamine (4.50 equiv.) were stirred at 90° C. for 16 h in a sealed vial. The mixture was allowed to cool and was then extracted with hot EtOAc×5. The combined organics were concentrated and the excess of 1,3-propanediamine was removed by co-evaporation with toluene. The crude material was used without further purification.

Step 2. The title compound was prepared according to general procedure 2 from material from step 1 and intermediate 3. LCMS [M+H]+ 446. ¹H NMR (400 MHz, METHANOL-$d_4$) δ ppm 7.38-7.42 (m, 1H), 7.28-7.34 (m, 1H), 7.20 (d, J=7.6 Hz, 2H), 7.11 (d, J=1.3 Hz, 2H), 6.87-6.94 (m, 1H), 5.82 (s, 1H), 3.44-3.55 (m, 2H), 3.21-3.27 (m, 3H), 3.05 (s, 3H), 2.31 (s, 3H), 1.93 (t, J=6.8 Hz, 2H).

Example 111

4-[2-[[2-amino-6-(3-chloro-2-methyl-phenyl)pyrimidin-4-yl]amino]ethyl]benzenecarbothioamide A mixture of 4-[2-[[2-amino-6-(3-chloro-2-methyl-phenyl)pyrimidin-4-yl]amino]ethyl]benzonitrile (1.0 equiv., intermediate 17), O,O'-Diethyl dithiophosphate (4.0 equiv.), and water was stirred at 20° C. for 2 days. The mixture was then diluted with water and extracted with DCM (×3). The combined organics were dried, concentrated, and purified by silica gel chromatography.
LCMS [M+H]⁺ 398.

Example 112

1-[4-[2-[[2-amino-6-(3-chloro-2-methyl-phenyl)pyrimidin-4-yl]amino]ethyl]phenyl]-3-ethyl-urea The title compound was prepared according to general procedure 8 from ethyl isocyanate and intermediate 13. LCMS [M+H]⁺ 425.

Example 113

1-[4-[2-[[2-amino-6-(3-chloro-2-methyl-phenyl)pyrimidin-4-yl]amino]ethyl]phenyl]-3-tert-butyl-urea The title compound was prepared according to general procedure 8 from t-butyl isocyanate and intermediate 13. LCMS [M+H]⁺ 453. ¹H NMR (400 MHz, METHANOL-$d_4$) δ ppm 7.57-7.62 (m, 1H), 7.33 (d, J=1.9 Hz, 2H), 7.23-7.27 (m, 2H), 7.16 (s, 2H), 5.99 (s, 1H), 3.70-3.77 (m, 2H), 2.85-2.91 (m, 2H), 2.37 (s, 3H), 1.34-1.38 (m, 9H).

Example 114

1-allyl-3-[4-[2-[[2-amino-6-(3-chloro-2-methyl-phenyl)pyrimidin-4-yl]amino]ethyl]phenyl]urea The title compound was prepared according to general procedure 8 from allyl isocyanate and intermediate 13. LCMS [M+H]⁺ 437. ¹H NMR (400 MHz, METHANOL-$d_4$) δ ppm 7.59 (d, J=7.3 Hz, 1H), 7.29-7.38 (m, 4H), 7.17 (d, J=8.5 Hz, 2H), 5.99 (s, 1H), 5.83-5.95 (m, 1H), 5.18-5.25 (m, 1H), 5.11 (dd, J=10.4, 1.6 Hz, 1H), 3.81 (dt, J=5.3, 1.6 Hz, 2H), 3.74 (t, J=7.3 Hz, 2H), 2.89 (t, J=7.1 Hz, 2H), 2.37 (s, 3H).

Example 115 ethyl N-[[4-[2-[[2-amino-6-(3-chloro-2-methyl-phenyl)pyrimidin-4-yl]amino]ethyl]phenyl]carbamoyl]carbamate The title compound was prepared according to general procedure 8 from ethyl N-(oxomethylene)carbamate and intermediate 13. LCMS [M+H]⁺ 469.

Example 116

1-[4-[2-[[2-amino-6-(3-chloro-2-methyl-phenyl)pyrimidin-4-yl]amino]ethyl]phenyl]-3-sec-butyl-urea The title compound was prepared according to general procedure 8 from sec-butyl isocyanate and intermediate 13. LCMS [M+H]⁺ 453. ¹H NMR (400 MHz, METHANOL-$d_4$) δ ppm 7.59 (d, J=7.3 Hz, 1H), 7.31-7.38 (m, 2H), 7.26-7.31 (m, 2H), 7.13-7.18 (m, 2H), 5.99 (s, 1H), 3.74 (t, J=7.3 Hz, 2H), 3.65-3.72 (m, 1H), 2.89 (t, J=7.3 Hz, 2H), 2.37 (s, 3H), 1.44-1.55 (m, 2H), 1.15 (d, J=6.3 Hz, 3H), 0.92-0.98 (m, 3H).

Example 117

1-[4-[2-[[2-amino-6-(3-chloro-2-methyl-phenyl)pyrimidin-4-yl]amino]ethyl]phenyl]-3-ethyl-thiourea A mixture of intermediate 13 (1.0 equiv.) and ethyl isothiocyanate (2.4 equiv.) in DCM was stirred at 20° C. for 48 h. The reaction mixture was then concentrated and purified by preparative LC. LCMS [M+H]⁺ 441.

Example 118

N-[4-[2-[[2-amino-6-(3-chloro-2-methyl-phenyl)pyrimidin-4-yl]amino]ethyl]phenyl]morpholine-4-carboxamide A mixture of intermediate 13 (1.0 equiv.), morpholine-4-carbonyl chloride (1.5 equiv.), and diisopropylethylamine (1.5 equiv.) in DCM was stirred at reflux for 2 h. The mixture was then concentrated and purified by preparative LC. LCMS [M+H]⁺ 467. ¹H NMR (400 MHz, METHANOL-$d_4$) δ ppm 7.60 (dd, J=7.4, 2.4 Hz, 1H), 7.33-7.38 (m, 2H), 7.29-7.32 (m, 2H), 7.16-7.21 (m, 2H), 5.99 (s, 1H), 3.75 (t, J=7.3 Hz, 2H), 3.68-3.72 (m, 4H), 3.48-3.52 (m, 4H), 2.91 (t, J=7.3 Hz, 2H), 2.37 (s, 3H).

Example 119 isopropyl N-[4-[2-[[2-amino-6-(3-chloro-2-methyl-phenyl)pyrimidin-4-yl]amino]ethyl]phenyl]carbamate The title compound was prepared according to general procedure 6 from intermediate 13 and isopropyl carbonochloridate. LCMS [M+H]⁺ 440. ¹H NMR (400 MHz, CHLOROFORM-d) δ ppm 7.44-7.49 (m, 1H), 7.32 (d, J=7.9 Hz, 2H), 7.07-7.25 (m, 4H), 6.62-6.78 (m, 1H), 6.37 (br. s., 1H), 5.79 (s, 1H), 5.00 (d, J=6.3 Hz, 1H), 3.72 (d, J=6.0 Hz, 2H), 2.87 (t, J=7.0 Hz, 3H), 2.31 (s, 3H), 1.27-1.34 (m, 6H).

Example 120 isobutyl N-[4-[2-[[2-amino-6-(3-chloro-2-methyl-phenyl)pyrimidin-4-yl]amino]ethyl]phenyl]carbamate The title compound was prepared according to general procedure 6 from intermediate 13 and isobutyl carbonochloridate. LCMS [M+H]⁺ 454. ¹H NMR (400 MHz, CHLOROFORM-d) δ ppm 7.45-7.49 (m, 1H), 7.31 (d, J=7.6 Hz, 2H), 7.11-7.22 (m, 5H), 6.71-6.88 (m, 1H), 6.44 (br. s., 1H), 5.81 (s, 1H), 3.94 (d, J=6.3 Hz, 2H), 3.73 (d, J=6.0 Hz, 2H), 2.87 (t, J=7.0 Hz, 2H), 2.29-2.33 (m, 3H), 1.97 (s, 1H), 0.93-0.99 (m, 6H).

Example 121

2,2-dimethylpropyl N-[4-[2-[[2-amino-6-(3-chloro-2-methyl-phenyl)pyrimidin-4-yl]amino]ethyl]phenyl]carbamate The title compound was prepared according to General procedure 6 from intermediate 13 and 2,2-dimethylpropyl carbonochloridate. LCMS [M+H]$^+$ 468. $^1$H NMR (400 MHz, CHLOROFORM-d) δ ppm 7.45 (d, J=7.6 Hz, 1H), 7.32 (d, J=7.6 Hz, 2H), 7.09-7.20 (m, 4H), 6.78-6.90 (m, 1H), 6.61-6.69 (m, 1H), 5.82 (s, 1H), 3.85 (s, 2H), 3.65-3.74 (m, 2H), 2.86 (br. s., 2H), 2.30 (s, 3H), 0.93-0.99 (m, 9H).

Example 122

2-methoxyethyl N-[4-[2-[[2-amino-6-(3-chloro-2-methyl-phenyl)pyrimidin-4-yl]amino]ethyl]phenyl]carbamate The title compound was prepared according to General procedure 6 from intermediate 13 and 2-methoxyethyl carbonochloridate. LCMS [M+H]$^+$ 456. $^1$H NMR (400 MHz, CHLOROFORM-d) δ ppm 7.45 (dd, J=7.6, 1.3 Hz, 1H), 7.32 (d, J=8.2 Hz, 2H), 7.10-7.21 (m, 4H), 6.89 (s, 1H), 6.36 (br. s., 1H), 5.75 (s, 1H), 4.29-4.35 (m, 2H), 3.67-3.74 (m, 2H), 3.63-3.67 (m, 2H), 3.41-3.44 (m, 3H), 2.87 (s, 2H), 2.31 (s, 3H).

Example 123 but-2-ynyl N-[4-[2-[[2-amino-6-(3-chloro-2-methyl-phenyl)pyrimidin-4-yl]amino]ethyl]phenyl]carbamate The title compound was prepared according to general procedure 6 from intermediate 13 and but-2-ynyl carbonochloridate. LCMS [M+H]$^+$ 450. $^1$H NMR (400 MHz, CHLOROFORM-d) δ ppm 7.45-7.49 (m, 1H), 7.32 (d, J=7.9 Hz, 2H), 7.11-7.23 (m, 4H), 6.83 (br. s., 1H), 6.33-6.40 (m, 1H), 5.80 (s, 1H), 4.74 (dt, J=4.4, 2.2 Hz, 2H), 3.73 (d, J=6.0 Hz, 2H), 2.88 (t, J=7.0 Hz, 2H), 2.29-2.34 (m, 3H), 1.84-1.89 (m, 3H).

Example 124

[4-[2-[[2-amino-6-(3-chloro-2-methyl-phenyl)pyrimidin-4-yl]amino]ethyl]phenyl]cyanamide A mixture of 4-[2-[[2-amino-6-(3-chloro-2-methyl-phenyl)pyrimidin-4-yl]amino]ethyl]-N'-hydroxy-benzamidine (1.0 equiv.), 4-toluenesulfonyl chloride (1.1 equiv.), and diisopropylethylamine (1.1 equiv.) in DCM was stirred at 20° C. for 2 h. The mixture was then diluted with NaHCO$_3$ (aq) and extracted with DCM×3. The combined organics were concentrated and purified by silica gel chromatography. LCMS [M+H]$^+$ 379. $^1$H NMR (400 MHz, METHANOL-d$_4$) δ ppm 7.39-7.44 (m, 1H), 7.15-7.26 (m, 4H), 6.91 (d, J=8.5 Hz, 2H), 5.76 (br. s., 1H), 3.50-3.65 (m, 2H), 2.85 (s, 2H), 2.31 (s, 3H).

Example 125

4-[2-[[2-amino-6-(3-chloro-2-methyl-phenyl)pyrimidin-4-yl]amino]ethyl]benzamidine A mixture of 4-[2-[[2-amino-6-(3-chloro-2-methyl-phenyl)pyrimidin-4-yl]amino]ethyl]benzenecarbothioamide and iodomethane (2.0 equiv.) in acetone was stirred at reflux for 2 h. Thereafter the mixture was concentrated and suspended in acetonitrile. Then ammonium acetate was added and the mixture was stirred at 20° C. for 16 h. The reaction mixture was then diluted with MeOH and purified by preparative LC. LCMS [M+H]$^+$ 381. $^1$H NMR (400 MHz, METHANOL-d$_4$) δ ppm 7.77-7.81 (m, 2H), 7.59-7.64 (m, 1H), 7.57 (d, J=8.5 Hz, 2H), 7.31-7.39 (m, 2H), 6.01 (s, 1H), 3.79-3.86 (m, 2H), 3.08-3.13 (m, 2H), 2.38 (s, 3H).

Example 126

4-N-(2-{[2-amino-6-(2,3-dimethylphenyl)pyrimidin-4-yl]amino}ethyl)pyrimidine-2,4-diamine The title compound was prepared according to general procedure 3 from intermediate 7 and 4-chloropyrimidin-2-amine. LCMS [M+H]$^+$ 351. $^1$H NMR (400 MHz, METHANOL-d4) δ ppm 7.57 (d, J=7.3 Hz, 1H), 7.36 (d, J=7.6 Hz, 1H), 7.25 (t, J=7.6 Hz, 1H), 7.15-7.19 (m, 1H), 6.09 (d, J=7.3 Hz, 1H), 6.01 (s, 1H), 3.77 (m, 4H), 2.36 (s, 3H), 2.25 (s, 3H).

Example 127

5-N-(2-{[2-amino-6-(2,3-dimethylphenyl)pyrimidin-4-yl]amino}ethyl)pyridine-2,5-diamine Step 1: N-[5-(2-aminoethylamino)-2-pyridyl]acetamide was prepared according to General procedure 4 from N-(5-bromo-2-pyridinyl)acetamide.

Step 2: A mixture of the crude material from step 1 (2.0 equiv.), intermediate 1 (1.0 equiv.), and diisopropylethylamine (9.0 equiv.) in methanol was stirred at 150° C. for 1 h. The N-acetyl group was hydrolyzed under these reaction conditions and the title compound was isolated after preparative LC. LCMS [M+H]$^+$ 350. $^1$H NMR (400 MHz, METHANOL-d4) δ ppm 7.52-7.57 (m, 1H), 7.34-7.38 (m, 1H), 7.22-7.27 (m, 1H), 7.16-7.20 (m, 1H), 7.13 (dd, J=2.8, 0.6 Hz, 1H), 6.91 (dd, J=9.5, 0.6 Hz, 1H), 6.04 (s, 1H), 3.73 (t, J=6.5 Hz, 2H), 3.30-3.35 (m, 2H, signal obscured by solvent), 2.36 (s, 3H), 2.25 (s, 3H).

Example 128

1-N-(2-{[2-amino-6-(2,3-dimethylphenyl)pyrimidin-4-yl]amino}ethyl)-2-fluorobenzene-1,4-diamine Step 1: N-[4-(2-aminoethylamino)-3-fluoro-phenyl]acetamide was prepared according to General procedure 4 from N-(4-bromo-3-fluorophenyl)acetamide.

Step 2: A mixture of the crude material from step 1 (2.0 equiv.), intermediate 1 (1.0 equiv.), and diisopropylethylamine (9.0 equiv.) in methanol was stirred at 150° C. for 1 h. The N-acetyl group was hydrolyzed under these reaction

Example 129 tert-butyl 4-(2-amino-6-{[2-(4-methanesulfonylphenyl)ethyl]amino}pyrimidin-4-yl)-1,2,3,6-tetrahydropyridine-1-carboxylate A mixture of tetrakis(triphenylphosphine) palladium (0) (0.050 equiv.), tert-butyl 4-(4,4,5,5-tetramethyl-1,3,2-dioxaborolan-2-yl)-3,6-dihydro-2H-pyridine-1-carboxylate (intermediate 6, 1.1 equiv.), potassium carbonate 1.0 M (2.5 equiv.), and dioxane was heated at 80° C. for 5 hours. The mixture was then purified by preparative LC to give the title compound. LCMS [M+H]$^+$ 474; $^1$H NMR (400 MHz, DMSO-d6) δ ppm 7.81-7.87 (m, 2H), 7.49-7.55 (m, 2H), 6.94 (br. s., 1H), 6.62 (br. s., 1H), 5.85 (s, 2H), 5.77 (s, 1H), 3.93-4.03 (m, 2H), 3.42-3.54 (m, 4H), 3.18 (s, 3H), 2.92 (t, J=7.1 Hz, 2H), 2.28-2.37 (m, 2H), 1.41 (s, 9H).

Example 130

4-N-[2-(4-methanesulfonylphenyl)ethyl]-6-[1-(4-methylbenzenesulfonyl)-1,2,3,6-tetrahydropyridin-4-yl]pyrimidine-2,4-diamine The title compound was prepared according to general procedure 9 from N4-[2-(4-methylsulfonylphenyl)ethyl]-6-(1,2,3,6-tetrahydropyridin-4-yl)pyrimidine-2,4-diamine hydrochloride and 4-methylbenzenesulfonyl chloride. LCMS [M+H]$^+$ 528. $^1$H NMR (400 MHz, DMSO-d$_6$) δ ppm 11.58 (br. s., 1H), 8.85 (t, J=5.7 Hz, 1H), 7.83-7.88 (m, 2H), 7.67-7.72 (m, 2H), 7.53 (d, J=8.3 Hz, 2H), 7.46 (dd, J=8.5, 0.6 Hz, 2H), 6.49 (br. s., 2H), 5.97 (s, 1H), 3.72-3.78 (m, 2H), 3.57-3.69 (m, 2H), 3.12-3.21 (m, 5H), 2.97 (t, J=7.1 Hz, 2H), 2.35-2.42 (m, 5H).

Example 131 tert-butyl 4-(2-amino-6-{[2-(4-sulfamoylphenyl)ethyl]amino}pyrimidin-4-yl)-1,2,3,6-tetrahydropyridine-1-carboxylate A mixture of tetrakis(triphenylphosphine) palladium (0) (0.050 equiv.), tert-butyl 4-(4,4,5,5-tetramethyl-1,3,2-dioxaborolan-2-yl)-3,6-dihydro-2H-pyridine-1-carboxylate (intermediate 4, 1.1 equiv.), potassium carbonate 1.0 M (2.5 equiv.), and dioxane was heated at 90° C. for 3 hours. The mixture was then purified by preparative LC to give the title compound. LCMS [M+H]$^+$ 475.

Example 132

4-(2-{[2-amino-6-(cyclohept-1-en-1-yl)pyrimidin-4-yl]amino}ethyl)benzene-1-sulfonamide A mixture of tetrakis(triphenylphosphine) palladium (0) (0.050 equiv.), 2-(cyclohepten-1-yl)-4,4,5,5-tetramethyl-1,3,2-dioxaborolane (intermediate 4, 1.2 equiv.), potassium carbonate 1.0 M (2.5 equiv.), and dioxane was heated at 90° C. for 16 hours. The mixture was then purified by preparative LC to give the title compound. LCMS [M+H]$^+$ 388.

conditions and the title compound was isolated after preparative LC. LCMS [M+H]$^+$ 367.

Example 133 tert-butyl 4-(2-amino-6-{[2-(4-sulfamoylphenyl)ethyl]amino}pyrimidin-4-yl)piperidine-1-carboxylate Palladium (10% on carbon) was added to tert-butyl 4-[2-amino-6-[2-(4-sulfamoylphenyl)ethylamino]pyrimidin-4-yl]-3,6-dihydro-2H-pyridine-1-carboxylate (example 131) in methanol. The solution was purged with N$_2$ for 5 minutes followed by dropwise addition of formic acid (3.0 equiv.) and the resulting mixture was stirred at 50° C. for 5 h. The mixture was then filtered and purified by preparative LC to give the title compound. LCMS [M+H]$^+$ 477.

Example 134

4-{2-[(2-amino-6-cycloheptylpyrimidin-4-yl)amino]ethyl}benzene-1-sulfonamide

Palladium (10% on carbon) was added to 4-[2-[[2-amino-6-(cyclohepten-1-yl)pyrimidin-4-yl]amino]ethyl]benzenesulfonamide (example 132) in methanol. The solution was purged with N$_2$ for 5 minutes followed by dropwise addition of formic acid (3.0 equiv.) and the resulting mixture was stirred at 90° C. for 4 h. The mixture was then filtered and purified by preparative LC to give the title compound. LCMS [M+H]$^+$ 390.

Example 135

4-(2-{[6-(1-acetyl-1,2,3,6-tetrahydropyridin-4-yl)-2-aminopyrimidin-4-yl]amino}ethyl)benzene-1-sulfonamide Prepared according to general procedure 9 from 4-[2-[[2-amino-6-(1,2,3,6-tetrahydropyridin-4-yl)pyrimidin-4-yl]amino]ethyl]benzenesulfonamide hydrochloride (intermediate 20) and acetyl chloride. LCMS [M+H] 417.

Example 136

4-[2-({2-amino-6-[1-(2-methylpropanoyl)-1,2,3,6-tetrahydropyridin-4-yl]pyrimidin-4-yl}amino)ethyl]benzene-1-sulfonamide Prepared according to general procedure 9 from 4-[2-[[2-amino-6-(1,2,3,6-tetrahydropyridin-4-yl)pyrimidin-4-yl]amino]ethyl]benzenesulfonamide hydrochloride and 2-methylpropanoyl chloride. LCMS [M+H]$^+$ 445.

Example 137

4-(2-{[2-amino-6-(1-methanesulfonyl-1,2,3,6-tetrahydropyridin-4-yl)pyrimidin-4-yl]amino}ethyl)benzene-1-sulfonamide Prepared according to general procedure 9 from 4-[2-[[2-amino-6-(1,2,3,6-tetrahydropyridin-4-yl)pyrimidin-4-yl]amino]ethyl]benzenesulfonamide hydrochloride (intermediate 20) and methanesulfonyl chloride. LCMS [M+H]$^+$ 453.

Example 138

4-[2-({2-amino-6-[1-(1,2-oxazole-5-carbonyl)-1,2,3,6-tetrahydropyridin-4-yl]pyrimidin-4-yl}amino)ethyl]benzene-1-sulfonamide Prepared according to general procedure 9 from 4-[2-[[2-amino-6-(1,2,3,6-tetrahydropyridin-4-yl)pyrimidin-4-yl]

amino]ethyl]benzenesulfonamide hydrochloride (intermediate 20) and (isoxazole-5-carbonyl chloride. LCMS [M+H]$^+$ 470.

Example 139

4-(2-{[2-amino-6-(1-cyclopentanecarbonyl-1,2,3,6-tetrahydropyridin-4-yl)pyrimidin-4-yl]amino}ethyl)benzene-1-sulfonamide Prepared according to general procedure 9 from 4-[2-[[2-amino-6-(1,2,3,6-tetrahydropyridin-4-yl)pyrimidin-4-yl]amino]ethyl]benzenesulfonamide hydrochloride (intermediate 20) and cyclopentanecarbonyl chloride. LCMS [M+H]$^+$ 471.

Example 140

4-[2-({2-amino-6-[1-(2-cyclopentylacetyl)-1,2,3,6-tetrahydropyridin-4-yl]pyrimidin-4-yl}amino)ethyl]benzene-1-sulfonamide Prepared according to general procedure 9 from 4-[2-[[2-amino-6-(1,2,3,6-tetrahydropyridin-4-yl)pyrimidin-4-yl]amino]ethyl]benzenesulfonamide hydrochloride (intermediate 20) and 2-cyclopentylacetyl chloride. LCMS [M+H]$^+$ 485.

Example 141

4-[2-({2-amino-6-[1-(4-methylbenzoyl)-1,2,3,6-tetrahydropyridin-4-yl]pyrimidin-4-yl}amino)ethyl]benzene-1-sulfonamide Prepared according to general procedure 9 from 4-[2-[[2-amino-6-(1,2,3,6-tetrahydropyridin-4-yl)pyrimidin-4-yl]amino]ethyl]benzenesulfonamide hydrochloride (intermediate 20) and 4-methylbenzoyl chloride. LCMS [M+H]$^+$ 493. $^1$H NMR (400 MHz, DMSO-d$_6$) δ ppm 11.59 (br. s., 1H), 8.70-8.94 (m, 1H), 7.70-7.79 (m, 2H), 7.45 (d, J=8.2 Hz, 2H), 7.23-7.38 (m, 6H), 6.60 (br. s., 2H), 6.03 (s, 1H), 4.14-4.41 (m, 2H), 3.57-3.71 (m, 4H), 2.94 (t, J=7.1 Hz, 2H), 2.38-2.43 (m, 2H), 2.35 (s, 3H).

Example 142

4-{2-[(2-amino-6-methylpyrimidin-4-yl)amino]ethyl}benzene-1-sulfonamide

Step 1: A mixture 2,4-dichloro-6-methyl-pyrimidine (1.0 equiv.), 4-(2-aminoethyl)benzenesulfonamide (1.2 equiv.), and diisopropylethylamine (2.0 equiv.) were suspended in 2-propanol and stirred at 90° C. for 16 h. The mixture was then diluted with NaHCO$_3$ (aq) and extracted with DCM×3. The combined organics were concentrated and the crude residue was purified by silica gel chromatography.
Step 2: the material from step 1 was suspended in ammonium hydroxide and stirred at 150° C. for 16 h. The mixture was concentrated and the title compound was isolated by preparative LC.
LCMS [M+H]$^+$ 308.

Example 143

4-[3-[[2-amino-6-(3-chloro-2-methyl-phenyl)pyrimidin-4-yl]amino]propylamino]benzamide Step 1. 4-(3-aminopropylamino)benzamide was prepared according to general procedure 4 from 4-iodobenzamide and propane-1,3-diamine.

Step 2. The title compound was produced according to general procedure 2 from 4-(3-aminopropylamino)benzamide and intermediate 3. [M+H]$^+$ 411. $^1$H NMR (400 MHz, METHANOL-d$_4$) δ ppm 7.63-7.69 (m, 2H), 7.40 (dd, J=7.7, 1.4 Hz, 1H), 7.13-7.24 (m, 2H), 6.62 (d, J=8.8 Hz, 2H), 5.82 (s, 1H), 3.48 (br. s., 2H), 3.24 (t, J=6.6 Hz, 2H), 2.31 (s, 3H), 1.92 (t, J=6.8 Hz, 2H).

Example 144

4-[3-[[2-amino-6-(3-chloro-2-methyl-phenyl)pyrimidin-4-yl]amino]propylamino]-N-methyl-benzenesulfonamide Step 1. 4-(3-aminopropylamino)-N-methyl-benzenesulfonamide was prepared according to general procedure 4 from 4-iodo-N-methyl-benzenesulfonamide and propane-1,3-diamine.
Step 2. The title compound was produced according to general procedure 2 from 4-(3-aminopropylamino)-N-methyl-benzenesulfonamide and intermediate 3. [M+H]$^+$ 461. $^1$H NMR (400 MHz, METHANOL-d$_4$) δ ppm 7.51-7.56 (m, 2H), 7.38-7.43 (m, 1H), 7.15-7.24 (m, 2H), 6.68 (d, J=8.8 Hz, 2H), 5.82 (s, 1H), 3.48 (br. s., 2H), 3.25 (t, J=6.8 Hz, 2H), 2.46 (s, 3H), 2.32 (s, 3H), 1.92 (quin, J=6.9 Hz, 2H).

Example 145

6-(3-chloro-2-methyl-phenyl)-N4-[3-[(2-methyl-1,3-benzothiazol-6-yl)amino]propyl]pyrimidine-2,4-diamine Step 1. N'-(2-methyl-1,3-benzothiazol-6-yl)propane-1,3-diamine was prepared according to general procedure 4 from 6-iodo-2-methyl-1,3-benzothiazole and propane-1,3-diamine.
Step 2. The title compound was produced according to general procedure 2 from N'-(2-methyl-1,3-benzothiazol-6-yl)propane-1,3-diamine and intermediate 3. [M+H]$^+$ 439. $^1$H NMR (400 MHz, METHANOL-d$_4$) δ ppm 7.83 (d, J=8.8 Hz, 1H), 7.58-7.63 (m, 2H), 7.30-7.39 (m, 2H), 7.26 (dd, J=8.8, 2.5 Hz, 1H), 6.04 (s, 1H), 3.67 (t, J=6.8 Hz, 2H), 3.40-3.46 (m, 2H), 2.84 (s, 3H), 2.37 (s, 3H), 2.07 (quin, J=7.1 Hz, 2H).

Example 146

2-[2-[[2-amino-6-(3-chloro-2-methyl-phenyl)pyrimidin-4-yl]amino]ethylamino]pyrimidine-4-carboxamide The title compound was produced according to general procedure 3 from intermediate 22 and 2-chloropyrimidine-4-carboxamide. LCMS [M+H]$^+$ 399. $^1$H NMR (400 MHz, METHANOL-d$_4$) δ ppm 8.49 (d, J=5.4 Hz, 1H), 7.60 (dd, J=8.1, 1.4 Hz, 1H), 7.28-7.39 (m, 2H), 7.18-7.22 (m, 1H), 5.97 (s, 1H), 3.77 (s, 4H), 2.35 (s, 3H).

Example 147

The title compound was produced according to general procedure 3 from intermediate 22 and 6-chloropyridine-3-carboxamide. LCMS [M+H]$^+$ 398. $^1$H NMR (400 MHz, METHANOL-d$_4$) δ ppm 8.48 (d, J=1.9 Hz, 1H), 8.23 (d, J=9.2 Hz, 1H), 7.61 (dd, J=7.6, 1.6 Hz, 1H), 7.30-7.40 (m, 2H), 7.01 (d, J=9.5 Hz, 1H), 6.06 (s, 1H), 3.80-3.87 (m, 2H), 3.70-3.78 (m, 2H), 2.37 (s, 3H).

Example 148

1-[3-[2-[[2-amino-6-(3-chloro-2-methyl-phenyl) pyrimidin-4-yl]amino]ethyl]phenyl]-3-ethyl-urea The title compound was produced according to general procedure 8 from intermediate 12 and ethyl isocyanate. LCMS [M+H]$^+$ 425. $^1$H NMR (400 MHz, METHANOL-d$_4$) δ ppm 7.40 (dd, J=7.4, 1.7 Hz, 1H), 7.32 (s, 1H), 7.14-7.24 (m, 4H), 6.88 (d, J=6.6 Hz, 1H), 5.78 (s, 1H), 3.59 (br. s., 2H), 3.22 (q, J=7.3 Hz, 2H), 2.85 (t, J=7.3 Hz, 2H), 2.32 (s, 3H), 1.12-1.17 (m, 3H).

Example 149

1-[3-[2-[[2-amino-6-(3-chloro-2-methyl-phenyl) pyrimidin-4-yl]amino]ethyl]phenyl]-3-tert-butyl-urea The title compound was produced according to general procedure 8 from intermediate 12 and tert-butyl isocyanate. LCMS [M+H]$^+$ 453. $^1$H NMR (400 MHz, METHANOL-d$_4$) δ ppm 7.56-7.62 (m, 1H), 7.45 (t, J=1.7 Hz, 1H), 7.32-7.36 (m, 2H), 7.14-7.19 (m, 1H), 6.99 (ddd, J=8.1, 2.2, 1.1 Hz, 1H), 6.87 (dq, J=7.6, 0.8 Hz, 1H), 6.01 (s, 1H), 3.77 (s, 2H), 2.90 (s, 2H), 2.37 (s, 3H), 1.34-1.37 (m, 9H).

Example 150

N-[3-[2-[[2-amino-6-(3-chloro-2-methyl-phenyl) pyrimidin-4-yl]amino]ethyl]phenyl]morpholine-4-carboxamide A mixture of N4-[2-(3-aminophenyl)ethyl]-6-(3-chloro-2-methyl-phenyl)pyrimidine-2,4-diamine (intermediate 12) (1 equiv.), morpholine-4-carbonyl chloride (1.4 equiv.), and diisopropylethylamine (1.6 equiv.) in DCM was stirred at reflux for 16 h. The reaction mixture was concentrated and purified by preparative LC. LCMS [M+H]$^+$ 467. $^1$H NMR (400 MHz, METHANOL-d$_4$) δ ppm 7.58-7.62 (m, 1H), 7.41 (t, J=1.7 Hz, 1H), 7.33-7.36 (m, 2H), 7.19-7.24 (m, 1H), 7.11-7.14 (m, 1H), 6.94-6.98 (m, 1H), 6.00 (s, 1H), 3.78 (t, J=7.1 Hz, 2H), 3.68-3.73 (m, 4H), 3.48-3.53 (m, 4H), 2.92 (t, J=7.1 Hz, 2H), 2.37 (s, 3H).

Example 151

3-[3-[2-[[2-amino-6-(3-chloro-2-methyl-phenyl) pyrimidin-4-yl]amino]ethyl]phenyl]-1,1-dimethyl-urea A mixture of N4-[2-(3-aminophenyl)ethyl]-6-(3-chloro-2-methyl-phenyl)pyrimidine-2,4-diamine (1 equiv.), N,N-dimethylcarbamoyl chloride (1.3 equiv.), and diisopropylethylamine (1.6 equiv.) was stirred at 150° C. for 10 min. The reaction mixture was concentrated and purified by preparative LC. LCMS [M+H]$^+$ 425. $^1$H NMR (400 MHz, METHANOL-d$_4$) δ ppm 7.58-7.62 (m, 1H), 7.41 (t, J=1.7 Hz, 1H), 7.33-7.36 (m, 2H), 7.18-7.24 (m, 1H), 7.11-7.15 (m, 1H), 6.92-6.96 (m, 1H), 6.01 (s, 1H), 3.78 (t, J=7.1 Hz, 2H), 3.01-3.03 (m, 6H), 2.89-2.94 (m, 2H), 2.37 (s, 3H).

Example 152

N-[3-[2-[[2-amino-6-(3-chloro-2-methyl-phenyl) pyrimidin-4-yl]amino]ethyl]phenyl]pyrrolidine-1-carboxamide A mixture of N4-[2-(3-aminophenyl)ethyl]-6-(3-chloro-2-methyl-phenyl)pyrimidine-2,4-diamine (1 equiv.), pyrrolidine-1-carbonyl chloride (1.3 equiv.), and diisopropylethylamine (1.6 equiv.) was stirred at 150° C. for 10 min. The reaction mixture was concentrated and purified by preparative LC. LCMS [M+H]$^+$ 451. $^1$H NMR (400 MHz, METHANOL-d$_4$) δ ppm 7.58-7.61 (m, 1H), 7.46 (t, J=1.6 Hz, 1H), 7.33-7.36 (m, 2H), 7.17-7.23 (m, 2H), 6.94 (dt, J=7.1, 1.7 Hz, 2H), 6.01 (s, 1H), 3.78 (t, J=7.1 Hz, 2H), 3.43-3.48 (m, 4H), 2.92 (t, J=7.1 Hz, 2H), 2.37 (s, 3H), 1.95-2.00 (m, 4H).

Example 153 isopropyl N-[3-[2-[[2-amino-6-(3-chloro-2-methyl-phenyl)pyrimidin-4-yl]amino]ethyl]phenyl]carbamate The title compound was produced according to general procedure 6 from intermediate 12 and isopropyl carbonochloridate. LCMS [M+H]$^+$ 440. $^1$H NMR (400 MHz, METHANOL-d$_4$) δ ppm 7.60 (dd, J=6.3, 2.8 Hz, 1H), 7.47 (s, 1H), 7.33-7.36 (m, 2H), 7.17-7.23 (m, 2H), 6.92-6.96 (m, 1H), 6.00 (s, 1H), 4.91-4.98 (m, 1H), 3.77 (t, J=7.1 Hz, 2H), 2.92 (t, J=7.1 Hz, 2H), 2.37 (s, 3H), 1.27-1.31 (m, 6H).

Example 154 isobutyl N-[3-[2-[[2-amino-6-(3-chloro-2-methyl-phenyl)pyrimidin-4-yl]amino]ethyl]phenyl]carbamate The title compound was produced according to general procedure 6 from intermediate 12 and isobutyl carbonochloridate. LCMS [M+H]$^+$ 454. $^1$H NMR (400 MHz, METHANOL-d$_4$) δ ppm 7.58-7.61 (m, 1H), 7.48 (s, 1H), 7.33-7.35 (m, 2H), 7.18-7.24 (m, 2H), 6.92-6.97 (m, 1H), 6.00 (s, 1H), 3.90 (d, J=6.6 Hz, 2H), 3.77 (t, J=7.1 Hz, 2H), 2.93 (t, J=7.1 Hz, 2H), 2.37 (s, 3H), 1.91-2.03 (m, 1H), 0.96-1.01 (m, 6H).

Example 155

2,2-dimethylpropyl N-[3-[2-[[2-amino-6-(3-chloro-2-methyl-phenyl)pyrimidin-4-yl]amino]ethyl]phenyl]carbamate The title compound was produced according to general procedure 6 from intermediate 12 and 2,2-dimethylpropyl carbonochloridate. LCMS [M+H]$^+$ 468. $^1$H NMR (400 MHz, METHANOL-d$_4$) δ ppm 7.57-7.61 (m, 1H), 7.49 (br. s., 1H), 7.33-7.35 (m, 2H), 7.19-7.24 (m, 2H), 6.95 (dt, J=6.2, 1.9 Hz, 1H), 6.00 (s, 1H), 3.83 (s, 2H), 3.77 (s, 2H), 2.93 (s, 2H), 2.37 (s, 3H), 0.97-1.01 (m, 9H).

Example 156

1-[6-[2-[[2-amino-6-(3-chloro-2-methyl-phenyl) pyrimidin-4-yl]amino]ethylamino]-3-pyridyl]-3-tert-butyl-urea Step 1. A mixture of intermediate 3 (1 equiv.), N-(2-aminoethyl)-5-nitropyridin-2-amine, (1.3 equiv.), and Hünig's base (1.5 equiv.) was stirred in 2-propanol at 120° C. for 16 h. The mixture was then poured into water and extracted with DCM×3. The combined organics were dried (MgSO₄) and concentrated. The crude material was used in step 2 without further purification.

Step 2. The crude material from step 1 (1 equiv.) was dissolved in EtOH, then SnCl₂ (5 equiv.) was added and the resulting mixture was stirred at reflux for 5 h. The mixture was then cooled and basified by addition of NaOH (5 M). The mixture was then extracted with DCM×3. The combined organics were dried (MgSO₄) and concentrated. The crude material was used in step 3 without further purification.

Step 3. A mixture of the crude material from step 2 (1 equiv.) and tert-butyl isocyanate (3 equiv.) in DCM was stirred at reflux for 16 h. The mixture was then concentrated and purified by prep-LC. LCMS [M+H]⁺ 469. ¹H NMR (400 MHz, METHANOL-d₄) δ ppm 8.18 (dd, J=2.5, 0.6 Hz, 1H), 7.77 (dd, J=9.5, 2.5 Hz, 1H), 7.60 (dd, J=7.7, 2.1 Hz, 1H), 7.30-7.38 (m, 2H), 7.07 (dd, J=9.6, 0.8 Hz, 1H), 6.07 (s, 1H), 3.82 (s, 2H), 3.66 (s, 2H), 2.36 (s, 3H), 1.36 (s, 9H).

Example 157 tert-butyl N-[6-[2-[[2-amino-6-(3-chloro-2-methyl-phenyl)pyrimidin-4-yl]amino]ethylamino]-3-pyridyl]carbamate Step 1. A mixture of intermediate 3 (1 equiv.), N-(2-aminoethyl)-5-nitropyridin-2-amine, (1.3 equiv.), and Hünig's base (1.5 equiv.) was stirred in 2-propanol at 120° C. for 16 h. The mixture was then poured into water and extracted with DCM×3. The combined organics were dried (MgSO4) and concentrated. The crude material was used in step 2 without further purification.

Step 2. The crude material from step 1 (1 equiv.) was dissolved in EtOH, then SnCl₂ (5 equiv.) was added and the resulting mixture was stirred at reflux for 5 h. The mixture was then cooled and basified by addition of NaOH (5 M). The mixture was then extracted with DCM×3. The combined organics were dried (MgSO₄) and concentrated. The crude material was used in step 3 without further purification.

Step 3. A mixture of the crude material from step 2 and di-tert-butyl dicarbonate in DCM was stirred at reflux for 16 h. The mixture was then concentrated and purified by prep-LC. LCMS [M+H]⁺ 470. ¹H NMR (400 MHz, METHANOL-d₄) δ ppm 8.23 (br. s., 1H), 7.84 (dd, J=9.5, 2.5 Hz, 1H), 7.58-7.62 (m, 1H), 7.28-7.38 (m, 2H), 7.09 (dd, J=9.8, 0.6 Hz, 1H), 6.07 (s, 1H), 3.80-3.86 (m, 2H), 3.64-3.70 (m, 2H), 2.36 (s, 3H), 1.51 (s, 9H).

Example 158

N2-[2-[[2-amino-6-(3-chloro-2-methyl-phenyl)pyrimidin-4-yl]amino]ethyl]-1,3,5-triazine-2,4,6-triamine The title compound was produced according to general procedure 3 from intermediate 22 and 6-chloro-1,3,5-triazine-2,4-diamine. LCMS [M+H]⁺ 387.

Example 159

2-[2-[[2-amino-6-(3-chloro-2-methyl-phenyl)pyrimidin-4-yl]amino]ethylamino]-4-(trifluoromethyl)pyrimidine-5-carboxamide The title compound was produced according to general procedure 3 from intermediate 22 and 2-chloro-4-(trifluoromethyl)pyrimidine-5-carboxamide. LCMS [M+H]⁺ 467. ¹H NMR (400 MHz, METHANOL-d₄) δ ppm 8.50-8.62 (m, 1H), 7.57-7.61 (m, 1H), 7.29-7.38 (m, 2H), 5.99 (d, J=7.3 Hz, 1H), 3.76 (br. s., 4H), 2.37 (s, 3H).

Example 160

6-(3-chloro-2-methyl-phenyl)-N4-[2-(4-isopropyl-sulfonylanilino)ethyl]pyrimidine-2,4-diamine Step 1. N'-(4-isopropylsulfonylphenyl)ethane-1,2-diamine was prepared according to general procedure 4 from 1-bromo-4-isopropylsulfonyl-benzene and ethylenediamine.

Step 2. The title compound was prepared according to general procedure 2 from the crude material of step 1 and intermediate 3. [M+H]⁺ 460. ¹H NMR (400 MHz, METHANOL-d₄) δ ppm 7.51-7.62 (m, 3H), 7.29-7.39 (m, 2H), 6.74-6.79 (m, 2H), 6.01 (s, 1H), 3.76 (t, J=6.2 Hz, 2H), 3.51 (t, J=6.2 Hz, 2H), 3.13-3.22 (m, 1H), 2.37 (s, 3H), 1.22 (d, J=7.0 Hz, 6H).

Example 161

6-(3-chloro-2-methyl-phenyl)-N4-[2-(4-methylsulfinylanilino)ethyl]pyrimidine-2,4-diamine Step 1. N'-(4-methylsulfinylphenyl)ethane-1,2-diamine was prepared according to general procedure 4 from 1-bromo-4-methylsulfinyl-benzene and ethylenediamine.

Step 2. The title compound was prepared according to general procedure 2 from the crude material of step 1 and intermediate 3. LCMS [M+H]⁺ 416.

Example 162

4-[2-[[2-amino-6-(3-chloro-2-methyl-phenyl)pyrimidin-4-yl]amino]ethyl]-3-fluoro-benzamide Step 1. 4-(2-aminoethyl)-3-fluoro-benzamide was prepared according to general procedure 10 from 4-bromo-3-fluoro-benzamide.

Step 2. The title compound was prepared according to general procedure 2 from the material from step 1 and intermediate 3. [M+H]⁺ 400.

Example 163

4-[3-[[2-amino-6-(3-chloro-2-methyl-phenyl)pyrimidin-4-yl]amino]propylamino]benzenesulfonamide Step 1. 4-(3-aminopropylamino)benzenesulfonamide was prepared according to general procedure 4 from 4-iodobenzenesulfonamide and propane-1,3-diamine.

Step 2. The title compound was prepared according to general procedure 2 from 4-(3-aminopropylamino)benzenesulfonamide and intermediate 3. LCMS [M+H]⁺ 447.

Example 164

4-[[3-[[2-amino-6-(3-chloro-2-methyl-phenyl)pyrimidin-4-yl]amino]-2,2-dimethyl-propyl]amino]benzenesulfonamide Step 1. A mixture of 4-bromobenzenesulfonamide (1 equiv.), CuCl (0.1 equiv.), and KOH (2 equiv.) were stirred in 2,2-dimethylpropane-1,3-diamine (5 equiv.) at 40° C. for 72 h. the reaction mixture was extracted with hot EtOAc and concentrated. The crude 4-[(3-amino-2,2-dimethyl-propyl)amino]benzenesulfonamide was then washed with diethyl ether and used in step 2.

Step 2. The title compound was prepared according to general procedure 2 from 4-[(3-amino-2,2-dimethyl-propyl)amino]benzenesulfonamide and intermediate 3. LCMS [M+H]$^+$ 475.

Example 165

6-(3-chloro-2-methyl-phenyl)-N4-[2,2-dimethyl-3-[(2-methyl-1,3-benzothiazol-6-yl)amino]propyl]pyrimidine-2,4-diamine Step 1. A mixture of 6-iodo-2-methyl-1,3-benzothiazole (1 equiv.), CuCl (0.1 equiv.), and KOH (2 equiv.) were stirred in 2,2-dimethylpropane-1,3-diamine (5 equiv.) at 40° C. for 72 h. the reaction mixture was extracted with hot EtOAc and concentrated. The crude residue was then purified by preparative LC to afford 2,2-dimethyl-N'-(2-methyl-1,3-benzothiazol-6-yl)propane-1,3-diamine. [M+H]$^+$ 250.

Step 2. The title compound was prepared according to general procedure 2 from 2,2-dimethyl-N'-(2-methyl-1,3-benzothiazol-6-yl)propane-1,3-diamine and intermediate 3. LCMS [M+H]$^+$ 467. $^1$H NMR (400 MHz, METHANOL-d4) δ ppm 7.56-7.61 (m, 2H), 7.31-7.37 (m, 1H), 7.25-7.30 (m, 1H), 7.12 (d, J=2.2 Hz, 1H), 6.92-6.97 (m, 1H), 6.09 (s, 1H), 3.59 (s, 2H), 3.08 (s, 2H), 2.75 (s, 3H), 2.32 (s, 3H), 1.11 (s, 6H).

Example 166

6-(3-Chloro-2-methyl-phenyl)-N4-[2-(3-isopropyl-sulfonylanilino)ethyl]pyrimidine-2,4-diamine Step 1. N'-(3-isopropylsulfonylphenyl)ethane-1,2-diamine was prepared according to general procedure 4 from 1-bromo-3-isopropylsulfonyl-benzene and ethylenediamine.

Step 2. The title compound was prepared according to general procedure 2 from N'-(3-isopropylsulfonylphenyl)ethane-1,2-diamine and 4-chloro-6-(3-chloro-2-methyl-phenyl)pyrimidin-2-amine. LCMS [M+H]$^+$ 460. $^1$H NMR (400 MHz, METHANOL-d$_4$) δ ppm 7.59-7.62 (m, 1H), 7.35 (s, 3H), 7.22-7.25 (m, 1H), 7.05-7.09 (m, 1H), 6.94-6.98 (m, 1H), 6.01 (s, 1H), 3.65-3.70 (m, 2H), 3.45-3.50 (m, 2H), 2.38 (s, 3H), 1.26 (d, J=7.0 Hz, 6H).

Example 167

6-[3-[[2-amino-6-(3-chloro-2-methyl-phenyl)pyrimidin-4-yl]amino]propylamino]pyridine-3-carboxamide The title compound was prepared according to general procedure 3 from 6-chloropyridine-3-carboxamide and intermediate 23. LCMS [M+H]$^+$ 412.

Example 168

2-[3-[[2-amino-6-(3-chloro-2-methyl-phenyl)pyrimidin-4-yl]amino]propylamino]pyrimidine-4-carboxamide The title compound was prepared according to general procedure 3 from 2-chloropyrimidine-4-carboxamide and intermediate 23. LCMS [M+H]$^+$ 413.

Example 169

6-(3-chloro-2-methyl-phenyl)-N4-[2-(4-isopropyl-sulfonylphenyl)ethyl]pyrimidine-2,4-diamine Step 1. 2-(4-isopropylsulfonylphenyl)ethanamine was prepared according to general procedure 10 from 1-bromo-4-isopropylsulfonyl-benzene.

Step 2. The title compound was prepared according to general procedure 2 from 2-(4-isopropylsulfonylphenyl)ethanamine and intermediate 3. LCMS [M+H]$^+$ 445.

Example 170

Step 1. 2-(3-isopropylsulfonylphenyl)ethanamine was prepared according to general procedure 10 from 1-bromo-3-isopropylsulfonyl-benzene.

Step 2. The title compound was prepared according to general procedure 2 from 2-(3-isopropylsulfonylphenyl)ethanamine and intermediate 3. LCMS [M+H]$^+$ 445. $^1$H NMR (400 MHz, METHANOL-d4) δ ppm 7.73-7.80 (m, 2H), 7.67 (s, 1H), 7.60 (t, J=7.4 Hz, 2H), 7.31-7.38 (m, 2H), 5.98 (d, J=1.6 Hz, 1H), 3.85 (t, J=7.0 Hz, 2H), 3.34 (obstructed by solvent signal, m, 1H), 3.10 (t, J=7.0 Hz, 2H), 2.36 (s, 3H), 1.24 (d, J=7.0 Hz, 6H).

Example 171

4-[2-[[2-amino-6-(3-chloro-2-methyl-phenyl)pyrimidin-4-yl]amino]ethyl]-2-fluoro-benzamide Step 1. 4-(2-aminoethyl)-2-fluoro-benzamide was prepared according to general procedure 10 from 4-bromo-2-fluoro-benzamide.

Step 2. The title compound was prepared according to general procedure 2 from 4-(2-aminoethyl)-2-fluoro-benzamide and intermediate 3. LCMS [M+H]$^+$ 400. $^1$H NMR (400 MHz, METHANOL-d4) δ ppm 7.79 (t, J=7.9 Hz, 1H), 7.58-7.62 (m, 1H), 7.30-7.38 (m, 2H), 7.22 (dd, J=7.9, 1.6 Hz, 1H), 7.18 (dd, J=12.2, 1.4 Hz, 1H), 6.00 (s, 1H), 3.82 (t, J=7.1 Hz, 2H), 3.03 (t, J=7.1 Hz, 2H), 2.37 (s, 3H).

Example 172

6-(3-chloro-2-methyl-phenyl)-N4-[2-(3-fluoro-4-methylsulfonyl-phenyl)ethyl]pyrimidine-2,4-diamine Step 1. 2-(3-fluoro-4-methylsulfonyl-phenyl)ethylamine was prepared according to general procedure 10 from 4-bromo-2-fluoro-1-methylsulfonyl-benzene.

Step 2. The title compound was prepared according to general procedure 2 from 2-(3-fluoro-4-methylsulfonyl-phenyl)ethylamine and intermediate 3. LCMS [M+H]$^+$ 435. $^1$H NMR (400 MHz, METHANOL-d4) δ ppm 7.86 (t, J=7.7 Hz, 1H), 7.58-7.62 (m, 1H), 7.31-7.38 (m, 4H), 6.00 (s, 1H), 3.84 (t, J=7.0 Hz, 2H), 3.22-3.24 (m, 3H), 3.08 (t, J=7.0 Hz, 2H), 2.37 (s, 3H).

Example 173

5-[2-[[2-amino-6-(3-chloro-2-methyl-phenyl)pyrimidin-4-yl]amino]ethyl]-2-hydroxy-benzamide Step 1. 2-(3-carbamoyl-4-hydroxy-phenyl)ethylamine was prepared according to general procedure 10 from 6-bromo-2,2-dimethyl-3H-1,3-benzoxazin-4-one.

Step 2. The title compound was prepared according to general procedure 2 from 2-(3-carbamoyl-4-hydroxy-phenyl)ethylamine and intermediate 3. LCMS [M+H]+ 398.

Example 174

2-[2-[[2-amino-6-(3-chloro-2-methyl-phenyl)pyrimidin-4-yl]amino]ethylsulfanyl]pyrimidine-4-carboxamide Step 1. A mixture of 2-(2-aminoethylsulfanyl)pyrimidine-4-carboxamide (1 equiv.), 2-(2-aminoethylsulfanyl)pyrimidine-4-carboxamide (1.2 equiv.), and Hünig's base (2 equiv.) in 2-propanol was stirred at 150° C. for 30 min. Thereafter the mixture was concentrated and purified by silica gel chromatography which afforded 2-(2-aminoethylsulfanyl)pyrimidine-4-carboxamide. LCMS [M+H]+ 299. $^1$H NMR (400 MHz, CHLOROFORM-d) δ ppm 8.80 (br. s., 1H), 8.74 (d, J=5.1 Hz, 1H), 7.80 (d, J=4.7 Hz, 1H), 5.67 (br. s., 1H), 5.01 (br. s., 1H), 3.44-3.52 (m, 2H), 3.23-3.30 (m, 2H), 1.45 (s, 9H).

Step 2. A mixture of 2-(2-aminoethylsulfanyl)pyrimidine-4-carboxamide and TFA was stirred at 20° C. for 1 h. Thereafter the mixture was concentrated to afford 2-(2-aminoethylsulfanyl)pyrimidine-4-carboxamide which was used without purification in step 3.

Step 3. The title compound was prepared according to general procedure 2 from 2-(2-aminoethylsulfanyl)pyrimidine-4-carboxamide and intermediate 3. LCMS [M+H]+ 416.

Example 175

6-(3-chloro-2-methyl-phenyl)-N4-[2-[[5-[(dimethylamino)methyl]-2-furyl]methylsulfanyl]ethyl]pyrimidine-2,4-diamine The title compound was prepared according to general procedure 2 from 2-[[5-[(dimethylamino)methyl]-2-furyl]methylsulfanyl]ethanamine and intermediate 3. LCMS [M+H]+ 432.

Example 176

6-(3-chloro-2-methyl-phenyl)-N4-[2-[(4-methylsulfonylphenyl)methylsulfanyl]ethyl]pyrimidine-2,4-diamine Step 1. A mixture of 1-(chloromethyl)-4-methylsulfonylbenzene (1 equiv.), tert-butyl N-(2-sulfanylethyl)carbamate (1 equiv.), and Cs$_2$CO$_3$ (1 equiv.) was stirred in DMF at 60° C. for 16 h. Then the mixture was poured into sat. NaHCO$_3$ and extracted with DCM×3. The combined organics were dried (MgSO$_4$), concentrated, and purified by silica gel chromatography to afford tert-butyl N-[2-[(4-methylsulfonylphenyl)methylsulfanyl]ethyl]carbamate. $^1$H NMR (400 MHz, CHLOROFORM-d) δ ppm 7.90 (d, J=8.5 Hz, 2H), 7.55 (d, J=8.5 Hz, 2H), 3.80 (s, 2H), 3.27-3.35 (m, 2H), 3.07 (s, 3H), 2.55 (t, J=6.8 Hz, 2H), 1.46 (s, 9H).

Step 2. A mixture of tert-butyl N-[2-[(4-methylsulfonylphenyl)methylsulfanyl]ethyl]carbamate and TFA was stirred at 20° C. for 1 h. Thereafter the mixture was concentrated to afford 2-[(4-methylsulfonylphenyl)methylsulfanyl]ethanamine which was used without purification in step 3.

Step 3. A mixture of 2-[(4-methylsulfonylphenyl)methylsulfanyl]ethanamine (1 equiv.), 4,6-dichloropyrimidin-2-amine (1 equiv.), and Hünig's base (3 equiv.) was stirred in 2-propanol at 120° C. for 16 h. Then the mixture was poured into sat. NaHCO$_3$ and extracted with DCM×3. The combined organics were dried (MgSO$_4$), concentrated, and purified by silica gel chromatography to afford 6-chloro-N4-[2-[(4-methylsulfonylphenyl)methylsulfanyl]ethyl]pyrimidine-2,4-diamine.

Step 4. The title compound was prepared according to general procedure 1 from 6-chloro-N4-[2-[(4-methylsulfonylphenyl)methylsulfanyl]ethyl]pyrimidine-2,4-diamine and (3-chloro-2-methyl)phenylboronic acid. LCMS [M+H]+ 463. $^1$H NMR (400 MHz, CHLOROFORM-d) δ ppm 7.88-7.93 (m, 2H), 7.52-7.56 (m, 2H), 7.39 (dd, J=7.1, 2.4 Hz, 1H), 7.14-7.21 (m, 2H), 5.78 (s, 1H), 4.98-5.06 (m, 1H), 4.84 (s, 2H), 3.82 (s, 2H), 3.49-3.58 (m, 2H), 3.06 (s, 3H), 2.68 (t, J=6.5 Hz, 2H), 2.37 (s, 3H).

Example 177

6-(3-chloro-2-methyl-phenyl)-N4-[2-[(4-methylsulfonylphenyl)methylsulfinyl]ethyl]pyrimidine-2,4-diamine A mixture of 6-(3-chloro-2-methyl-phenyl)-N4-[2-[(4-methylsulfonylphenyl)methylsulfanyl]ethyl]pyrimidine-2,4-diamine prepared in example 176 (1 equiv.) and H$_2$O$_2$ (3 equiv.) in MeOH was stirred at 20° C. for 2 h. Thereafter the mixture was concentrated and purified by silica gel chromatography to afford the title compound. LCMS [M+H]+ 479. $^1$H NMR (400 MHz, CHLOROFORM-d) δ ppm 7.95-8.00 (m, 2H), 7.51-7.55 (m, 2H), 7.36-7.40 (m, 1H), 7.13-7.19 (m, 2H), 5.81 (s, 1H), 5.37 (t, J=5.7 Hz, 1H), 4.92 (s, 2H), 4.16 (d, J=13.0 Hz, 1H), 4.04 (d, J=13.3 Hz, 1H), 3.83-4.01 (m, 2H), 3.09-3.17 (m, 1H), 3.08 (s, 3H), 2.84 (dt, J=13.1, 5.1 Hz, 1H), 2.36 (s, 3H).

Example 178

Isopropyl 4-[2-[[2-amino-6-(3-chloro-2-methyl-phenyl)pyrimidin-4-yl]amino]ethyl]benzoate Step 1. A mixture of 2-(4-carboxyphenyl)ethylammonium chloride (1 equiv.) and H$_2$SO$_4$ (1 equiv.) was stirred in 2-propanol at reflux for 16 h. The mixture was poured into sat. NaHCO$_3$ and extracted with DCM×3. The combined organics were dried (MgSO$_4$) and concentrated. The crude isopropyl 4-(2-aminoethyl)benzoate was used in step 2 without further purification. LCMS [M+H]+ 208.

Step 2. The title compound was prepared according to general procedure 2 from isopropyl 4-(2-aminoethyl)benzoate and intermediate 3. LCMS [M+H]+ 425. $^1$H NMR (400 MHz, DMSO-d6) δ ppm 7.88 (d, J=8.2 Hz, 2H), 7.42 (d, J=8.2 Hz, 2H), 7.34-7.38 (m, 1H), 7.20-7.27 (m, 2H), 7.06 (br. s., 1H), 6.06 (br. s., 2H), 5.84 (s, 1H), 5.13 (spt, J=6.3 Hz, 1H), 3.52 (br. s., 2H), 2.92 (t, J=7.4 Hz, 2H), 2.38 (s, 3H), 1.32 (d, J=6.3 Hz, 6H).

Example 179

1-[3-[2-[[2-amino-6-(3-chloro-2-methyl-phenyl)pyrimidin-4-yl]amino]ethyl]phenyl]guanidine A mixture of Intermediate 12 (1 equiv.) and tert-butyl (NZ)—N-[(tert-butoxycarbonylamino)-pyrazol-1-yl-methylene]carbamate (1.4 equiv.) in 2-propanol was stirred at 150° C. for 1 h. The mixture was then concentrated and thereafter dissolved in TFA. The resulting mixture was stirred at 150° C. for 30 min. after which it was concentrated and purified by preparative LC. [M+H]+ 396. $^1$H NMR (400 MHz, METHANOL-d4) δ ppm 7.58-7.63 (m, 1H), 7.41-7.47 (m, 1H), 7.29-7.38 (m, 3H), 7.22 (t, J=1.7 Hz, 1H), 7.17 (ddd, J=7.9, 2.2, 1.3 Hz, 1H), 6.02 (s, 1H), 3.80 (t, J=7.3 Hz, 2H), 3.01 (t, J=7.3 Hz, 2H), 2.38 (s, 3H).

Example 180

6-[2-[[2-amino-6-(3-chloro-2-methyl-phenyl)pyrimidin-4-yl]amino]ethylsulfanyl]pyridine-3-sulfonamide Step 1. A mixture of 6-chloropyridine-3-sulfonamide (1 equiv.), tert-butyl N-(2-sulfanylethyl)carbamate (1.2 equiv.), and Hünig's base (2 equiv.) in 2-propanol was stirred at 120° C. for 16 h. The mixture was then concentrated, dissolved in DCM and passed through a short plug of silica. After concentration the crude residue was used without further purification in step 2.

Step 2. The crude residue from step 1 was stirred in TFA at 20° C. for 2 h. The TFA was then removed by co-evaporation with 2-propanol. Used without further purification in step 3. LCMS [M+H]+ 234.

Step 3. The title compound was prepared according to general procedure 2 from the material from step 2 and intermediate 3. LCMS [M+H]+ 451.

Example 181 methyl 4-[2-[[2-amino-6-(3-chloro-2-methyl-phenyl)pyrimidin-4-yl]amino]ethylsulfanylmethyl]benzoate Step 1. A mixture of methyl 4-(bromomethyl)benzoate (1 equiv.), tert-butyl N-(2-sulfanylethyl)carbamate (1.3 equiv.), and K$_2$CO$_3$ (1.1 equiv.) were stirred in DMF at 60° C. for 16 h. The mixture was poured into water and extracted with DCM×3. The combined organics were dried (MgSO$_4$), concentrated, and purified by silica gel chromatography to afford methyl 4-[2-(tert-butoxycarbonylamino)ethylsulfanylmethyl]benzoate.

Step 2. Methyl 4-[2-(tert-butoxycarbonylamino)ethylsulfanylmethyl]benzoate was stirred in TFA at 20° C. for 2 h. The TFA was then removed by co-evaporation with 2-propanol. Used without further purification in step 3.

Step 3. The title compound was prepared according to general procedure 2 from the material from step 2 and intermediate 3. LCMS [M+H]+ 443. $^1$H NMR (400 MHz, METHANOL-d4) δ ppm 7.94-7.98 (m, 2H), 7.60 (dd, J=7.0, 2.5 Hz, 1H), 7.47-7.51 (m, 2H), 7.33-7.37 (m, 2H), 6.02 (s, 1H), 3.89 (s, 3H), 3.87 (s, 2H), 3.66 (t, J=6.8 Hz, 2H), 2.71 (t, J=6.8 Hz, 2H), 2.38 (s, 3H).

Example 182 methyl 4-[2-[[2-amino-6-(3-chloro-2-methyl-phenyl)pyrimidin-4-yl]amino]ethyl]benzoate Step 1. A mixture of 2-(4-carboxyphenyl)ethylammonium chloride (1 equiv.) and H$_2$SO$_4$ (1 equiv.) was stirred in methanol at reflux for 16 h. The mixture was poured into sat. NaHCO$_3$ and extracted with DCM×3. The combined organics were dried (MgSO4) and concentrated. The crude methyl 4-(2-aminoethyl)benzoate was used in step 2 without further purification. LCMS [M+H]+ 180.

Step 2. The title compound was prepared according to general procedure 2 from methyl 4-(2-aminoethyl)benzoate and intermediate 3. LCMS [M+H]+ 397. $^1$H NMR (400 MHz, METHANOL-d4) δ ppm 7.94 (d, J=8.2 Hz, 2H), 7.35-7.43 (m, 3H), 7.13-7.25 (m, 2H), 5.76 (s, 1H), 3.89 (s, 3H), 3.60-3.71 (m, 2H), 2.98 (t, J=7.1 Hz, 2H), 2.30 (s, 3H).

Example 183 ethyl 4-[2-[[2-amino-6-(3-chloro-2-methyl-phenyl)pyrimidin-4-yl]amino]ethyl]benzoate Step 1. A mixture of 2-(4-carboxyphenyl)ethylammonium chloride (1 equiv.) and H$_2$SO$_4$ (1 equiv.) was stirred in ethanol at reflux for 16 h. The mixture was poured into sat. NaHCO$_3$ and extracted with DCM×3. The combined organics were dried (MgSO$_4$) and concentrated. The crude ethyl 4-(2-aminoethyl)benzoate was used in step 2 without further purification. LCMS [M+H]+ 194.

Step 2. The title compound was prepared according to general procedure 2 from ethyl 4-(2-aminoethyl)benzoate and intermediate 3. LCMS [M+H]+ 411. $^1$H NMR (400 MHz, METHANOL-d4) δ ppm 7.94 (d, J=8.2 Hz, 2H), 7.35-7.43 (m, 3H), 7.13-7.24 (m, 2H), 5.75 (s, 1H), 4.35 (q, J=7.3 Hz, 2H), 3.64 (br. s., 2H), 2.98 (t, J=7.1 Hz, 2H), 2.30 (s, 3H), 1.38 (t, J=7.1 Hz, 3H).

Example 184 propyl 4-[2-[[2-amino-6-(3-chloro-2-methyl-phenyl)pyrimidin-4-yl]amino]ethyl]benzoate Step 1. A mixture of 2-(4-carboxyphenyl)ethylammonium chloride (1 equiv.) and H$_2$SO$_4$ (1 equiv.) was stirred in 1-propanol at 90° C. for 16 h. The mixture was poured into sat. NaHCO$_3$ and extracted with DCM×3. The combined organics were dried (MgSO4) and concentrated. The crude propyl 4-(2-aminoethyl)benzoate was used in step 2 without further purification. LCMS [M+H]+ 208.

Step 2. The title compound was prepared according to general procedure 2 from propyl 4-(2-aminoethyl)benzoate and intermediate 3. LCMS [M+H]+ 425. $^1$H NMR (400 MHz, METHANOL-d4) δ ppm 7.95 (d, J=8.2 Hz, 2H), 7.36-7.43 (m, 3H), 7.14-7.24 (m, 2H), 5.76 (s, 1H), 4.23-4.29 (m, 2H), 3.60-3.70 (m, 2H), 2.99 (t, J=7.1 Hz, 2H), 2.30 (s, 3H), 1.73-1.85 (m, 2H), 1.04 (t, J=7.4 Hz, 3H).

Example 185

2-hydroxyethyl 4-[2-[[2-amino-6-(3-chloro-2-methyl-phenyl)pyrimidin-4-yl]amino]ethyl]benzoate A mixture of 4-[2-[[2-amino-6-(3-chloro-2-methyl-phenyl)pyrimidin-4-yl]amino]ethyl]benzoic acid (prepared in example 9) (1 equiv.) and H$_2$SO$_4$ (1 equiv.) was stirred in ethylene glycol at 120° C. for 2 h. The mixture was then purified by preparative LC. LCMS [M+H]+ 427.

Example 186

2-methylsulfonylethyl 4-[2-[[2-amino-6-(3-chloro-2-methyl-phenyl)pyrimidin-4-yl]amino]ethyl]benzoate A mixture of 4-[2-[[2-amino-6-(3-chloro-2-methyl-phenyl)pyrimidin-4-yl]amino]ethyl]benzoic acid (prepared in example 9) (1 equiv.) and H$_2$SO$_4$ (1 equiv.) was stirred in 2-methylsulfonylethanol at 120° C. for 2 h. The mixture was then purified by preparative LC. LCMS [M+H]+ 489.

Example 187

2,3-dihydroxypropyl 4-[2-[[2-amino-6-(3-chloro-2-methyl-phenyl)pyrimidin-4-yl]amino]ethyl]benzoate A mixture of 4-[2-[[2-amino-6-(3-chloro-2-methyl-phenyl)pyrimidin-4-yl]amino]ethyl]benzoic acid (prepared in example 9) (1 equiv.) and $H_2SO_4$ (1 equiv.) was stirred in glycerol at 120° C. for 2 h. The mixture was then purified by preparative LC. LCMS [M+H]$^+$ 457.

Example 188

6-(3-chloro-2-methyl-phenyl)-N4-[2-[(6-methylsulfonyl-3-pyridyl)amino]ethyl]pyrimidine-2,4-diamine Step 1. N'-(6-methylsulfonyl-3-pyridyl)ethane-1,2-diamine was prepared according to general procedure 4 from 5-bromo-2-methylsulfonyl-pyridine and ethylenediamine.

Step 2. The title compound was prepared according to general procedure 2 from N'-(6-methylsulfonyl-3-pyridyl)ethane-1,2-diamine and intermediate 3. LCMS [M+H]$^+$ 433. $^1$H NMR (400 MHz, METHANOL-d4) δ ppm 8.11 (d, J=2.8 Hz, 1H), 7.83 (d, J=8.8 Hz, 1H), 7.60 (dd, J=7.6, 1.6 Hz, 1H), 7.30-7.39 (m, 2H), 7.15 (dd, J=8.8, 2.8 Hz, 1H), 6.03 (s, 1H), 3.73-3.79 (m, 2H), 3.53 (t, J=6.3 Hz, 2H), 3.10 (s, 3H), 2.37 (s, 3H).

Example 189

N-[4-[2-[[2-amino-6-(3-chloro-2-methyl-phenyl)pyrimidin-4-yl]amino]ethylamino]-2-methyl-phenyl]acetamide Step 1. N-[4-(2-aminoethylamino)-2-methyl-phenyl]acetamide was prepared according to general procedure 4 from N-(4-iodo-2-methyl-phenyl)acetamide and ethylenediamine.

Step 2. The title compound was prepared according to general procedure 2 from N-[4-(2-aminoethylamino)-2-methyl-phenyl]acetamide and intermediate 3. LCMS [M+H]$^+$ 425. $^1$H NMR (400 MHz, METHANOL-d4) δ ppm 7.61 (dd, J=7.6, 1.6 Hz, 1H), 7.30-7.40 (m, 2H), 7.15 (d, J=8.2 Hz, 1H), 6.75 (d, J=12.6 Hz, 2H), 6.05 (s, 1H), 3.77 (t, J=6.0 Hz, 2H), 3.50 (d, J=5.1 Hz, 2H), 2.38 (s, 3H), 2.19 (s, 3H), 2.13 (s, 3H).

Example 190 methyl 4-[2-[[2-amino-6-(3-chloro-2-methyl-phenyl)pyrimidin-4-yl]amino]ethylsulfinylmethyl]benzoate A mixture of methyl 4-[2-[[2-amino-6-(3-chloro-2-methyl-phenyl)pyrimidin-4-yl]amino]ethylsulfanylmethyl]benzoate (prepared in example 181) (1 equiv.) and $H_2O_2$ (5 equiv.) in MeOH was stirred at 20° C. for 16 h. Thereafter the mixture was concentrated and purified by preparative LC to afford the title compound. LCMS [M+H]$^+$ 459. $^1$H NMR (400 MHz, METHANOL-d4) δ ppm 8.03-8.06 (m, 2H), 7.61 (dd, J=7.6, 1.9 Hz, 1H), 7.49-7.53 (m, 2H), 7.31-7.39 (m, 2H), 6.06 (s, 1H), 4.33 (d, J=13.0 Hz, 1H), 4.19 (d, J=13.0 Hz, 1H), 3.94-4.00 (m, 2H), 3.23 (ddd, J=13.7, 7.7, 6.3 Hz, 1H), 3.00 (dt, J=13.4, 5.4 Hz, 1H), 2.37 (s, 3H).

Example 191

6-(3-chloro-2-methyl-phenyl)-N4-[2-(4-ethylphenyl)ethyl]pyrimidine-2,4-diamine

The title compound was prepared according to general procedure 2 from 2-(4-ethylphenyl)ethanamine and intermediate 3. LCMS [M+H]$^+$ 367. $^1$H NMR (400 MHz, METHANOL-d4) δ ppm 7.59 (dd, J=7.6, 1.9 Hz, 1H), 7.30-7.38 (m, 2H), 7.12-7.20 (m, 4H), 6.00 (s, 1H), 3.75 (t, J=7.3 Hz, 2H), 2.91 (t, J=7.3 Hz, 2H), 2.61 (q, J=7.6 Hz, 2H), 2.37 (s, 3H), 1.20 (t, J=7.6 Hz, 3H).

Example 192 methyl 4-[2-[[2-amino-6-(3-chloro-2-methyl-phenyl)pyrimidin-4-yl]amino]ethylsulfonylmethyl]benzoate A mixture of methyl 4-[2-[[2-amino-6-(3-chloro-2-methyl-phenyl)pyrimidin-4-yl]amino]ethylsulfinylmethyl]benzoate prepared in example 190, (1 equiv.) and 3-chloroperbenzoic acid (1.5 equiv.) in DCM was stirred at 20° C. for 2 h. The mixture was concentrated and purified by silica gel chromatography to afford the title compound. LCMS [M+H]$^+$ 475. $^1$H NMR (400 MHz, METHANOL-d4) δ ppm 8.00-8.04 (m, 2H), 7.53-7.57 (m, 2H), 7.42 (dd, J=7.1, 2.1 Hz, 1H), 7.17-7.25 (m, 2H), 5.85 (s, 1H), 4.55 (s, 2H), 3.91 (s, 3H), 3.85 (t, J=6.5 Hz, 2H), 3.37 (t, J=6.3 Hz, 2H), 2.32 (s, 3H).

Example 193

4-[4-[[2-amino-6-(3-chloro-2-methyl-phenyl)pyrimidin-4-yl]amino]but-2-ynylsulfanyl]benzoic acid Step 1. A mixture of 3-sulfanylbenzoic acid (3 equiv.), 4-chlorobut-2-yn-1-amine hydrochloride (1 equiv.), and Hünig's base (6 equiv.) in 2-propanol was stirred at 120° C. for 16 h. A precipitate formed which was collected by filtration and washed with MeOH and DCM to afford 3-(4-aminobut-2-ynylsulfanyl)benzoic acid. LCMS [M+H]$^+$ 222.

Step 2. The title compound was prepared according to general procedure 2 from 3-(4-aminobut-2-ynylsulfanyl)benzoic acid and intermediate 3. LCMS [M+H]$^+$ 439. $^1$H NMR (400 MHz, METHANOL-d4) δ ppm 8.07-8.10 (m, 1H), 7.85-7.88 (m, 1H), 7.59-7.66 (m, 2H), 7.39-7.45 (m, 1H), 7.35-7.38 (m, 2H), 6.03 (s, 1H), 4.29 (t, J=2.1 Hz, 2H), 3.78 (t, J=2.2 Hz, 2H), 2.37 (s, 3H).

Example 194

4-(2-{[2-amino-6-(3-chloro-2-methylphenyl)pyrimidin-4-yl]amino}ethyl)-N-(1-hydroxypropan-2-yl)benzamide Step 1: A mixture of 4,6-dichloropyrimidin-2-amine (600 mg, 3.66 mmol), 4-(2-aminoethyl)benzoic acid hydrochloride (812 mg, 4.02 mmol) and triethylamine (1.53 mL, 10.98 mmol) in n-butanol (20 mL) was heated in a sealed tube at 110° C. overnight and then concentrated. The residue was recrystallized from a mixture of 2-propanol, methanol and water. The solid material was collected by filtration and dried to give 4-{2-[(2-amino-6-chloropyrimidin-4-yl)amino]ethyl}benzoic acid. LCMS [M+H]$^+$ 293.

Step 2: A mixture of 4-{2-[(2-amino-6-chloropyrimidin-4-yl)amino]ethyl}benzoic acid (58 mg, 0.20 mmol), 2-aminopropan-1-ol (30 µL, 0.39 mmol), HATU coupling reagent (91 mg, 0.24 mmol) and triethylamine (80 µL, 0.59 mmol) in DMF (3 mL) was stirred at r.t. for 2 h. Purified by preparative HPLC to give 4-{2-[(2-amino-6-chloropyrimidin-4-yl)amino]ethyl}-N-(1-hydroxypropan-2-yl)benzamide.

Step 3: A mixture of 4-{2-[(2-amino-6-chloropyrimidin-4-yl)amino]ethyl}-N-(1-hydroxypropan-2-yl)benzamide (40 mg, 0.11 mmol), (3-chloro-2-methylphenyl)boronic acid (25 mg, 0.15 mmol), Pd(PPh$_3$)$_4$ (7 mg, 0.010 mmol) and potassium carbonate (32 mg, 0.23 mmol) in 1,4-dioxane/water (5 mL; 4:1) was heated in a sealed tube at 90° C. overnight. The mixture was concentrated and purified by preparative HPLC to give 4-(2-{[2-amino-6-(3-chloro-2-methylphenyl)pyrimidin-4-yl]amino}ethyl)-N-(1-hydroxypropan-2-yl)benzamide.
LCMS [M+H]$^+$ 440.

Example 195

6-(3-chloro-2-methylphenyl)-4-N-{2-[4-(4-methylpiperazine-1-carbonyl)phenyl]ethyl}pyrimidine-2,4-diamine Step 1: A mixture of 4-{2-[(2-amino-6-chloropyrimidin-4-yl)amino]ethyl}benzoic acid (59 mg, 0.20 mmol) prepared in example 194, Step 1, 1-methylpiperazine (40 µL, 0.36 mmol), HATU coupling reagent (91 mg, 0.24 mmol) and triethylamine (80 µL, 0.59 mmol) in DMF (3 mL) was stirred at r.t. for 2 h. Purified by preparative HPLC to give 6-chloro-4-N-{2-[4-(4-methylpiperazine-1-carbonyl)phenyl]ethyl}pyrimidine-2,4-diamine. LCMS [M+H]$^+$ 375.

Step 2: A mixture of 6-chloro-4-N-{2-[4-(4-methylpiperazine-1-carbonyl)phenyl]ethyl}pyrimidine-2,4-diamine (30 mg, 0.080 mmol), (3-chloro-2-methylphenyl)boronic acid (18 mg, 0.10 mmol), Pd(PPh$_3$)$_4$ (5 mg, 0.0043 mmol) and potassium carbonate (22 mg, 0.16 mmol) in 1,4-dioxane/water (5 mL; 4:1) was heated in a sealed tube at 90° C. overnight. The mixture was concentrated and purified by preparative HPLC to give 6-(3-chloro-2-methylphenyl)-4-N-{2-[4-(4-methylpiperazine-1-carbonyl)phenyl]ethyl}pyrimidine-2,4-diamine. LCMS [M+H]$^+$ 465.

Example 196

6-(3-chloro-2-methylphenyl)-N4-[2-(4-methanesulfinylphenyl)ethyl]pyrimidine-2,4-diamine Step 1: A mixture of 1-bromo-4-methanesulfinylbenzene (88 mg, 0.40 mmol), potassium benzyl N-[2-(trifluoroboranuidyl)ethyl]carbamate (160 mg, 0.56 mmol), caesium carbonate (261 mg, 0.80 mmol), Pd(OAc)$_2$ (9 mg, 0.040 mmol) and 2-dicyclohexylphosphino-2',6'-diisopropoxybiphenyl (37 mg, 0.080 mmol) in 1,4-dioxane/water (5 mL; 4:1) was heated in a sealed tube at 100° C. overnight. The mixture was concentrated and purified by preparative HPLC to give benzyl N-[2-(4-methanesulfinylphenyl)ethyl]carbamate. LCMS [M+H]$^+$ 318.

Step 2: Benzyl N-[2-(4-methanesulfinylphenyl)ethyl]carbamate (39 mg, 0.12 mmol) was heated in TFA (1 mL) at 70° C. overnight. The mixture was concentrated and dried under vacuum to give 2-(4-methanesulfinylphenyl)ethan-1-amine; trifluoroacetic acid. LCMS [M+H]$^+$ 184.

Step 3: A mixture of 4-chloro-6-(3-chloro-2-methylphenyl)pyrimidin-2-amine (25 mg, 0.10 mmol; intermediate 3), 2-(4-methanesulfinylphenyl)ethan-1-amine; trifluoroacetic acid (33 mg, 0.11 mmol) and potassium carbonate (34 mg, 0.25 mmol) in acetonitrile (2 mL) was heated at 150° C. for 1 h using microwave irradiation. The mixture was concentrated and purified by preparative HPLC to give 6-(3-chloro-2-methylphenyl)-N4-[2-(4-methanesulfinylphenyl)ethyl]pyrimidine-2,4-diamine. LCMS [M+H]$^+$ 401.

Example 197

4-[2-({2-amino-6-[2-methyl-3-(trifluoromethyl)phenyl]pyrimidin-4-yl}amino)ethyl]benzene-1-sulfonamide Step 1: A mixture of 1-bromo-2-methyl-3-(trifluoromethyl)benzene (100 µL, 0.64 mmol), 4,4,5,5-tetramethyl-2-(tetramethyl-1,3,2-dioxaborolan-2-yl)-1,3,2-dioxaborolane (327 mg, 1.29 mmol), PdCl$_2$dppf.DCM (26 mg, 0.030 mmol) and potassium acetate (158 mg, 1.61 mmol) in 1,4-dioxane (5 mL) was heated in a sealed tube at 80° C. overnight. The mixture was run through a plug of silica (EtOAc), concentrated and purified by preparative HPLC to give 4,4,5,5-tetramethyl-2-[2-methyl-3-(trifluoromethyl)phenyl]-1,3,2-dioxaborolane.

Step 2: A mixture of 4-{2-[(2-amino-6-chloropyrimidin-4-yl)amino]ethyl}benzene-1-sulfonamide (25 mg, 0.080 mmol; Intermediate 4), 4,4,5,5-tetramethyl-2-[2-methyl-3-(trifluoromethyl)phenyl]-1,3,2-dioxaborolane (26 mg, 0.090 mmol), Pd(PPh$_3$)$_4$ (9 mg, 0.010 mmol) and potassium carbonate (21 mg, 0.15 mmol) in 1,4-dioxane/water (5 mL; 4:1) was heated in a sealed tube at 90° C. overnight. The mixture was concentrated and purified by preparative HPLC to give 4-[2-({2-amino-6-[2-methyl-3-(trifluoromethyl)phenyl]pyrimidin-4-yl}amino)ethyl]benzene-1-sulfonamide. LCMS [M+H]$^+$ 452.

Example 198

N4-[2-(4-methanesulfonylphenyl)ethyl]-6-[2-methyl-3-(trifluoromethyl)phenyl]pyrimidine-2,4-diamine A mixture of 6-chloro-4-N-[2-(4-methanesulfonylphenyl)ethyl]pyrimidine-2,4-diamine (25 mg, 0.080 mmol; intermediate 6), 4,4,5,5-tetramethyl-2-[2-methyl-3-(trifluoromethyl)phenyl]-1,3,2-dioxaborolane (26 mg, 0.090 mmol) prepared in example 197 step 1, Pd(PPh$_3$)$_4$ (9 mg, 0.010 mmol) and potassium carbonate (21 mg, 0.15 mmol) in 1,4-dioxane/water (5 mL; 4:1) was heated in a sealed tube at 90° C. overnight. The mixture was concentrated and purified by preparative HPLC to give N4-[2-(4-methanesulfonylphenyl)ethyl]-6-[2-methyl-3-(trifluoromethyl)phenyl]pyrimidine-2,4-diamine. LCMS [M+H]$^+$ 451.

Example 199

6-(3-chloro-2-methylphenyl)-N4-(2-{[5-(trifluoromethyl)pyridin-2-yl]oxy}ethyl)pyrimidine-2,4-diamine A mixture of 2-[[2-amino-6-(3-chloro-2-methyl-phenyl)pyrimidin-4-yl]amino]ethanol (intermediate 19), 2-chloro-5-(trifluoromethyl)pyridine (1.5 equiv.) and Cs$_2$CO$_3$ (2.0 equiv.) in DMSO was heated in a sealed tube at 90° C. for 16 h. After cooling was methanol added, followed by filtration and purification by preparative LC to give the title compound. LCMS [M+H]$^+$ 424. $^1$H NMR (400 MHz, METHANOL-d$_4$) δ ppm 8.43-8.53 (m, 1H), 7.88-8.03 (m, 1H), 7.52-7.67 (m, 1H), 7.29-7.39 (m, 2H), 6.95-7.00 (m, 1H), 6.07 (s, 1H), 4.50-4.69 (m, 1H), 3.96 (t, J=5.4 Hz, 2H), 2.38 (s, 3H).

Example 200

6-(3-chloro-2-methylphenyl)-N4-(2-{furo[3,2-c]pyridin-4-yloxy}ethyl)pyrimidine-2,4-diamine A mixture of 2-[[2-amino-6-(3-chloro-2-methyl-phenyl)pyrimidin-4-yl]amino]ethanol (intermediate 19), 4-chlorofuro[3,2-c]pyridine (1.5 equiv.) and $Cs_2CO_3$ (2.0 equiv.) in DMSO was heated in a sealed tube at 110° C. for 16 h. After cooling was methanol added, followed by filtration and purification by preparative LC to give the title compound. LCMS [M+H]$^+$ 396. $^1$H NMR (400 MHz, METHANOL-$d_4$) δ ppm 7.97 (d, J=6.0 Hz, 1H), 7.79 (d, J=2.2 Hz, 1H), 7.60 (dd, J=7.3, 2.2 Hz, 1H), 7.29-7.38 (m, 2H), 7.22 (dd, J=6.0, 0.9 Hz, 1H), 6.92 (dd, J=2.2, 0.9 Hz, 1H), 6.07 (s, 1H), 4.69 (t, J=5.2 Hz, 2H), 4.01 (t, J=5.4 Hz, 2H), 2.36 (s, 3H)

Example 201

(Z)-4-(2-{[2-amino-6-(3-chloro-2-methylphenyl)pyrimidin-4-yl]amino}ethoxy)-N'-hydroxybenzene-1-carboximidamide 4-(2-{[2-amino-6-(3-chloro-2-methylphenyl)pyrimidin-4-yl]amino}ethoxy)benzonitrile (intermediate 25) was dissolved in DMSO (1 mL). $H_2O_2$ (4.0 equiv.) and 5M NaOH was added and the reaction was stirred at room temperature for 30 min. Methanol was added followed, by filtration and purification by preparative LC to give the title compound. LCMS [M+H]$^+$ 398. $^1$H NMR (400 MHz, DMSO-$d_6$) δ ppm 7.80-7.89 (m, 4H), 7.44 (dd, J=7.7, 1.7 Hz, 1H), 7.22-7.27 (m, 1H), 7.20 (dd, J=7.7, 1.7 Hz, 2H), 7.01 (d, J=8.8 Hz, 2H), 6.10 (s, 2H), 5.80 (s, 1H), 4.16 (t, J=5.7 Hz, 2H), 3.59-3.76 (m, 2H), 2.29 (s, 3H).

Example 202

6-(3-chloro-2-methylphenyl)-N4-{2-[4-(2H-1,2,3,4-tetrazol-5-yl)phenoxy]ethyl}pyrimidine-2,4-diamine A mixture of 4-[2-[[2-amino-6-(3-chloro-2-methyl-phenyl)pyrimidin-4-yl]amino]ethoxy]benzonitrile (intermediate 25) sodium azide (1.2 equiv), ammonium chloride (1.2 equiv.) in DMF was heated in a sealed dry tube at 130° C. for 24 hours. After cooling methanol was added followed by filtration and purification by preparative LC to give the title compound. LCMS [M+H]$^+$ 423. $^1$H NMR (400 MHz, METHANOL-$d_4$) δ ppm 7.91-7.99 (m, 2H), 7.35-7.45 (m, 1H), 7.17-7.24 (m, 2H), 6.99-7.08 (m, 2H), 5.90 (s, 1H), 4.21 (t, J=5.5 Hz, 2H), 3.73-3.86 (m, 2H), 2.32 (s, 3H)

Example 203

(Z)-4-(2-{[2-amino-6-(3-chloro-2-methylphenyl)pyrimidin-4-yl]amino}ethoxy)-N'-hydroxybenzene-1-carboximidamide To a solution of 4-[2-[[2-amino-6-(3-chloro-2-methylphenyl)pyrimidin-4-yl]amino]ethoxy]benzonitrile (intermediate 25) methanol was added the hydroxylamine hydrochloride (3.0 equiv.) and N,N-diisopropylethylamine (3.2 equiv.) and stirred at 80° C. for 90 min. The reaction mixture was cooled to 23° C. and concentrated in vacuo. Dichloromethane and water were added, the phases were separated, and the organic layer was washed with brine, dried ($Na_2SO_4$), filtered, and concentrated in vacuo. The crude was dissolved in methanol, followed by filtration and purification by preparative LC to give the title compound. LCMS [M+H]$^+$ 413.

Example 204

6-(3-chloro-2-methylphenyl)-N4-[3-(4-methanesulfonylphenoxy)propyl]pyrimidine-2,4-diamine A mixture of 3-{[2-amino-6-(3-chloro-2-methylphenyl)pyrimidin-4-yl]amino}propan-1-ol (intermediate 24), 1-fluoro-4-methylsulfonyl-benzene (1.1 equiv.) and $Cs_2CO_3$ (2.0 equiv.) in DMSO was heated in a sealed tube at 90° C. for 1 h. After cooling was methanol added to the solution, followed by filtration and purification by preparative LC to furnish the title compound. LCMS [M+H]$^+$ 447. $^1$H NMR (400 MHz, METHANOL-$d_4$) δ ppm 7.85-7.91 (m, 2H), 7.60 (dd, J=7.4, 2.1 Hz, 1H), 7.34 (d, J=5.7 Hz, 2H), 7.10-7.18 (m, 2H), 6.04 (s, 1H), 4.22 (t, J=6.0 Hz, 2H), 3.75 (t, J=6.6 Hz, 2H), 3.08 (s, 3H), 2.37 (s, 3H), 2.18 (quin, J=6.3 Hz, 2H)

Example 205

2-(3-{[2-amino-6-(3-chloro-2-methylphenyl)pyrimidin-4-yl]amino}propoxy)pyrimidine-4-carboxamide A mixture of 3-{[2-amino-6-(3-chloro-2-methylphenyl)pyrimidin-4-yl]amino}propan-1-ol (intermediate 24), 2-chloropyrimidine-4-carboxamide (1.1 equiv.) and $Cs_2CO_3$ (2.0 equiv.) in DMSO was heated in a sealed tube at 90° C. for 2 h. After cooling was methanol added to the solution, followed by filtration and purification by preparative LC to furnish the title compound. LCMS [M+H] 414. $^1$H NMR (400 MHz, METHANOL-$d_4$) δ ppm 8.79 (d, J=5.1 Hz, 1H), 7.69 (s, 1H), 7.55-7.63 (m, 1H), 7.30-7.41 (m, 3H), 6.04 (s, 1H), 4.59 (t, J=6.0 Hz, 2H), 3.76 (t, J=6.8 Hz, 2H), 2.18 (quin, J=6.3 Hz, 3H).

Example 206

6-(3-{[2-amino-6-(3-chloro-2-methylphenyl)pyrimidin-4-yl]amino}propoxy)pyridine-3-carboxamide A mixture of 3-{[2-amino-6-(3-chloro-2-methylphenyl)pyrimidin-4-yl]amino}propan-1-ol (intermediate 24) 6-chloropyridine-3-carboxamide (1.1 equiv.) and $Cs_2CO_3$ (2.0 equiv.) in DMSO was heated in a sealed tube at 90° C. for 2 h. After cooling was methanol added to the solution, followed by filtration and purification by preparative LC to furnish the title compound. LCMS [M+H] 413. $^1$H NMR (400 MHz, METHANOL-$d_4$) δ ppm 8.67 (dd, J=2.5, 0.6 Hz, 1H), 8.13 (dd, J=8.8, 2.5 Hz, 1H), 7.58-7.63 (m, 1H), 7.29-7.40 (m, 2H), 6.86 (dd, J=8.8, 0.6 Hz, 1H), 6.03 (s, 1H), 4.48 (t, J=6.2 Hz, 2H), 3.72 (t, J=6.6 Hz, 2H), 2.37 (s, 3H), 2.15 (quin, J=6.4 Hz, 2H).

Example 207

6-(3-chloro-2-methylphenyl)-N4-{2-[4-(morpholine-4-sulfonyl)phenyl]ethyl}pyrimidine-2,4-diamine Morpholine (6 equiv.) and 4-(2-acetamidoethyl)benzene-1-sulfonyl chloride (intermediate 26) (1 equiv.) were heated neat at 70° C. for 30 min. 2.5 M NaOH (26 equiv.) was added and the reaction was heated in a microwave oven for 15 min at 150° C. The mixture was extracted with DCM and the organic phase was dried over MgSO4 and removed in vacuo. The crude product was dissolved in MeOH and 4-chloro-6-(3-chloro-2-methylphenyl)pyrimidin-2-amine (intermediate 3) (1 equiv.) was added. The solvent was removed and the mixture was melted for 15 min at 160° C. The crude material was dissolved in MeOH and purified by preparative LC to afford the title compound. LCMS [M+H]$^+$ 488. $^1$H NMR (400 MHz, DMSO-d6) δ ppm 2.29 (3H, s) 2.78-2.88 (4H, m) 2.96 (2H, t, J=7.19 Hz) 3.45-3.59 (2H, m) 3.59-3.67 (4H, m) 5.74 (1H, s) 6.06 (2H, br. s.) 7.07 (1H, br. s.) 7.17-7.27 (2H, m) 7.40-7.47 (1H, m) 7.53-7.59 (2H, m) 7.63-7.70 (2H, m)

Example 208

4-(2-{[2-amino-6-(3-chloro-2-methylphenyl)pyrimidin-4-yl]amino}ethyl)-N-(2-methoxyethyl)benzene-1-sulfonamide 2-methoxyethan-1-amine (6 equiv.) and 4-(2-acetamidoethyl)benzene-1-sulfonyl chloride (intermediate 26) (1 equiv.) were heated neat at 70° C. for 30 min. 2,5M NaOH (26 equiv.) was added and the reaction was heated in a microwave for 15 min at 150° C. 12M HCl (26 equiv.) was added and the solvent was removed in vacuo. MeOH was added and NaCl was removed by filtration. 4-chloro-6-(3-chloro-2-methylphenyl)pyrimidin-2-amine (intermediate 3) (1 equiv.) was added and the solvent was evaporated at 80° C. The crude material was melted at 160° C. for 30 min. The crude material was dissolved in MeOH and purified by preparative LC to afford the title compound. LCMS [M+H]$^+$ 476.

Example 209

4-(2-{[2-amino-6-(3-chloro-2-methylphenyl)pyrimidin-4-yl]amino}ethyl)-N-(oxetan-3-yl)benzene-1-sulfonamide Oxetan-3-amine (6 equiv.) and 4-(2-acetamidoethyl)benzene-1-sulfonyl chloride intermediate 26 (1 equiv.) were heated neat at 70° C. for 30 min. 2,5M NaOH (26 equiv.) was added and the reaction was heated in the micro for 15 min at 150° C. 12M HCl (26 equiv.) was added and the solvent was removed in vacuo. MeOH was added and NaCl was removed by filtration. 4-chloro-6-(3-chloro-2-methylphenyl)pyrimidin-2-amine (intermediate 3) (1 equiv.) was added and the solvent was evaporated at 80° C. The crude material was melted at 160° C. for 30 min. The crude material was dissolved in MeOH and purified by preparative LC to afford the title compound. LCMS [M+H]$^+$ 474.

Example 210

4-(2-{[2-amino-6-(3-chloro-2-methylphenyl)pyrimidin-4-yl]amino}ethyl)-N-(oxan-4-yl)benzene-1-sulfonamide Oxan-4-amine (6 equiv.) and 4-(2-acetamidoethyl)benzene-1-sulfonyl chloride intermediate 26 (1 equiv.) were heated neat at 70° C. for 30 min. 2,5M NaOH (26 equiv.) was added and the reaction was heated in the micro for 15 min at 150° C. 12M HCl (26 equiv.) was added and the solvent was removed in vacuo. MeOH was added and NaCl was removed by filtration. 4-chloro-6-(3-chloro-2-methylphenyl)pyrimidin-2-amine (intermediate 3) (1 equiv.) was added and the solvent was evaporated at 80° C. The crude material was melted at 160° C. for 30 min. The crude material was dissolved in MeOH and purified by preparative LC to afford the title compound. LCMS [M+H]$^+$ 502.

Example 211

4-(2-{[2-amino-6-(3-chloro-2-methylphenyl)pyrimidin-4-yl]amino}ethyl)-N-methyl-N-(prop-2-yn-1-yl)benzamide Step 1 sodium 4-(2-{[2-amino-6-(3-chloro-2-methylphenyl)pyrimidin-4-yl]amino}ethyl)benzoate Methyl 4-(2-{[2-amino-6-(3-chloro-2-methylphenyl)pyrimidin-4-yl]amino}ethyl)benzoate (prepared in example 9) (1 eq), MeOH and 5M NaOH (1.1 eq) were heated in a sealed tube for 8 hours at 115° C. The title compound was isolated by removing the solvent in vacuo. LCMS [M+H]$^+$ 383.

Step 2 TBTU (1.5 eq) was added to a stirred mixture of sodium 4-(2-{[2-amino-6-(3-chloro-2-methylphenyl)pyrimidin-4-yl]amino}ethyl)benzoate (1 eq), methyl(prop-2-yn-1-yl)amine (3 eq), Hynigs (5 eq) and dry DMF. The mixture was stirred at r.t. in a sealed tube for 4 hours. The mixture was purified by preparative LC to give the title compound. LCMS [M+H]$^+$ 434 1H NMR (400 MHz, DMSO-d6) δ ppm 2.26-2.31 (3H, m) 2.88 (1H, t, J=7.35 Hz) 2.97 (3H, br. s.) 3.23-3.40 (1H, m) 3.51 (2H, br. s.) 3.95-4.41 (2H, m) 5.74 (1H, s) 6.06 (2H, br. s.) 7.08 (1H, br. s.) 7.18-7.28 (2H, m) 7.32-7.40 (4H, m) 7.44 (1H, dd, J=7.58, 1.74 Hz)

Example 212

6-(3-chloro-2-methylphenyl)-N4-[2-(4-ethynylphenyl)ethyl]pyrimidine-2,4-diamine

Step 1: A mixture of 4-chloro-6-(3-chloro-2-methylphenyl)pyrimidin-2-amine (200 mg, 0.79 mmol) intermediate 3, 2-(4-bromophenyl)ethan-1-amine (183 μL, 1.18 mmol) and triethylamine (200 μl, 1.43 mmol) in n-butanol (3 mL) was heated in a sealed tube at 120° C. for 72 h. The mixture was left at r.t. for 4 h and the solid material was removed by filtration. The filtrate was concentrated and purified by preparative HPLC. To give N4-[2-(4-bromophenyl)ethyl]-6-(3-chloro-2-methylphenyl)pyrimidine-2,4-diamine LCMS [M+H]$^+$ 417.

Step 2: N$_2$ was bubbled through s mixture of N4-[2-(4-bromophenyl)ethyl]-6-(3-chloro-2-methylphenyl)pyrimidine-2,4-diamine, prepared in step 1 (1 eq), Et2N (1 eq), PPh3 (0.2 eq), CuI (0.05 eq) and DMF for 3 min. PdCl2(PPh3)$_2$ (0.05 eq) and ethynyltrimethylsilane (2 eq) was added and the reaction was heated in a sealed tube for 1 hour at 120° C. The mixture was cold to r.t. and 1M tetrabutyl ammonium fluoride in THF (5 eq) was added. The reaction was stirred for 1 hour at r.t. MeOH was added followed by filtration and purified by preparative LC to give the title compound. LCMS [M+H]$^+$ 363. $^1$H NMR (400 MHz, DMSO-d6) δ ppm 2.29 (3H, s) 2.84 (2H, t, J=7.27 Hz) 3.48 (2H, br. s.) 4.13 (1H, s) 5.72 (1H, s) 6.05 (2H, br. s.) 7.03 (1H, br. s.) 7.17-7.31 (4H, m) 7.38-7.46 (3H, m)

Example 213

6-(2-(2-amino-6-(3-chloro-2-methylphenyl)pyrimidin-4-ylamino)ethoxy)pyridine-3-sulfonamide

Step 1: 6-Chloropyridine-3-sulfonamide $SOCl_2$ (24 mL) was added to water (145 mL) containing CuCl (87 mg) at 0° C. over a period of 30 min. The solution was then stirred at RT overnight. 3-amino-6-chloropyridine (10.0 g, 77.8 mmol) was added with stirring to conc. HCl (80 mL) portionwise. The mixture was stirred until all solid was dissolved. At −5° C. a solution of $NaNO_2$ (5.9 g, 85.5 mmol, in 24 mL $H_2O$) was added dropwise while the temperature was kept between −5° C. and 0° C. The resulting mixture was stirred for 30 min after completion of the addition and then added dropwise into the aqueous solution of $SOCl_2$. The temperature was kept below 0° C. during the addition. After the addition the mixture was stirred for 1 h below 0° C. and then filtered. The cake was washed with ice-cold water (5 mL). A yellow solid was obtained as crude product (16 g), which was added with stirring into 50% aqueous ammonia (80 mL) portionwise at 10° C. The mixture was then stirred at RT for 30 min, then was extracted with EA (150 mL×1.50 mL x 2), the combined organic layers were washed with brine (50 mL) and dried over $Na_2SO_4$. Removal of solvent under reduced pressure afforded the product $^1$H NMR (400 MHz, DMSO-$d_6$): b=7.73 (s, 2H), 7.78 (d, J=8.4 Hz, 1H), 8.22 (m, 1H), 8.80 (d, J=2.0 Hz, 1H) ppm.

Step 2: 6-(2-Aminoethoxy)pyridine-3-sulfonamide

To the solution of 2-aminoethanol (2.4 g, 38.9 mmol) in dioxane (60 mL) was added NaH (60%, 1.40 g, 35.1 mmol) in portions at 10° C. After 30 min stirring at RT, 6-Chloropyridine-3-sulfonamide (1.50 g, 7.8 mmol) was added. The mixture was stirred for 30 min under reflux. After cooling to RT, the reaction was quenched by adding $H_2O$ (0.5 mL). The organic layer was separated and dried over $Na_2SO_4$. After removal of solvent under reduced pressure, the residue was purified by column chromatography. Recrystallization from MeCN afforded a yellow the product (0.42 g). $^1$H NMR (400 MHz, DMSO-$d_6$): b=2.89 (t, J=6.0 Hz, 2H), 4.27 (t, J=6.0 Hz, 2H), 4.62 (br, 2H), 6.99 (m, 1H), 8.05 (m, 1H), 8.55 (m, 1H) ppm.

Step 3: 6-(2-(2-amino-6-(3-chloro-2-methylphenyl) pyrimidin-4-ylamino)ethoxy)pyridine-3-sulfonamide The mixture of 6-(2-Aminoethoxy)pyridine-3-sulfonamide (0.42 g, 1.9 mmol), and intermediate 3 (0.98 g, 3.8 mmol) and TEA (0.59 g, 5.8 mmol) in i-PrOH (15 mL) was stirred at 95° C. overnight. After cooling to RT and removal of solvent under reduced pressure, the residue was purified by column chromatography (to afford a white solid which was purified by prep HPLC to provide the title compound. $^1$H NMR (400 MHz, DMSO-$d_6$): b=2.29 (s, 2H), 3.67 (s, 2H), 4.46 (t, J=5.6 Hz, 2H), 5.79 (s, 1H), 6.09 (s, 2H), 7.01 (d, J=8.8 Hz, 1H), 7.24 (m, 3H), 7.44 (m, 1H), 8.07 (m, 1H), 8.56 (d, J=2.4 Hz, 1H) ppm.

Example 214

6-(3-Chloro-2-methylphenyl)-N4-(2-(5-(methylsulfonyl)pyridin-2-yloxy)ethyl)pyrimidine-2,4-diamine

Step 1 2-Bromo-5-(methylsulfonyl)pyridine

Isopropylmagnesium chloride (2.0 M, 13.7 mL, 27.4 mmol) was added to a solution of 3,6-dibromopyridine (5.00 g, 21.1 mmol) in THF (18 mL) at 0° C. at a rate which maintained the temperature below 8° C. The reaction mixture was stirred at 0° C. for 45 min. At −15° C. the solution of methanesulfonyl chloride (3.22 g, 28.1 mmol) in THF (4 mL) was added at a rate which maintained the temperature below 5° C. The reaction mixture was allowed to warm up to room temperature and then quenched by adding water (50 mL) and ethyl acetate (30 mL) to it. After separation, the organic layer was dried over $Na_2SO_4$. After removal of solvent, the residue was purified by column chromatography to afford a the expected product (2.4 g). 1H NMR (400 MHz, DMSO-d6): b=3.37 (s, 3H), 7.98 (m, 1H), 8.26 (m, 1H), 8.89 (d, J=0.4 Hz, 1H) ppm.

Step 2 6-(3-Chloro-2-methylphenyl)-N4-(2-(5-(methylsulfonyl)pyridin-2-yloxy)ethyl)pyrimidine-2,4-diamine NaH (60%, 86 mg, 2.154 mmol) was added to the solution of 2-[[2-amino-6-(3-chloro-2-methyl-phenyl)pyrimidin-4-yl]amino]ethanol (intermediate 19) (337 mg, 1.44 mmol) in THF (15 mL). The reaction mixture was stirred for 10 min at RT.

After addition of bromo-5-(methylsulfonyl)pyridine (200 mg, 0.72 mmol), the reaction mixture was stirred for 30 min at RT. The reaction was quenched by adding 6 drops of water. After removal of solvent under reduced pressure, the residue was purified by prep HPLC (eluent: mixture of MeCN and 0.1% aqueous $NH_4HCO_3$ solution) to afford the product. 1H NMR (400 MHz, DMSO-d6): b=2.29 (s, 3H), 3.26 (s, 3H), 3.69 (s, 2H), 4.50 (t, J=6.4 Hz, 2H), 5.78 (s, 1H), 6.11 (s, 2H), 7.19 (m, 1H), 7.22 (m, 3H), 7.44 (m, 1H), 8.19 (m, 1H), 8.67 (s, 1H) ppm.

Example 215

2-(2-amino-6-(3-chloro-2-methylphenyl)pyrimidin-4-ylamino)-1-(4-(methylsulfonyl)phenyl)ethanol

Step 1: 2-Bromo-1-(4-(methylsulfonyl)phenyl)ethanone

To the solution of 1-(4-(methylsulfonyl)phenyl)ethan-1-one (5.00 g, 25.2 mmol) in $CHCl_3$ (100 mL) was added $Br_2$ (4.0 0 g, 25.2 mmol) in $CHCl_3$ (15 mL) dropwise over period of 1 h, the mixture was stirred for 1 h at RT (15° C.). The solution was washed with saturated $NaHCO_3$ (30 mL) and brine (30 mL), dried over $Na_2SO_4$. After removal of solvent under reduced pressure, the crude product was recrystallized from EtOH (50 mL) at RT to afford a white solid as product 20 (4.60 g, 16.6 mmol, 66%). $^1$H NMR (300 MHz, $CDCl_3$): δ=3.12 (s, 3H), 4.48 (s, 2H), 8.10 (m, 2H), 8.18 (m, 2H) ppm.

Step 2: To the solution of 2-Bromo-1-(4-(methylsulfonyl)phenyl)ethanone (5.30 g, 19.1 mmol) in MeCN (53 mL) was added hexamethylenetetramine (2.70 g, 19.3 mmol), the mixture was stirred for 2 h. at R.T. The product was isolated by filtration and dried under high vacuum (7.20 g), and used for next step without further purification.

Step 3: 2-Amino-1-(4-(methylsulfonyl)phenyl)ethanone hydrochloride

To the solution of concentrated HCl (10 mL) in EtOH (40 mL) was added 2-amino-1-(4-(methylsulfonyl)phenyl)ethanone (7.2 g, 17.3 mmol) at RT. The mixture was stirred for 2 h at 50° C. After cooling to 5° C., the resulting white solid was collected by filtration, washed with EtOH (10 mL). The solid was dissolved in the mixture of H₂O (12 mL) and concentrated HCl (0.5 mL) at 70° C., the hot solution was filtered and the filtrate was cooled to 5° C., the crystalline white solid was isolated by filtration, washed with ice-cold H₂O (5 mL) and EtOH (5 mL), dried under high vacuum to afford the product (2.30 g, 9.2 mmol, 53%). ¹H NMR (400 MHz, D₂O): (=3.17 (d, J=2.8 Hz, 2H), 4.64 (s, 3H), 7.99 (m, 2H), 8.09 (m, 2H) ppm.

Step 4:
2-amino-1-(4-(methylsulfonyl)phenyl)ethan-1-ol

At 0° C., NaBH₄ (0.30 g, 8.0 mmol) was dissolved in MeOH (30 mL), KOH (0.22 g, 3.9 mmol) in MeOH (4 mL) was added carefully, then 2-Amino-1-(4-(methylsulfonyl)phenyl)ethanone hydrochloride (1.00 g, 4.0 mmol) was added in small portions. The mixture was stirred for 30 min at 0° C. and 30 min at RT. After removal of solvent under reduced pressure, the residue was treated with saturated NaHCO₃ (10 mL). After extraction with DCM (20 mL×4), the combined organic layers was washed with brine (5 mL), dried over Na₂SO₄. Removal of solvent under reduced pressure, gave the product (0.25 g). ¹H NMR (300 MHz, CDCl₃): δ=2.76 (m, 1H), 3.07 (s, 3H), 3.12 (m, 1H), 4.73 (m, 1H), 7.59 (d, J=8.4 Hz, 2H), 7.93 (d, J=8.4 Hz, 2H) ppm.

Step 5: 2-(2-amino-6-(3-chloro-2-methylphenyl)pyrimidin-4-ylamino)-1-(4-(methylsulfonyl)phenyl)ethanol A mixture of 2-amino-1-(4-(methylsulfonyl)phenyl)ethan-1-ol (190 mg, 0.88 mmol), intermediate 3 (266 mg, 1.05 mmol) and triethylamine (0.19 mL, 1.32 mmol) in isopropanol (5 mL) was stirred overnight at 95° C. After cooling to RT and removal of solvent under reduced pressure, the residue was purified by preparative HPLC to yield the product (65 mg). ¹H NMR (300 MHz, DMSO-d₆): δ=2.08 (s, 3H), 3.20 (s, 3H), 3.61 (br, 1H), 4.90 (s, 1H), 5.81 (s, 1H), 5.84 (m, 1H), 6.11 (s, 2H), 7.20 (m, 3H), 7.26 (m, 1H), 7.70 (m, 2H), 7.90 (m, 2H) ppm.

Example 216

4-(2-(2-Amino-6-(3-chloro-2-methylphenyl)pyrimidin-4-ylamino)-1-hydroxyethyl)benzenesulfonamide Step 1: 4-(2-Bromoacetyl)benzenesulfonamide Br₂ (7.2 g, 45.0 mmol, in 10 mL HOAc) was added dropwise to the solution of 4-acetylbenzenesulfonamide (9.0 g, 45.0 mmol) in HOAc (250 mL) at 40° C. The reaction mixture was stirred for 1 h at 40° C. After removal of solvent under reduced pressure, the residue was purified by recrystallization from EtOH (20 mL) to yield the product (6.60 g). ¹H NMR (300 MHz, CDCl₃): δ=4.99 (s, 2H), 7.59 (s, 2H), 7.98 (m, 2H), 8.16 (m, 2H) ppm.

Step 2:
4-(2-Bromo-1-hydroxyethyl)benzenesulfonamide

To the mixture of 4-(2-Bromoacetyl)benzenesulfonamide (1.00 g, 3.6 mmol) in THF (20 mL) was added borane-dimethylsulphide complex (0.33 g, 4.3 mmol) at 0° C. The mixture was stirred for 24 h. at R.T. After removal of solvent under reduced pressure, the residue was purified by column chromatography to afford the product (0.30 g). ¹H NMR (300 MHz, CDCl₃): δ=3.63 (m, 1H), 3.72 (m, 1H), 4.91 (m, 1H), 6.00 (d, J=4.8 Hz, 1H), 7.34 (s, 2H), 7.57 (d, J=8.4 Hz, 1H), 7.78 (d, J=8.4 Hz, 2H) ppm.

Step 3:
4-(2-Amino-1-hydroxyethyl)benzenesulfonamide

The mixture of 4-(2-Bromo-1-hydroxyethyl)benzenesulfonamide (0.30 g, 1.1 mmol) and NH₄OH (15 mL) was stirred for 60 h. at R.T. Removal of solvent under reduced pressure afforded the crude product as yellow solid (100%), which was used for next step without further purification. ¹H NMR (400 MHz, D₂O): b=3.08 (m, 1H), 3.24 (m, 1H), 4.99 (m, 1H), 7.54 (m, 2H), 7.82 (m, 2H) ppm.

Step 4: 4-(2-(2-Amino-6-(3-chloro-2-methylphenyl)pyrimidin-4-ylamino)-1-hydroxyethyl)benzenesulfonamide The mixture of 4-(2-Amino-1-hydroxyethyl)benzenesulfonamide (0.23 g, 1.0 mmol), intermediate 3 (0.27 g, 1.0 mmol) and NEt₃ (0.20 g, 2.0 mmol) in i-PrOH (12 mL) was stirred at 95° C. overnight. After removal of solvent, the residue was purified by preparative HPLC to afford the title compound as white solid (44 mg). ¹H NMR (400 MHz, D₂O): (=2.29 (s, 3H), 3.22 (m, 1H), 3.31 (s, 1H), 3.61 (br, 1H), 4.86 (s, 1H), 5.77 (m, 1H), 5.83 (s, 1H), 6.12 (s, 2H), 7.21 (m, 2H), 7.27 (s, 1H), 7.43 (m, 1H), 7.59 (m, 2H), 7.81 (m, 2H) ppm.

Example 217

(2-(2-Amino-6-(4-(methylsulfonyl)phenethylamino)pyrimidin-4-yl)-6-chlorophenyl)methanol A solution of (2-(2-Amino-6-chloropyrimidin-4-yl)-6-chlorophenyl)methanol (prepared in example 218 step 2) (55.3 mg, 0.21 mmol), 13 (104 mg, 0.45 mmol) and DIPEA (86.3 mg, 0.67 mmol) in n-BuOH (3 mL) was stirred overnight under reflux. After removal the solvent under the reduced pressure, the residue was purified by preparative HPLC to give the product (14.2 mg). ¹H NMR (300 MHz, DMSO-d₆) b=2.97 (t, J=7.5 Hz, 2H), 3.19 (s, 3H), 3.31 (s, 1H), 3.54 (m, 2H), 4.45 (s, 2H), 5.95 (br, 1H), 6.34 (s, 1H), 7.38 (m, 2H), 7.55 (m, 3H), 7.86 (m, 2H) ppm.

Example 218

4-(2-(2-Amino-6-(3-chloro-2-(hydroxymethyl)phenyl)pyrimidin-4-ylamino)ethyl)benzenesulfonamide Step 1: (3-Chloro-2-(hydroxymethyl)phenylboronic acid The solution of 2-borono-6-chlorobenzoic acid (1.40 g, 7.0 mmol) in THF (5 mL) was added dropwise to a stirred suspension of LiAlH₄ (1.60 g, 42.0 mmol) in THF (20 mL) at 0° C. The mixture was stirred under reflux for 3 h. The solvent was removed under reduced pressure to give white solid. 1M HCl was added dropwise at 0° C. The mixture was filtered to give the product (0.80 g). ¹H NMR (400 MHz, DMSO-d₆): δ=4.99 (s, 2H), 7.41 (m, 1H), 7.53 (m, 1H), 7.70 (m, 1H), 9.45 (s, 1H) ppm.

Step 2: (2-(2-Amino-6-chloropyrimidin-4-yl)-6-chlorophenyl)methanol

To the solution of (3-Chloro-2-(hydroxymethyl)phenylboronic acid (0.80 g, 4.3 mmol), 4,6-dichloropyrimidin-2- amine (1.40 g, 8.6 mmol), and Na$_2$CO$_3$ (1.00 g, 9.5 mmol) in dioxane/H$_2$O (32 mL/8 mL), Pd(PPh$_3$)$_4$ (150 mg, 0.13 mmol, 3 mol %) was then added. The mixture was stirred for h at 90° C. The solvent was removed under the reduced pressure. The residue was treated with DCM (10 mL×3). The organic layer was washed with brine (10 mL). After removal of solvent under the reduced pressure, the residue was purified by column chromatography (silica gel, petroleum ether/ethyl acetate=5/1) to give the product (0.10 g). $^1$H NMR (400 MHz, CDCl$_3$): δ=4.69 (s, 2H), 5.52 (m, 1H), 6.93 (s, 1H), 7.36 (m, 3H), 7.55 (m, 1H) ppm. LC-MS (ESI): m/z 269.97 [M+H]$^+$.

Step 3: 4-(2-(2-Amino-6-(3-chloro-2-(hydroxymethyl)phenyl)pyrimidin-4-ylamino)ethyl)benzenesulfonamide To the solution of (2-(2-Amino-6-chloropyrimidin-4-yl)-6-chlorophenyl)methanol (42.7 mg, 0.16 mmol), 4-(2-aminoethyl)benzenesulfonamide (47.6 mg, 0.24 mmol) and DIPEA (41.3 mg, 0.32 mmol), the mixture was refluxed overnight.

After removal the solvent under reduced pressure, the residue was purified by preparative TLC to afford the product as white solid (20.3 mg). $^1$H NMR (400 MHz, CDCl$_3$): δ=3.06 (t, J=6.3 Hz, 2H), 3.82 (t, J=6.6 Hz, 2H), 4.75 (s, 2H), 6.20 (s, 1H), 7.48 (m, 4H), 7.67 (m, 1H), 7.86 (m, 2H) ppm.

Example 1

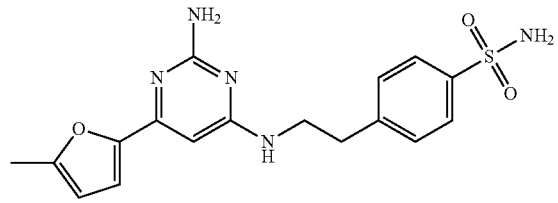

Example 2

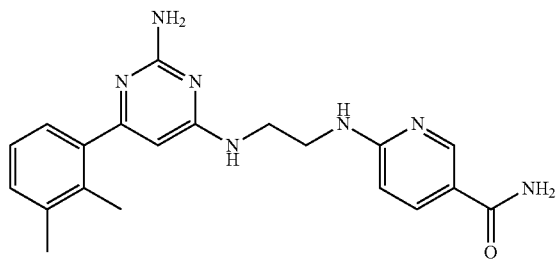

Example 3

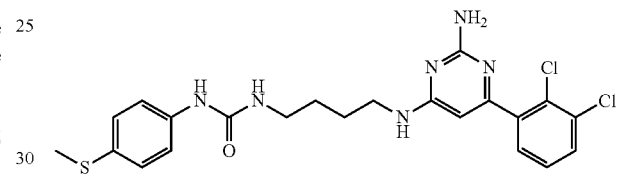

Example 4

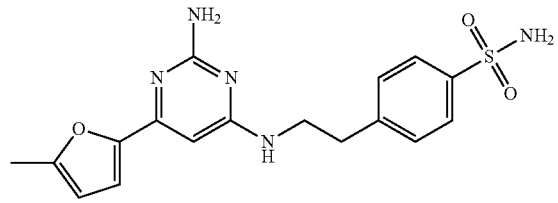

Example 5

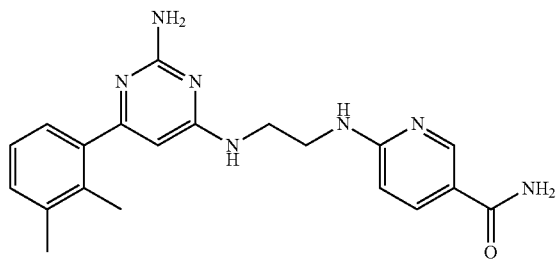

Example 6

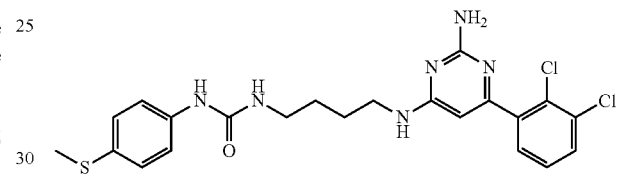

Example 7

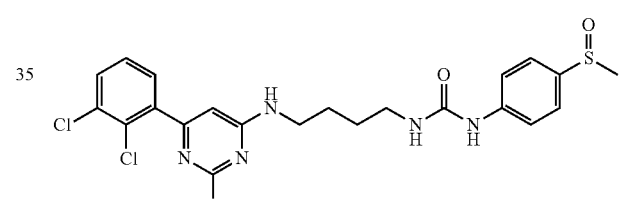

Example 8

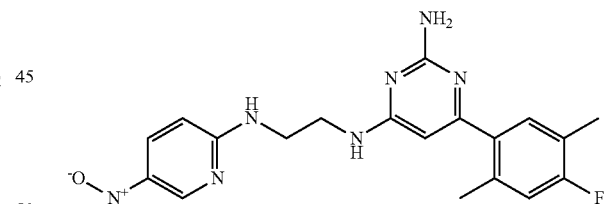

Example 9

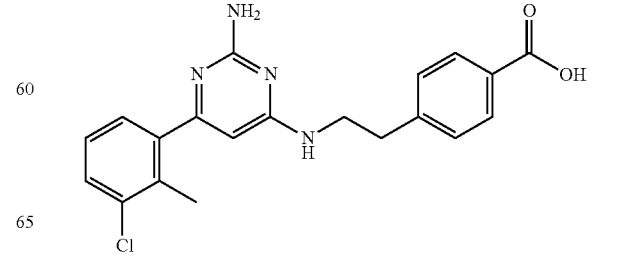

Example 10
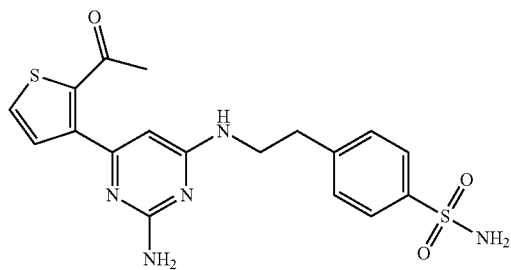
Example 11
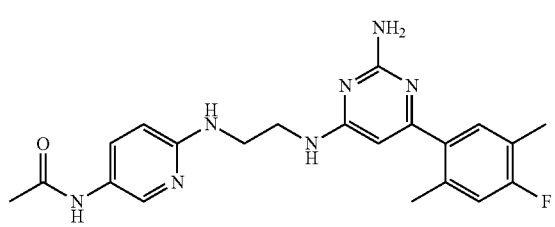
Example 12
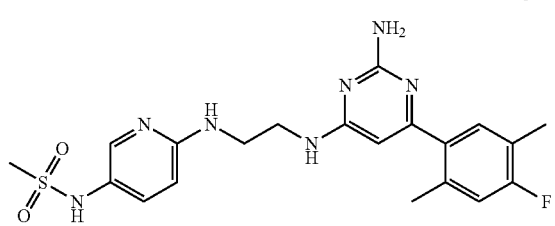
Example 13
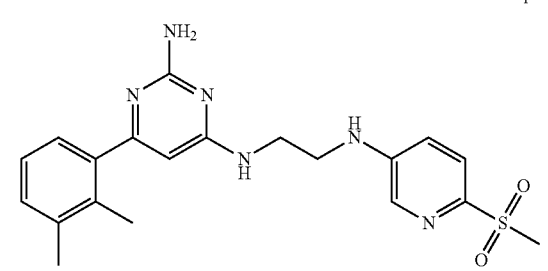
Example 14
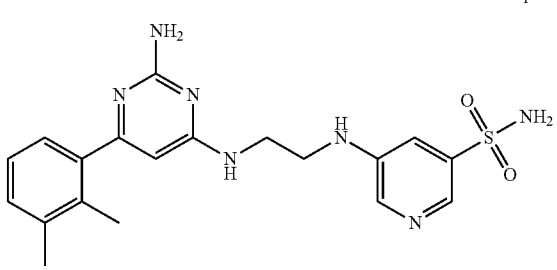
Example 15
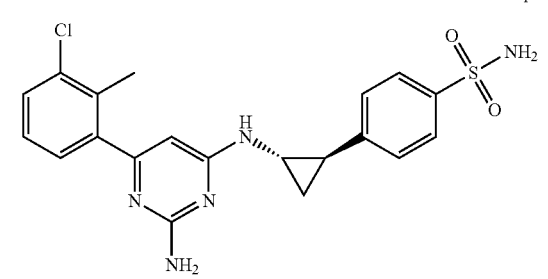
Example 16
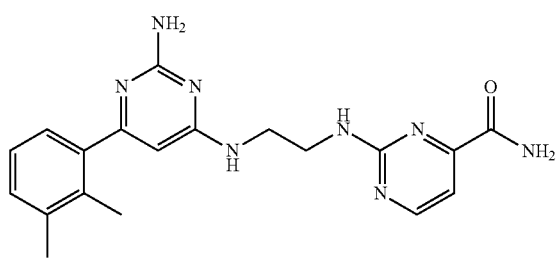
Example 17
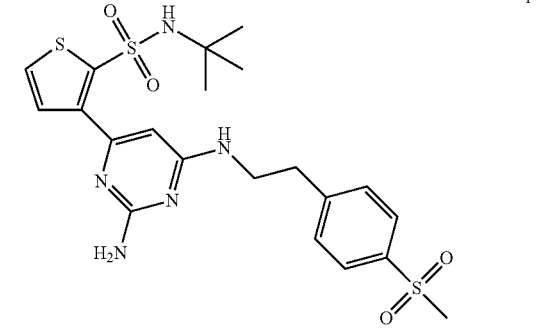
Example 18
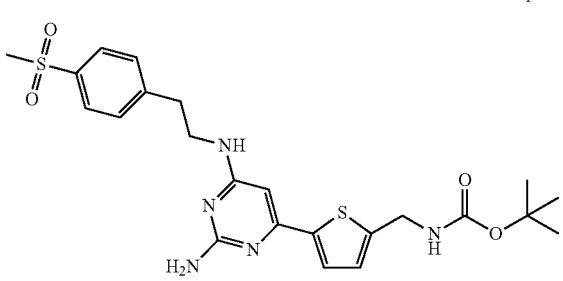
Example 19
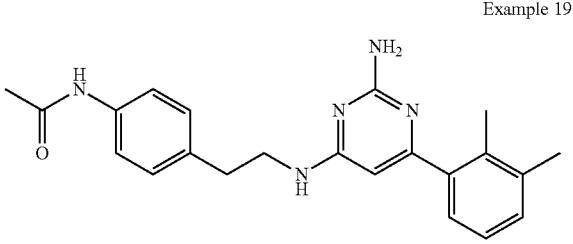
Example 20
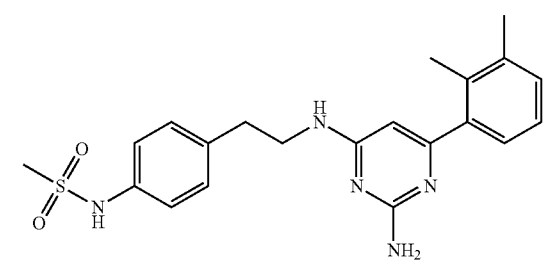

Example 21
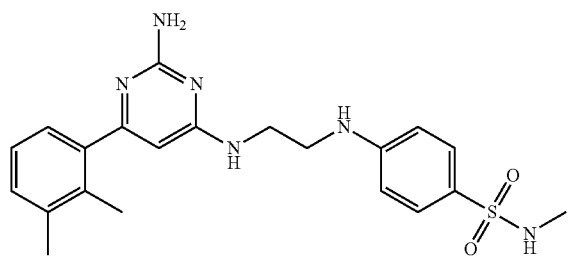
Example 22
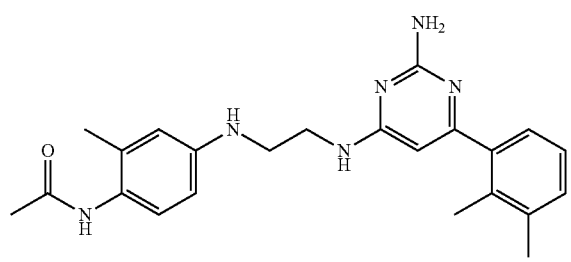
Example 23
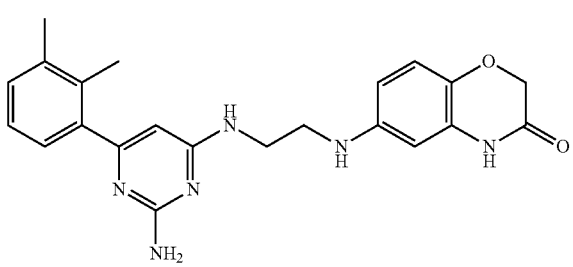
Example 24
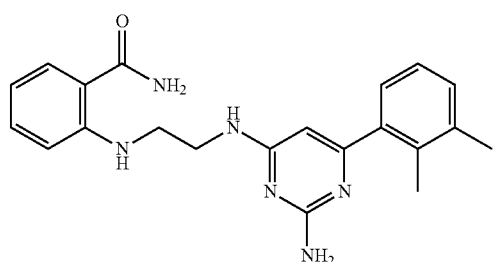
Example 25
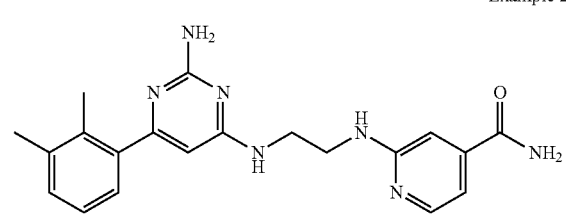
Example 26
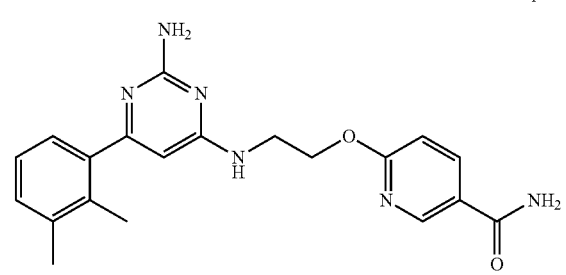
Example 27
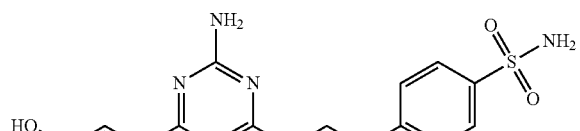
Example 28
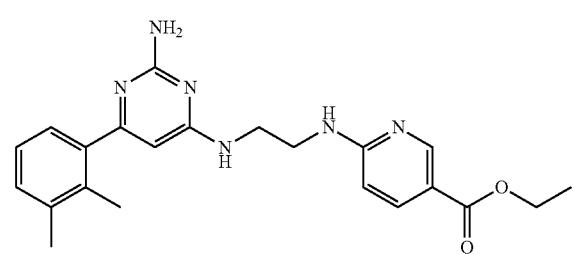
Example 29
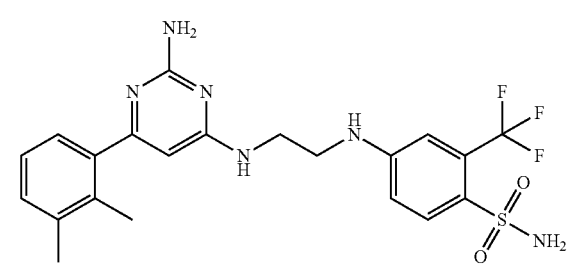
Example 30
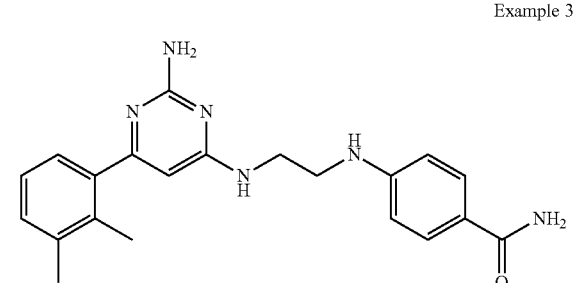
Example 31
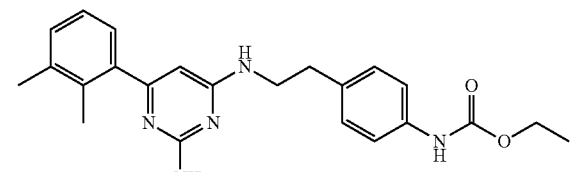
Example 32
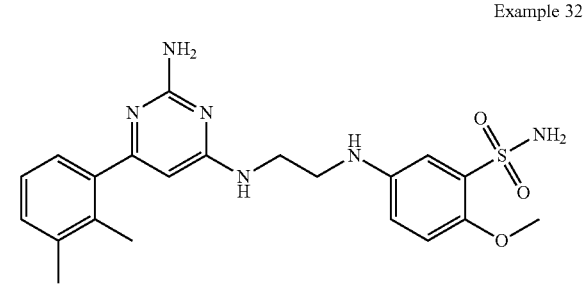

Example 33
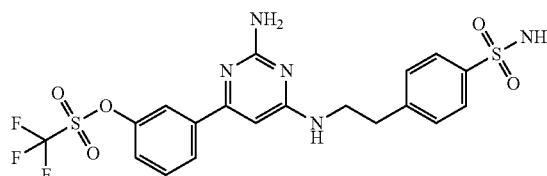
Example 34
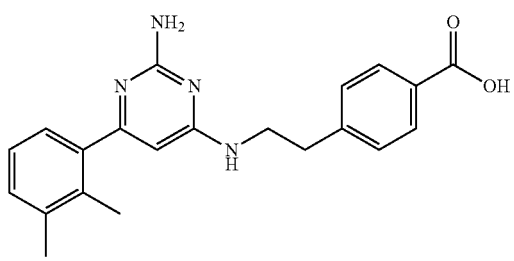
Example 35
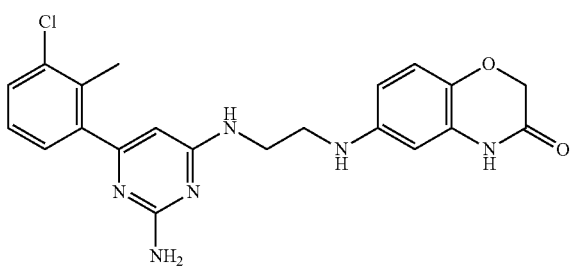
Example 36
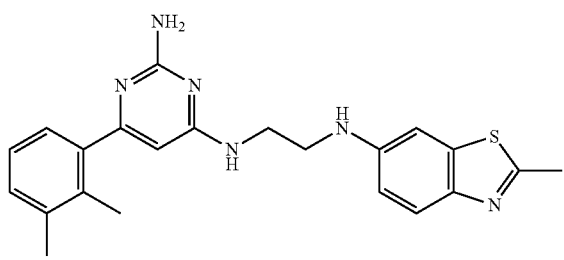
Example 37
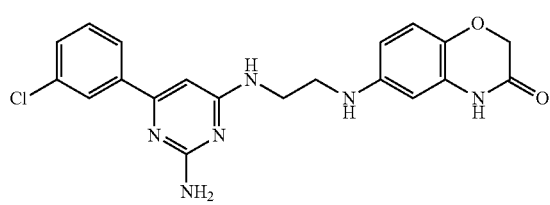
Example 38
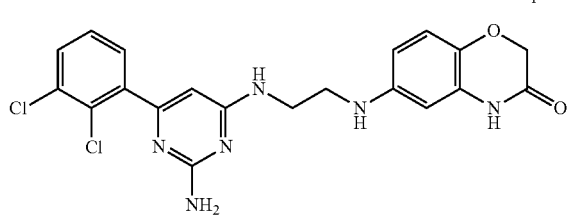
Example 39
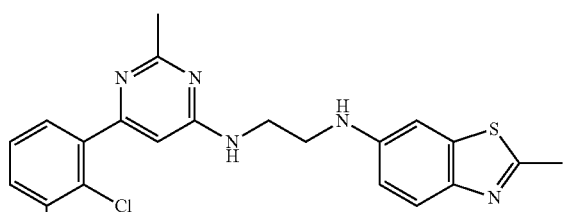
Example 40
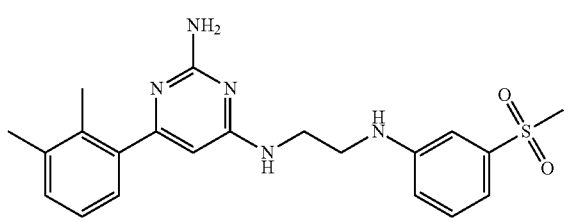
Example 41
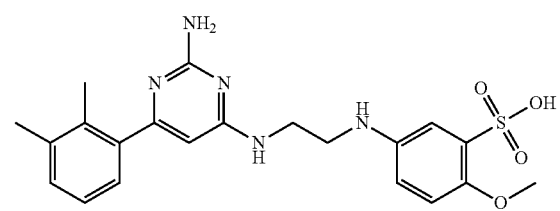
Example 42
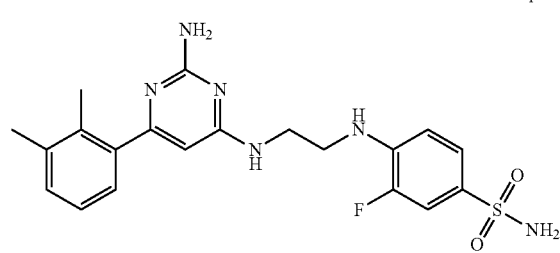
Example 43
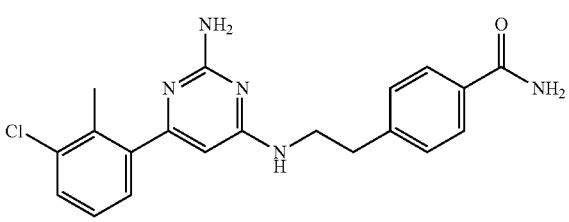
Example 44
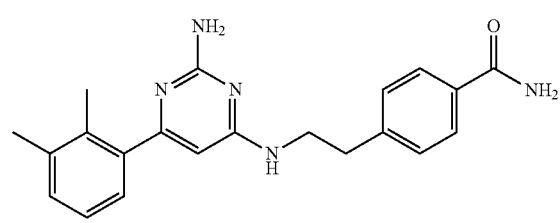

Example 45
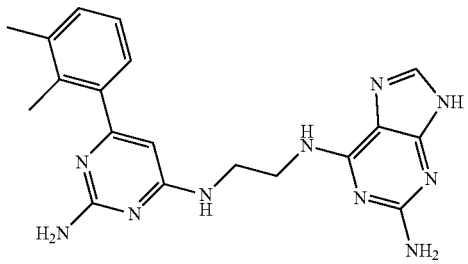
Example 51
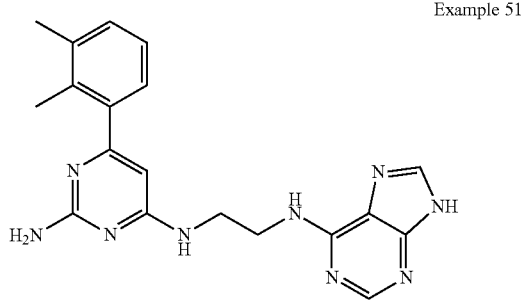
Example 46
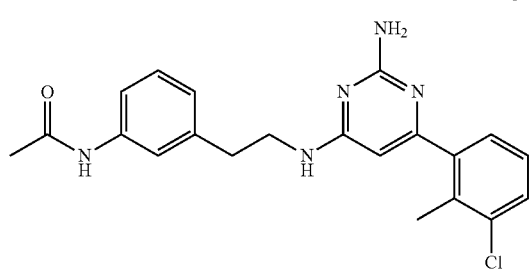
Example 52
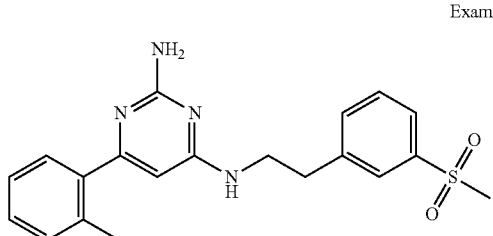
Example 47
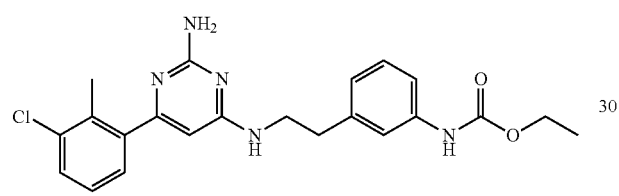
Example 53
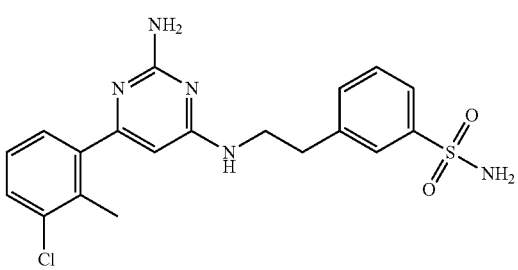
Example 48
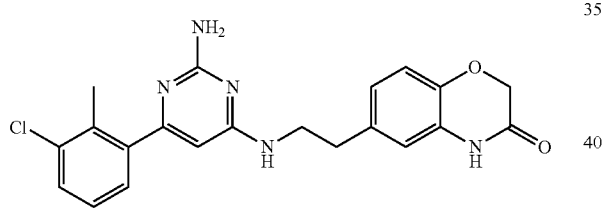
Example 49
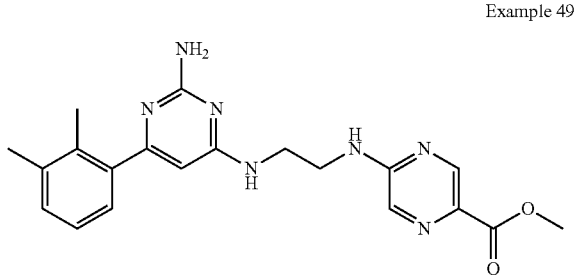
Example 54
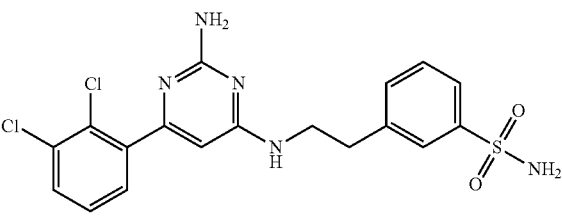
Example 50
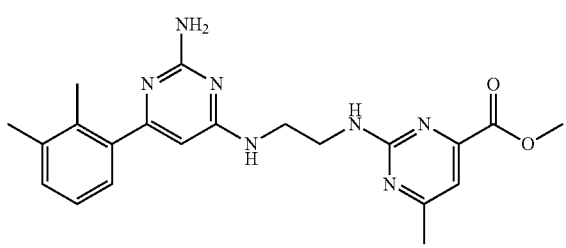
Example 55
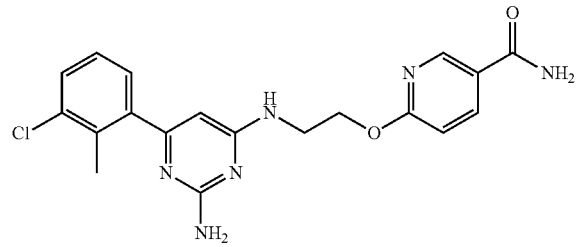

Example 56
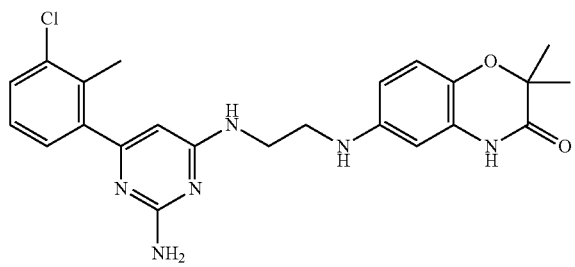
Example 57
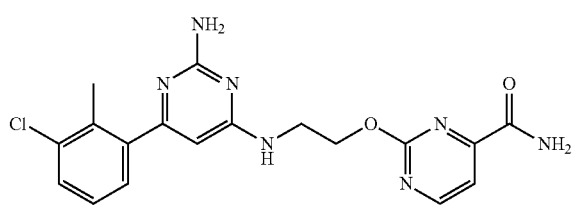
Example 58
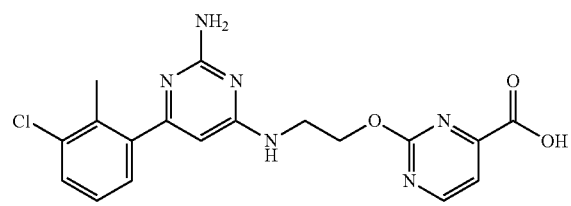
Example 59
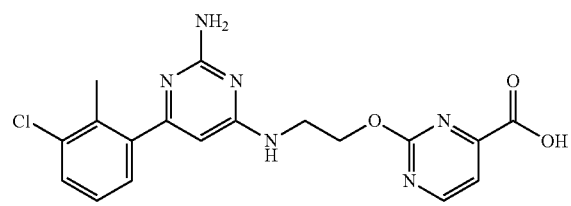
Example 60
Example 61
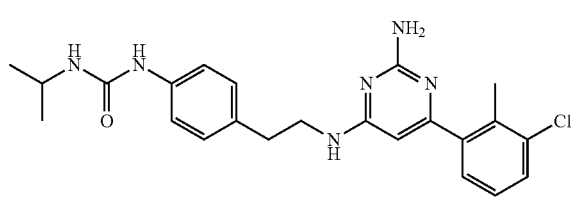
Example 62
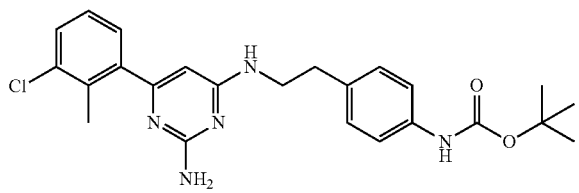
Example 63
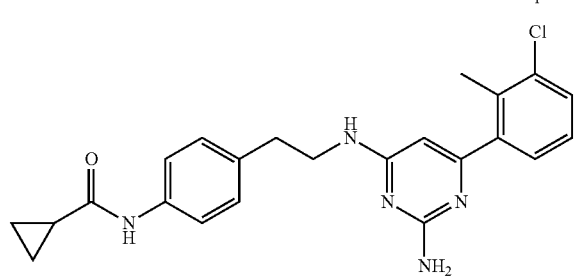
Example 64
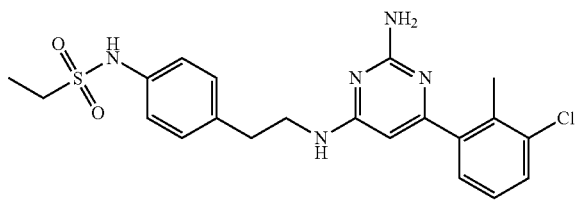
Example 65
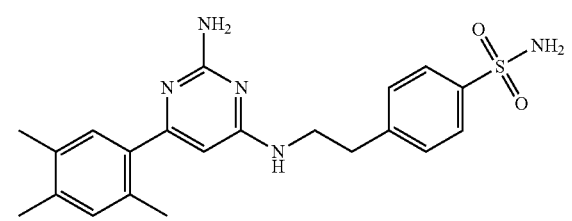
Example 66
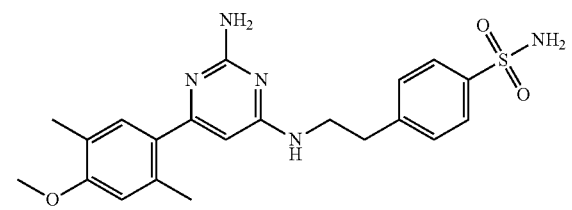
Example 67
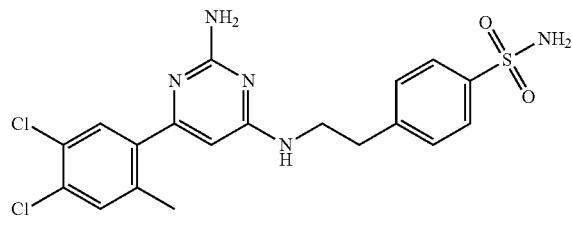

Example 68
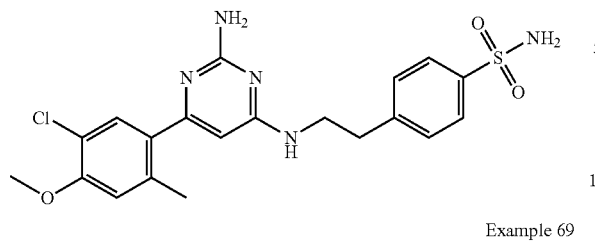
Example 69
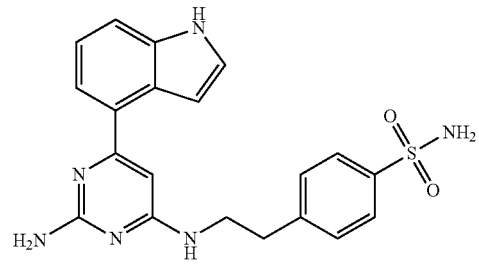
Example 70
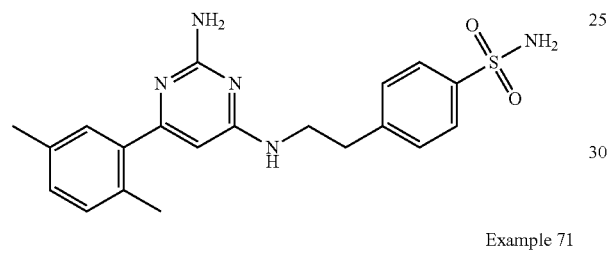
Example 71
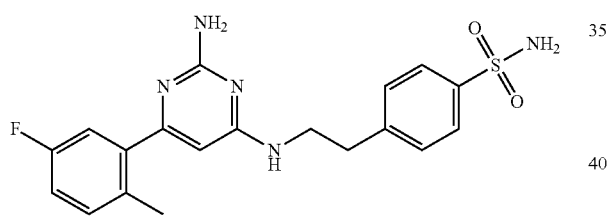
Example 72
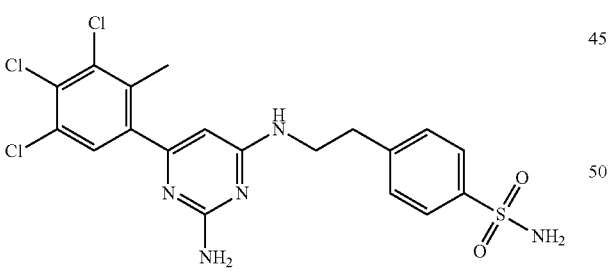
Example 73
Example 74
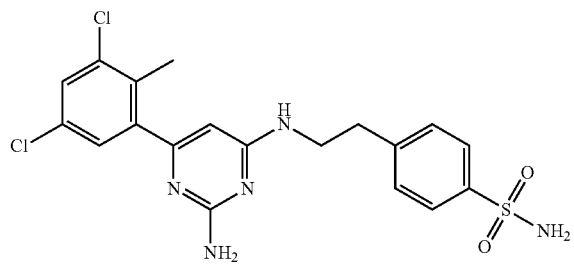
Example 75
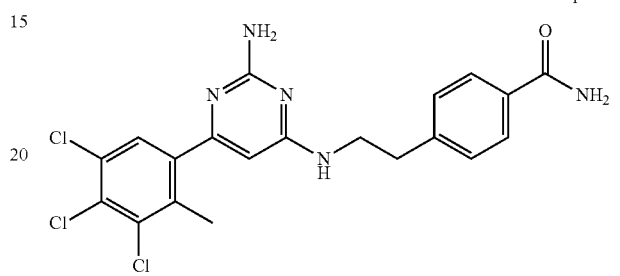
Example 76
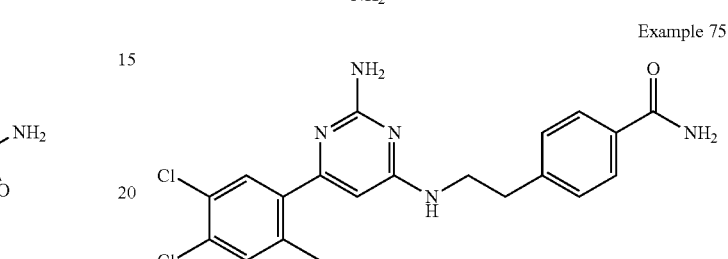
Example 77
Example 78
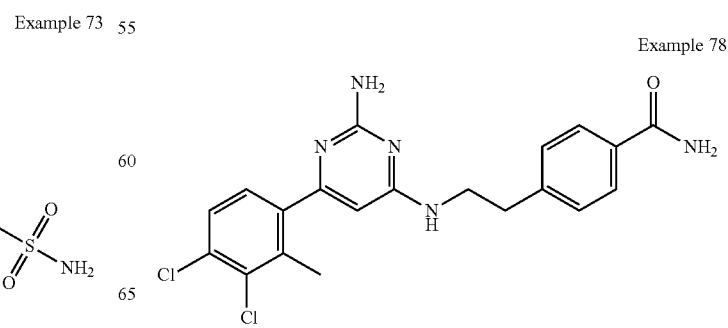

Example 79
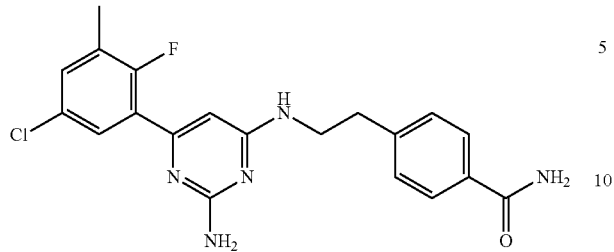
Example 80
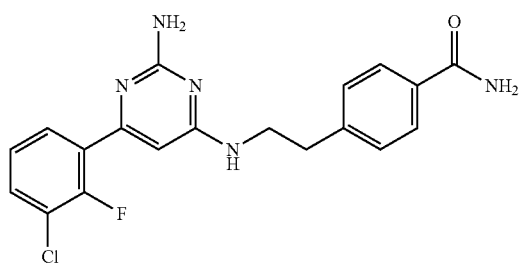
Example 81
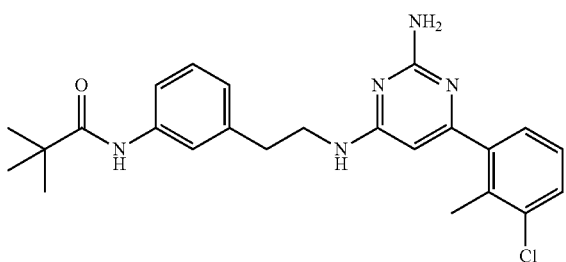
Example 82
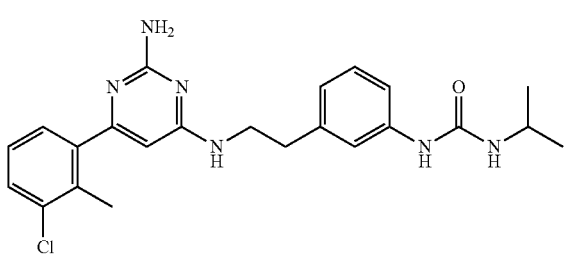
Example 83
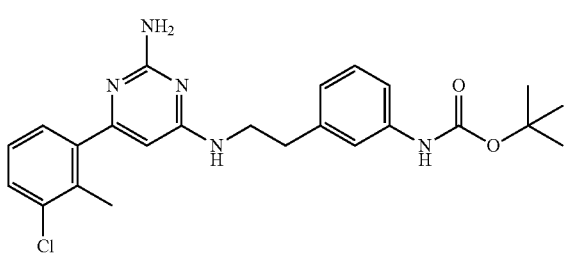
Example 84
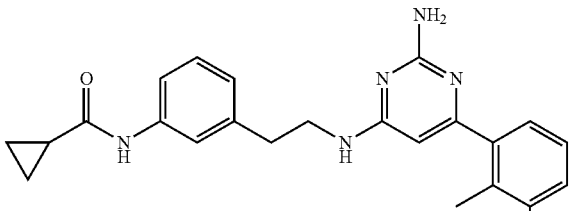
Example 85
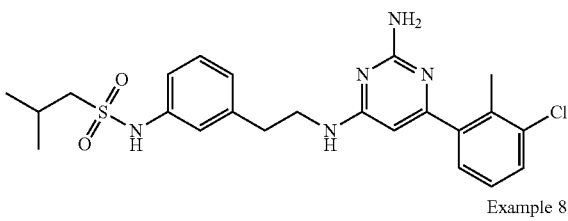
Example 86
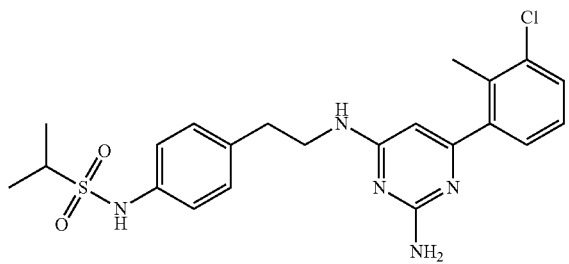
Example 87
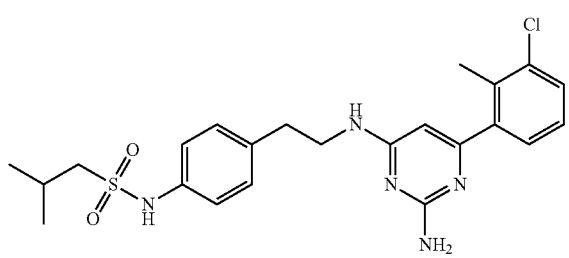
Example 88
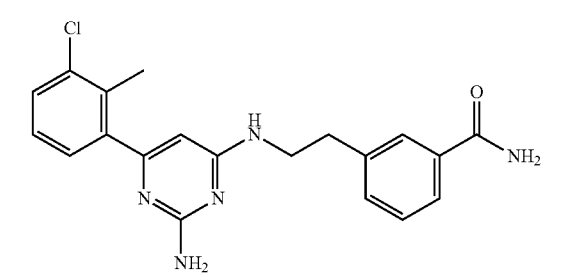
Example 89
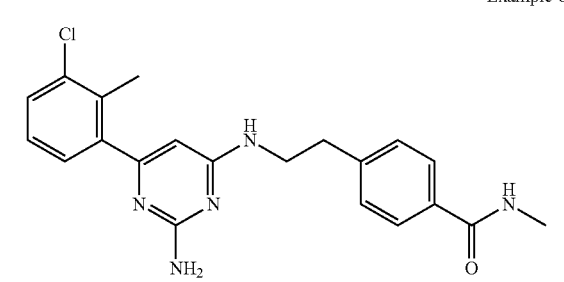

Example 90
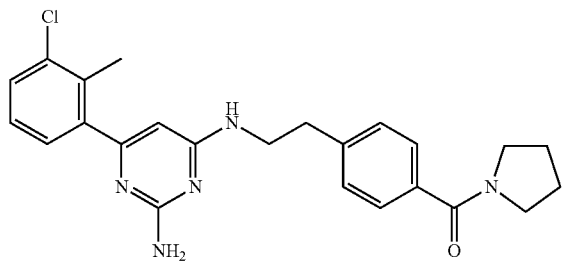
Example 91
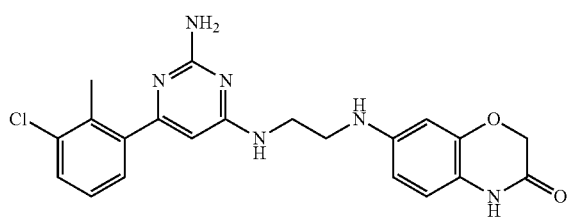
Example 92
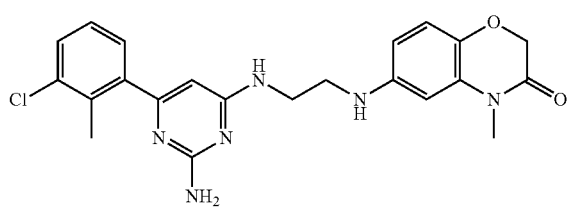
Example 93
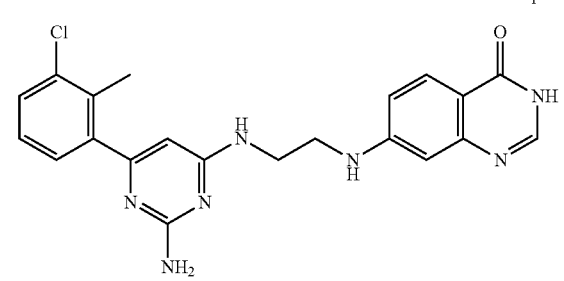
Example 94
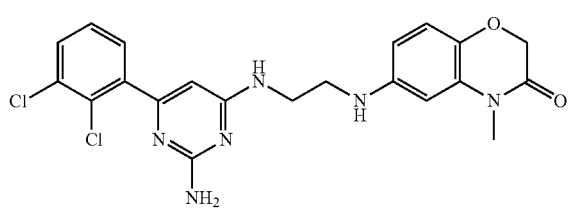
Example 95
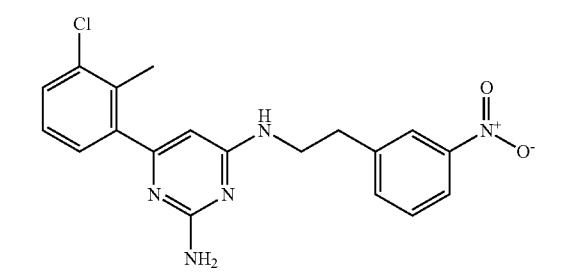
Example 96
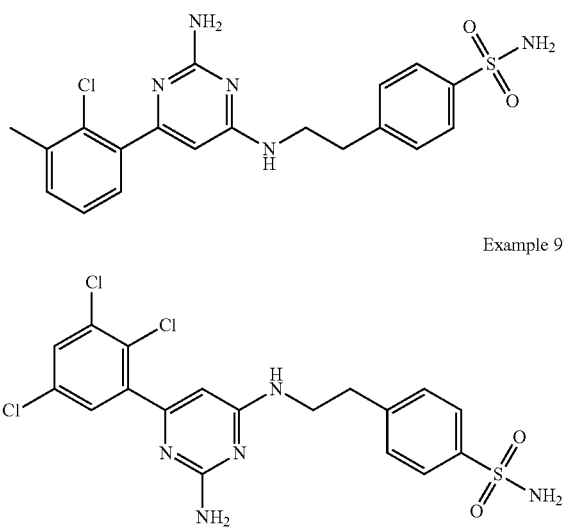
Example 97
Example 98
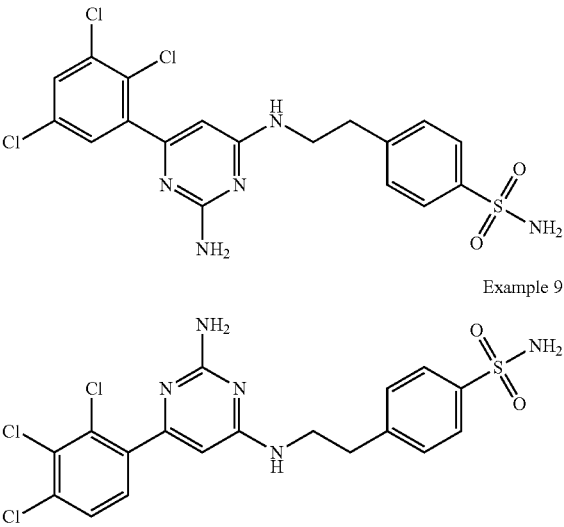
Example 99
Example 100
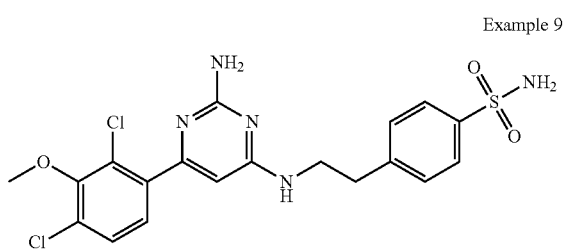
Example 101
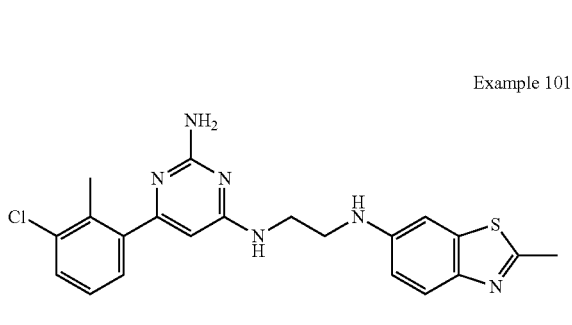

Example 102
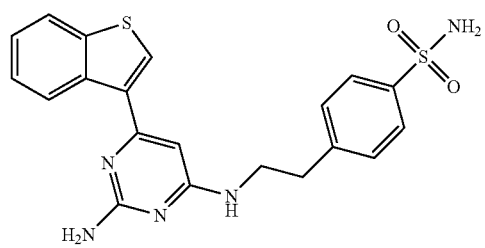
Example 103
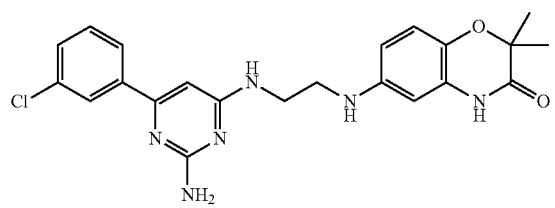
Example 104
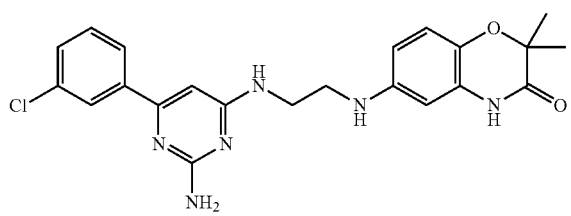
Example 105
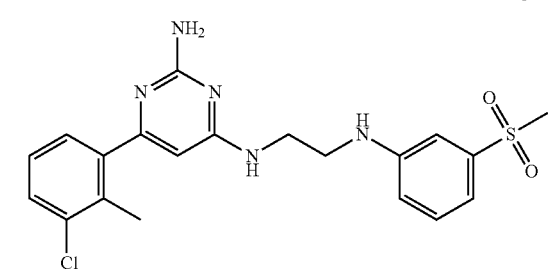
Example 106
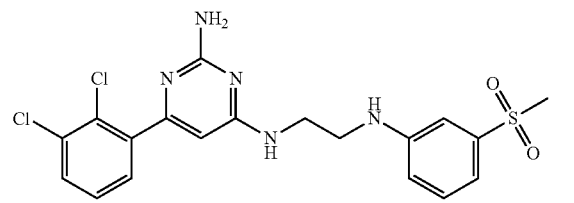
Example 107
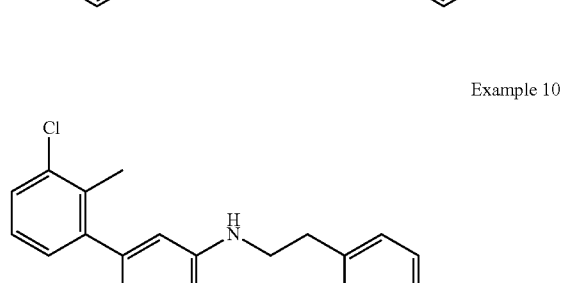
Example 108
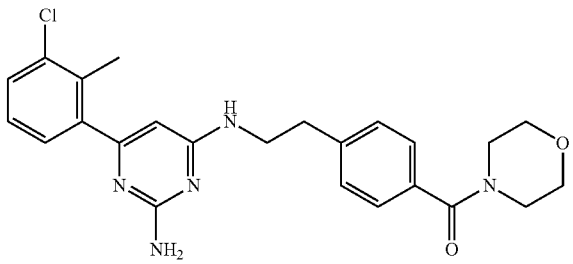
Example 109
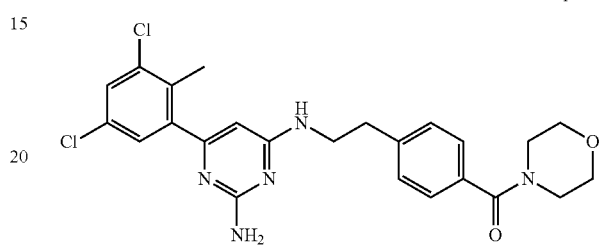
Example 110
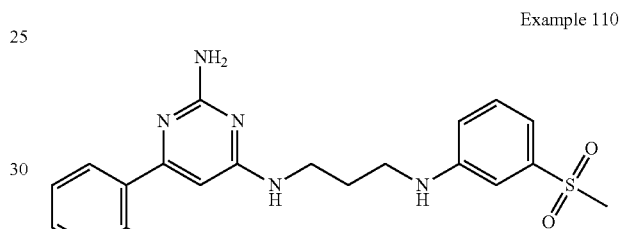
Example 111
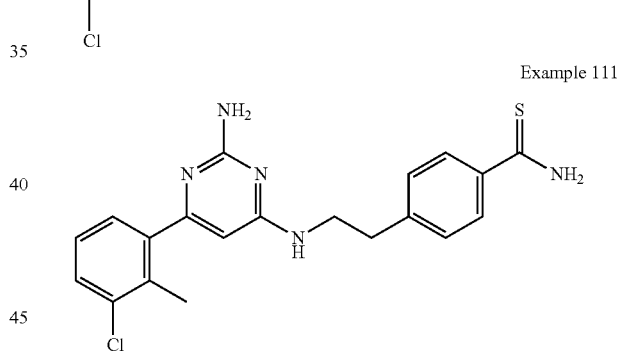
Example 112
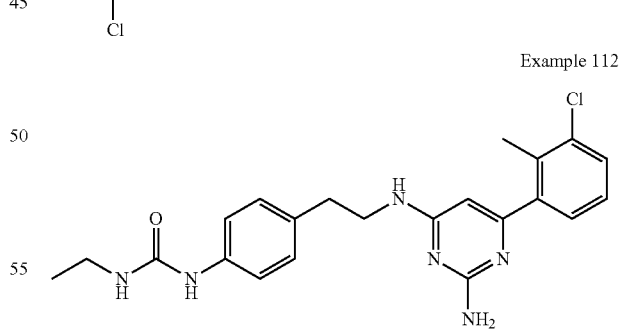
Example 113
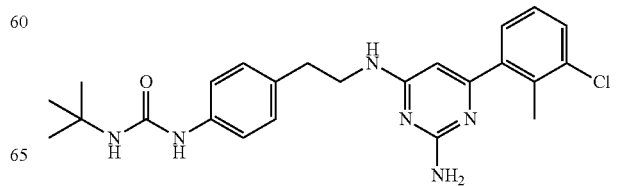

Example 114
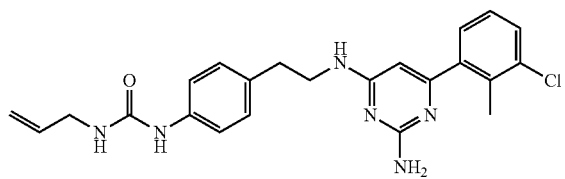
Example 115
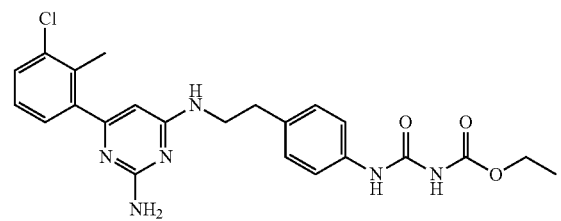
Example 116
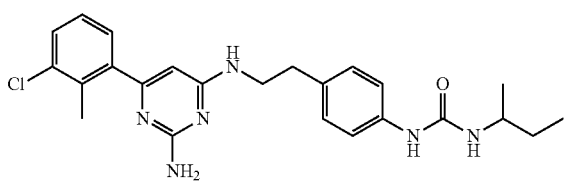
Example 117
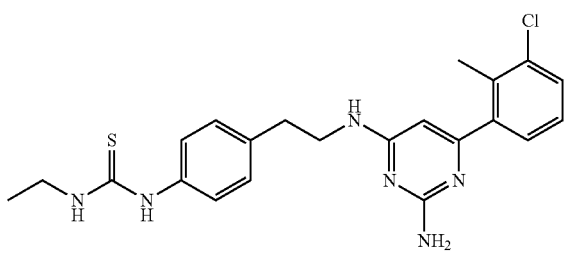
Example 118
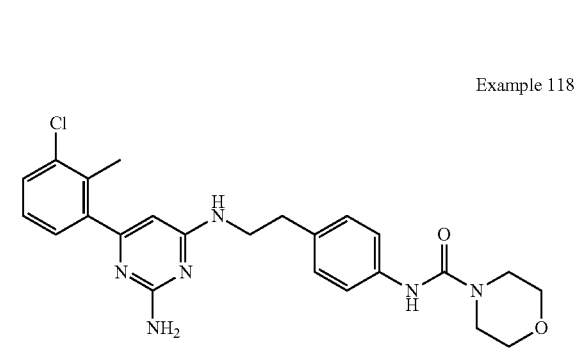
Example 119
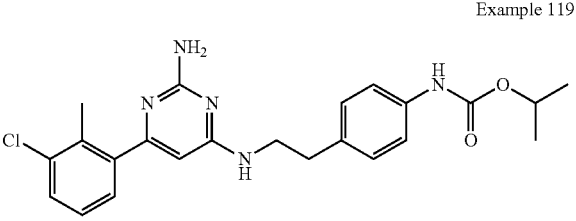
Example 120
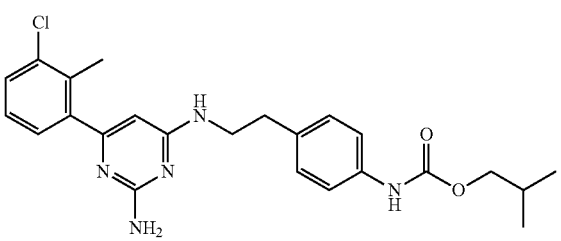
Example 121
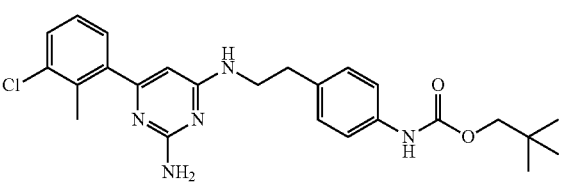
Example 122
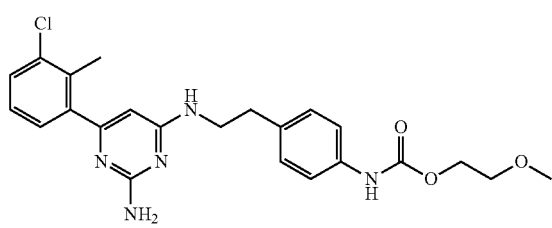
Example 123
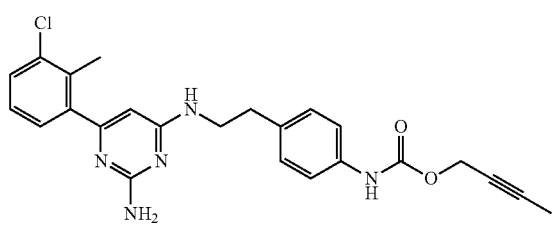
Example 124
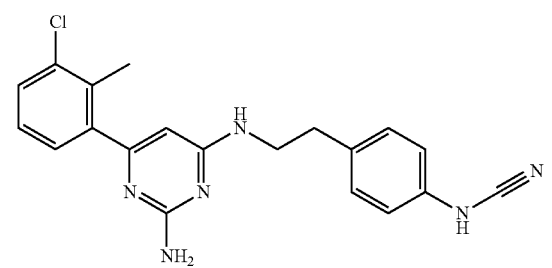
Example 125
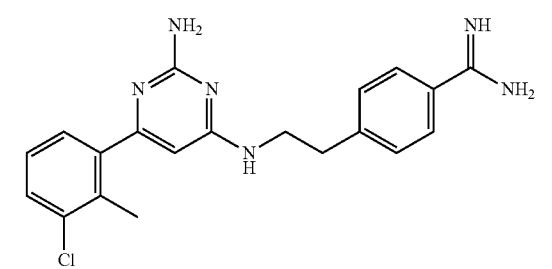

Example 126
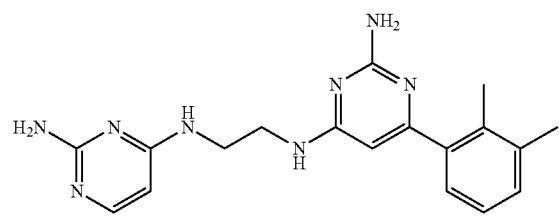
Example 127
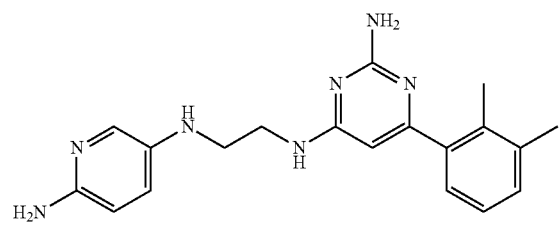
Example 128
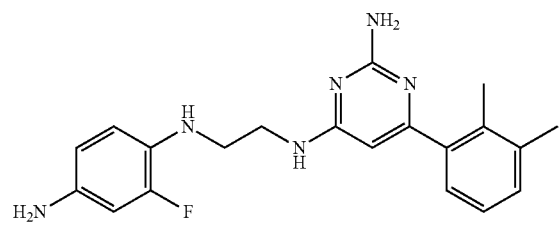
Example 129
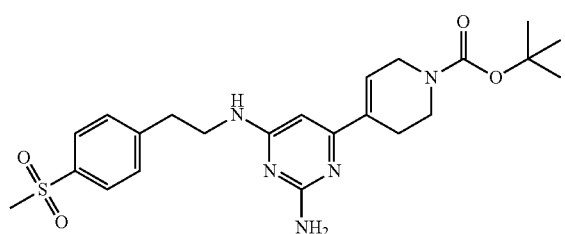
Example 130
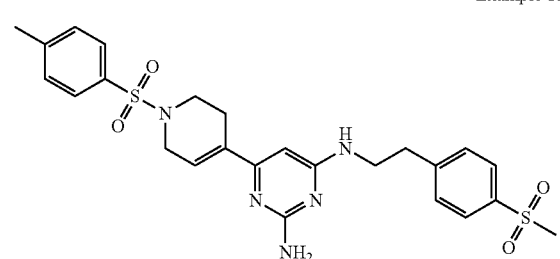
Example 131
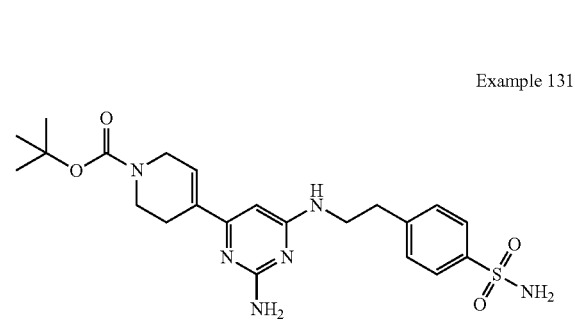
Example 132
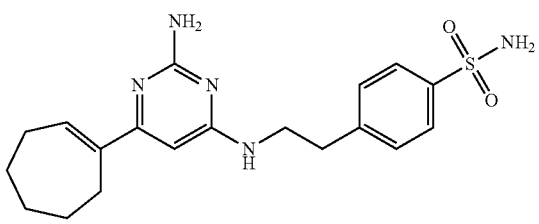
Example 133
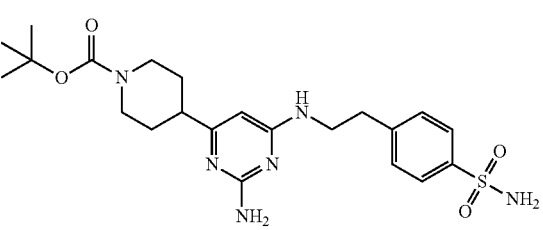
Example 134
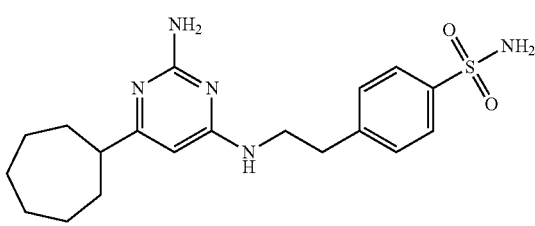
Example 135
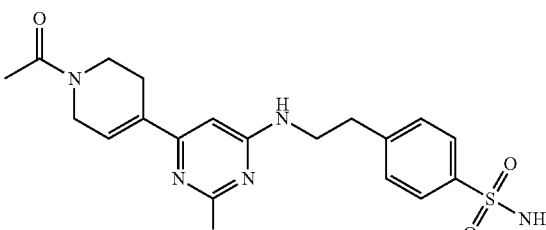
Example 136
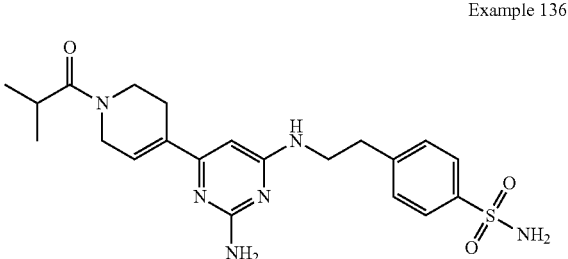
Example 137
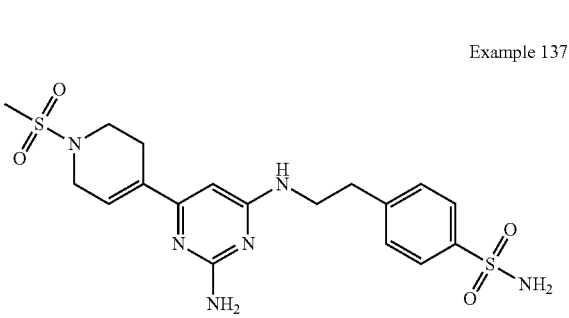

Example 138
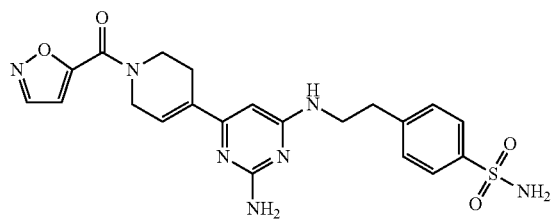
Example 145
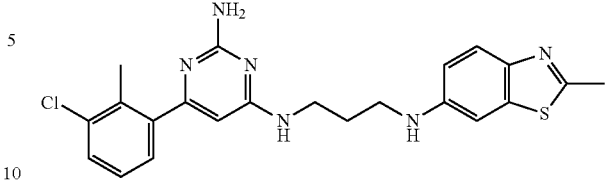
Example 139
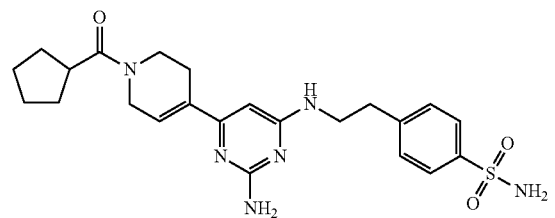
Example 146
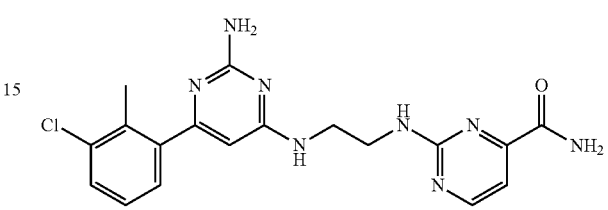
Example 140
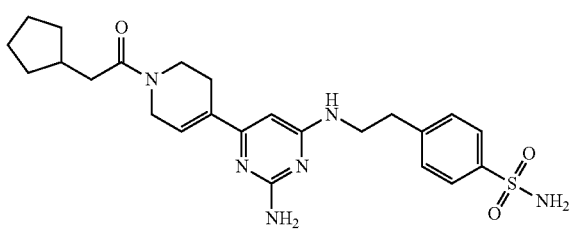
Example 147
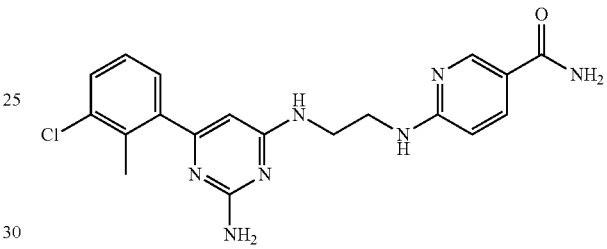
Example 141
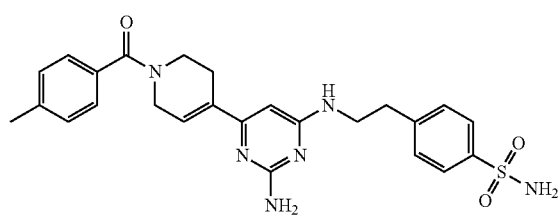
Example 148
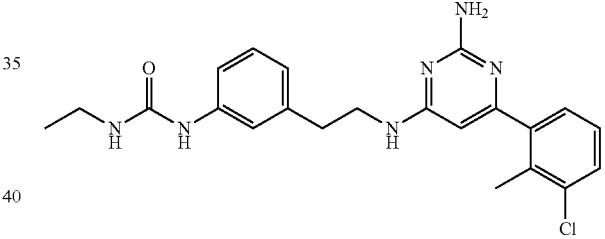
Example 142
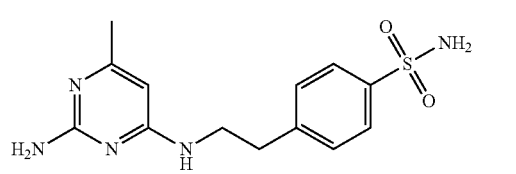
Example 149
Example 143
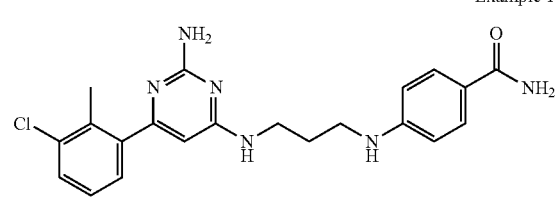
Example 150
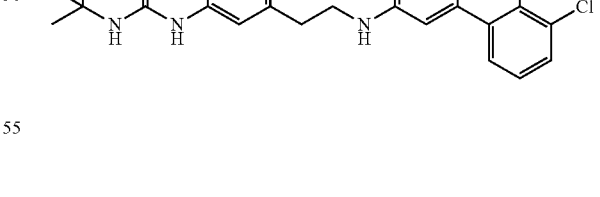
Example 144
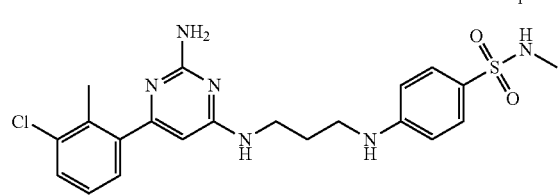
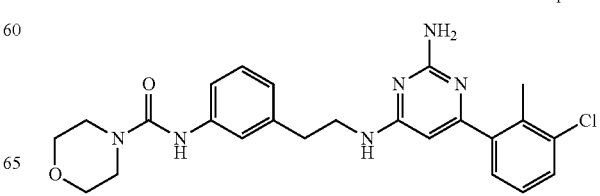

Example 151
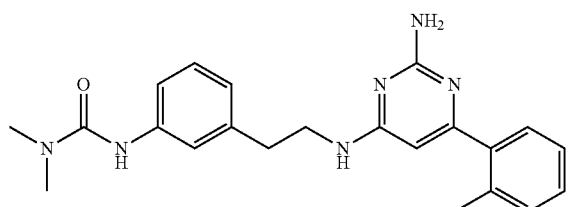
Example 152
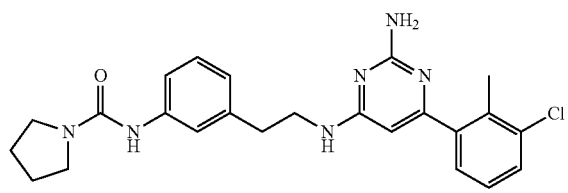
Example 153
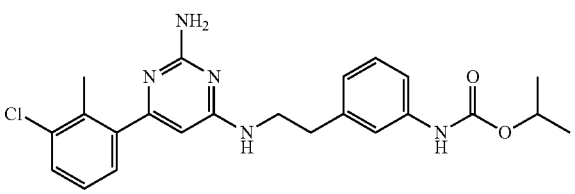
Example 154
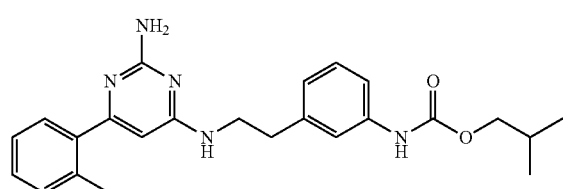
Example 155
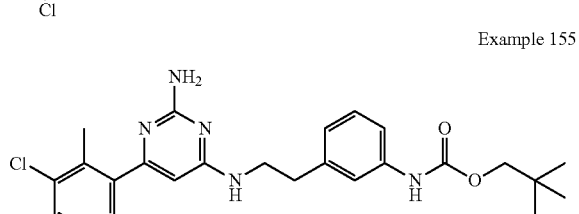
Example 156
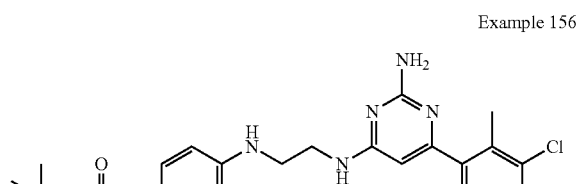
Example 157
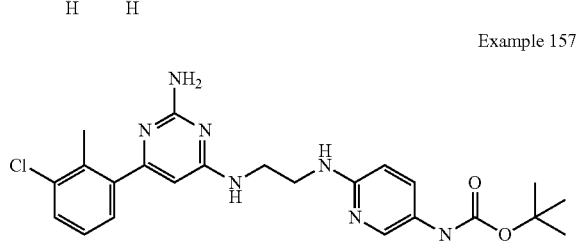
Example 158
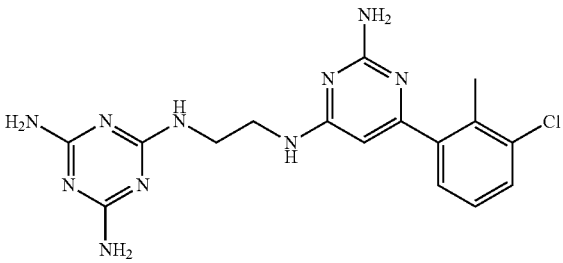
Example 159
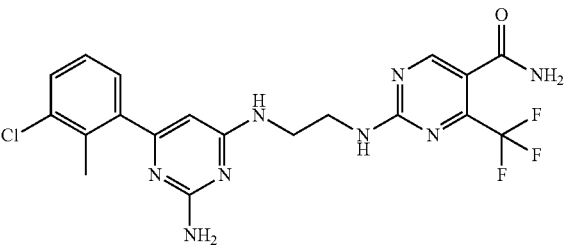
Example 160
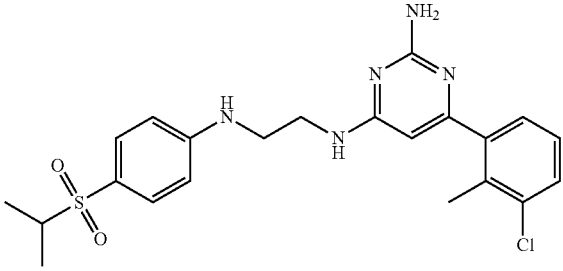
Example 161
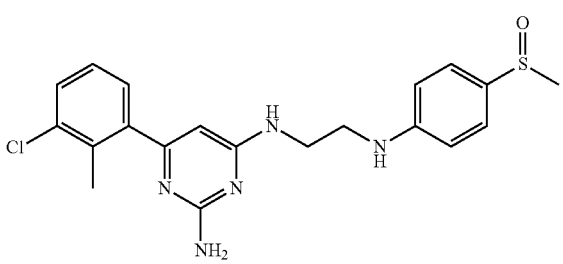
Example 162
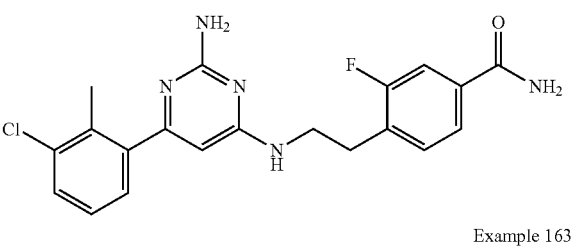
Example 163
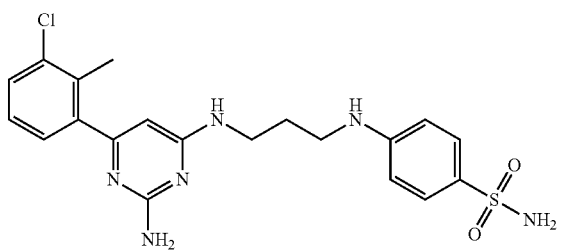

Example 164
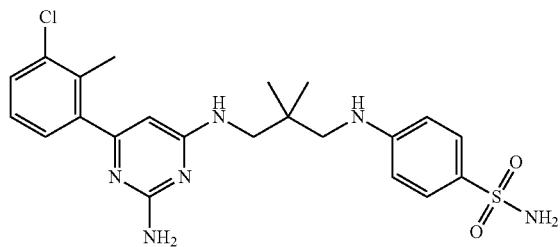
Example 165
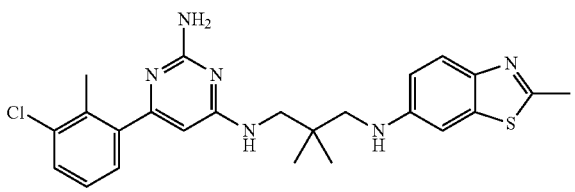
Example 166
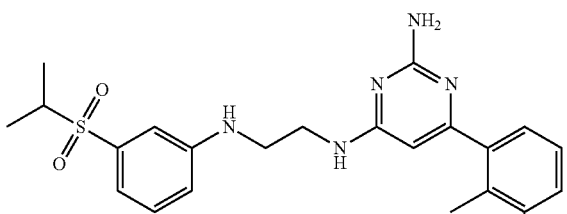
Example 167
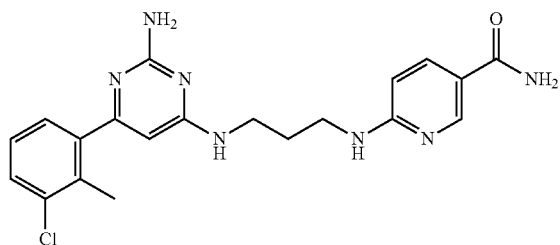
Example 168
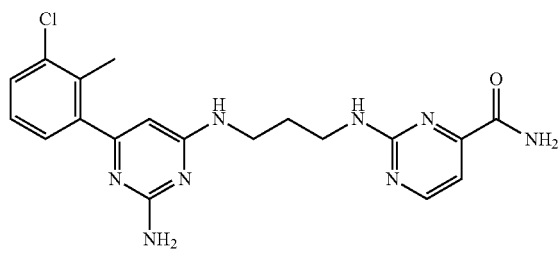
Example 169
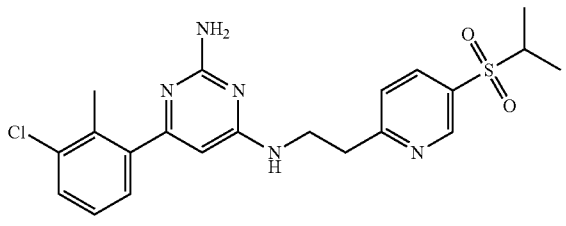
Example 170
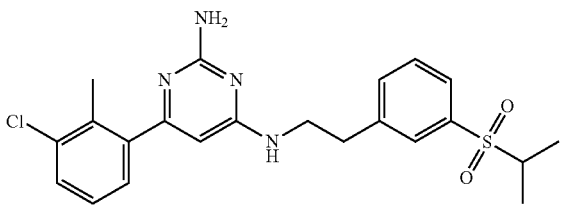
Example 171
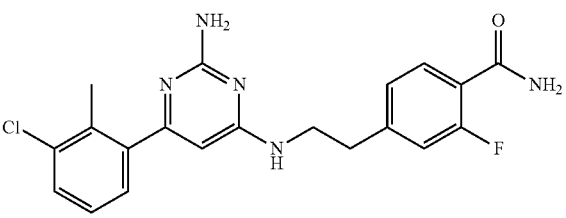
Example 172
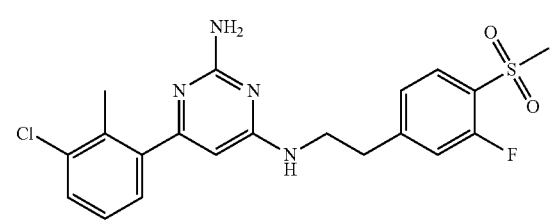
Example 173
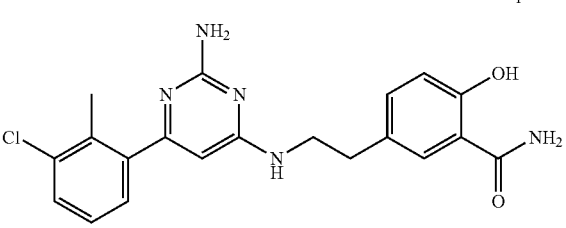
Example 174
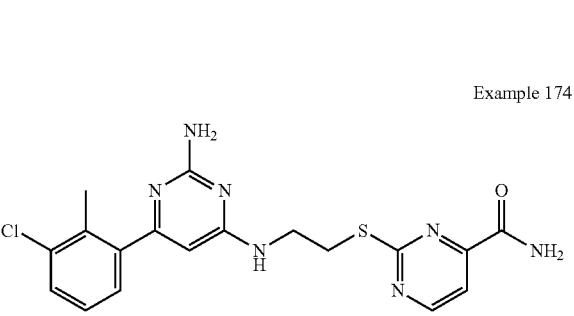
Example 175
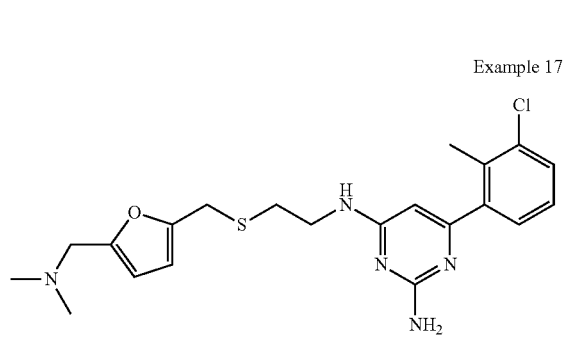

Example 176
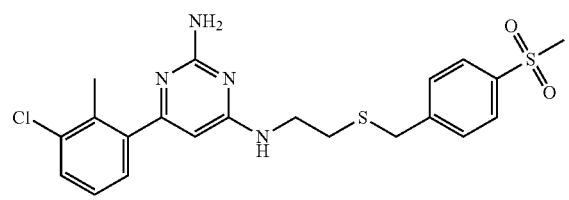
Example 177
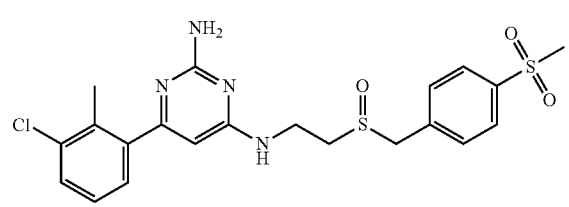
Example 178
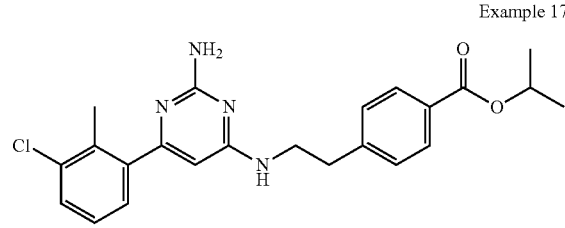
Exampl 179
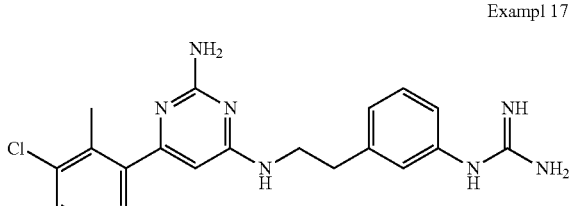
Example 180
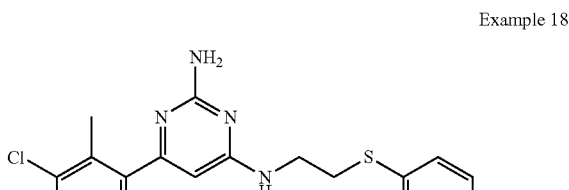
Example 181
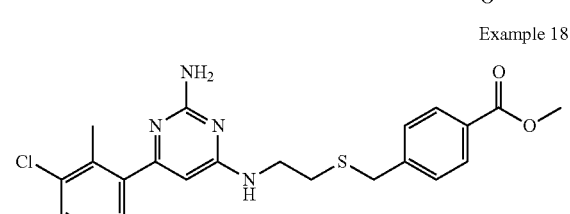
Example 182
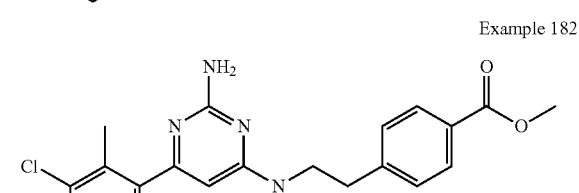
Example 183
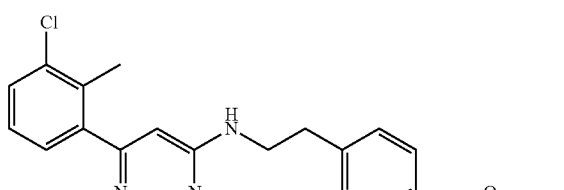
Example 184
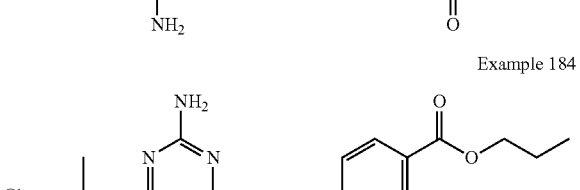
Example 185
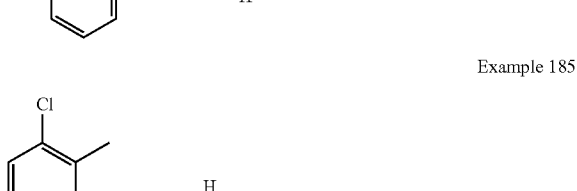
Example 186
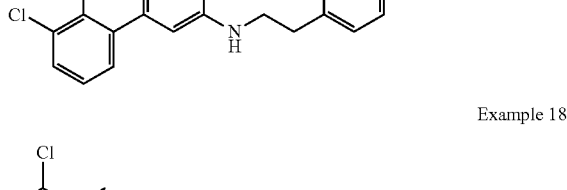
Example 187
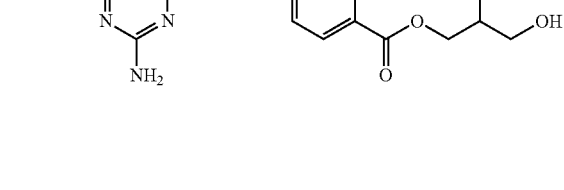
Example 188
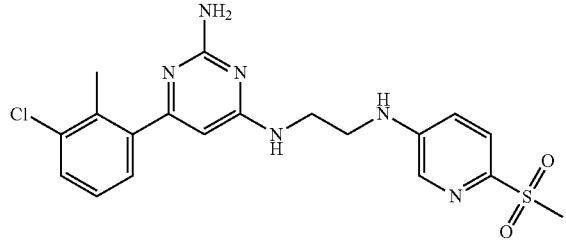

-continued
Example 189
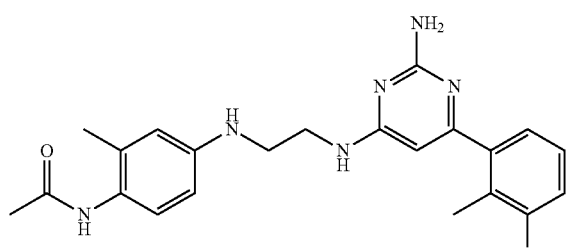
Example 190
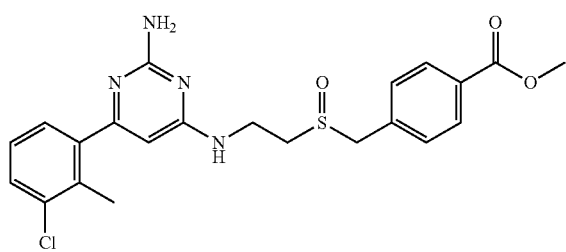
Example 191
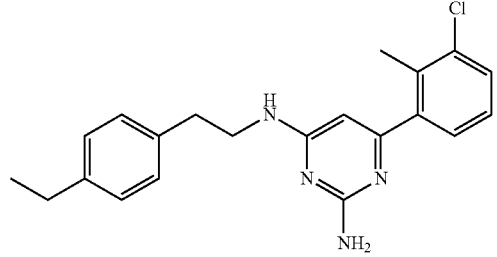
Example 192
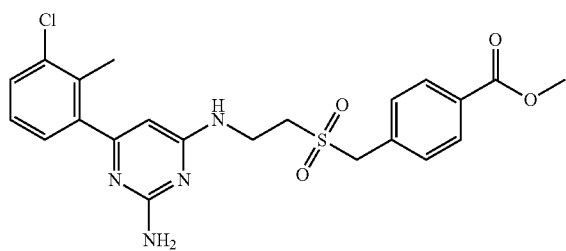
Example 193
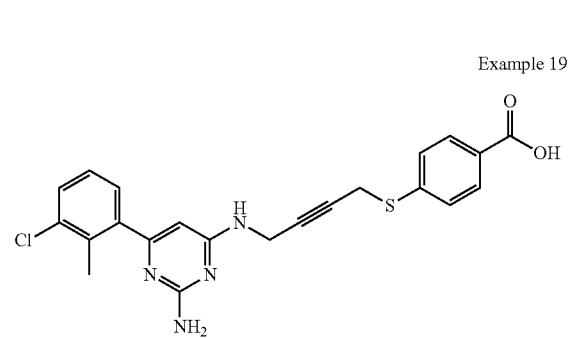
-continued
Example 194
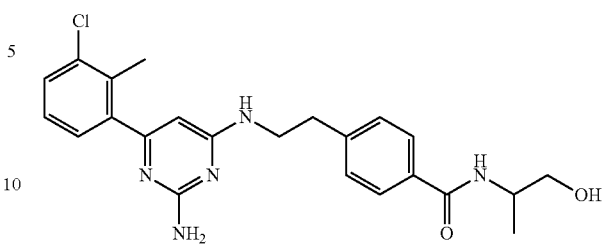
Example 195
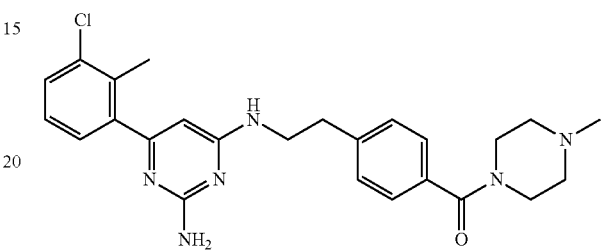
Example 196
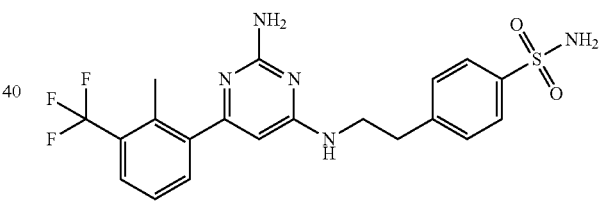
Example 197
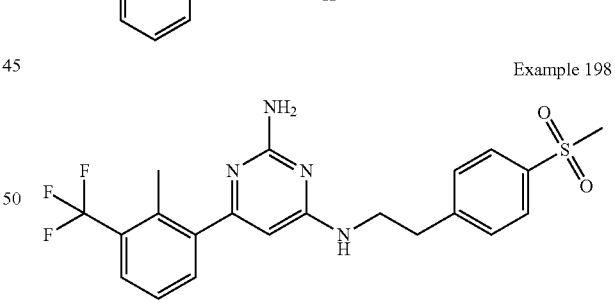
Example 198
Example 199
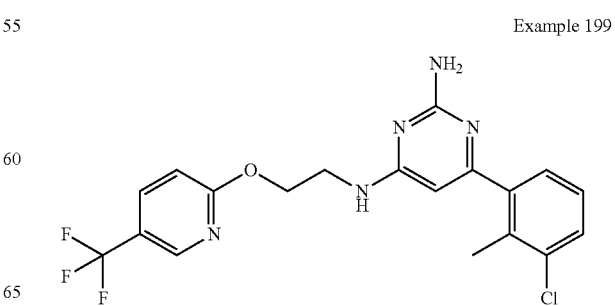

Example 200
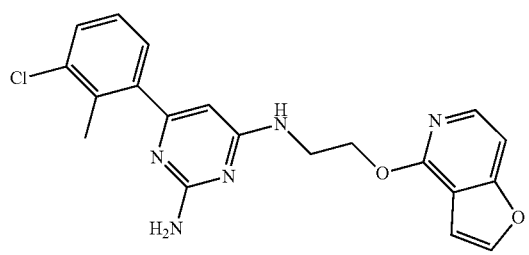
Example 201
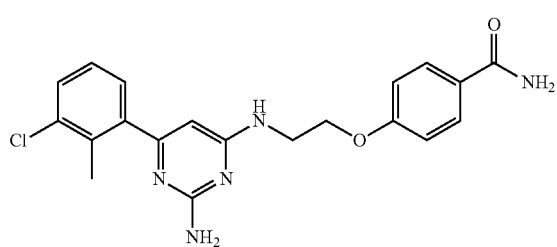
Example 202
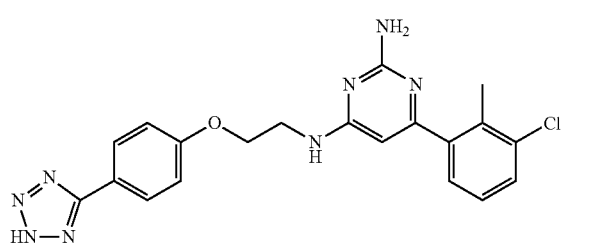
Example 203
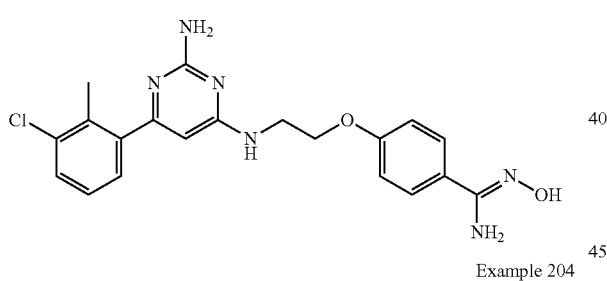
Example 204
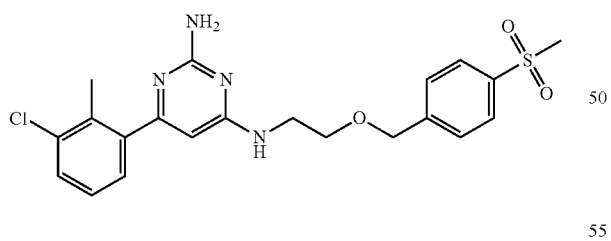
Example 205
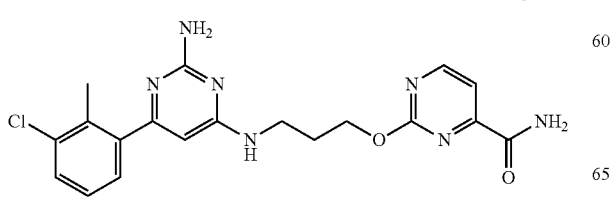
Example 206
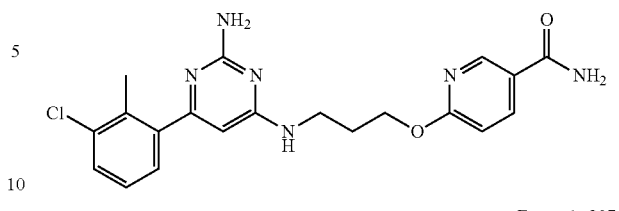
Example 207
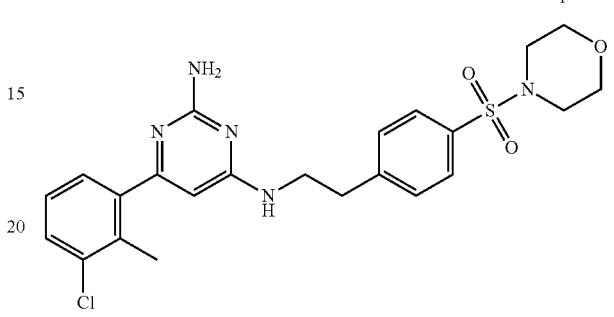
Example 208
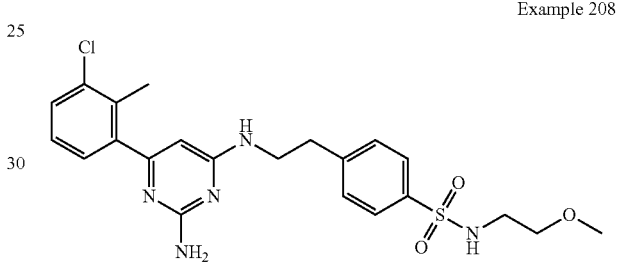
Example 209
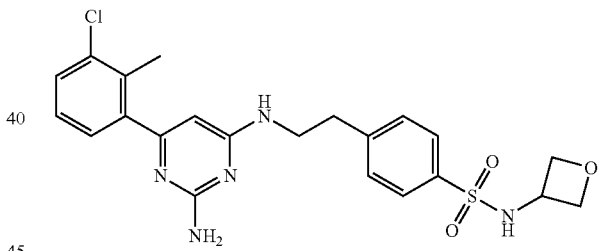
Example 210
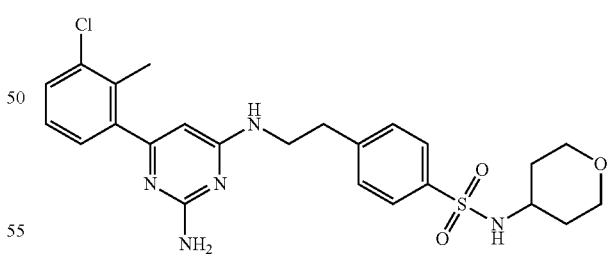
Example 211
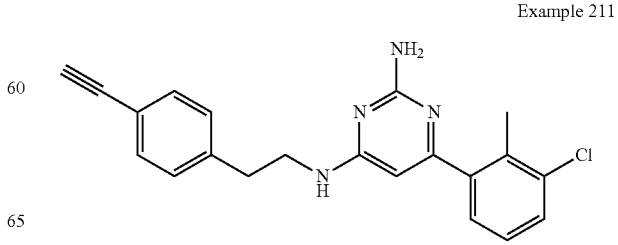

-continued

Example 212

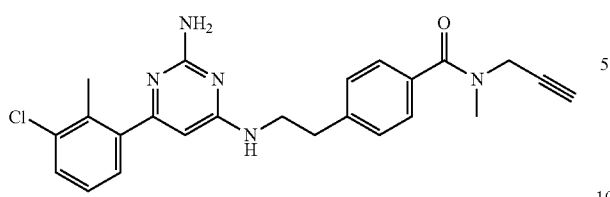

Example 213

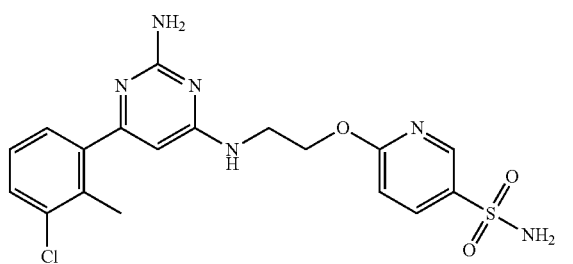

Example 214

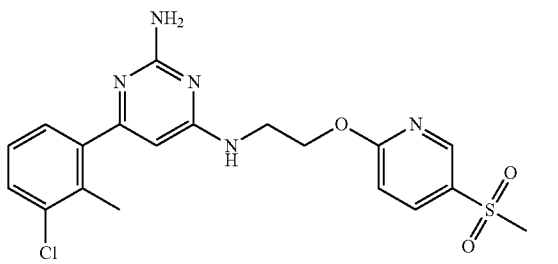

Example 215

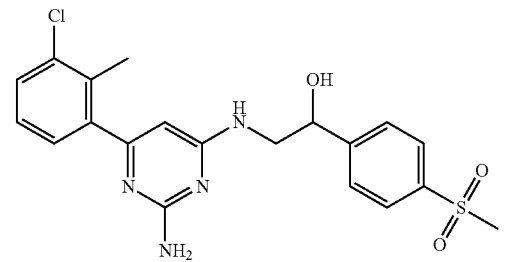

Example 216

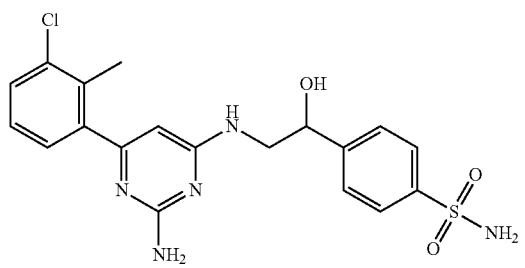

Example 217

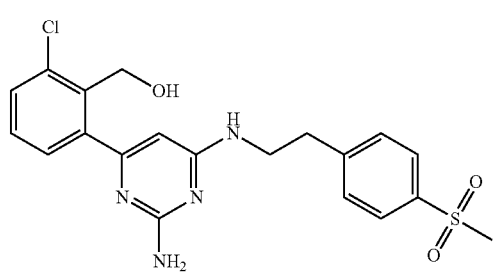

-continued

Example 218

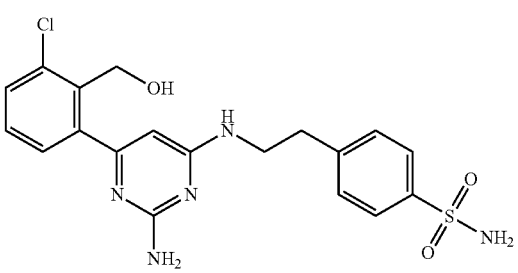

BIOLOGICAL EXAMPLES

Biological Example 1

MTH1 Enzymatic Assay and IC50 Value Determination

MTH1 catalyzes the hydrolysis of dGTP to dGMP and PPi. By coupling the reaction to pyrophosphatase added in excess PPi is converted to Pi that can be detected by using the malachite green assay reagent. Two different formats were used for IC50 determinations in the enzymatic assay, 96- and 384-well format. 96-Well Method:

Briefly, the compound to be analyzed is diluted in DMSO in a 1:3 dilution series generating 12 different compound concentrations giving a final DMSO concentration of 1% in the assay well. MTH1 diluted in assay buffer (100 mM Tris-acetate, 40 mM NaCl, 10 mM magnesium acetate, 1 mM DTT and 0.005% Tween 20) fortified with *E. coli* pyrophosphatase (0.2 U/ml) is added to a final concentration of 6 nM. dGTP diluted in assay buffer is added to a final concentration of 100 μM. The reaction mixture is incubated for 15 minutes at 22° C. To 100 μl reaction mixture, 25 μl Malachite green assay regent (0.095% Malachite green in 17% H2SO4, 1.5% Ammonium molybdate, 0.17% Tween 20) is added, followed by incubation with shaking for 15 minutes at 22° C. The absorbance of the assay plate is read at 630 nm using a Hidex Sense Multilabel plate reader. The IC50 value is determined by fitting a dose response curve to the data points using nonlinear regression analysis and the equation $Y = Bottom + (Top - Bottom)/(1 + 10^{((Log\ IC50-X)*HillSlope)})$, where Y is the read absorbance at 630 nm and X is log [compound].

384-Well Method:

The compounds to be tested are nano-dispensed, in 11 concentrations, directly in assay plates, with a final DMSO concentration <1%. The protocol and the reaction mixture are the same as for the 96-well assay, with a total reaction volume of 50 μl/well to which 10 μl of Malachite green reagent is added. All additions to the assay plates are made with multidrop.

Using this approach the following representative IC50 values were derived.

Examples—1, 2, 3, 4, 5, 6, 7, 8, 9, 10, 11, 12, 13, 14, 15, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 134, 135, 136, 137, 138, 139, 140, 141, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 178, 179, 180, 181, 182, 183, 184, 185, 186, 187, 188, 189, 191, 193, 194, 195, 196, 197, 198, 199, 200, 201, 202, 203, 204, 205, 206, 207, 208, 209, 210, 211, 212, 213, 214, 215, 216, 217 and 218 had IC50's of less than 200 nM.

Biological Example 2: Cell Viability Assay

Method 1:
Cells are seeded into 96 well plates (1000-3000 cells/well) in DMEM GlutaMAX™ or other suitable media dependent on cell line and incubated overnight in 5% $CO_2$, 37° C. Thereafter cells are treated with compound or vehicle and left in incubator for 3 days until staining with resazurin. Cells are incubated in resazurin (diluted in suitable media) at 37° C. for 2 hours before measuring the fluorescence (Ex544/Em590).

Method 2:
The compounds to be tested are nano-dispensed in 11 concentrations, directly in 384-well cell plates, with a final DMSO concentration <1%. Cells are seeded in cell plates, pre-dispensed with compounds, 50 µl/well (600-1200 cells/well). After 3 days culture in 5% CO2, 37° C., resazurin diluted in PBS is added, 10 µl/well, and cells are incubated 3 hours before measuring fluorescence (Ex544/Em590).

Using these approaches the following representative IC50 values were derived.

Examples—1, 2, 3, 13, 16, 19, 20, 21, 22, 23, 24, 26, 28, 29, 30, 31, 32, 35, 36, 38, 39, 40, 42, 43, 44, 46, 47, 48, 49, 52, 53, 54, 55, 56, 57, 59, 60, 61, 62, 63, 64, 65, 66, 70, 72, 73, 74, 75, 76, 77, 78, 79, 81, 82, 83, 84, 85, 86, 87, 89, 90, 91, 92, 93, 95, 96, 97, 101, 103, 104, 105, 106, 107, 108, 109, 110, 111, 112, 113, 114, 115, 116, 117, 118, 119, 120, 121, 122, 123, 124, 126, 127, 128, 143, 144, 145, 146, 148, 149, 150, 151, 152, 153, 154, 155, 159, 160, 161, 163, 164, 165, 166, 167, 168, 169, 170, 171, 172, 173, 174, 176, 178, 180, 181, 182, 183, 184, 185, 186, 187, 188, 189, 191, 194, 195, 196, 198, 200, 201, 203, 204, 205, 206, 207, 208, 209, 210, 211, 212, 213 and 214 had IC50's of less than 500 nM Biological Example 3: MTH1 siRNA Knock Down and Cell Survival Cells were cultivated in suitable medium supplemented with 10% FBS and 10 U/ml PeSt. On day 1, cells were seeded at approximately 30% confluency in 6-well plates in complete medium. The day after, the medium was aspired and fresh medium without antibiotics was added. The cells were transfected with All-stars Non-targeting RNA (NT RNA, Qiagen) and MTH1 siRNA (5'-CGACGACAGC-UACUGGUUU-3') and Interferin (Polyplus) according to the manufacturer's protocol. On day 5, cells were either trypsinized, counted and re-seeded for clonogenic outgrowth on 10-cm plates at 500 cells/plate or washed with PBS and scraped in lysis buffer (10 mM Hepes pH 7.1, 50 mM NaCl, 0.3 M sucrose, 0.1 mM EDTA, 0.5% Triton X100, 1 mM DTT and 1× protease inhib, cocktail (Pierce)) and processed for Western blot. Blots were stained with anti-MTH1 antibody (rabbit polyclonal, HPA, KTH, Sweden) and anti-tubulin (mouse monoclonal, Sigma Aldrich). After additional 7-10 days, survival plates were fixed/stained with 4% methylene blue in MeOH and colonies were counted manually. FIG. 1 shows the effect on cell survival following MTH1 siRNA depletion in various human cancer and normal cell lines.

The invention claimed is:
1. A compound of formula I,

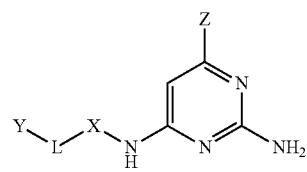

(I)

or a pharmaceutically acceptable salt thereof,
wherein:
X represents —$C_{2-6}$alkylene- optionally substituted by one or more $T^1$, or a saturated or partially unsaturated —$(C(R^A)_2)_p$—$C_{2-5}$heterocycloalkylene-$(C(R^A)_2)_q$— where the heterocycloalkylene is optionally substituted by one or more $T^2$;
L represents a single bond or -$L^1$-$L^2$-;
$L^1$ represents —N($R^B$)—, —O—, —S(O)$_m$—, —C(O)N($R^C$)—, —N($R^D$)C(O)— or —N($R^E$)C(O)N($R^F$)—;
$L^2$ represents a single bond;
Y represents
(i) a 6- to 10-membered aryl substituted by $D^1$ and optionally substituted by one or more groups selected from $R^1$, or
(ii) a 6-membered heteroaryl substituted by $D^2$ and optionally substituted by one or more groups selected from $R^2$, or
(iii) a 5-membered heteroaryl substituted by $D^3$ and optionally substituted by one or more groups selected from $R^3$, or
(iv) a 9-membered bicyclic heteroaryl, in which one ring is 5-membered and the other 6-membered, which heteroaryl is connected to L via its 5-membered ring and substituted by one or more groups selected from $D^4$, and optionally substituted by one or more groups selected from $R^4$, or
(v) a 9- to 11-membered bicyclic heteroaryl, in which one ring is 6-membered and the other 5-7-membered, which heteroaryl is connected to L via its 6-membered ring and optionally substituted by one or more groups selected from $D^5$, or
(vi) an 8-membered bicyclic heteroaryl optionally substituted by one or more groups selected from $D^6$;
$D^1$ represents $R^a$, -A-C(Q)$R^c$, -A-C(Q)N($R^d$)$R^e$, -A-C(Q)O$R^f$, -A-S(O)$_n$$R^g$, -A-S(O)$_n$C(O)$R^h$, -A-S(N$R^i$)(O)$R^j$, -A-S(O)$_n$N($R^k$)$R^l$, -A-S(O)$_n$O$R^m$, —B(O$R^n$)$_2$, —$N_3$, —N($R^o$)$R^p$, —N(H)CN, —$NO_2$, —$ONO_2$, —O$R^q$, —S$R^r$ or, when Y is partly aromatic, =Q;
$D^2$ represents $R^b$, -A-C(Q)$R^c$, -A-C(Q)N($R^d$)$R^e$, -A-C(Q)O$R^f$, -A-S(O)$_n$$R^g$, -A-S(O)$_n$C(O)$R^h$, -A-S(N$R^i$)(O)$R^j$, -A-S(O)$_n$N($R^k$)$R^l$, -A-S(O)$_n$O$R^m$, —B(O$R^n$)$_2$, —$N_3$, —N($R^o$)$R^p$, —N(H)CN, —$NO_2$, —$ONO_2$, —O$R^q$ or —S$R^r$;
$D^3$ represents —CN, $R^a$, -A-C(Q)$R^c$, -A-C(Q)N($R^d$)$R^e$, -A-C(Q)O$R^f$, -A-S(O)$_n$$R^g$, -A-S(O)$_n$C(O)$R^h$, -A-S(N$R^i$)(O)$R^j$, -A-S(O)$_n$N($R^k$)$R^l$, -A-S(O)$_n$O$R^m$, —B(O$R^n$)$_2$, —$N_3$, —N($R^o$)$R^p$, —N(H)CN, —$NO_2$, —$ONO_2$, —O$R^q$ or —S$R^r$;
$D^4$ represents —CN, $R^b$, -A-C(Q)$R^c$, -A-C(Q)N($R^d$)$R^e$, -A-C(Q)O$R^f$, -A-S(O)$_n$$R^g$, -A-S(O)$_n$C(O)$R^h$, -A-S(N$R^i$)(O)$R^j$, -A-S(O)$_n$N($R^k$)$R^l$, -A-S(O)$_n$O$R^m$, —B(O$R^n$)$_2$, —$N_3$, —N($R^o$)$R^p$, —N(H)CN, —$NO_2$, —$ONO_2$, —O$R^q$, —S$R^r$ or, when Y is partly aromatic, =Q;

$D^5$ and $D^6$ represent halogen, —CN, $R^b$, -A-C(Q)$R^c$, -A-C(Q)N($R^d$)$R^e$, -A-C(Q)O$R^f$, -A-S(O)$_n$$R^g$, -A-S(O)$_n$C(O)$R^h$, -A-S(N$R^i$)(O)$R^j$, -A-S(O)$_n$N($R^k$)$R^l$, -A-S(O)$_n$O$R^m$, —B(O$R^n$)$_2$, —N$_3$, —N($R^o$)$R^p$, —N(H)CN, —NO$_2$, —ONO$_2$, —O$R^q$, —S$R^r$ or, when Y is partly aromatic, =Q;

each $R^1$, $R^2$, $R^3$ and $R^4$ independently represents halogen, —CN, $R^y$, —NO$_2$, —O$R^z$ or =O;

A represents a single bond, —N($R^G$)—, —C(Q)N($R^H$)— or —O—;

Q represents =O, =S, =N$R^s$, =NN($R^t$)$R^u$, =N(O$R^v$), =NS(O)$_2$N($R^w$)$R^x$ or =C(H)NO$_2$;

Z represents
  (i) a 6- to 10-membered aryl optionally substituted by one or more groups selected from $D^7$, or
  (ii) a 5- to 10-membered monocyclic or bicyclic heteroaryl selected from benzothiophenyl furanyl, indolyl, pyrazolyl, and thiophenyl, and optionally substituted by one or more groups selected from $D^8$, or
  (iii) a 3- to 8-membered nonaromatic ring, which ring is connected via a carbon atom to the pyrimidine core of formula I and optionally contains one or two heteroatoms and/or one or two double bonds, and which ring is optionally substituted by one or more groups selected from $D^9$;

$D^7$ represents halogen, —CN, $R^{a1}$, -$A^1$-C($Q^1$)$R^{b1}$, -$A^1$-C($Q^1$)N($R^{c1}$)$R^{d1}$, -$A^1$-C($Q^1$)O$R^{e1}$, -$A^1$-S(O)$_n$$R^{f1}$, -$A^1$-S(O)$_n$C(O)$R^{g1}$, -$A^1$-S(N$R^{h1}$)(O)$R^{i1}$, -$A^1$-S(O)$_n$N($R^{j1}$)$R^{k1}$, -$A^1$-S(O)$_n$O$R^{l1}$, —B(O$R^{m1}$)$_2$, —N$_3$, —N($R^{n1}$)$R^{o1}$, —N(H)CN, —NO$_2$, —ONO$_2$, —O$R^{p1}$, —S$R^{q1}$ or, when Z is partly aromatic, =$Q^1$;

$D^8$ represents halogen, —CN, -$A^1$-C(O)$R^{b1}$, -A-C(O)N($R^{c1}$)$R^{d1}$, -$A^1$-S(O)$_n$$R^{f1}$, -$A^1$-SO$_2$N($R^j$)$R^{k1}$, —NO$_2$, —O$R^{p1}$, or, when Z is partly aromatic, =O;

$D^9$ represents halogen, —CN, $R^{a1}$, -$A^1$-C($Q^1$)$R^{b1}$, -$A^1$-C($Q^1$)N($R^{c1}$)$R^{d1}$, -$A^1$-C($Q^1$)O$R^{e1}$, -$A^1$-S(O)$_n$$R^{f1}$, -$A^1$-S(O)$_n$N($R^{j1}$)$R^{k1}$, —N($R^{n1}$)$R^{o1}$, —O$R^{p1}$ or =$Q^1$;

$A^1$ represents a single bond, —N($R^I$)— or —C($Q^J$)N($R^J$)—;

$Q^1$ represents =O, =S, =N$R^{r1}$, =NN($R^{s1}$)$R^{t1}$, =N(O$R^{u1}$), =NS(O)$_2$N($R^{v1}$)$R^{w1}$ or =C(H)NO$_2$;

$R^a$ and $R^q$ represent C$_1$alkyl substituted by one or more groups selected from $G^1$, C$_{2-6}$alkyl optionally substituted by one or more groups selected from $G^1$, heterocycloalkyl optionally substituted by one or more groups selected from $G^2$, aryl optionally substituted by one or more groups selected from $G^3$ or heteroaryl optionally substituted by one or more groups selected from $G^4$;

$R^d$ represents hydrogen, $R^b$, —C(O)O$R^f$, —S(O)$_n$$R^g$, —S(O)$_n$N($R^k$)$R^l$, —N($R^o$)$R^p$ or —O$R^q$;

each $R^c$, $R^e$, $R^f$, $R^h$, $R^i$, $R^k$, $R^l$, $R^m$, $R^n$, $R^o$, $R^p$, $R^r$, $R^s$, $R^u$, $R^t$, $R^u$, $R^v$, $R^w$, $R^x$, $R^y$ and $R^z$ independently represents hydrogen, C$_{1-6}$alkyl optionally substituted by one or more groups selected from $G^1$, heterocycloalkyl optionally substituted by one or more groups selected from $G^2$, aryl optionally substituted by one or more groups selected from $G^3$ or heteroaryl optionally substituted by one or more groups selected from $G^4$; or any two $R^d$ and $R^e$, $R^k$ and $R^l$, $R^o$ and $R^p$, $R^t$ and $R^u$ and/or $R^w$ and $R^x$ are linked together to form, along with the nitrogen atom to which they are attached, a 3- to 6-membered ring, which ring optionally contains one further heteroatom and which ring optionally is substituted by one or more groups selected from halogen, C$_{1-3}$alkyl optionally substituted by one or more halogens, and =O; or two $R^m$ are linked together to form, along with the boron, and the oxygen atoms to which they are attached, a 5- to 8-membered heterocyclic ring, which ring optionally contains one or more further heteroatoms and which ring optionally is substituted by one or more groups independently selected from halogen, C$_{1-3}$alkyl optionally substituted by one or more halogens, and/or =O;

each $R^b$, $R^g$ and $R^j$ independently represents C$_{1-6}$alkyl optionally substituted by one or more groups selected from $G^1$, heterocycloalkyl optionally substituted by one or more groups selected from $G^2$, aryl optionally substituted by one or more groups selected from $G^3$ or heteroaryl optionally substituted by one or more groups selected from $G^4$;

$R^{c1}$ represents $R^{a1}$, —S(O)$_n$$R^{g1}$, —S(O)$_n$N($R^{j1}$)$R^{k1}$, —N($R^{n1}$)$R^{o1}$ or —O$R^{p1}$;

each $R^{b1}$, $R^{d1}$, $R^{e1}$, $R^{g1}$, $R^{h1}$, $R^{j1}$, $R^{k1}$, $R^{l1}$, $R^{m1}$, $R^{n1}$, $R^{o1}$, $R^{p1}$, $R^{q1}$, $R^{r1}$, $R^{s1}$, $R^{t1}$, $R^{u1}$, $R^{v1}$ and $R^{w1}$ independently represents hydrogen, C$_{1-6}$alkyl optionally substituted by one or more groups selected from $G^5$, heterocycloalkyl optionally substituted by one or more groups selected from $G^6$, aryl optionally substituted by one or more groups selected from $G^7$ or heteroaryl optionally substituted by one or more groups selected from $G^8$; or any two $R^{c1}$ and $R^{d1}$, $R^{j1}$ and $R^{k1}$, $R^{n1}$ and $R^{o1}$, $R^{s1}$ and $R^{t1}$ and/or $R^{v1}$ and $R^{w1}$ are linked together to form, along with the nitrogen atom to which they are attached, a 3- to 6-membered ring, which ring optionally contains one further heteroatom and which ring optionally is substituted by one or more groups selected from halogen, C$_{1-3}$alkyl optionally substituted by one or more halogens, and =O; or two $R^{m1}$ are linked together to form, along with the boron, and the oxygen atoms to which they are attached, a 5- to 8-membered heterocyclic ring, which ring optionally contains one or more further heteroatoms and which ring optionally is substituted by one or more groups independently selected from halogen, C$_{1-3}$alkyl optionally substituted by one or more halogens, and/or =O;

each $R^{a1}$, $R^{f1}$ and $R^{i1}$ independently represents C$_{1-6}$alkyl optionally substituted by one or more groups selected from $G^5$, heterocycloalkyl optionally substituted by one or more groups selected from $G^6$, aryl optionally substituted by one or more groups selected from $G^7$ or heteroaryl optionally substituted by one or more groups selected from $G^8$;

each $G^1$ and $G^5$ independently represent a group selected from halogen, —CN, —N$_3$, —N($R^{b2}$)$R^{c2}$, —N(H)C(O)$R^{d2}$, —N(H)S(O)$_n$$R^{h2}$, —O$R^{k2}$, —S(O)$_m$$R^{l2}$ or =O;

each $G^2$ and $G^6$ independently represents a group selected from halogen, $R^{a2}$, —CN, —N$_3$, —N($R^{b2}$)$R^{c2}$, —N(H)C(O)$R^{d2}$, —N(H)S(O)$_n$$R^{h2}$, —O$R^{k2}$, —S(O)$_m$$R^{l2}$ or =O;

each $G^3$, $G^4$, $G^7$ and $G^8$ independently represents a group selected from halogen, —CN, $R^{a2}$, —N($R^{b2}$)$R^{c2}$, -$A^2$-C(O)$R^{d2}$, -$A^2$-C(O)N($R^{e2}$)$R^{f2}$, -$A^2$-C(O)O$R^{g2}$, -$A^2$-S(O)$_n$$R^{h2}$, -$A^2$-S(O)$_n$N($R^{i2}$)$R^{j2}$, —O$R^{k2}$ or =O;

$A^2$ represents a single bond or —N(H)—;

each $R^{a2}$ and $R^{h2}$ independently represents C$_{1-6}$ alkyl optionally substituted by one or more halogens;

each $R^{b2}$, $R^{c2}$, $R^{d2}$, $R^{e2}$, $R^{f2}$, $R^{g2}$, $R^{i2}$, $R^{j2}$, $R^{k2}$ and $R^{l2}$ independently represents hydrogen or C$_{1-6}$ alkyl optionally substituted by one or more halogens; or any two $R^{b2}$ and $R^{c2}$, $R^{e2}$ and $R^{f2}$ and/or $R^{i2}$ and $R^{j2}$ are linked together to form, along with the nitrogen atom to which they are attached, a 3- to 6-membered ring, which ring optionally contains one further heteroatom and which ring optionally is substituted by one or more groups selected from halogen, $C_{1-3}$alkyl optionally substituted by one or more halogens, and =O;

each $R^A$, $R^B$, $R^C$, $R^D$, $R^E$, $R^F$, $R^G$, $R^H$, $R^I$ and $R^J$ independently represents hydrogen or $C_{1-3}$ alkyl optionally substituted by one or more halogens;

$T^1$ represents halogen, —CN, —N($R^{b3}$)$R^{c3}$ or —OR$^{d3}$;

$T^2$ represents halogen, —CN, $R^{a3}$, —OR$^{d3}$ or =O;

each $R^{a3}$ independently represents $C_{1-6}$alkyl optionally substituted by one or more halogens;

each $R^{b3}$, $R^{c3}$ and $R^{d3}$ independently represents hydrogen or $C_{1-6}$alkyl optionally substituted by one or more halogens; or $R^{b3}$ and $R^{c3}$ are linked together to form, along with the nitrogen atom to which they are attached, a 3- to 6-membered ring;

each p and q independently represents 0, 1 or 2, provided that the sum of p and q is 0, 1 or 2;

each m independently represents 0, 1 or 2; and each n independently represents 1 or 2;

provided that when X represents —CH$_2$CH$_2$—, Y represents pyrimidin-4-yl,

L represents -L$^1$-L$^2$-, L$^1$ represents —N(H)—, and

Z represents phenyl, 3-chlorophenyl, 3,5-dichlorophenyl or 5-chloro-2-methoxyphenyl, then $R^b$ does not represent —CH$_3$, $R^o$ does not represent hydrogen and $R^p$ does not represent hydrogen or —CH$_2$CH(CH$_3$)$_2$, and provided that when X represents —CH$_2$CH$_2$—, Y represents pyrimidin-4-yl, L represents -L$^1$-L$^2$-, L$^1$ represents —N(Me)-, and Z represents phenyl, then $R^o$ does not represent hydrogen; and provided that formula I does not represent 4-(2-{[2-amino-6-(2,3-dichlorophenyl)pyrimidin-4-yl]amino}ethyl)benzene-1-sulfonamide, 4-(2-{[2-amino-6-(3-chloro-2-methylphenyl)pyrimidin-4-yl]amino}ethyl)benzene-1-sulfonamide, 4-(2-{[2-amino-6-(2,3-dimethylphenyl)pyrimidin-4-yl]amino}ethyl)benzene-1-sulfonamide, 6-(2,3-dimethylphenyl)-4-N-[2-(4-methanesulfonylphenyl)ethyl]pyrimidine-2,4-diamine, N-[3-(3-{[2-amino-6-(2,3-dimethylphenyl)pyrimidin-4-yl]amino}propoxy)phenyl]-acetamide, 6-(2,3-dimethylphenyl)-4-N-{2-[5-(4-fluorophenyl)-1,3,4-oxadiazol-2-yl]ethyl}-pyrimidine-2,4-diamine, 4-(2-{[2-amino-6-(3-chloro-2-methylphenyl)pyrimidin-4-yl]amino}ethyl)-N,N-dimethylbenzene-1-sulfonamide, 4-(2-{[2-amino-6-(2,3-dichlorophenyl)pyrimidin-4-yl]amino}ethyl)-N,N-dimethylbenzene-1-sulfonamide, 4-(2-{[2-amino-6-(2,3-dimethylphenyl)pyrimidin-4-yl]amino}ethyl)-N,N-dimethylbenzene-1-sulfonamide, 4-(2-{[2-amino-6-(4-fluoro-2,3-dimethylphenyl)pyrimidin-4-yl]amino}ethyl)benzene-1-sulfonamide, 4-(2-{[2-amino-6-(3-cyano-2-methylphenyl)pyrimidin-4-yl]amino}ethyl)benzene-1-sulfonamide, 4-(2-{[2-amino-6-(5-chloro-2-methylphenyl)pyrimidin-4-yl]amino}ethyl)benzene-1-sulfonamide, 4-(2-{[2-amino-6-(3,4-dichloro-2-methylphenyl)pyrimidin-4-yl]amino}ethyl)benzene-1-sulfonamide, 6-(4-fluoro-2,3-dimethylphenyl)-4-N-[2-(4-methanesulfonylphenyl)ethyl]pyrimidine-2,4-diamine, 6-(3,4-dichloro-2-methylphenyl)-4-N-[2-(4-methanesulfonylphenyl)ethyl]pyrimidine-2,4-diamine, 4-(2-{[2-amino-6-(4-chloro-2-methylphenyl)pyrimidin-4-yl]amino}ethyl)benzene-1-sulfonamide, 4-(2-{[2-amino-6-(2-chloro-4-fluorophenyl)pyrimidin-4-yl]amino}ethyl)benzene-1-sulfonamide, 4-(2-{[2-amino-6-(2,3,4-trifluorophenyl)pyrimidin-4-yl]amino}ethyl)benzene-1-sulfonamide, 4-(2-{[2-amino-6-(4-fluoro-3-methylphenyl)pyrimidin-4-yl]amino}ethyl)benzene-1-sulfonamide, 4-(2-{[2-amino-6-(4-fluoro-2,5-dimethylphenyl)pyrimidin-4-yl]amino}ethyl)benzene-1-sulfonamide, 6-[(2-{[2-amino-6-(2,3-dimethylphenyl)pyrimidin-4-yl]amino}ethyl)amino]pyridine-3-sulfonamide, 6-(2,3-dichlorophenyl)-4-N-[2-(4-methanesulfonylphenyl)ethyl]pyrimidine-2,4-diamine or 4-[(2-{[2-amino-6-(2,3-dimethylphenyl)pyrimidin-4-yl]amino}ethyl)amino]benzene-1-sulfonamide.

2. The compound as claimed in claim 1 wherein
X represents —CH$_2$CH$_2$—, —CH$_2$CH$_2$CH$_2$—, —CH$_2$CH$_2$CH$_2$CH$_2$—, —CH$_2$C(CH$_3$)$_2$CH$_2$—, -cyclopropylene- or —CH$_2$—≡—CH$_2$—.

3. The compound as claimed in claim 1 wherein X represents —CH$_2$CH$_2$—.

4. The compound as claimed in claim 1 wherein L represents -L$^1$-L$^2$-.

5. The compound as claimed in claim 4 wherein L$^1$ represents —N(H)—, —O—, —C(O)N(H)—, —N(H)C(O)N(H)— or —S(O)$_m$—.

6. The compound as claimed in claim 4 wherein L$^1$ represents —O—.

7. The compound as claimed in claim 4 wherein L$^1$ represents —S— or —S(O)—.

8. The compound as claimed in claim 1 wherein L represents a single bond.

9. The compound as claimed in claim 1 wherein Y represents phenyl, substituted by D$^1$ and optionally substituted by one or more groups selected from R$^1$;

D$^1$ represents R$^a$, -A-C(Q)R$^c$, -A-C(Q)N(R$^d$)R$^e$, -A-C(Q)OR$^f$, -A-S(O)$_n$R$^g$, -A-S(O)$_n$C(O)R$^h$, -A-S(NR$^i$)(O)R$^j$, -A-S(O)$_n$N(R$^k$)R$^l$, -A-S(O)$_n$OR$^m$, —B(OR$^n$)$_2$, —N(R$^o$)R$^p$, —N(H)CN, —NO$_2$, —SR$^r$ or a 5-membered heteroaryl;

Q represents =O, =S, =NR$^s$ or =N(OR$^v$); and each R$^1$ independently represents halogen, R$^y$ or —OR$^z$.

10. The compound as claimed in claim 9 wherein
D$^1$ represents R$^a$, -A-C(Q)R$^c$, -A-C(Q)N(R$^d$)R$^e$, -A-C(O)OR$^f$, -A-S(O)$_n$R$^g$, —S(O)$_n$N(R$^k$)R$^l$, —S(O)$_2$OR$^m$, —N(H)CN, —NO$_2$ or —SR$^r$;

Q represents =O, =S, =NR$^s$ or =N(OR$^o$);

each R$^1$ independently represents halogen, R$^y$ or —OR$^z$;

R$^e$, R$^l$, R$^m$, R$^s$ and R$^v$ represents hydrogen;

each R$^b$, R$^f$, R$^k$, R$^r$, and R$^z$ independently represents hydrogen or $C_{1-6}$alkyl optionally substituted by one or more groups selected from G$^1$;

R$^c$, R$^g$ and R$^y$ represents $C_{1-6}$alkyl optionally substituted by one or more groups selected from G$^1$;

R$^d$ represents R$^b$ or —C(O)OR$^f$; or

R$^d$ and R$^e$ are linked together to form, along with the nitrogen atom to which they are attached, a 5- to 6-membered ring, which ring optionally contains one further heteroatom;

G$^1$ represents fluoro, —OR$^{k2}$ or —S(O)$_2$R$^{l2}$; and

R$^{k2}$ and R$^{l2}$ represent $C_{1-3}$alkyl.

11. The compound as claimed in claim 10 wherein
Y is phenyl substituted by D$^1$ in 3- or 4-position and optionally substituted by one or more groups selected from R$^1$;

D$^1$ represents ethyl, ethynyl, trifluoromethyl, —C(O)NH$_2$, —C(NH)NH$_2$, —C(NOH)NH$_2$, —C(S)NH$_2$, —C(O)N(H)Me, —C(O)NHCH(CH$_3$)CH$_2$OH, —C(O)N(CH₃)propargyl, —C(O)OH, —C(O)OCH₃, —C(O)OCH₂CH₃, —C(O)OCH₂CH₂CH₃, —C(O)OCH₂CH(CH₃)₂, —C(O)OCH₂CH₂OH, —C(O)OCH₂CH₂SO₂Me, —C(O)OCH₂CH(OH)CH₂OH, —NH₂, —N(H)CN, —NHC(O)Me, —NH(CO)cyclopropyl, —NH(CO)C(Me)₃, —NHC(O)OEt, —NHC(O)OCH(Me)₂, —NHC(O)OC(Me)₃, —NHC(O)OCH₂CH(Me)₂, —NHC(O)OCH₂C(Me)₃, —NHC(O)OCH₂CH₂OMe, —N(H)C(O)N(H)Et, —N(H)C(O)N(H)CH(Me)₂, —N(H)C(O)N(H)C(Me)₃, —N(H)C(O)N(H)CH₂CH=CH₂, —N(H)C(O)N(CH₃)₂, —N(H)C(O)N(H)C(O)OEt, —N(H)C(S)N(H)Et, —NO₂, —NHSO₂Me, —NHSO₂Et, —NHSO₂CH(Me)₂, —NHSO₂CH₂CH(Me)₂, —NHSO₂CH₂CF₃, —SMe, —S(O)Me, —SO₂Me, —SO₂CF₃, —SO₂CH(Me)₂, —SO₂CH₂CH₂N(Me)₂, —SO₂NH₂, —SO₂NHMe, —SO₂NHCH₂CH₂OMe, —SO₂OH, tetrazolyl,

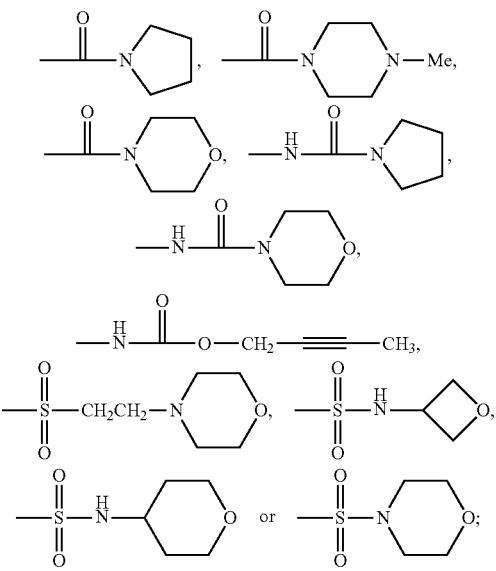

and R¹ represents fluoro, —CH₃, —CF₃, —OH or —OCH₃.

12. The compound as claimed in claim 11 wherein D¹ represents —C(O)NH₂, —C(O)N(H)Me, —NHC(O)Me, —NH(CO)cyclopropyl, —NH(CO)C(Me)₃, —NHSO₂Me, —NHS(O)₂Et, —NHS(O)₂CH(Me)₂, —NHSO₂CH₂CF₃, —SO₂Me, —SO₂NH₂ or —SO₂NHMe.

13. The compound as claimed in claim 11 wherein D¹ represents —C(O)OCH₃, —C(O)OCH₂CH₃, —C(O)OCH₂CH₂CH₃, —C(O)OCH₂CH(CH₃)₂, —C(O)OCH₂CH₂OH, —C(O)OCH₂CH₂SO₂Me or —C(O)OCH₂CH(OH)CH₂OH.

14. The compound as claimed in claim 11 wherein D¹ represents —SO₂CH(CH₃)₂, —SO₂CH₂CH₂NMe)₂, —SO₂NHCH₂CH₂OMe,

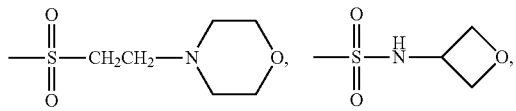

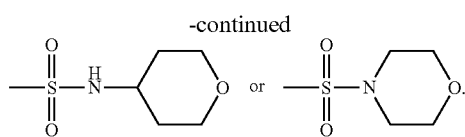

15. The compound as claimed in claim 1 wherein Y represents pyridinyl substituted by D² and optionally substituted by one or more groups selected from R²; D² represents Rᵇ, -A-C(Q)Rᶜ, -A-C(Q)N(Rᵈ)Rᵉ, -A-C(Q)ORᶠ, -A-S(O)ₙRᵍ, -A-S(O)ₙC(O)Rʰ, -A-S(O)ₙN(Rᵏ)Rⁱ, -A-S(O)ₙORᵐ, —B(ORⁿ)₂, —C(O)ORᶠ, —N(Rᵒ)Rᵖ, or —NO₂;
Q represents =O, =S, =NRˢ or =N(ORᵛ); and
each R² independently represents halogen or C₁₋₃ alkyl optionally substituted by one or more fluoro.

16. The compound as claimed in claim 15 wherein D² represents Rᵇ, -A-C(Q)Rᶜ, -A-C(O)N(Rᵈ)Rᵉ, -A-C(O)ORᶠ, -A-S(O)ₙRᵍ, —S(O)ₙN(Rᵏ)Rⁱ or —NO₂;
each Rᵈ, Rᵉ and Rⁱ represents hydrogen;
each Rᶜ, Rᶠ, Rᵍ and Rʸ represents C₁₋₆alkyl; and
Rᵏ represent hydrogen or C₁₋₆alkyl.

17. The compound as claimed in claim 16 wherein D² represents C₁₋₆ alkyl optionally substituted by one or more fluoro, —C(O)NH₂, —C(O)ORᶠ, —N(H)C(O)Rᶜ, —N(H)C(O)N(Rᵈ)Rᵉ, —N(H)C(O)ORᶠ, —N(H)S(O)ₙRᵍ, —S(O)ₙRᵍ, —N(Rᵒ)Rᵖ or —NO₂.

18. The compound as claimed in claim 16 wherein Y represents 2-pyridinyl substituted in the 4-position by —C(O)NH₂ or in the 5-position by —CF₃, —C(O)NH₂, —C(O)OEt, —N(H)C(O)Me, —N(H)C(O)N(H)C(CH₃)₃, —N(H)C(O)OC(CH₃)₃, —N(H)SO₂Me, —NO₂, —SO₂Me, —SO₂NH₂ or —SO₂N(H)Me, 3-pyridinyl substituted in the 4-position by —NH₂ or —SO₂Me, substituted in the 5-position by —SO₂NH₂ or substituted in the 6-position by —SO₂Me, or 4-pyridinyl substituted in the 2-position by —C(O)NH₂.

19. The compound as claimed in claim 1 wherein Y represents pyrimidinyl substituted by D² and optionally substituted by one or more groups selected from R²;
D² represents -A-C(Q)Rᶜ, -A-C(Q)N(Rᵈ)Rᵉ, -A-C(Q)ORᶠ, -A-S(O)ₙRᵍ, -A-S(O)ₙN(Rᵏ)Rⁱ, -A-S(O)ₙORᵐ, —B(ORⁿ)₂, —C(O)ORᶠ or —N(Rᵒ)Rᵖ;
Q represents =O, =S, =NRˢ or =N(ORᵛ); and
each R² independently represents halogen or C₁₋₃ alkyl optionally substituted by one or more fluoro.

20. The compound as claimed in claim 19 wherein Y represents 2-pyrimidinyl substituted in the 4-position by —C(O)NH₂, —C(O)OH or —C(O)OMe, —NH₂, —S(O)₂Me or —S(O)₂NH₂, substituted in the 5-position by —C(O)NH₂, or 4-pyrimidinyl substituted in the 2-position by —C(O)NH₂, —NH₂, —S(O)₂Me or —S(O)₂NH₂; and
R² represents halogen or C₁₋₃alkyl optionally substituted by one or more fluoro.

21. The compound as claimed in claim 20 wherein Y represents 2-pyrimidinyl substituted in the 4-position by —C(O)NH₂, —C(O)OH or —C(O)OMe.

22. The compound as claimed in claim 1 wherein Y represents pyrazinyl substituted by D² and optionally substituted by one or more groups selected from R²;
D² represents -A-C(Q)Rᶜ, -A-C(Q)N(Rᵈ)Rᵉ, -A-C(Q)ORᶠ, -A-S(O)ₙRᵍ, -A-S(O)ₙN(Rᵏ)Rⁱ, -A-S(O)ₙORᵐ, —B(ORⁿ)₂, —C(O)ORᶠ or —N(Rᵒ)Rᵖ; and
Q represents =O, =S, =NRʷ or =N(ORᶻ).

23. The compound as claimed in claim 22 wherein
Y represents pyrazinyl substituted by —C(O)OR$^f$ or —C(O)N(R$^d$)R$^e$ or —C(O)OR$^f$;
R$^d$ and R$^e$ represent hydrogen; and
R$^f$ represents C$_{1-6}$alkyl.

24. The compound as claimed in claim 1 wherein
Y represents a 5-membered heteroaryl substituted by D$^3$ and optionally substituted by one or more groups selected from R$^3$;
D$^3$ represents —CN, -A-C(Q)R$^c$, -A-C(Q)N(R$^d$)R$^e$, -A-C(Q)OR$^f$, -A-S(O)$_n$R$^g$, -A-S(O)$_n$N(R$^k$)R$^l$, —B(OR$^o$)$_2$, —C(O)OR$^f$, —N(R$^p$)R$^q$, or —NO$_2$;
Q represents =O, =S, =NR$^s$ or =N(OR$^v$); and
each R$^3$ independently represents halogen or C$_{1-3}$ alkyl optionally substituted by one or more fluoro.

25. The compound as claimed in claim 24 wherein
Y represents imidazolyl, isoxazolyl, oxazolyl, 1, 2, 4-oxadiazolyl, 1, 3, 4-oxadiazolyl, 1, 3, 4-thiadiazolyl, thiazolyl, 1, 2, 3-triazolyl or thiophenyl, each substituted by halogen, —C(O)NH$_2$, —C(O)OMe, —NH$_2$, —NO$_2$, —S(O)$_2$Me or —S(O)$_2$NH$_2$ and each optionally substituted by halogen or C$_{1-3}$ alkyl optionally substituted by one or more fluoro.

26. The compound as claimed in claim 1 wherein
Y represents a 9-membered bicyclic heteroaryl connected to L via its 5-membered ring; substituted by D$^4$ and optionally substituted by one or more groups selected from R$^4$;
D$^4$ represents —CN, R$^b$, -A-C(O)R$^c$, -A-C(O)N(R$^d$)R$^e$, -A-C(Q)OR$^f$, -A-S(O)$_n$R$^g$, -A-S(O)$_n$N(R$^k$)R$^l$, —C(O)OR$^f$, —N(R$^o$)R$^p$, —OR$^q$, and, when Y is partly aromatic, also =O; and
each R$^4$ independently represents halogen, C$_{1-3}$ alkyl optionally substituted by one or more fluoro or —OC$_{1-3}$ alkyl optionally substituted by one or more fluoro.

27. The compound as claimed in claim 26 wherein
said heteroaryl is selected from 2-benzimidazolyl, 2-benzoxazolyl, 2-benzothiazolyl, 2-indolyl, 2-indolinyl or 2-isoindolinyl;
D$^4$ represents -Me, —CHF$_2$, —CF$_3$, —NH$_2$, —NHMe, —NMe$_2$, —OH, —OMe, —OCF$_3$, and, in the case of 2-indolinyl or 2-isoindolinyl, also =O; and
each R$^4$ independently selected from fluoro, chloro, -Me, —CHF$_2$, —CF$_3$, —NH$_2$, —NHMe, —NMe$_2$, —OH and —OMe.

28. The compound as claimed in claim 1 wherein
Y represents a 9- or 10-membered bicyclic heteroaryl connected to L via its 6-membered ring, said heteroaryl optionally being substituted by one or more D$^5$; and
each D$^5$ is independently selected from halogen, —CN, R$^b$, -A-C(O)R$^c$, -A-C(O)N(R$^d$)R$^e$, -A-C(Q)OR$^f$, -A-S(O)$_n$R$^g$, -A-S(O)$_n$N(R$^k$)R$^l$, —C(O)OR$^f$, —N(R$^o$)R$^p$, —OR$^q$, and, when Y is partly aromatic, also =O.

29. The compound as claimed in claim 28 wherein
Y is selected from benzimidazol-5-yl, benzoxazol-5-yl, benzothiazol-5-yl, benzothiazol-6-yl, benzothiophen-6-yl, 2, 3-dihydrobenz[1,3]oxazin-6-yl, 3,4-dihydrobenz[1,4]oxazin-6-yl, dihydrobenzothiophen-6-yl, indol-5-yl, indol-6-yl, indolin-5-yl, indolin-6-yl, isoindolin-5-yl, isoquinolin-6-yl, isoquinolin-7-yl, tetrahydroquinolin-6-yl, tetrahydroquinolin-7-yl, tetrahydroisoquinolin-6-yl, tetrahydroisoquinolin-6-yl, tetrahydroquinazolin-6-yl, tetrahydroquinazolin-7-yl, thiochroman-7-yl, quinolin-6-yl, quinolin-7-yl, quinazolin-6-yl, quinazolin-7-yl, or purin-6-yl; and
each D$^5$ is independently selected from fluoro, chloro, -Me, —CHF$_2$, —CF$_3$, —NH$_2$, —NHMe, —NMe$_2$, —OH, —OMe, =NH and =O.

30. The compound as claimed in claim 1 wherein Z represents phenyl optionally substituted by one or more groups selected from D$^7$;
D$^7$ represents halogen, —CN, R$^{a1}$, -A$^1$-C(Q$^1$)R$^{b1}$, -A$^1$-C(Q$^1$)N(R$^{c1}$)R$^{d1}$, -A$^1$-S(O)$_n$R$^{f1}$, -A$^1$-S(O)$_n$N(R$^{j1}$)R$^{k1}$, —NO$_2$ or —OR$^{p1}$;
each R$^{a1}$, R$^{b1}$, R$^{c1}$, R$^{d1}$, R$^{j1}$, R$^{k1}$ and R$^{p1}$ independently represents hydrogen or C$_{1-6}$alkyl optionally substituted by one or more fluoro; or
any two R$^{c1}$ and R$^{d1}$ and/or R$^{j1}$ and R$^{k1}$ are linked together to form, along with the nitrogen atom to which they are attached, a 3- to 6-membered ring, which ring optionally contains one further heteroatom and which ring optionally is substituted by one or more fluoro, C$_{1-3}$alkyl optionally substituted by one or more fluoro or =O; and
R$^{f1}$ represents C$_{1-3}$ alkyl optionally substituted by one or more fluoro.

31. The compound as claimed in claim 30 wherein Z represents phenyl substituted:
(i) by one substituent in the 3-position selected from fluoro, chloro, —CF$_3$, —CH$_2$OH, —OH, —OS(O)$_2$CH$_3$ or —OS(O)$_2$CF$_3$,
(ii) by two substituents selected from fluoro, chloro, -Me, —CF$_3$ or —OMe, or
(ii) by three substituents selected from fluoro, chloro, -Me, —CF$_3$ or —OMe, or
(iv) by four substituents selected from fluoro, chloro, or -Me.

32. The compound as claimed in claim 31 wherein Z represents 2,3-dichlorophenyl, 3-chloro-2-fluorophenyl, 2-chloro-3-methylphenyl, 3-chloro-2-methylphenyl, 5-fluoro-2-methylphenyl, 2,5-dimethylphenyl, 2, 3-dimethylphenyl 5-chloro-2-fluoro-3-methylphenyl, 3,4-dichloro-2-methylphenyl, 3,5-dichloro-2-methylphenyl, 4,5-dichloro-2-methylphenyl, 2,3-dimethyl-4-fluorophenyl, 2,5-dimethyl-4-fluorophenyl, 2-methyl-3-trifluoromethyl, 2,3,4-trichlorophenyl, 2,3,5-trichlorophenyl or 2,4,5-trimethylphenyl.

33. The compound as claimed in claim 32 wherein
Z represents 3-chloro-2-fluorophenyl, 2-chloro-3-methylphenyl, 3-chloro-2-methyl-phenyl, 2,3-dichlorophenyl or 2,3-dimethylphenyl.

34. A compound as claimed in claim 1 wherein Z represents benzothiophenyl, furanyl, indolyl, pyrazolyl or thiophenyl, optionally substituted by one or more groups selected from D$^8$;
each D$^8$ independently represents halogen, —CN, -A$^1$-C(O)R$^{b1}$, -A$^1$-C(O)N(R$^{c1}$)R$^{d1}$, -A$^1$-S(O)$_n$R$^{f1}$, -A$^1$-SO$_2$N(R$^j$)R$^{k1}$, —NO$_2$ or —OR$^{p1}$;
each R$^{b1}$, R$^{c1}$, R$^{d1}$, R$^{j1}$, R$^{k1}$ and R$^{p1}$ independently represents hydrogen or C$_{1-6}$alkyl optionally substituted by one or more fluoro; or
any two R$^{c1}$ and R$^{d1}$ and/or R$^{j1}$ and R$^{k1}$ are linked together to form, along with the nitrogen atom to which they are attached, a 3- to 6-membered ring, which ring optionally contains one further heteroatom and which ring optionally is substituted by one or more fluoro, C$_{1-3}$alkyl optionally substituted by one or more fluoro, or =O; and
R$^{f1}$ represents C$_{1-3}$ alkyl optionally substituted by one or more fluoro.

35. The compound as claimed in claim 1 wherein
Z is a 5- to 7-membered nonaromatic ring, which ring optionally contains one heteroatom, optionally contains one double bond and is optionally substituted by one or more groups selected from $D^9$;
each $D^9$ independently represents $R^{a1}$, $-C(O)R^{b1}$, $-C(O)N(R^{c1})R^{d1}$, $-C(O)OR^{e1}$, $-SO_2R^f$, $-SO_2N(R^{j1})R^{k1}$ or =O;
each $R^{a1}$, $R^{b1}$, $R^{c1}$, $R^{d1}$, $R^{e1}$, $R^{f1}$, $R^{j1}$ and $R^{k1}$ independently represents $C_{1-6}$alkyl optionally substituted by one or more fluoro, phenyl optionally substituted by one or more groups selected from halogen or $C_{1-3}$alkyl optionally substituted by one or more fluoro, or heteroaryl optionally substituted by one or more groups selected from halogen or $C_{1-3}$alkyl optionally substituted by one or more fluoro; or
any two $R^{c1}$ and $R^{d1}$ and/or $R^{j1}$ and $R^{k1}$ are linked together to form, along with the nitrogen atom to which they are attached, a 5- to 6-membered ring, which ring optionally contains one further heteroatom and which ring optionally is substituted by one or more $C_{1-3}$alkyl or =O; and
$R^{e1}$ represent $C_{1-6}$alkyl optionally substituted by one or more fluoro.

36. The compound as claimed in claim 35 wherein
Z represents cycloheptanyl, cyclohexanyl, cyclopentanyl, piperidin-3-yl, pyrrolidin-3-yl, cyclohepten-1-yl, piperidin-4-yl or 1, 2, 3, 6-tetrahydropiperidin-4-yl and where the piperidine, pyrrolidine and the 1, 2, 3, 6-tetrahydropiperidine are substituted by $-R^{a1}$, $-C(O)R^{b1}$, $-C(O)N(R^{c1})R^{d1}$, $-C(O)OR^{e1}$, $-SO_2R^{f1}$, $-SO_2N(R^{j1})R^{k1}$ or =O.

37. A pharmaceutical formulation comprising a compound as claimed in claim 1, or a pharmaceutically acceptable salt thereof, in admixture with a pharmaceutically acceptable adjuvant, diluent or carrier.

38. A combination product comprising:
(A) a compound as claimed in claim 1, or a pharmaceutically acceptable salt thereof; and
(B) one or more other therapeutic agent(s) that is/are useful in the treatment of cancer
wherein each one of components (A) and (B) is formulated in admixture with a pharmaceutically-acceptable adjuvant, diluent or carrier.

39. The combination product as claimed in claim 38, wherein component (B) is selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors; kinase inhibitors; angiogenesis inhibitors; immunotherapeutic agents; pro-apoptotic agents; and cell cycle signaling inhibitors.

40. A method of treatment of cancer, which method comprises administration of a therapeutically effective amount of a compound as claimed in claim 1, or a pharmaceutically acceptable salt thereof, to a patient in need of such treatment.

41. The method as claimed in claim 40, wherein the treatment further comprises radiation therapy.

42. The method as claimed in claim 40, wherein the treatment further comprises immunotherapy.

43. The method as claimed in claim 40, wherein the treatment further comprises surgery.

44. The method as claimed in claim 40, wherein the cancer is selected from:

Soft Tissue Cancers selected from sarcoma, myxoma, rhabdomyoma, fibroma, lipoma and teratoma;
Lung cancers selected from bronchogenic carcinoma, alveolar carcinoma, bronchial adenoma, sarcoma, lymphoma, chondromatous hamartoma, and mesothelioma;
Gastrointestinal cancers selected from cancers of the esophagus, stomach, pancreas, small bowel, and large bowel;
Genitourinary tract cancers selected from cancers of the kidney, bladder and urethra, prostate, and testis;
Liver cancers selected from hepatoma, cholangiocarcinoma, hepatoblastoma, angiosarcoma, hepatocellular adenoma, and hemangioma;
Bone cancers selected from osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors;
Nervous system cancers selected from cancer of the skull, meninges brain, and the spinal cord;
Gynecological cancers selected from cancers of the uterus, cervix, ovaries, vulva, vagina, and fallopian tubes;
Hematologic cancers;
Skin cancers selected from malignant melanoma, basal cell carcinoma, squamous cell carcinoma, Kaposi's sarcoma, moles dysplastic nevi, lipoma, angioma, dermatofibroma, and keloids;
Adrenal glands cancers, neuroblastoma, neurofibromatosis and head and neck cancers, and
breast cancer.

45. The method as claimed in claim 40, wherein the cancer is selected from the group consisting of breast cancers, prostate cancers, lung cancers, oesophageal cancers, colon cancers, brain cancers, skin cancers, ovarian cancers, testicular cancers, neurofibromatosis and leukemias.

46. A compound as claimed in claim 1, selected from
6-(3-chloro-2-methylphenyl)-4-N-[2-(4-methanesulfonylphenyl)ethyl]pyrimidine-2,4-diamine;
6-[(3-{[2-amino-6-(2,3-dimethylphenyl)pyrimidin-4-yl]amino}propyl)amino]pyridine-3-sulfonamide;
6-[(2-{[2-amino-6-(2,3-dimethylphenyl)pyrimidin-4-yl]amino}ethyl)amino]-N-methylpyridine-3-sulfonamide;
6-[(2-{[2-amino-6-(2,3-dimethylphenyl)pyrimidin-4-yl]amino}ethyl)amino]pyridine-3-carboxamide;
3-(4-{[2-amino-6-(2,3-dichlorophenyl)pyrimidin-4-yl]amino}butyl)-1-[4-(methyl sulfanyl)phenyl]urea;
3-(4-{[2-amino-6-(2,3-dichlorophenyl)pyrimidin-4-yl]amino}butyl)-1-(4-methanesulfinylphenyl)urea;
6-(4-fluoro-2,5-dimethylphenyl)-4-N-{2-[(5-nitropyridin-2-yl)amino]ethyl}pyrimidine-2,4-diamine;
4-(2-{[2-amino-6-(3-chloro-2-methylphenyl)pyrimidin-4-yl]amino}ethyl)benzoic acid;
4-(2-{[6-(2-acetylthiophen-3-yl)-2-aminopyrimidin-4-yl]amino}ethyl)benzene-1-sulfonamide;
N-{6-[(2-{[2-amino-6-(4-fluoro-2,5-dimethylphenyl)pyrimidin-4-yl]amino}ethyl)amino]pyridin-3-yl}acetamide;
N-{6-[(2-{[2-amino-6-(4-fluoro-2,5-dimethylphenyl)pyrimidin-4-yl]amino}ethyl)amino]pyridin-3-yl}methanesulfonamide;

6-(2,3-dimethylphenyl)-4-N-{2-[(6-methanesulfonylpyridin-3-yl)amino]ethyl}pyrimidine-2,4-diamine;

5-[(2-{[2-amino-6-(2,3-dimethylphenyl)pyrimidin-4-yl]amino}ethyl)amino]pyridine-3-sulfonamide;

4-[(1R,2S)-2-{[2-amino-6-(3-chloro-2-methylphenyl)pyrimidin-4-yl]amino}cyclopropyl]benzene-1-sulfonamide;

2-[(2-{[2-amino-6-(2,3-dimethylphenyl)pyrimidin-4-yl]amino}ethyl)amino]pyrimidine-4-carboxamide;

4-(2-amino-6-{[2-(4-methanesulfonylphenyl)ethyl]amino}pyrimidin-4-yl)-N-tert-butylthiophene-2-sulfonamide;

tert-butyl N-{[5-(2-amino-6-{[2-(4-methanesulfonylphenyl)ethyl]amino}pyrimidin-4-yl)thiophen-2-yl]methyl}carbamate;

N-[4-(2-{[2-amino-6-(2,3-dimethylphenyl)pyrimidin-4-yl]amino}ethyl)phenyl]acetamide;

N-[4-(2-{[2-amino-6-(2,3-dimethylphenyl)pyrimidin-4-yl]amino}ethyl)phenyl]methanesulfonamide;

4-[(2-{[2-amino-6-(2,3-dimethylphenyl)pyrimidin-4-yl]amino}ethyl)amino]-N-methylbenzene-1-sulfonamide;

N-{4-[(2-{[2-amino-6-(2,3-dimethylphenyl)pyrimidin-4-yl]amino}ethyl)amino]-2-methylphenyl}acetamide;

6-[(2-{[2-amino-6-(2,3-dimethylphenyl)pyrimidin-4-yl]amino}ethyl)amino]-3,4-dihydro-2H-1,4-benzoxazin-3-one;

2-[(2-{[2-amino-6-(2,3-dimethylphenyl)pyrimidin-4-yl]amino}ethyl)amino]benzamide;

2-[(2-{[2-amino-6-(2,3-dimethylphenyl)pyrimidin-4-yl]amino}ethyl)amino]pyridine-4-carboxamide;

6-(2-{[2-amino-6-(2,3-dimethylphenyl)pyrimidin-4-yl]amino}ethoxy)pyridine-3-carboxamide;

4-(2-{[2-amino-6-(3-hydroxyphenyl)pyrimidin-4-yl]amino}ethyl)benzene-1-sulfonamide;

ethyl 6-[(2-{[2-amino-6-(2,3-dimethylphenyl)pyrimidin-4-yl]amino}ethyl)amino]pyridine-3-carboxylate;

4-[(2-{[2-amino-6-(2,3-dimethylphenyl)pyrimidin-4-yl]amino}ethyl)amino]-2-(trifluoromethyl)benzene-1-sulfonamide;

4-[(2-{[2-amino-6-(2,3-dimethylphenyl)pyrimidin-4-yl]amino}ethyl)amino]benzamide;

ethyl N-[4-(2-{[2-amino-6-(2,3-dimethylphenyl)pyrimidin-4-yl]amino}ethyl)phenyl]carbamate;

5-[(2-{[2-amino-6-(2,3-dimethylphenyl)pyrimidin-4-yl]amino}ethyl)amino]-2-methoxybenzene-1-sulfonamide;

3-(2-amino-6-{[2-(4-sulfamoylphenyl)ethyl]amino}pyrimidin-4-yl)phenyl trifluoromethanesulfonate;

4-(2-{[2-amino-6-(2,3-dimethylphenyl)pyrimidin-4-yl]amino}ethyl)benzoic acid;

6-[(2-{[2-amino-6-(3-chloro-2-methylphenyl)pyrimidin-4-yl]amino}ethyl)amino]-3,4-dihydro-2H-1,4-benzoxazin-3-one;

6-(2,3-dimethylphenyl)-4-N-{2-[(2-methyl-1,3-benzothiazol-6-yl)amino]ethyl}pyrimidine-2,4-diamine;

6-[(2-{[2-amino-6-(3-chlorophenyl)pyrimidin-4-yl]amino}ethyl)amino]-3,4-dihydro-2H-1,4-benzoxazin-3-one;

6-[(2-{[2-amino-6-(2,3-dichlorophenyl)pyrimidin-4-yl]amino}ethyl)amino]-3,4-dihydro-2H-1,4-benzoxazin-3-one;

6-(2,3-dichlorophenyl)-4-N-{2-[(2-methyl-1,3-benzothiazol-6-yl)amino]ethyl}pyrimidine-2,4-diamine;

6-(2,3-dimethylphenyl)-4-N-{2-[(3-methanesulfonylphenyl)amino]ethyl}pyrimidine-2,4-diamine;

5-[(2-{[2-amino-6-(2,3-dimethylphenyl)pyrimidin-4-yl]amino}ethyl)amino]-2-methoxybenzene-1-sulfonic acid;

4-[(2-{[2-amino-6-(2,3-dimethylphenyl)pyrimidin-4-yl]amino}ethyl)amino]-3-fluorobenzene-1-sulfonamide;

4-(2-{[2-amino-6-(3-chloro-2-methylphenyl)pyrimidin-4-yl]amino}ethyl)benzamide;

4-(2-{[2-amino-6-(2,3-dimethylphenyl)pyrimidin-4-yl]amino}ethyl)benzamide;

4-N-{2-[(2-amino-9H-purin-6-yl)amino]ethyl}-6-(2,3-dimethylphenyl)pyrimidine-2,4-diamine;

N-[3-(2-{[2-amino-6-(3-chloro-2-methylphenyl)pyrimidin-4-yl]amino}ethyl)phenyl]acetamide;

ethyl N-[3-(2-{[2-amino-6-(3-chloro-2-methylphenyl)pyrimidin-4-yl]amino}ethyl)phenyl]carbamate;

6-(2-{[2-amino-6-(3-chloro-2-methylphenyl)pyrimidin-4-yl]amino}ethyl)-3,4-dihydro-2H-,4-benzoxazin-3-one;

methyl 5-[(2-{[2-amino-6-(2,3-dimethylphenyl)pyrimidin-4-yl]amino}ethyl)amino]pyrazine-2-carboxylate;

methyl 2-[(2-{[2-amino-6-(2,3-dimethylphenyl)pyrimidin-4-yl]amino}ethyl)amino]-6-methylpyrimidine-4-carboxylate;

6-(2,3-dimethylphenyl)-4-N-{2-[(9H-purin-6-yl)amino]ethyl}pyrimidine-2,4-diamine;

6-(3-chloro-2-methylphenyl)-4-N-[2-(3-methanesulfonylphenyl)ethyl]pyrimidine-2,4-diamine;

3-(2-{[2-amino-6-(3-chloro-2-methylphenyl)pyrimidin-4-yl]amino}ethyl)benzene-1-sulfonamide;

3-(2-{[2-amino-6-(2,3-dichlorophenyl)pyrimidin-4-yl]amino}ethyl)benzene-1-sulfonamide;

6-(2-{[2-amino-6-(3-chloro-2-methylphenyl)pyrimidin-4-yl]amino}ethoxy)pyridine-3-carboxamide;

6-[(2-{[2-amino-6-(3-chloro-2-methylphenyl)pyrimidin-4-yl]amino}ethyl)amino]-2,2-dimethyl-3,4-dihydro-2H-1,4-benzoxazin-3-one;

2-(2-{[2-amino-6-(3-chloro-2-methylphenyl)pyrimidin-4-yl]amino}ethoxy)pyrimidine-4-carboxamide;

2-(2-{[2-amino-6-(3-chloro-2-methylphenyl)pyrimidin-4-yl]amino}ethoxy)pyrimidine-4-carboxylic acid;

N-[4-(2-{[2-amino-6-(3-chloro-2-methylphenyl)pyrimidin-4-yl]amino}ethyl)phenyl]-2,2-dimethylpropanamide;

N-[4-(2-{[2-amino-6-(3-chloro-2-methylphenyl)pyrimidin-4-yl]amino}ethyl)phenyl]-2,2,2-trifluoroethane-1-sulfonamide;

1-[4-(2-{[2-amino-6-(3-chloro-2-methylphenyl)pyrimidin-4-yl]amino}ethyl)phenyl]-3-(propan-2-yl)urea;

tert-butyl N-[4-(2-{[2-amino-6-(3-chloro-2-methylphenyl)pyrimidin-4-yl]amino}ethyl)phenyl]carbamate;

N-[4-(2-{[2-amino-6-(3-chloro-2-methylphenyl)pyrimidin-4-yl]amino}ethyl)phenyl]cyclopropanecarboxamide;

N-[4-(2-{[2-amino-6-(3-chloro-2-methylphenyl)pyrimidin-4-yl]amino}ethyl)phenyl]ethane-1-sulfonamide;

4-(2-{[2-amino-6-(2,4,5-trimethylphenyl)pyrimidin-4-yl]amino}ethyl)benzene-1-sulfonamide;

4-(2-{[2-amino-6-(4-methoxy-2,5-dimethylphenyl)pyrimidin-4-yl]amino}ethyl)benzene-1-sulfonamide;

4-(2-{[2-amino-6-(4,5-dichloro-2-methylphenyl)pyrimidin-4-yl]amino}ethyl)benzene-1-sulfonamide;

4-(2-{[2-amino-6-(5-chloro-4-methoxy-2-methylphenyl)pyrimidin-4-yl]amino}ethyl)benzene-1-sulfonamide;

4-(2-{[2-amino-6-(1H-indol-4-yl)pyrimidin-4-yl]amino}ethyl)benzene-1-sulfonamide;

4-(2-{[2-amino-6-(2,5-dimethylphenyl)pyrimidin-4-yl]amino}ethyl)benzene-1-sulfonamide;

4-(2-{[2-amino-6-(5-fluoro-2-methylphenyl)pyrimidin-4-yl]amino}ethyl)benzene-1-sulfonamide;
4-(2-{[2-amino-6-(3,4,5-trichloro-2-methylphenyl)pyrimidin-4-yl]amino}ethyl)benzene-1-sulfonamide;
4-(2-{[2-amino-6-(5-chloro-2-fluoro-3-methylphenyl)pyrimidin-4-yl]amino}ethyl)benzene-1-sulfonamide;
4-(2-{[2-amino-6-(3,5-dichloro-2-methylphenyl)pyrimidin-4-yl]amino}ethyl)benzene-1-sulfonamide;
4-(2-{[2-amino-6-(3,4,5-trichloro-2-methylphenyl)pyrimidin-4-yl]amino}ethyl)benzamide;
4-(2-{[2-amino-6-(3,5-dichloro-2-methylphenyl)pyrimidin-4-yl]amino}ethyl)benzamide;
4-(2-{[2-amino-6-(4-fluoro-2,3-dimethylphenyl)pyrimidin-4-yl]amino}ethyl)benzamide;
4-(2-{[2-amino-6-(3,4-dichloro-2-methylphenyl)pyrimidin-4-yl]amino}ethyl)benzamide;
4-(2-{[2-amino-6-(5-chloro-2-fluoro-3-methylphenyl)pyrimidin-4-yl]amino}ethyl)benzamide;
4-(2-{[2-amino-6-(3-chloro-2-fluorophenyl)pyrimidin-4-yl]amino}ethyl)benzamide;
N-[3-(2-{[2-amino-6-(3-chloro-2-methylphenyl)pyrimidin-4-yl]amino}ethyl)phenyl]-2,2-dimethylpropanamide;
1-[3-(2-{[2-amino-6-(3-chloro-2-methylphenyl)pyrimidin-4-yl]amino}ethyl)phenyl]-3-(propan-2-yl)urea;
tert-butyl N-[3-(2-{[2-amino-6-(3-chloro-2-methylphenyl)pyrimidin-4-yl]amino}ethyl)phenyl]carbamate;
N-[3-(2-{[2-amino-6-(3-chloro-2-methylphenyl)pyrimidin-4-yl]amino}ethyl)phenyl]cyclopropanecarboxamide;
N-[3-(2-{[2-amino-6-(3-chloro-2-methylphenyl)pyrimidin-4-yl]amino}ethyl)phenyl]-2-methylpropane-1-sulfonamide;
N-[4-(2-{[2-amino-6-(3-chloro-2-methylphenyl)pyrimidin-4-yl]amino}ethyl)phenyl]propane-2-sulfonamide;
N-[4-(2-{[2-amino-6-(3-chloro-2-methylphenyl)pyrimidin-4-yl]amino)}ethyl)phenyl]-2-methylpropane-1-sulfonamide;
3-[2-[[2-amino-6-(3-chloro-2-methyl-phenyl)pyrimidin-4-yl]amino]ethyl]benzamide;
4-[2-[[2-amino-6-(3-chloro-2-methyl-phenyl)pyrimidin-4-yl]amino]ethyl]-N-methyl-benzamide;
[4-[2-[[2-amino-6-(3-chloro-2-methyl-phenyl)pyrimidin-4-yl]amino]ethyl]phenyl]-pyrrolidin-1-yl-methanone;
7-[2-[[2-amino-6-(3-chloro-2-methyl-phenyl)pyrimidin-4-yl]amino]ethylamino]-4H-1,4-benzoxazin-3-one;
6-[2-[[2-amino-6-(3-chloro-2-methyl-phenyl)pyrimidin-4-yl]amino]ethylamino]-4-methyl-1,4-benzoxazin-3-one;
7-[2-[[2-amino-6-(3-chloro-2-methyl-phenyl)pyrimidin-4-yl]amino]ethylamino]-3H-quinazolin-4-one;
6-[2-[[2-amino-6-(2,3-dichlorophenyl)pyrimidin-4-yl]amino]ethylamino]-4-methyl-1,4-benzoxazin-3-one;
6-(3-chloro-2-methylphenyl)-4-N-[2-(3-nitrophenyl)ethyl]pyrimidine-2,4-diamine;
4-[2-[[2-amino-6-(2-chloro-3-methyl-phenyl)pyrimidin-4-yl]amino]ethyl]benzenesulfonamide;
4-[2-[[2-amino-6-(2,3,5-trichlorophenyl)pyrimidin-4-yl]amino]ethyl]benzenesulfonamide;
4-[2-[[2-amino-6-(2,3,4-trichlorophenyl)pyrimidin-4-yl]amino]ethyl]benzenesulfonamide;
4-[2-[[2-amino-6-(2,4-dichloro-3-methoxy-phenyl)pyrimidin-4-yl]amino]ethyl]benzenesulfonamide;
6-(3-chloro-2-methyl-phenyl)-N4-[2-(2-methyl-5-nitro-imidazol-1-yl)ethyl]pyrimidine-2,4-diamine;
6-(3-chloro-2-methyl-phenyl)-N4-[2-[(2-methyl-1,3-benzothiazol-6-yl)amino]ethyl]pyrimidine-2,4-diamine;
4-[2-[[2-amino-6-(benzothiophen-3-yl)pyrimidin-4-yl]amino]ethyl]benzenesulfonamide;
6-[2-[[2-amino-6-(3-chlorophenyl)pyrimidin-4-yl]amino]ethylamino]-2,2-dimethyl-4H-1,4-benzoxazin-3-one;
6-[2-[[2-amino-6-(2,3-dichlorophenyl)pyrimidin-4-yl]amino]ethylamino]-3,3-dimethyl-4H-1,4-benzoxazin-2-one; 6-(3-chloro-2-methyl-phenyl)-N4-[2-(3-methylsulfonylanilino)ethyl]pyrimidine-2,4-diamine;
6-(2,3-dichlorophenyl)-N4-[2-(3-methylsulfonylanilino)ethyl]pyrimidine-2,4-diamine;
4-[2-[[2-amino-6-(3-chloro-2-methyl-phenyl)pyrimidin-4-yl]amino]ethyl]-N'-hydroxy-benzamidine;
[4-[2-[[2-amino-6-(3-chloro-2-methyl-phenyl)pyrimidin-4-yl]amino]ethyl]phenyl]-morpholino-methanone;
[4-[2-[[2-amino-6-(3,5-dichloro-2-methyl-phenyl)pyrimidin-4-yl]amino]ethyl]phenyl]-morpholino-methanone;
6-(3-chloro-2-methyl-phenyl)-N4-[3-(3-methylsulfonylanilino)propyl]pyrimidine-2,4-diamine;
4-[2-[[2-amino-6-(3-chloro-2-methyl-phenyl)pyrimidin-4-yl]amino]ethyl]benzenecarbothioamide;
1-[4-[2-[[2-amino-6-(3-chloro-2-methyl-phenyl)pyrimidin-4-yl]amino]ethyl]phenyl]-3-ethyl-urea;
1-[4-[2-[[2-amino-6-(3-chloro-2-methyl-phenyl)pyrimidin-4-yl]amino]ethyl]phenyl]-3-tert-butyl-urea;
1-allyl-3-[4-[2-[[2-amino-6-(3-chloro-2-methyl-phenyl)pyrimidin-4-yl]amino]ethyl]phenyl]urea;
ethyl N-[[4-[2-[[2-amino-6-(3-chloro-2-methyl-phenyl)pyrimidin-4-yl]amino]ethyl]phenyl]carbamoyl]carbamate;
1-[4-[2-[[2-amino-6-(3-chloro-2-methyl-phenyl)pyrimidin-4-yl]amino]ethyl]phenyl]-3-sec-butyl-urea;
1-[4-[2-[[2-amino-6-(3-chloro-2-methyl-phenyl)pyrimidin-4-yl]amino]ethyl]phenyl]-3-ethyl-thiourea;
N-[4-[2-[[2-amino-6-(3-chloro-2-methyl-phenyl)pyrimidin-4-yl]amino]ethyl]phenyl]morpholine-4-carboxamide;
isopropyl N-[4-[2-[[2-amino-6-(3-chloro-2-methyl-phenyl)pyrimidin-4-yl]amino]ethyl]phenyl]carbamate;
Isobutyl N-[4-[2-[[2-amino-6-(3-chloro-2-methyl-phenyl)pyrimidin-4-yl]amino]ethyl]phenyl]carbamate;
2,2-dimethylpropyl N-[4-[2-[[2-amino-6-(3-chloro-2-methyl-phenyl)pyrimidin-4-yl]amino]ethyl]phenyl]carbamate;
2-methoxyethyl N-[4-[2-[[2-amino-6-(3-chloro-2-methyl-phenyl)pyrimidin-4-yl]amino]ethyl]phenyl]carbamate;
But-2-ynyl N-[4-[2-[[2-amino-6-(3-chloro-2-methyl-phenyl)pyrimidin-4-yl]amino]ethyl]phenyl]carbamate;
[4-[2-[[2-amino-6-(3-chloro-2-methyl-phenyl)pyrimidin-4-yl]amino]ethyl]phenyl]cyanamide;
4-[2-[[2-amino-6-(3-chloro-2-methyl-phenyl)pyrimidin-4-yl]amino]ethyl]benzamidine;
4-N-(2-{[2-amino-6-(2,3-dimethylphenyl)pyrimidin-4-yl]amino}ethyl)pyrimidine-2,4-diamine;
5-N-(2-{[2-amino-6-(2,3-dimethylphenyl)pyrimidin-4-yl]amino}ethyl)pyridine-2,5-diamine;
1-N-(2-{[2-amino-6-(2,3-dimethylphenyl)pyrimidin-4-yl]amino}ethyl)-2-fluorobenzene-1,4-diamine;
tert-butyl 4-(2-amino-6-{[2-(4-methanesulfonylphenyl)ethyl]amino}pyrimidin-4-yl)-1,2,3,6-tetrahydropyridine-1-carboxylate;
4-N-[2-(4-methanesulfonylphenyl)ethyl]-6-[1-(4-methylbenzenesulfonyl)-1,2,3,6-tetrahydropyridin-4-yl]pyrimidine-2,4-diamine;

tert-butyl 4-(2-amino-6-{[2-(4-sulfamoylphenyl)ethyl]amino}pyrimidin-4-yl)-1,2,3,6-tetrahydropyridine-1-carboxylate;
4-(2-{[2-amino-6-(cyclohept-1-en-1-yl)pyrimidin-4-yl]amino}ethyl)benzene-1-sulfonamide;
tert-butyl 4-(2-amino-6-{[2-(4-sulfamoylphenyl)ethyl]amino}pyrimidin-4-yl)piperidine-1-carboxylate;
4-{2-[(2-amino-6-cycloheptylpyrimidin-4-yl)amino]ethyl}benzene-1-sulfonamide;
4-(2-{[6-(1-acetyl-1,2,3,6-tetrahydropyridin-4-yl)-2-aminopyrimidin-4-yl]amino}ethyl)benzene-1-sulfonamide;
4-[2-({2-amino-6-[1-(2-methylpropanoyl)-1,2,3,6-tetrahydropyridin-4-yl]pyrimidin-4-yl}amino)ethyl]benzene-1-sulfonamide;
4-(2-{[2-amino-6-(1-methanesulfonyl-1,2,3,6-tetrahydropyridin-4-yl)pyrimidin-4-yl]amino}ethyl)benzene-1-sulfonamide;
4-[2-({2-amino-6-[1-(1,2-oxazole-5-carbonyl)-1,2,3,6-tetrahydropyridin-4-yl]pyrimidin-4-yl}amino)ethyl]benzene-1-sulfonamide;
4-(2-{[2-amino-6-(1-cyclopentanecarbonyl-1,2,3,6-tetrahydropyridin-4-yl)pyrimidin-4-yl]amino}ethyl)benzene-1-sulfonamide;
4-[2-({2-amino-6-[1-(2-cyclopentylacetyl)-1,2,3,6-tetrahydropyridin-4-yl]pyrimidin-4-yl}amino)ethyl]benzene-1-sulfonamide;
4-[2-({2-amino-6-[1-(4-methylbenzoyl)-1,2,3,6-tetrahydropyridin-4-yl]pyrimidin-4-yl}amino)ethyl]benzene-1-sulfonamide;
4-[3-[[2-amino-6-(3-chloro-2-methyl-phenyl)pyrimidin-4-yl]amino]propylamino]benzamide;
4-[3-[[2-amino-6-(3-chloro-2-methyl-phenyl)pyrimidin-4-yl]amino]propylamino]-N-methyl-benzenesulfonamide;
6-(3-chloro-2-methyl-phenyl)-N4-[3-[(2-methyl-1,3-benzothiazol-6-yl)amino]propyl]pyrimidine-2,4-diamine;
2-[2-[[2-amino-6-(3-chloro-2-methyl-phenyl)pyrimidin-4-yl]amino]ethylamino]pyrimidine-4-carboxamide;
6-[2-[[2-amino-6-(3-chloro-2-methyl-phenyl)pyrimidin-4-yl]amino]ethylamino]pyridine-3-carboxamide;
1-[3-[2-[[2-amino-6-(3-chloro-2-methyl-phenyl)pyrimidin-4-yl]amino]ethyl]phenyl]-3-ethyl-urea;
1-[3-[2-[[2-amino-6-(3-chloro-2-methyl-phenyl)pyrimidin-4-yl]amino]ethyl]phenyl]-3-tert-butyl-urea;
N-[3-[2-[[2-amino-6-(3-chloro-2-methyl-phenyl)pyrimidin-4-yl]amino]ethyl]phenyl]morpholine-4-carboxamide;
3-[3-[2-[[2-amino-6-(3-chloro-2-methyl-phenyl)pyrimidin-4-yl]amino]ethyl]phenyl]-1,1-dimethyl-urea;
N-[3-[2-[[2-amino-6-(3-chloro-2-methyl-phenyl)pyrimidin-4-yl]amino]ethyl]phenyl]pyrrolidine-1-carboxamide;
isopropyl N-[3-[2-[[2-amino-6-(3-chloro-2-methyl-phenyl)pyrimidin-4-yl]amino]ethyl]phenyl]carbamate;
isobutyl N-[3-[2-[[2-amino-6-(3-chloro-2-methyl-phenyl)pyrimidin-4-yl]amino]ethyl]phenyl]carbamate;
2,2-dimethylpropyl N-[3-[2-[[2-amino-6-(3-chloro-2-methyl-phenyl)pyrimidin-4-yl]amino]ethyl]phenyl]carbamate;
1-[6-[2-[[2-amino-6-(3-chloro-2-methyl-phenyl)pyrimidin-4-yl]amino]ethylamino]-3-pyridyl]-3-tert-butyl-urea;
tert-butyl N-[6-[2-[[2-amino-6-(3-chloro-2-methyl-phenyl)pyrimidin-4-yl]amino]ethylamino]-3-pyridyl]carbamate;
N2-[2-[[2-amino-6-(3-chloro-2-methyl-phenyl)pyrimidin-4-yl]amino]ethyl]-1,3,5-triazine-2,4,6-triamine;
2-[2-[[2-amino-6-(3-chloro-2-methyl-phenyl)pyrimidin-4-yl]amino]ethylamino]-4-(trifluoromethyl)pyrimidine-5-carboxamide;
6-(3-chloro-2-methyl-phenyl)-N4-[2-(4-isopropylsulfonylanilino)ethyl]pyrimidine-2,4-diamine;
6-(3-chloro-2-methyl-phenyl)-N4-[2-(4-methylsulfinylanilino)ethyl]pyrimidine-2,4-diamine;
4-[2-[[2-amino-6-(3-chloro-2-methyl-phenyl)pyrimidin-4-yl]amino]ethyl]-3-fluoro-benzamide;
4-[3-[[2-amino-6-(3-chloro-2-methyl-phenyl)pyrimidin-4-yl]amino]propylamino]benzenesulfonamide;
4-[[3-[[2-amino-6-(3-chloro-2-methyl-phenyl)pyrimidin-4-yl]amino]-2,2-dimethyl-propyl]amino]benzenesulfonamide;
6-(3-chloro-2-methyl-phenyl)-N4-[2,2-dimethyl-3-[(2-methyl-1,3-benzothiazol-6-yl)amino]propyl]pyrimidine-2,4-diamine;
6-(3-Chloro-2-methyl-phenyl)-N4-[2-(3-isopropylsulfonylanilino)ethyl]pyrimidine-2,4-diamine;
6-[3-[[2-amino-6-(3-chloro-2-methyl-phenyl)pyrimidin-4-yl]amino]propylamino]pyridine-3-carboxamide;
2-[3-[[2-amino-6-(3-chloro-2-methyl-phenyl)pyrimidin-4-yl]amino]propylamino]pyrimidine-4-carboxamide;
6-(3-chloro-2-methyl-phenyl)-N4-[2-(4-isopropylsulfonylphenyl)ethyl]pyrimidine-2,4-diamine;
6-(3-chloro-2-methyl-phenyl)-N4-[2-(3-isopropylsulfonylphenyl)ethyl]pyrimidine-2,4-diamine;
4-[2-[[2-amino-6-(3-chloro-2-methyl-phenyl)pyrimidin-4-yl]amino]ethyl]-2-fluoro-benzamide;
6-(3-chloro-2-methyl-phenyl)-N4-[2-(3-fluoro-4-methylsulfonyl-phenyl)ethyl]pyrimidine-2,4-diamine;
5-[2-[[2-amino-6-(3-chloro-2-methyl-phenyl)pyrimidin-4-yl]amino]ethyl]-2-hydroxy-benzamide;
2-[2-[[2-amino-6-(3-chloro-2-methyl-phenyl)pyrimidin-4-yl]amino]ethylsulfanyl]pyrimidine-4-carboxamide;
Isopropyl 4-[2-[[2-amino-6-(3-chloro-2-methyl-phenyl)pyrimidin-4-yl]amino]ethyl]benzoate;
1-[3-[2-[[2-amino-6-(3-chloro-2-methyl-phenyl)pyrimidin-4-yl]amino]ethyl]phenyl]guanidine;
6-[2-[[2-amino-6-(3-chloro-2-methyl-phenyl)pyrimidin-4-yl]amino]ethylsulfanyl]pyridine-3-sulfonamide;
methyl 4-[2-[[2-amino-6-(3-chloro-2-methyl-phenyl)pyrimidin-4-yl]amino]ethyl]benzoate;
ethyl 4-[2-[[2-amino-6-(3-chloro-2-methyl-phenyl)pyrimidin-4-yl]amino]ethyl]benzoate;
propyl 4-[2-[[2-amino-6-(3-chloro-2-methyl-phenyl)pyrimidin-4-yl]amino]ethyl]benzoate;
2-hydroxyethyl 4-[2-[[2-amino-6-(3-chloro-2-methyl-phenyl)pyrimidin-4-yl]amino]ethyl]benzoate;
2-methylsulfonylethyl 4-[2-[[2-amino-6-(3-chloro-2-methyl-phenyl)pyrimidin-4-yl]amino]ethyl]benzoate;
2,3-dihydroxypropyl 4-[2-[[2-amino-6-(3-chloro-2-methyl-phenyl)pyrimidin-4-yl]amino]ethyl]benzoate;
6-(3-chloro-2-methyl-phenyl)-N4-[2-[(6-methyl sulfonyl-3-pyridyl)amino]ethyl]pyrimidine-2,4-diamine;
N-[4-[2-[[2-amino-6-(3-chloro-2-methyl-phenyl)pyrimidin-4-yl]amino]ethylamino]-2-methyl-phenyl]acetamide;
6-(3-chloro-2-methyl-phenyl)-N4-[2-(4-ethylphenyl)ethyl]pyrimidine-2,4-diamine;
4-[4-[[2-amino-6-(3-chloro-2-methyl-phenyl)pyrimidin-4-yl]amino]but-2-ynylsulfanyl]benzoic acid;
4-(2-{[2-amino-6-(3-chloro-2-methylphenyl)pyrimidin-4-yl]amino}ethyl)-N-(1-hydroxypropan-2-yl)benzamide;

6-(3-chloro-2-methylphenyl)-4-N-{2-[4-(4-methylpiperazine-1-carbonyl)phenyl]ethyl}pyrimidine-2,4-diamine;

6-(3-chloro-2-methylphenyl)-N4-[2-(4-methanesulfinylphenyl)ethyl]pyrimidine-2,4-diamine;

4-[2-({2-amino-6-[2-methyl-3-(trifluoromethyl)phenyl]pyrimidin-4-yl}amino)ethyl]benzene-1-sulfonamide;

N4-[2-(4-methanesulfonylphenyl)ethyl]-6-[2-methyl-3-(trifluoromethyl)phenyl]pyrimidine-2,4-diamine;

6-(3-chloro-2-methylphenyl)-N4-(2-{[5-(trifluoromethyl)pyridin-2-yl]oxy}ethyl)pyrimidine-2,4-diamine;

6-(3-chloro-2-methylphenyl)-N4-(2-{furo[3,2-c]pyridin-4-yloxy}ethyl)pyrimidine-2,4-diamine;

4-(2-{[2-amino-6-(3-chloro-2-methylphenyl)pyrimidin-4-yl]amino}ethoxy)benzamide;

6-(3-chloro-2-methylphenyl)-N4-{2-[4-(2H-1,2,3,4-tetrazol-5-yl)phenoxy]ethyl}pyrimidine-2,4-diamine;

(Z)-4-(2-{[2-amino-6-(3-chloro-2-methylphenyl)pyrimidin-4-yl]amino}ethoxy)-N'-hydroxybenzene-1-carboximidamide;

6-(3-chloro-2-methylphenyl)-N4-[3-(4-methanesulfonylphenoxy)propyl]pyrimidine-2,4-diamine;

2-(3-{[2-amino-6-(3-chloro-2-methylphenyl)pyrimidin-4-yl]amino}propoxy)pyrimidine-4-carboxamide;

6-(3-{[2-amino-6-(3-chloro-2-methylphenyl)pyrimidin-4-yl]amino}propoxy)pyridine-3-carboxamide;

6-(3-chloro-2-methylphenyl)-N4-{2-[4-(morpholine-4-sulfonyl)phenyl]ethyl}pyrimidine-2,4-diamine;

4-(2-{[2-amino-6-(3-chloro-2-methylphenyl)pyrimidin-4-yl]amino}ethyl)-N-(2-methoxyethyl)benzene-1-sulfonamide;

4-(2-{[2-amino-6-(3-chloro-2-methylphenyl)pyrimidin-4-yl]amino}ethyl)-N-(oxetan-3-yl)benzene-1-sulfonamide;

4-(2-{[2-amino-6-(3-chloro-2-methylphenyl)pyrimidin-4-yl]amino}ethyl)-N-(oxan-4-yl)benzene-1-sulfonamide;

6-(3-chloro-2-methylphenyl)-N4-[2-(4-ethynylphenyl)ethyl]pyrimidine-2,4-diamine;

4-(2-{[2-amino-6-(3-chloro-2-methylphenyl)pyrimidin-4-yl]amino}ethyl)-N-methyl-N-(prop-2-yn-1-yl)benzamide;

6-(2-(2-amino-6-(3-chloro-2-methylphenyl)pyrimidin-4-ylamino)ethoxy)pyridine-3-sulfonamide;

6-(3-chloro-2-methylphenyl)-N4-(2-((5-(methylsulfonyl)pyridin-2-yl)oxy)ethyl)pyrimidine-2,4-diamine;

2-(2-amino-6-(3-chloro-2-methylphenyl)pyrimidin-4-ylamino)-1-(4-(methyl sulfonyl)phenyl)ethanol;

4-(2-(2-Amino-6-(3-chloro-2-methylphenyl)pyrimidin-4-ylamino)-1-hydroxyethyl)benzenesulfonamide;

(2-(2-Amino-6-(4-(methylsulfonyl)phenethylamino)pyrimidin-4-yl)-6-chlorophenyl)methanol; and 4-(2-(2-Amino-6-(3-chloro-2-(hydroxymethyl)phenyl)pyrimidin-4-ylamino)ethyl)benzenesulfonamide:

or a pharmaceutically acceptable salt thereof.

\* \* \* \* \*